United States Patent
Zhao et al.

(10) Patent No.: US 11,779,663 B2
(45) Date of Patent: *Oct. 10, 2023

(54) SPECIFIC CONJUGATION LINKERS, SPECIFIC IMMUNOCONJUGATES THEREOF, METHODS OF MAKING AND USES SUCH CONJUGATES THEREOF

(71) Applicants: Hangzhou DAC Biotech Co., Ltd., Hangzhou (CN); Robert Yongxin Zhao, Lexington, MA (US)

(72) Inventors: Robert Yongxin Zhao, Lexington, MA (US); Qingliang Yang, Hangzhou (CN); Yuanyuan Huang, Hangzhou (CN); Shun Gai, Hangzhou (CN); Linyao Zhao, Hangzhou (CN); Hangbo Ye, Hangzhou (CN); Huihui Guo, Hangzhou (CN); Qianqian Tong, Hangzhou (CN); Minjun Cao, Hangzhou (CN); Junxiang Jia, Hangzhou (CN); Chengyu Yang, Hangzhou (CN); Wenjun Li, Hangzhou (CN); Xiaomai Zhou, Hangzhou (CN); Hongsheng Xie, Hangzhou (CN); Chen Lin, Hangzhou (CN); Zhixiang Guo, Hangzhou (CN); Zhicang Ye, Hangzhou (CN)

(73) Assignee: HANGZHOU DAC BIOTECH CO., LTD., Hangzhou (CN)

( * ) Notice: Subject to any disclaimer, the term of this patent is extended or adjusted under 35 U.S.C. 154(b) by 228 days.

This patent is subject to a terminal disclaimer.

(21) Appl. No.: 17/093,184

(22) Filed: Nov. 9, 2020

(65) Prior Publication Data

US 2021/0052747 A1 Feb. 25, 2021

Related U.S. Application Data

(62) Division of application No. 16/074,981, filed as application No. PCT/IB2016/050580 on Feb. 4, 2016, now Pat. No. 11,129,910.

(51) Int. Cl.
| | |
|---|---|
| *A61B 5/00* | (2006.01) |
| *A61B 8/00* | (2006.01) |
| *A61B 10/00* | (2006.01) |
| *A61K 49/00* | (2006.01) |
| *A61K 47/68* | (2017.01) |
| *C07D 417/12* | (2006.01) |
| *C07D 417/14* | (2006.01) |
| *C07D 498/18* | (2006.01) |
| *C07D 513/22* | (2006.01) |
| *C07D 519/00* | (2006.01) |
| *A61K 45/06* | (2006.01) |
| *A61K 31/194* | (2006.01) |

(52) U.S. Cl.
CPC ...... *A61K 49/0058* (2013.01); *A61K 47/6809* (2017.08); *A61K 47/6829* (2017.08); *A61K 47/6889* (2017.08); *A61K 49/0032* (2013.01); *A61K 49/0043* (2013.01); *C07D 417/12* (2013.01); *C07D 417/14* (2013.01); *C07D 498/18* (2013.01); *C07D 513/22* (2013.01); *C07D 519/00* (2013.01); *A61K 31/194* (2013.01); *A61K 45/06* (2013.01)

(58) Field of Classification Search
CPC ............ A61K 49/0058; A61K 47/6809; A61K 47/6829; A61K 47/6889; A61K 49/0032; A61K 49/0043; A61K 31/194; A61K 45/06; A61K 47/6803; A61K 47/6817; A61K 49/0021; C07D 417/12; C07D 417/14; C07D 498/18; C07D 513/22; C07D 519/00; C07D 207/08; C07D 277/56; A61P 31/00; A61P 35/00; A61P 37/00

See application file for complete search history.

(56) References Cited

U.S. PATENT DOCUMENTS

| 9,839,687 B2 * | 12/2017 | Zhao | ........... A61K 31/5517 |
| 10,293,055 B2 | 5/2019 | Zhao | |
| 10,836,796 B2 | 11/2020 | Zhao et al. | |

(Continued)

FOREIGN PATENT DOCUMENTS

| WO | 2005/037992 A2 | 4/2005 |
| WO | 2014197854 A1 | 12/2014 |
| WO | 2015151080 A2 | 10/2015 |

(Continued)

OTHER PUBLICATIONS

Thiele (1910).*

(Continued)

*Primary Examiner* — Johann R Richter
*Assistant Examiner* — Melissa J Perreira
(74) *Attorney, Agent, or Firm* — BUCHANAN INGERSOLL & ROONEY PC

(57) ABSTRACT

The present invention relates to novel linkers containing a 2,3-disubstituted succinic group, or 2-monosubstituted, or 2,3-disubstituted fumaric or maleic (trans (E)- or cis (Z)-butenedioic), or acetylenedicarboxyl group for conjugation of a cytotoxic agent, and/or one or more different functional molecules per linker to a cell-binding molecule, through bridge linking pairs of thiols on the cell-binding molecule specifically. The invention also relates to methods of making such linkers, and of using such linkers in making homogeneous conjugates, as well as of application of the conjugates in treatment of cancers, infections and autoimmune disorders.

10 Claims, 39 Drawing Sheets

(56) References Cited

U.S. PATENT DOCUMENTS

2015/0322155 A1   11/2015  Zhao
2020/0215206 A1    7/2020  Zhao et al.

FOREIGN PATENT DOCUMENTS

WO        2015151081 A2   10/2015
WO        2015155753 A2   10/2015

OTHER PUBLICATIONS

International Search Report (PCT/ISA/210) dated Oct. 21, 2016, by the State Intellectual Property Office of the P.R. China as the International Searching Authority for International Application No. PCT/IB2016/050580.

Written Opinion (PCT/ISA/237) dated Oct. 21, 2016, by the State Intellectual Property Office of the P.R. China as the International Searching Authority for International Application No. PCT/IB2016/050580.

Examination Report No. 1 dated Aug. 31, 2020, by the Australian Patent Office in corresponding Australian Patent Application No. 2016202632. (5 pages).

Office Action dated Apr. 14, 2020, by the Canadian Patent Office in corresponding Canadian Patent Application No. 3,013,412. (5 pages).

The extended European search report dated Aug. 7, 2019, by the European Patent Office in corresponding European Patent Application No. 16715987.0. (6 pages).

International Preliminary Report on Patentability dated Oct. 11, 2018 by the State Intellectual Property Office of the People's Republic of China in corresponding International Patent Application No. PCT/IB2016/050580.

Adams et al., "Generating improved single-chain Fv molecules for tumor targeting," Journal of Immunological Methods (1999), vol. 231, pp. 249-260.

Adem et al., "Auristatin Antibody Drug Conjugate Physical Instability and the Role of Drug Payload," Bioconjugate Chemistry, (2014), vol. 25, No. 4, pp. 656-664.

Afar et al., "Preclinical validation of anti-TMEFF2-auristatin E-conjugated antibodies in the treatment of prostate cancer," Molecular Cancer Therapeutics, (2004), vol. 3, No. 8, pp. 921-932.

Albelda et al., "Integrin Distribution in Malignant Melanoma: Association of the β3 Subunit with Tumor Progression," Cancer Research, (Oct. 15, 1990), vol. 50, No. 20, pp. 6757-6764.

Almagro et al., "Humanization of antibodies," Frontiers in Bioscience, (Jan. 1, 2008), vol. 13, pp. 1619-1633.

Almutairi et al., "Biodegradable dendritic positron-emitting nanoprobes for the noninvasive imaging of angiogenesis," Proceedings of the National Academy of Sciences, (Jan. 20, 2009), vol. 106, No. 3, pp. 685-690.

Anderl et al., "Chemical modification allows phallotoxins and amatoxins to be used as tools in cell biology," Beilstein Journal of Organic Chemistry, (2012), vol. 8, pp. 2072-2084.

Anderson et al., "A Solid-Phase Approach to the Phallotoxins: Total Synthesis of [Ala7]-Phalloidin," Journal of Organic Chemistry, (2005), vol. 70, pp. 4578-4584.

Arrillaga-Romany et al., "Current status of antiangiogenic therapies for glioblastomas," Expert Opinion on Investigational Drugs, (2014), vol. 23, No. 2, pp. 199-210.

Axup et al., "Synthesis of site-specific antibody-drug conjugates using unnatural amino acids," Proceedings of the National Academy of Sciences, (Oct. 2, 2012), vol. 109, No. 40, pp. 16101-16106.

Badescu et al., "Bridging Disulfides for Stable and Defined Antibody Drug Conjugates," Bioconjugate Chemistry, (2014), vol. 25, No. 6, pp. 1124-1136.

Balasubramanian et al., "Total Synthesis and Biological Evaluation of Tubulysin U, Tubulysin V, and Their Analogues," Journal of Medicinal Chemistry, (2009), vol. 52, No. 2, pp. 238-240.

Barak et al., "Differential staining of actin in metaphase spindles with 7-nitrobenz-2-oxa-1,3-diazole-phallacidin and fluorescent DNase: Is actin involved in chromosomal movement?," Proceedings of the National Academy of Sciences(May 1981), vol. 78, No. 5, pp. 3034-3038.

Barbanti-Brodano et al., "Selective Killing of Macrophages by Amanitin-Albumin Conjugates," Nature New Biology, (Jun. 27, 1973), vol. 243, pp. 281-283.

Bartlett et al., "Stereoselective Synthesis of the Dihydroxyisoleucine Constituent of the Amanita Mushroom Toxins," Tetrahedron Letters, (1982), vol. 23, No. 6., pp. 619-622.

Batori et al., "Exploring the potential of the monobody scaffold: effects of loop elongation on the stability of a fibronectin type III domain," Protein Engineering, (2002), vol. 15, No. 12, pp. 1015-1020.

Brannigan et al., "Protein engineering 20 years on," Nature Reviews: Molecular Cell Biology, (Dec. 2002), vol. 3, pp. 964-970.

Brueckner et al., "Structural basis of transcription inhibition by α-amanitin and implications for RNA polymerase II translocation," Nature Structural & Molecular Biology, (Aug. 2008), vol. 15, No. 8, pp. 811-818.

Baumann et al., "Identification of Structural Features Involved in Binding of α-Amanitin to a Monoclonal Antibody," Biochemistry, (1993), vol. 32, No. 15, pp. 4043-4050.

Bermbach et al., "Epidermal Growth Factor Labeled β-Amanitin-Poly-L-ornithine: Preparation and Evidence for a Specific Cytotoxicity," (1990), vol. 29, pp. 6839-6845.

Beste et al., "Small antibody-like proteins with prescribed ligand specificities derived from the lipocalin fold," Proceedings of the National Academy of Sciences, vol. 96, No. 5, pp. 1898-1903.

Birker-Robaczewska et al., "The Expression of Urotensin II Receptor (U2R) is Up-regulated by Interferon-γ," Journal of Receptors and Signal Transduction, (2003), vol. 23, No. 4, pp. 289-305.

Boccon-Gibod et al., "An update on the use of gonadotropin-releasing hormone antagonists in prostate cancer," Therapeutic Advances in Urology, (2011), vol. 3, No. 3, pp. 127-140.

Boersma et al., "Bispecific Designed Ankyrin Request Proteins (DARPins) Targeting Epidermal Growth Factor Receptor Inhibit A431 Cell Proliferation and Receptor Recycling," The Journal of Biological Chemistry, (Dec. 2, 2011), vol. 286, No. 48, pp. 41273-41285.

Boersma et al., "DARPins and other repeat protein scaffolds: advances in engineering and applications," Current Opinion in Biotechnology, (2011), vol. 22, pp. 849-857.

Boger et al., "Parallel Synthesis and Evaluation of 132 (+)-1,2,9,9a-Tetrahydrocyclopropa[c]benz[e]indol-4-one (CBI) Analogues of CC-1065 and the Duocarmycins Defining the Contribution of the DNA-Binding Domain," Journal of Organic Chemistry, (2001), vol. 66, pp. 6654-6661.

Bonetti et al., "Increased Penetration of Amanitine into Hepatocytes when Conjugated with Albumin," Archives of Toxicology, (1976) vol. 35, pp. 69-73.

Botos et al., "The Structural Biology of Toll-like Receptors," Structure, (Apr. 13, 2011), vol. 19, pp. 447-459.

Bouvier et al., "Leishmanolysin: Surface Metalloproteinase of Leishmania," Methods in Enzymology, (1995), vol. 248, pp. 614-633.

Boylan et al., "Conjugation Site Heterogeneity Causes Variable Electrostatic Properties in Fc Conjugates," Bioconjugate Chemistry, (2013), vol. 24, pp. 1008-1016.

Brich et al., "Preparation and characterization of a water soluble dextran immunoconjugate of doxorubicin and the monoclonal antibody (ABL 364)," Journal of Controlled Release, (1992), vol. 19, pp. 245-258.

Brodner et al., "Identification of the Amatoxin-Binding Subunit of RNA Polymersa B by Affinity Labeling Experiments. Subunit B 3—the True Amatoxin Receptor Protein of Multiple RNA Polymerase B," Biochemistry, (1976), vol. 15, No. 16, pp. 3480-3484.

Burg et al., "NG2 Proteoglycan-binding Peptides Target Tumor Neovasculature," Cancer Research, (Jun. 15, 1999), vol. 59, pp. 2869-2874.

Burgess et al., "The complex mediators of cell growth and differentiation," Immunology Today, (Jun. 1984), vol. 5, No. 6, pp. 155-158.

(56) References Cited

OTHER PUBLICATIONS

Camacho, Luis H., "CTLA-4 blockade with ipilimumab: biology, safety, efficacy, and future considerations," Cancer Medicine, (2015), vol. 4, No. 5, pp. 661-672.
Chafin et al., "Action of α-Amanitin during Pyrophosphorolysis and Elongation by RNA Polymerase II," The Journal of Biological Chemistry, (Aug. 11, 1995), vol. 270, No. 32, pp. 19114-19119.
Chai et al., "Discovery of 23 Natural Tubulysins from Angiococcus disciformis an d48 and Cystobacter SBCb004," Chemistry & Biology, (Mar. 26, 2010), vol. 17, pp. 296-309.
Chandrasekhar et al., "Toward Tubulysin: Gram-Scale Synthesis of Tubuvaline-Tubuphenylalanine Fragment," Journal of Organic Chemistry, (2009), vol. 74, pp. 9531-9534.
Chari et al., "Antibody-Drug Conjugates: An Emerging Concept in Cancer Therapy," Angewandte Chemie International Edition, (2014), vol. 53, pp. 3796-3827.
Chari et al., "Targeted Cancer Therapy: Conferring Specificity to Cytotxic Drugs," Accounts of Chemical Research, (Jan. 2008), vol. 41, No. 1, pp. 98-107.
Chen et al., "Integrin Targeted Delivery of Chemotherapeutics," Theranostics, (2011), vol. 1, pp. 189-200.
Chen et al., "Synthesis of Doxorubicin Conjugates Through Hydrazone Bonds to Melanotransferrin P97," Synthetic Communications: An International Journal for Rapid Communication of Synthetic Organic Chemistry, (2003), vol. 33, No. 14, pp. 2377-2390.
Cochlovius et al., "Cure of Burkitt's Lymphoma in Severe Combined Immunodeficiency Mice by T Cells, Tetravalent CD3×CD19 Tandem Diabody, and CD28 Costimulation," Cancer Research, (Aug. 15, 2000), vol. 60, pp. 4336-4341.
Clackson et al., "Making antibody fragments using phage display libraries," Letters to Nature, (Aug. 15, 1991), vol. 352, pp. 624-628.
Davis et al., "A Conjugate of α-Amanitin and Monoclonal Immunoglobulin G to Thy 1.2 Antigen is Selectively Toxic to T Lymphoma Cells," Science, (Sep. 18, 1981), vol. 213, pp. 1385-1388.
Debruyne et al., "Abarelix for injectable suspension: first-in-class gonadotropin-releasing hormone antagonist for prostate cancer," Future Oncology, (2006), vol. 2, No. 6, pp. 677-696.
Dechantsrelter et al., "N-Methylated Cyclic RGD Peptides as Highly Active and Selective αVβ3 Integrin Antagonists," Journal of Medicinal Chemistry, (1999), vol. 42, No. 16, pp. 3033-3040.
Dennler et al., "Transglutaminase-Based Chemo-Enzymatic Conjugation Approach Yields Homogeneous Antibody-Drug Conjugates," Bioconjugate Chemistry, (2014), vol. 25, pp. 569-578.
Dente et al., "Monoclonal antibodies that recognise filamentous phage: tools for phage display technology," Gene (Oct. 11, 1994), vol. 148, No. 1, pp. 7-13.
Dhar et al., "Targeted delivery of cisplatin to prostate cancer cells by aptamer functionalized Pt(IV) prodrug-PLGA-PEG nanoparticles," Proceedings of the National Academy of Sciences, (Nov. 11, 2008), vol. 105, No. 45, pp. 17356-17361.
Dillman, Robert O., "Cancer Immunotherapy," Cancer Biotherapy and Radiopharmaceuticals, (2011), vol. 26, No. 1. (64 pages).
Dömling et al., "Total Synthesis of Tubulysin U and V," Angewandte Chemie International Edition, (2006), vol. 45, pp. 7235-7239.
Drake et al., "Aldehyde Tag Coupled with HIPS Chemistry Enables the Production of ADCs Conjugated Site-Specifically to Different Antibody Regions with Distinct in Vivo Efficacy and PK Outcomes," Bioconjugate Chemistry, (2014), vol. 25, pp. 1331-1341.
Dudek et al., "First Human Phase I Trial of 852A, a Novel Systemic Toll-like Receptor 7 Agonist, to Activate Innate Immune Responses in Patients with Advanced Cancer," Clinical Cancer Research, (Dec. 1, 2007), vol. 13, No. 23, pp. 7119-7125.
Dunn et al., "Subsite Preferences of Retroviral Proteinases," Methods in Enzymology, (1994), vol. 241. (33 pages).
Edelman et al., "The Covalent Structure of an Entire γG Immunoglobulin Molecule," (May 1969), vol. 63, No. 1, pp. 78-85.
Epelbaum et al., "Molecular and Pharmacological Characterization of Somatostatin Receptor Subtypes in Adrenal, Extraadrenal, and Malignant Pheochromocytomas," Journal of Clinical Endocrinology and Metabolism, (Jun. 1995), vol. 80, No. 6, pp. 1837-1844.

Epenetos et al., "Limitations of Radiolabeled Monoclonal Antibodies for Localization of Human Neoplasms," Cancer Research, (Jun. 1986), vol. 46, pp. 3183-3191.
Faulstich et al., "Ether Derivatives of α-Amanitin. Introduction of Spacer Moieties, Lipophilic Residues, and Radioactive Labels," Biochemistry, (1981), vol. 20, pp. 6498-6504.
Faulstich et al., "Protein Conjugates of Fungal Toxins," Methods in Enzymology, (1985), vol. 112, pp. 225-237.
Fekete et al., "Receptors for Luteinizing Hormone-Releasing Hormone, Somatostatin, Prolactin, and Epidermal Growth Factor in Rat and Human Prostate Cancers and in Benign Prostate Hyperplasia," The Prostate, (1989), vol. 14, pp. 191-208.
Ferris et al., "Tumor Antigen-Targeted, Monoclonal Antibody-Based Immunotherapy: Clinical Response, Cellular Immunity, and Immunoescape," Journal of Clinical Oncology, (Oct. 1, 2010), vol. 28, No. 28, pp. 4390-4399.
Fiume, Luigi, "Penetration of a Beta-Amanitin/Rabbit-Albumin Conjugate into Hepatic Parenchymal Cells," The Lancet, (Oct. 18, 1969), pp. 853-854.
Francis et al., "A phase I trial of antibody directed enzyme prodrug therapy (ADEPT) in patients with advanced colorectal carcinoma or other CEA producing tumours," British Journal of Cancer, (2002), vol. 87, pp. 600-607.
Frangione et al., "Disulphide Bridges of Immunoglobin GI Heavy Chains," Nature, (Dec. 2, 1967), vol. 216, pp. 939-941.
Frangione et al., "Intrachain Disulphide Bridges in Immunoglobulin G Heavy Chains," Biochemical Journal, (1968), vol. 106, pp. 15-21.
Frangione et al., "Structural Studies of Immunoglobulin G," Nature, (Jan. 11, 1969), vol. 221, pp. 145-148.
Frangione et al., "Variations in the S-S Bridges of Immunoglobins G: Interchain Disulphide Bridges of γG3 Myeloma Proteins," Journal of Molecular Biology, (1968), vol. 33, pp. 893-906.
Frankel et al., "Cell Surface Receptor-Targeted Therapy of Acute Myeloid Leukemia: A Review," Cancer Biotherapy & Radiopharmaceuticals, (2000), vol. 15, No. 5, pp. 459-476.
Friestad et al., "Stereoselective Mn-Mediated Coupling of Functionalized Iodides and Hydrazones: a Synthetic Entry to the Tubulysin γ-Amino Acids," Organic Letters, (2004), vol. 6, No. 19, pp. 3249-3252.
Friestad et al., "Synthesis of γ-Amino Esters via Mn-Mediated Radical Addition to Chiral γ- Hydrazonoesters," Organic Letters, (2009), vol. 11, No. 5, pp. 1095-1098.
Fukata et al., "Toll-like receptors (TLRs) and Nod-like receptors (NLRs) in inflammatory disorders," Seminars in Immunology, (2009), vol. 21, pp. 242-253.
Garanger et al., "Tumor Targeting with RGD Peptide Ligands-Design of New Molecular Conjugates for Imaging and Therapy of Cancers," Anti-Cancer Agents in Medicinal Chemistry, (2007), vol. 7, pp. 552-558.
Gerber et al., "Antibody drug-conjugates targeting the tumor vasculature," mAbs, (May/Jun. 2009), vol. 1, No. 3, pp. 247-253.
Geysen et al., "Small peptides induce antibodies with a sequence and structural requirement for binding antigen comparable to antibodies raised against the native protein," Proceedings of the National Academy of Sciences, (Jan. 1985), vol. 82, pp. 178-182.
Ginj et al., "Radiolabeled somatostatin receptor antagonist are preferable to agonists for in vivo peptide receptor targeting of tumors," Proceedings of the National Academy of Sciences, (Oct. 31, 2016), vol. 103, No. 44, pp. 16436-16441.
Gonzalez et al., "Bombesin-Related Peptides and their receptors: recent advances in their role in physiology and disease states," Current Opinion in Endocrinology, Diabetes and Obesity, (Feb. 2008), vol. 15, No. 1, pp. 58-64.
Goodman et al., "Nanomolar Small Molecule Inhibitors for αvβ6, αvβ5, and αvβ3 Integrins," Journal of Medicinal Chemistry, (2002), vol. 45, pp. 1045-1051.
Gorn et al., "Expression of two human skeletal calcitonin receptor isoforms cloned from a giant cell tumor of bone. The first intracellular domain modulates ligand binding and signal transduction," The Journal of Clinical Investigation, (1995), vol. 95, No. 6, pp. 2680-2691.

(56) References Cited

OTHER PUBLICATIONS

Govellino, et al., "A listing of human tumor antigens recognized by T cells: Mar. 2004 update", Cancer Immunology Immunotherapy, vol. 54, 2005, pp. 187-207.
Guo et al., "Culture conditions and analysis of amanitins on Amanita spissa," Acta Microbiologica Sinica, (Jun. 4, 2006), vol. 46, No. 3, pp. 373-378.
Hackel et al., "The full amino acid repertoire is superior to serine/tyrosine for selection of high affinity immunoglobulin G binders from the fibronectin scaffold," Protein Engineering Design & Selection, (2010), vol. 23, No. 4, pp. 211-219.
Hallen et al., "Gene family encoding the major toxins of lethal Amanita mushrooms," Proceedings of the National Academy of Sciences, (Nov. 27, 2007), vol. 104, No. 48, pp. 19097-19101.
Halmos et al., "High Expression of Somatostatin Receptors and Messenger Ribonucleic Acid for Its Receptor Subtypes in Organ-Confined and Locally Advanced Human Prostate Cancers," The Journal of Clinical Endocrinology & Metabolism, (2000), vol. 85, No. 7, pp. 2564-2571.
Halmos et al., "Human Ovarian Cancers Express Somatostatin Receptors," The Journal of Clinical Endocrinology & Metabolism, (2000), vol. 85, No. 10, pp. 3509-3512.
Hamblett et al., "Effects of Drug Loading on the Antitumor Activity of a Monoclonal Antibody Drug Conjugate," Clinical Cancer Research, (Oct. 15, 2004), vol. 10, pp. 7063-7070.
Harlow et al., "Antibodies: A Laboratory Manual," Cold Spring Harbor Laboratory, (1988). (742 pages).
Henning et al., "Substance-p. Receptors in Human Primary Neoplasms: Tumoral and Vascular Localization," International Journal of Cancer, (1995), vol. 61, pp. 786-792.
Heyl et al., "Facile Direct Synthesis of Acetylenedicarbonxamides," Synthesis, (Mar. 17, 2014), vol. 46, No. 11, pp. 1463-1468.
Hillier et al., "Preclinical Evaluation of Novel Glutamate-Urea-Lysin Analogues That Target Prostate-Specific Membrane Antigen as Molecular Imaging Pharmaceuticals for Prostate Cancer," Cancer Research, (Sep. 1, 2009), vol. 69, No. 17, pp. 6932-6940.
Hinman et al., "Preparation and Characterization of Monoclonal Antibody Conjugates of the Calicheamicins: A Novel and Potent Family of Antitumor Antibiotics," Cancer Research, (Jul. 15, 1993), vol. 53, pp. 3336-3342.
Hofer et al., "Molecularly Defined Antibody Conjugation through a Selenocysteine Interface," Biochemistry, (2009), vol. 48, pp. 12047-12057.
Holt et al., "Domain antibodies: proteins for therapy," Trends in Biotechnology, (Nov. 2003), vol. 21, No. 11, pp. 484-490.
Horgen et al., "The Insensitivity of Mushroom Nuclear RNA Polymerase Activity to Inhibition by Amatoxins," Archives of Microbiology, vol. 118, No. 3, pp. 317-319.
Hotz et al., "Systemic cancer immunotherapy with Toll-like receptor 7 agonists," OncoImmunology, (2012), vol. 1, No. 2, pp. 227-228.
Houdebine, Louis-Marie, "Antibody manufacture in transgenic animals and comparisons with other systems," Current Opinion in Biotechnology, (Dec. 1, 2002), vol. 13, No. 6, pp. 625-629.
Hurwitz et al., "The Covalent Binding of Daunomycin and Adriamycin to Antibodies, with Retention of Both Drug and Antibody Activities," Cancer Research, (May 1975), vol. 35, pp. 1175-1181.
Huse et al., "Generation of a Large Combinatorial Library of the Immunoglobulin Repertoire in Phage Lambda," Research Article, (Dec. 8, 1989), pp. 1275-1281.
Javier et al., "Aptamer-Targeted Gold Nanoparticles as Molecular-Specific Contrast Agents for Reflectance Imaging," Bioconjugate Chemistry, (2008), vol. 19, pp. 1309-1312.
Jreston, et al., "Preparation and Characterization of an a-Amanitin Azo Derivative with a Free Carboxyl Group and its Bovine Serum Albumin Conjugate", Archives of Biochemistry and Biophysics, vol. 209, No. 1, Jun. 1981, pp. 63-71.
Junutula et al., "Engineered Thio-Trastuzumab-DM1 Conjugate with an Improved Therapeutic Index to Target Human Epidermal Growth Factor Receptor 2-Positive Breast Cancer," Clinical Cancer Research, (2010), vol. 16, No. 19, pp. 4769-4778.
Junutula et al., "Site-specific conjugation of a cytotoxic drug to an antibody improves the therapeutic index," Nature Biotechnology, (Aug. 2008), vol. 26, No. 8, pp. 925-932.
Karlson-Stiber et al., "Cytotoxic fungi—an overview," Toxicon, (2003), vol. 42, pp. 339-349.
Kasturi et al., "Programming the magnitude and persistence of antibody responses with innate immunity," Nature (Feb. 24, 2011), vol. 470, pp. 543-547.
Kim et al., "C-2 Modified Taxol Analogs with Improved Aqueous Solubility," Bulletin—Korean Chemical Society, (1999), vol. 20, No. 12, pp. 1389-1390.
King et al., "Monoclonal Antibody Conjugates of Doxorubicin Prepared with Branched Linkers: A Novel Method for Increasing the Potency of Doxorubicin Immunoconjugates," Bioconjugate Chemical, (1999), vol. 10, pp. 279-288.
King et al., "Monoclonal Antibody Conjugates of Doxorubicin Prepared with Branched Peptide Linkers: Inhibition of Aggregation by Methoxytriethyleneglycol Chains," Journal of Medicinal Chemistry, (2002), vol. 45, pp. 4336-4343.
Kiprijanov et al., "Generation and Production of Engineered Antibodies," Molecular Biotechnology, (Feb. 2004), vol. 26, No. 1, pp. 39-60.
Köhler et al., "Continuous cultures of fused cells secreting antibody of predefined specificity," Nature, (Aug. 7, 1975), vol. 256, pp. 495-497.
Koide et al., "The Fibronectin Type III Domain as a Scaffold for Novel Binding Proteins," Journal of Molecular Biology, (1998), vol. 284, No. 4, pp. 1141-1151.
Koppán et al., "Targeted Cytotoxic Analog of Luteinizing Hormone-Releasing Hormone AN-207 Inhibits the Growth of PC-82 Human Prostate Cancer in Nude Mice," The Prostate, (1999), vol. 38, pp. 151-158.
Kouroumalis et al., "Treatment of hepatocellular carcinoma with octreotide: a randomised controlled study," Gut, (1998), vol. 42, pp. 442-447.
Kratz et al., "Preparation, Characterization and in Vitro Efficacy of Albumin Conjugates of Doxorubicin," Biological & Pharmaceutical Bulletin, (1998), vol. 21, No. 1, pp. 56-61.
Kratz et al., "Probing the Cysteine-34 Position of Endogenous Serum Albumin with Thiol-Binding Doxorubicin Derivatives. Improved Efficacy of an Acid-Sensitive Doxorubicin Derviative with Specific Albumin-Binding Properties Compared to That of the Parent Compound," Journal of Medicinal Chemistry, (2002), vol. 45, pp. 5523-5533.
Kubicek et al., "The Tubulin-Bound Structure of the Antimitotic Drug Tubulysin," Angewandte Chemie International Edition, (2010), vol. 49, pp. 4809-4812.
Laakkonen et al., "Homing peptides as targeted delivery vehicles," Integrative Biology, (2010), vol. 2, pp. 326-337.
Laguzza et al., "New Antitumor Monoclonal Antibody-Vinca Conjugates LY203725 and Related Compounds: Design, Preparation, and Representative in Vivo Activity," Journal of Medicinal Chemistry, (1989), vol. 32, pp. 548-555.
De Lamo Marin et al., "A Practical and Efficient Total Synthesis of Potent Insulinotropic (2S,3R,4S)-4-Hydroxyisoleucine through a Chiral N-Protected γ-Keto-α-aminoester," European Journal of Organic Chemistry, (2010), pp. 3985-3989.
Lane, Tim, "BCG immunotherapy for superficial bladder cancer," Journal of the Royal Society of Medicine, (Jun. 2001), vol. 94, p. 316.
Lau et al., "Novel Doxorubicin-Monoclonal Anti-carcinoembryonic Antigen Antibody Immunoconjugate Activity in vitro," Bioorganic & Medicinal Chemistry, (1995), vol. 3, No. 10, pp. 1305-1312.
Lazar et al., "A molecular immunology approach to antibody humanization and functional optimization," Molecular Immunology, (2007), vol. 44, pp. 1986-1998.
Lee et al., "Designing dendrimers for biological applications," Nature Biotechnology, (Dec. 2005), vol. 23, No. 12, pp. 1517-1526.
Lei et al., "Binding of Monoclonal Antibodies against the Carboxyl Terminal Segment of the Nicotinic Receptor o Subunit Suggests an

(56) References Cited

OTHER PUBLICATIONS

Unusual Transmembrane Disposition of This Sequence Region," Biochemistry, (1995), vol. 34, pp. 6675-6688.
Li et al., "Human antibodies for immunotherapy development generated via a human B cell hybridoma technology," Proceedings of the National Academy of Sciences, (Mar. 7, 2006), vol. 103, No. 10, pp. 3557-3562.
Liong et al., "Multifunctional Inorganic Nanoparticles for Imaging, Targeting, and Drug Delivery," ACS Nano, (2008), vol. 2, No. 5, pp. 889-896.
Litten, Walter, "The Most Poisonous Mushrooms," Scientific American, Inc., (1975), vol. 232, No. 3, pp. 90-101.
Little et al., "Surface Display of Antibodies," Biotechnology Advances, (1994), vol. 12, No. 3, pp. 539-555.
Liu et al., "Disulfide bond structures of IgG molecules: Structural variations, chemical modifications and possible impacts to stability and biological function," mAbs, (Jan./Feb. 2012), vol. 4, No. 1, pp. 17-23.
Liu et al., "Ranking the Susceptibility of Disulfide Bonds in Human IgG1 Antibodies by Reduction, Differential Alkylation, and LC-MS Analysis," Analytical Chemistry, (Jun. 15, 2010), vol. 82, No. 12, pp. 5219-5226.
Liu et al., "Targeting Cell Surface Alpha(v)beta(3) Integrin Increases Therapeutic Efficacies of a Legumain Protease-Activated Auristatin Prodrug," Molecular Pharmaceutics, (2012), vol. 9, pp. 168-175.
Liu et al., "Engineering therapeutic monoclonal antibodies," Immunological Reviews, (2008), vol. 222, pp. 9-27.
Loh et al., "Somatostatin receptors in nasopharyngeal carcinoma," Virchows Archiv, (2002), vol. 441, pp. 444-448.
Low et al., "Discovery and Development of Folic-Acid-Based Receptor Targeting for Imaging and Therapy of Cancer and Inflammatory Diseases," Accounts of Chemical Research, (Jan. 2008), vol. 41, No. 1, pp. 120-129.
Lundholm et al., "Plaque Production by the Polyoma Virus," Letters to the Editors, (1959) pp. 396-397.
Luo et al., "Peptide Macrocyclization Catalyzed by a Prolyl Oligopeptidase Involved in α-Amanitin Biosynthesis," Chemistry & Biology, (Dec. 18, 2014), vol. 21, pp. 1610-1617.
Lutz et al., "Efficient construction of therapeutics, bioconjugates, biomaterials and bioactive surfaces using azide-alkyne "click" chemistry," Advanced Drug Delivery Reviews, (2008), vol. 60, pp. 958-970.
Lyon et al., "Self-hydrolyzing maleimides improve the stability and pharmacological properties of antibody-drug conjugates," Nature Biotechnology, (2014), vol. 32, pp. 1059-1062.
Maisonneuve et al., "Unleashing the potential of NOD- and Toll-like agonists as vaccine adjuvants," Proceedings of the National Academy of Sciences, (Aug. 26, 2014), vol. 111, No. 34, pp. 12294-12299.
Martin-Killias et al., "A Novel Fusion Toxin Derived from an EpCam-Specific Designed Ankyrin Repeat Protein Has Potent Antitumor Activity," Clinical Cancer Research, (Jan. 1, 2011), vol. 17, No. 1, pp. 100-110.
Matayoshi et al., "Novel Fluorogenic Substrates for Assaying Retroviral Proteases by Resonance Energy Transfer," Science, (1999), vol. 247, No. 4945, pp. 954-958.
May et al., "High Yielding Synthesis of 3α-Hydroxypyrrolo[2,3-b]indoline Dipeptide Methyl Esters: Synthons for Expedient Introduction of the Hydroxypyrroloindoline Moiety into Larger Peptide-Based Natural Products and for the Creation of Tryptathionine Bridges," Journal of Organic Chemistry, (2005), vol. 70, pp. 8424-8430.
May et al., "Intraannular Savige-Fontana Reaction: One-Step Conversion of One Class of Monocyclic Peptides into Another Class of Bicyclic Peptides," Chemistry: A European Journal, (2008), vol. 14, pp. 3404-3409.
May et al., "Synthesis, Characterisation, and In Vitro Evaluation of Pro2-Ile3-S-Deoxo-Amaninamide and Pro2-D-allo-Ile3-S-Deoxo-Amaninamide: Implications for Structure-Activity Relationships in Amanitin Conformation and Toxicity," Chemistry: A European Journal, (2008), vol. 14, pp. 3410-3417.
May et al., "Tryptathionine Bridges in Peptide Synthesis," PeptideScience, (2007), vol. 88, No. 5, pp. 714-724.
Means et al., "Structure and function of Toll-like receptor proteins," Life Sciences, (2000), vol. 68, pp. 241-258.
Medarova et al., "In vivo imaging of siRNA delivery and silencing in tumors," Nature Medicine, (Mar. 2007), vol. 13, No. 3, pp. 372-377.
Medina et al., "Targeted Liposomal Drug Delivery in Cancer," Current Pharmaceutical Design, (2004), vol. 10, pp. 2981-2989.
Mehrling, Thomas, "Chemotherapy is getting 'smarter,'" Future Oncology, (2015), vol. 11, No. 4, pp. 549-552.
Metzger et al., "Synthesis of Nα-Fmoc protected derivatives of S-(2,3-dihydroxypropyl)-cysteine and their application in peptide synthesis," International Journal of Peptide and Protein Research, (1991), vol. 38, pp. 545-554.
Miller et al., "Somatostatin binding in normal and malignant human gastrointestinal mucosa," British Journal of Cancer, (1992), vol. 66, No. 2, pp. 391-395.
Miller et al., "Design, Construction, and In Vitro Analyses of Multivalent Antibodies," The Journal of Immunology, (2003), vol. 170, pp. 4854-4861.
Miller et al., "Synthesis of Taxoids with Improved Cytotoxicity and Solubility for Use in Tumor-Specific Delivery," Journal of Medicinal Chemistry, (2004), vol. 47, pp. 4802-4805.
Milstein, C., "The Disulphide Bridges of Immunoglobulin ϰ-Chains," Biochemical Journal, (1966), vol. 101, pp. 338-351.
Moertel et al., "Expression of Somatostatin Receptors in Childhood Neuroblastoma," American Journal of Clinical Pathology: Anatomic Pathology, (Dec. 1, 1994), vol. 102, No. 6, pp. 752-756.
Mohammad et al., "A new tubulin polymerization inhibitor, auristatin PE, induces tumor regression in a human Waldenstrom's macroglobulinemia xenograft model," International Journal of Oncology, (1999), vol. 15, pp. 367-372.
Moldenhauer et al., "Therapeutic Potential of Amanitin-Conjugated Anti-Epithelial Cell Adhesion Molecule Monoclonal Antibody Against Pancreatic Carcinoma," Journal of the National Cancer Institute, (Apr. 18, 2012), vol. 104, No. 8, pp. 622-634.
Moore et al., "Application of dual affinity retargeting molecules to achieve optimal redirected T-cell killing of B-cell lymphoma," Blood, (Apr. 28, 2011), vol. 117, No. 17, pp. 4542-4551.
Moshnikova et al., "Antiproliferative Effect of pHLIP-Amanitin," Biochemistry, (2013), vol. 52, pp. 1171-1178.
Moyse et al., "Somatostatin Receptors in Human Growth Hormone and Prolactin-Secreting Pituitary Adenomas," Journal of Clinical Endocrinology and Metabolism, (1985), vol. 61, No. 1, pp. 98-103.
Mullard, Asher, "Maturing antibody-drug conjugate pipeline hits 30," Nature Reviews, (May 2013), vol. 12, pp. 329-332.
Mullersman et al., "Conjugation of N-acylated amino sugars to protein by reductive alkylation using sodium cyanoborohydride: application to an azo derivative of α-amanitin," Biochemistry and Cell Biology, (1991), vol. 69, No. 7, pp. 418-427.
Mullersman et al., "Periodate oxidation products derived from methylated α-amanitin: evidence for distinct aldehydic and non-aldehydic forms," International Journal of Peptide and Protein Research, (1991), vol. 38, pp. 409-416.
Muraoka et al., "Effective Production of Amanitins by Two-Step Cultivation of the Basidiomycete, Galerina fasciculata GF-060," Journal of Bioscience and Bioengineering, (2000), vol. 89, No. 1, pp. 73-76.
Muyldermans et al., "Nanobodies: Natural Single-Domain Antibodies," The Annual Review of Biochemistry, (2013), vol. 82, pp. 775-797.
Nakase et al., "Accumulation of arginine-rich cell-penetrating peptides in tumors and the potential for anticancer drug delivery in vivo," Journal of Controlled Release, (2012), vol. 159, pp. 181-188.
Neri et al., "Interfering with pH regulation in tumours as a therapeutic strategy," Nature Reviews, (Oct. 2011), vol. 10, pp. 767-777.
Nicolaou et al., "Calicheamicin ↓1 I: A Rationally Designed Molecule with Extremely Potent and Selective DNA Cleaving Properties and Apoptosis Inducing Activity," Angewandte Chemie International Edition, (1994), vol. 33, No. 2, pp. 183-186.

(56) References Cited

OTHER PUBLICATIONS

Nicolaou et al., "Chemical Synthesis and Biological Evaluation of C-2 Taxoids," Journal of the American Chemical Society, (1995), vol. 117, pp. 2409-2420.
Nicolaou et al., "Chemistry and biology of natural and designed enediynes," Proceedings of the National Academy of Sciences, (Jul. 1993), vol. 90, pp. 5881-5888.
Nicolaou et al., "Designed Enediynes: A New Class of DNA-Cleaving Molecules with Potent and Selective Anticancer Activity," Science, (May 22, 1992), vol. 256, pp. 1172-1178.
Niman et al., "Generation of protein-reactive antibodies by short peptides is an event of high frequency: Implications for the structural basis of immune recognition," Proceedings of the National Academy of Sciences, (Aug. 1983), vol. 80, pp. 4949-4953.
Novellino et al., "A listing of human tumor antigens recognized by T cells: Mar. 2004 update," Cancer Immunology Immunotherapy, (2005), vol. 54, pp. 187-207.
O'Keefe et al., "Characterization of a Transferrin-Diphtheria Toxin Conjugate," The Journal of Biological Chemistry, (Jan. 25, 1985), vol. 260, No. 2, pp. 932-937.
Ohlsson et al., "The Effect of Bombesin, Cholecystokinin, Gastrin, and Their Antagonists on Proliferation of Pancreatic Cancer Cell Lines," Scandinavian Journal of Gastroenterology, (1999), vol. 34, No. 12, pp. 1224-1229.
Ojima et al., "A common pharmacophore for cytotoxic natural products that stabilize microtubules," Proceedings of the National Academy of Sciences, (Apr. 1999), vol. 96, pp. 4256-4261.
Ojima et al., "Syntheses and Structure—Activity Relationships of the Second-Generation Antitumor Taxoids: Exceptional Activity against Drug-Resistant Cancer Cells," Journal of Medicinal Chemistry, (1996), vol. 39, pp. 3889-3896.
Ojima et al., "Syntheses and Structure—Activity Relationships of Taxoids Derived from 14β-Hydroxy-10-deacetylbaccatin III," Journal of Medicinal Chemistry, (1997), vol. 40, pp. 267-278.
Ojima et al., "Tumor-Specific Novel Taxoid-Monoclonal Antibody Conjugates," Journal of Medicinal Chemistry, (2002), vol. 45, pp. 5620-5623.
O'Keefe, et al., "Characterization of a Transferrin-Diphtheria Toxin Conjugate", The Journal of Biological Chemistry, vol. 260, No. 2, Jan. 25, 1985, pp. 932-937.
Okeley et al., "Metabolic Engineering of Monoclonal Antibody Carbohydrates for Antibody-Drug Conjugation," Bioconjugate Chemistry, (2013), vol. 24, pp. 1650-1655.
Pando et al., "First Total Synthesis of Tubulysin B," Organic Letters, (2009), vol. 11, No. 24, pp. 5567-5569.
Pando et al., "The Multiple Multicomponent Approach to Natural Product Mimics: Tubugis, N-Substituted Anticancer Peptides with Picomolar Activity," Journal of the American Chemical Society, (2011), vol. 133, pp. 7692-7695.
Panowski et al., "Site-specific antibody drug conjugates for cancer therapy," mAbs, (Jan./Feb. 2014), vol. 6, No. 1, pp. 34-45.
Parham, P., "One the fragmentation of monoclonal IgG1, IgG2a, and IgG2b from BALB/c mice," The Journal of Immunology, (Dec. 1983), vol. 131, No. 6, pp. 2895-2902.
Patterson et al., "Expedient Synthesis of N-Methyl Tubulysin Analogues with High Cytotoxicity," Journal of Organic Chemistry, (2008), vol. 73, pp. 4362-4369.
PCT/IB2016/050580, "International Preliminary Report on Patentability".
Peltier et al., "The Total Synthesis of Tubulysin D," Journal of the American Chemical Society, (2006), vol. 128, pp. 16018-16019.
Pietersz et al., "Immunochemotherapy of a Murine Thymoma with the Use of Idarubicin Monoclonal Antibody Conjugates," Cancer Research, (Feb. 15, 1988), vol. 48, pp. 926-931.
Pink et al., "Disulphide Bridges of a Human Immunoglobulin G Protein," Nature, (Dec. 2, 1967), vol. 216, pp. 941-942.
Pink et al., "Inter Heavy-Light Chain Disulphide Bridge in Immune Globulins," Nature, (Apr. 1, 1967), vol. 214, pp. 92-94.

Porkka et al., "A fragment of the HMGN2 protein homes to the nuclei of tumor cells and tumor endothelial cells in vivo," Proceedings of the National Academy of Sciences, (May 28, 2002), vol. 99, No. 11, pp. 7444-7449.
Pousse et al., "Brønsted Acid Catalyzed Asymmetric Aldol Reaction: A Complementary Approach to Enamine Catalysis," Organic Letters, (2010), vol. 12, No. 16, pp. 3582-3585.
Preston et al., "Preparation and Characterization of an α-Amanitin Azo Derivative with a Free Carboxyl Group and Its Bovine Serum Albumin Conjugate," Archives of Biochemistry and Biophysics, (Jun. 1981), vol. 209, No. 1, pp. 63-71.
Prèvost et al., "Somatostatin-14 Mainly Binds the Somatostatin Receptor Subtype 2 in Human Neuroblastoma Tumors," Neuroendocrinology, (1996), vol. 63, pp. 188-197.
Rabuka et al., "Site-specific chemical protein conjugation using genetically encoded aldehyde tags," Nature Protocols, (2012), vol. 7, No. 6, pp. 1052-1067.
Raghavan et al., "Cytotoxic Simplified Tubulysin Analogues," Journal of Medicinal Chemistry, (2008), vol. 51, pp. 1530-1533.
Reddy et al., "In Vivo Structural Activity and Optimization Studies of Folate-Tubulysin Conjugates," Molecular Pharmaceutics, (2009), vol. 6, No. 5, pp. 1518-1525.
Reubi et al., "Detection of Somatostatin Receptors in Surgical and Percutaneous Needle Biopsy Samples of Carcinoids and Islet Cell Carcinomas," Cancer Research, (Sep. 15, 1990), vol. 50, pp. 5969-5977.
Reubi et al., "High Density of Somatostatin Receptors in Pituitary Tumors from Acromegalic Patients," Journal of Clinical Endocrinology and Metabolism, (1984), vol. 59, No. 6, pp. 1148-1151.
Reubi et al., "Hormone-Producing Gastrointestinal Tumors Contain a High Density of Somatostatin Receptors," Journal of Endocrinology and Metabolism, (1987), vol. 65, No. 6, pp. 1127-1134.
Reubi et al., "In Vitro and In Vivo Detection of Somatostatin Receptors in Human Malignant Lymphomas," International Journal of Cancer, (1992), vol. 50, pp. 895-900.
Reubi et al., "In Vitro and in Vivo Detection of Somatostatin Receptors in Pheochromocytomas and Paragangliomas," Journal of Clinical Endocrinology and Metabolism, (1992), vol. 74, No. 5, pp. 1082-1089.
Reubi et al., "Receptor Autoradiographic Evaluation of Cholecystokinin, Neurotensin, Somatostatin and Vasoactive Intestinal Peptide Receptors in Gastro-Intestinal Adenocarcinoma Samples: Where Are They Really Located?" International Journal of Cancer, (1999), vol. 81, pp. 376-386.
Reubi et al., "Regulatory peptide receptors in human hepatocellular carcinomas," Gut, (1999), vol. 45 pp. 766-774.
Reubi et al., "Somatostatin Receptors in Human Prostate and Prostate Cancer," Journal of Clinical Endocrinology and Metabolism, (1995), vol. 80, No. 9, pp. 2806-2814.
Reubi et al., "Somatostatin Receptors in Differentiated Ovarian Tumors," American Journal of Pathology, (May 1991), vol. 138, No. 5, pp. 1267-1272.
Reubi et al., "Somatostatin Receptor Incidence and Distribution in Breast Cancer Using Receptor Autoradiography: Relationship to EGF Receptors," International Journal of Cancer, (1990), vol. 46, pp. 416-420.
Reubi et al., "Somatostatin Receptors in Human Renal Cell Carcinomas," Cancer Research, (Nov. 1, 1992), vol. 52, pp. 6074-6078.
Reubi et al., "Visualization of Somatostatin Receptors and Correlation with Immunoreactive Growth Hormone and Prolactin in Human Pituitary Adenomas: Evidence for Different Tumor Subclasses," Journal of Clinical Endocrinology and Metabolism, (1987), vol. 65, No. 1, pp. 65-73.
Ruoslahti et al., "Anchorage Dependence, Integrins, and Apoptosis," Cell, (May 20, 1994), vol. 77, pp. 477-478.
Sagman et al., "Indentification of Somatostatin Receptors in Human Small Cell Lung Carcinoma," Cancer, (Nov. 15, 1990), vol. 66, No. 10, pp. 2129-2133.
Sani et al., "Total Synthesis of Tubulysins U and V," Angewandte Chemie International Edition, (2007), vol. 46, pp. 3526-3529.

(56) References Cited

OTHER PUBLICATIONS

Savige et al., "New Method of Linking Tryptophan to Cysteine Sulphydryle Groups in Peptides and Proteins," Journal of the Chemical Society, Chemical Communications, (1976), No. 15, pp. 600-601.
Schally et al., "Cancer chemotherapy based on targeting of cytotoxic peptide conjugates to their receptors on tumors," European Journal of Endocrinology, (1999), vol. 141, pp. 1-14.
Schmitt et al., "Conformation of Different S-Deoxo-Xaa3-amaninamide Analogues in DMSO Solution as Determined by NMR Spectroscopy. Strong CD Effects Induced by βI, βII Conformation Change," Journal of the American Chemical Society, (1996), vol. 118, No. 18, pp. 4380-4387.
Schumacher et al., "Next generation maleimides enable the controlled assembly of antibody-drug conjugates via native disulfide bond bridging," Organic & Biomolecular Chemistry, (2014), vol. 12, pp. 7261-7269.
Scott et al., "Synthesis of Reagents for the One Step Incorporation of Hydrazide Functionality onto the Lysine Residues of Proteins, and Their Use as Linkers for Carbonyl Containing Molecules," Bioorganic & Medicinal Chemistry Letters, (1996), vol. 6, No. 13, pp. 1491-1496.
Seidah et al., "Pro-Protein Convertases of Subtilisin/Kexin Family," Methods in Enzymology, (1994), vol. 244, pp. 175-188.
Shen et al., "Conjugation site modulates the in vivo stability and therapeutic activity of antibody-drug conjugates," Nature Biotechnology, (Feb. 2012), vol. 30, No. 2, pp. 184-189.
Sievers et al., "Antibody-Drug Conjugates in Cancer Therapy," The Annual Review of Medicine, (2013), vol. 64, pp. 15-29.
Silverman et al., "Multivalent avimer proteins evolved by exon shuffling of a family of human receptor domains," Nature Biotechnology, (Dec. 2005), vol. 23, No. 12, pp. 1556-1561.
Skerra, Arne, "Alternative binding proteins: Anticalins—harnessing the structural plasticity of the lipocalin ligand pocket to engineer novel binding activities," The FEBS Journal, (2008), vol. 275, pp. 2677-2683.
Skerra, Arne, "Alternative non-antibody scaffolds for molecular recognition," Current Opinion in Biotechnology, (2007), vol. 18, pp. 295-304.
Skerre, Arne, "Lipocalins as a scaffold," Biochimica et Biophysica Acta (BBA)—Protein Structure and Molecular Enzymology, (2000), vol. 1482, pp. 337-350.
Sletten et al., "From Mechanism to Mouse: A Tale of Two Bioorthogonal Reactions," Accounts of Chemical Research, (2011), vol. 44, No. 9, pp. 666-676.
Smith et al., "The Enediyne Antibiotics," Journal of Medicinal Chemistry, (May 24, 1996), vol. 39, No. 11, pp. 2103-2117.
Smith et al., "Purification and Kinetic Characterization of Human Cytomegalovirus Assemblin," Methods in Enzymology, (1994), vol. 244, pp. 412-423.
Spiegelberg et al., "Human Myeloma IgG Half-Molecules. Structural and Antigenic Analyses," Biochemistry, (1975), vol. 14, No. 10, pp. 2157-2163.
Srkalovic et al., "Evaluation of Receptors for Somatostatin in Various Tumors Using Different Analogs," Journal of Clinical Endocrinology and Metabolism, (1990), vol. 70, No. 3, pp. 661-669.
Strop et al., "Location Matters: Site of Conjugation Modulates Stability and Pharmacokinetics of Antibody Drug Conjugates," Chemistry & Biology, (Feb. 21, 2013), vol. 20, pp. 161-167.
Strop, Pavel, "Versatility of Microbial Transglutaminase," Bioconjugate Chemistry, (2014), vol. 25, pp. 855-862.
Temming et al., "RGD-based strategies for selective delivery of therapeutics and imaging agents to the tumour vasculature," Drug Resistance Updates, (2005), vol. 8, pp. 381-402.
Thornberry, Nancy, "Interleukin-1β Converting Enzyme," Methods in Enzymology, (1994), vol. 244, pp. 615-631.
Thumshirn et al., "Multimeric Cyclic RGD Peptides as Potential Tools for Tumor Targeting: Solid-Phase Peptide Synthesis and Chemoselective Oxime Ligation," Chemistry: A European Journal, (2003), vol. 9, pp. 2717-2725.
Thundimadathil, Jyothi, "Cancer Treatment Using Peptides: Current Therapies and Future Prospects," Journal of Amino Acids, (2012), vol. 2012. (14 pages).
Tian et al., "A general approach to site-specific antibody drug conjugates," Proceedings of the National Academy of Sciences, (Feb. 4, 2014), vol. 111, No. 5, pp. 1766-1771.
Tolcher et al., "Phase I and Pharmacokinetic Study of CT-322 (BMS-844203), a Targeted Adnectin Inhibitor of VEGFR-2 Based on a Domain of Human Fibronectin," Clinical Cancer Research, (Jan. 2011), vol. 17, No. 2, pp. 363-371.
Trail et al., "Effect of Linker Variation on the Stability, Potency, and Efficacy of Carcinoma- reactive BR64-Doxorubicin Immunoconjugates," Cancer Research, (Jan. 1, 1997), vol. 57, pp. 100-105.
Trouet et al., "A covalent linkage between daunorubicin and proteins that is stable in serum and reversible by lysosomal hydrolases, as required for a lysosomotropic drug-carrier conjugate: In vitro and in vivo studies," Proceedings of the National Academy of Sciences, (Jan. 1982), vol. 79, pp. 626-629.
Tumey et al., "Mild Method for Succinimide Hydrolysis on ADCs: Impact on ADC Potency, Stability, Exposure, and Efficacy," Bioconjugate Chemistry, (2014), vol. 25, pp. 1871-1880.
Ullrich et al., "Pretubulysin, a Potent and Chemically Accessible Tubulysin Precursor from Angiococcus disciformis," Angewandte Chemie International Edition, (2009), vol. 48, pp. 4422-4425.
Van Den Mooter, et al., "Trastuzumab emtansine in advanced human epidermal growth factor receptor 2-positive breast cancer," Expert Opinion on Biological Therapy, (2015), vol. 15, No. 5, pp. 749-760.
Van Wuytswinkel et al., "A convergent synthesis of heterocyclic dendrimers using the 1,3-dipolar cycloaddition reaction of organic azides and acetylenedicarboxylate esters," Journal of the Chemical Society, Perkin Transactions 1, (Jan. 1, 2000), vol. 1, No. 9, pp. 1337-1340.
Villaruz et al., "Immunotherapy in lung cancer," Translational Lung Cancer Research, (2014), vol. 3, No. 1, pp. 2-14.
Wakankar et al., "Analytical methods for physicochemical characterization of antibody drug conjugates," mAbs, (Mar./Apr. 2011), vol. 3, No. 2, pp. 161-172.
Wang et al., "Structural characterization on the maytansinoid-monoclonal antibody immunoconjugate, huN901-DM1, by mass spectrometry," Protein Science, (2005), vol. 14, pp. 2436-2446.
Wang et al., "A Practical Synthesis of (2S,3R,4S)-4-Hydroxyisoleucine, A Potent Insulinotropic α-Amino Acid from Fenugreek," European Journal of Organic Chemistry, (2002), vol. 2002, No. 5, pp. 834-839.
Warpehoski et al., "Stereoelectronic Factors Influencing the Biological Activity and DNA Interaction of Synthetic Antitumor Agents Modeled on CC-1065," Journal of Medicinal Chemistry, (1988), vol. 31, pp. 590-603.
Weber, Christian H., "Regulation and signaling of human bombesin receptors and their biological effects, Current Opinion in Endocrinology, Diabetes & Obesity," (2009), vol. 16, pp. 66-71.
Weber et al., "Adenovirus Endopeptidases," Methods in Enzymology, (1994), vol. 244, pp. 595-604.
Wieland et al., "The Effect of the Chemical Nature of the Side Chains of Amatoxins in the Inhibition of Eukaryotic RNA Polymerase B," European Journal of Biochemistry, (1981), vol. 117, pp. 161-164.
Wieland, Theodor, "The toxic peptides from Amanita mushrooms," International Journal of Peptide and Protein Research, (1983), vol. 22, pp. 257-276.
Winkler et al., "EpCAM-targeted delivery of nanocomplexed siRNA to tumor cells with designed ankyrin repeat proteins," Molecular Cancer Therapeutics, (Sep. 2009), vol. 8, No. 9, pp. 2674-2683.
Wipf et al., "Synthesis of the Tubuvaline-Tubuphenylalanine (Tuv-Tup) Fragment of Tubulysin," Organic Letters, (2004), vol. 6, No. 22, pp. 4057-4060.
Wipf et al., "Total Synthesis of N14-Desacetoxytubulysin H," Organic Letters, (2007), vol. 9, No. 8, pp. 1605-1607.
Wu et al., "Site-specific chemical modification of recombinant proteins produced in mammalian cells by using the genetically

(56) References Cited

OTHER PUBLICATIONS encoded aldehyde tag," Proceedings of the National Academy of Sciences, (Mar. 3, 2009), vol. 106, No. 9, pp. 3000-3005.
Yang et al., "Doxorubicin conjugated with a monoclonal antibody directed to a human melanoma-associated proteoglycan suppresses the growth of established tumor xenografts in nude mice," Proceedings of the National Academy of Sciences, (Feb. 1988), vol. 85, pp. 1189-1193.
Yocum, R. Rogers, "New Laboratory Scale Purification of β-Amanitin from American Amanita phalloides," Biochemistry, (Sep. 5, 1978), vol. 17, No. 18, pp. 3786-3789.
Zaidi et al., "The Calcitonin Gene Peptides: Biology and Clinical Relevance," Clinical Reviews in Clinical Laboratory Sciences, (1990), vol. 28, No. 2, pp. 109-174.
Zanotti et al., "Analogs of Amanin," International Journal of Peptide and Protein Research, (1981), vol. 18, pp. 162-168.
Zanotti et al., "S-deoxo-Abu1, Ile3-amaninamide, an inactive amatoxin analogue," International Journal of Peptide and Protein Research, (1990), vol. 35, pp. 263-270.
Zanotti et al., "Structure-toxicity relationships in the amatoxin series," International Journal of Peptide and Protein Research, (1989), vol. 34, pp. 222-228.
Zanotti et al., "Structure-toxicity relationships in the amatoxin series," International Journal of Peptide and Protein Research, (1992), vol. 40, pp. 551-558.
Zanotti et al., "Synthesis of analogues of amaninamide, an amatoxin from the white Amanita virosa mushroom," International Journal of Peptide and Protein Research, (1987), vol. 30, pp. 450-459.
Zanotti et al., "Synthesis of cyclic tryptathionine peptides," International Journal of Peptide and Protein Research, (1987), vol. 30, pp. 323-329.
Zanotti et al., "Synthetic amatoxin analogues," International Journal of Peptide and Protein Research, (1988), vol. 32, pp. 9-20.
Zhang et al., "Production and characterization of Amanitin toxins from a pure culture of Amanita exitialis," FEMS Microbiology Letters, (2005), vol. 252, pp. 223-228.
Zhao et al., "Synthesis and Biological Evaluation of Antibody Conjugates of Phosphate Prodrugs of Cytotoxic DNA Alkylators for the Targeted Treatment of Cancer," Journal of Medicinal Chemistry, (2012), vol. 55, pp. 766-782.
Zhao et al., "Synthesis and Evaluation of Hydrophilic Linkers for Antibody-Maytansinoid Conjugates," Journal of Medicinal Chemistry, (2011), vol. 54, pp. 3606-3623.
Zhao et al., "Synthesis of a Cytotoxic Amanitin for Biorthogonal Conjugation," ChemBioChem, (2015), vol. 16, pp. 1420-1425.
Zhelev et al., "Preparation of a β-Amanitin-Concanavalin a Conjugate of Low Toxicity," Toxicon, (1987) vol. 25, No. 9, pp. 981-987.
Zhou et al., "Cell-Specific Delivery of a Chemotherapeutic to Lung Cancer Cells," Journal of the American Chemical Society, (2004), vol. 126, pp. 15656-15657.
Zhou et al., "Imaging of nucleolar RNA in living cells using a highly photostable deep-red fluorescent prode," Biosensors and Bioelectronics, (2015), vol. 68, pp. 189-196.
Zhou et al., "Site-Specific Antibody-Drug Conjugation through Glycoengineenng," Bioconjugate Chemistry, (2014), vol. 25, pp. 510-520.
Zimmerman et al., "Production of Site-Specific Antibody-Drug Conjugates Using Optimized Non-Natural Amino Acids in a Cell-Free Expression System," Bioconjugate Chemistry, (2014), vol. 25, pp. 351-361.
Zitzmann et al., "Arginine-Glycine-Aspartic Acid (RGD)-Peptide Binds to Both Tumor and Tumor-Endothelial Cells in Vivo," Cancer Research, (Sep. 15, 2002), vol. 62, pp. 5139-5143.
Notice of Grant for Patent dated Dec. 23, 2021, by the Australian Patent Office in corresponding Australian Patent No. 2016202632. (1 page).
Office Action dated Feb. 24, 2021, by the U.S. Patent and Trademark Office in U.S. Appl. No. 16/074,981. (11 pages).
Clayden et al. "Organic Chemistry," Oxford University Press, 2012, 2nd Edition. (1,469 pages).
Wang et al., "Antibody-Drug Conjugates: The 21st Century Magic Bullets for Cancer," AAPS Advances in the Pharmaceutical Science Series, vol. 17, Springer International Publishing, 2015. (248 pages).
Wuytswinkel et al., "A convergent synthesis of heterocyclic dendrimers using the 1,3-dipolar cycloaddition reaction of organic azides and acetylenedicarboxylate esters," Journal of the Chemical Society, Perkin Transactions 1, No. 9, 2000, pp. 1337-1340.
Office Action dated Jun. 28, 2021, by the Canadian Patent Office in corresponding Canadian Patent Application No. 3,013,412. (5 pages).
Examination Report dated May 31, 2021, by the Indian Patent Office in corresponding Indian Patent Application No. 201817029224 and an English translation of the Report. (8 pages).
Substantive Examination Adverse Report dated Aug. 13, 2021, by the Intellectual Property Corporation of Malaysia in corresponding Malaysian Patent Application No. PI 2018001395. (2 pages).
Patent examination report 1 dated Mar. 3, 2021, by the New Zealand Intellectual Property Office in corresponding New Zealand Patent Application No. 744940. (10 pages).
Patent examination report 2 dated Sep. 16, 2021, by the New Zealand Intellectual Property Office in corresponding New Zealand Patent Application No. 744940. (10 pages).
Substantive Examination Report dated Oct. 15, 2020, by the Intellectual Property Office of the Philippines Bureau of Patents in corresponding Philippine Patent Application No. 1/2018/501638. (5 pages).
Examination Review Report dated Mar. 23, 2021, by the Intellectual Property Office of Singapore in corresponding Singaporean Patent Application No. 11201806594Q. (5 pages).
Written Opinion dated Nov. 11, 2019, by the Intellectual Property Office of Singapore in corresponding Singaporean Patent Application No. 11201806594Q. (8 pages).
Notice of Acceptance for Patent Application dated Aug. 31, 2021, by the Australian Patent Office in corresponding Australian Patent Application No. 2016202632. (3 pages).
Communication pursuant to Article 94(3) EPC dated Dec. 12, 2021, by the European Patent Office in corresponding European Patent Application No. 16715987.0. (5 pages).
Office Action dated Nov. 10, 2020, by the Canadian Patent Office in corresponding Canadian Patent pplication No. 3,013,412. (4 pages).
Notice of Allowance dated May 19, 2021, by the U.S. Patent and Trademark Office in U.S. Appl. No. 16/074,981. (7 pages).
Examination Report No. 1 dated Sep. 28, 2022, by the Australian Patent Office in corresponding Australian Patent Application No. 2021266317. (4 pages).
Office Action (Examination report No. 2 for standard patent application) dated Jun. 20, 2023, by the Australian Government, IP Australia in corresponding Australian Patent Application No. 2021266317. (4 pages).

* cited by examiner

ST1

ST2

ST3

ST4

ST5

ST6

ST7

ST8

SPECIFIC CONJUGATION LINKERS, SPECIFIC IMMUNOCONJUGATES THEREOF, METHODS OF MAKING AND USES SUCH CONJUGATES THEREOF

CROSS REFERENCE OF RELATED APPLICATIONS

This application is a divisional of U.S. patent application Ser. No. 16/074,981, filed on Aug. 2, 2018, now U.S. Pat. No. 11,129,910, entitled "SPECIFIC CONJUGATION LINKERS, SPECIFIC IMMUNOCONJUGATES THEREOF, METHODS OF MAKING AND USES SUCH CONJUGATES THEREOF," which in turn is a national stage application of PCT/IB2016/050580, filed on Feb. 4, 2016. The entire content of each of the prior applications is hereby incorporated by reference.

FIELD OF THE INVENTION

The present invention relates to linkers used for the conjugation of compounds, in particular, cytotoxic agents to specific pairs of sulfur atoms of a cell-binding molecule. The present invention also relates to methods of making cell-binding agent-drug (cytotoxic agent) conjugates in a specific manner comprising either modification of drugs with these linkers first, followed by reaction with prepared cell-binding agents; or modification of cell-binding agents with these linkers first, followed by reaction with drugs.

BACKGROUND OF THE INVENTION

The targeted delivery of highly active or potent pharmaceutical drugs by antibodies or other biological ligands to specific sites of disease in human body is an exciting approach in cancer treatment that has gained significant interest over the past few years. In particular, since US FDA approvals of Adcetris (brentuximab vedotin) in 2011 and Kadcyla (ado-trastuzumab emtansine) in 2013, almost every major pharmaceutical and biotech company has adopted the applications of antibody-drug conjugate (ADC) for targeted treatment of cancers (Chari, R. et al, Angew. Chem., Int. Ed. 2014, 53, 3796-3827; Sievers, E. L. et al. Annu Rev Med. 2013, 64, 15-29; Mehrling, T. Future Oncol, 2015, 11, 549). In conjugated form, the cytotoxic agents exhibit more selective therapeutic activity, sparing non-target cells from many of the toxic effects and improving the safety profile (Van den Mooter, T. et al Expert Opin Biol Ther. 2015, 15, 749-60).

The big challenge of chemotherapeutic drugs is their narrow therapeutic windows due to they normally cannot discriminate between normal and malignant cells, thus causes side effects which limit the tolerated doses below the clinically effective ones. In contrast, immunotherapy, normally in the form of monoclonal antibodies (mAb) can specifically bind to certain proteins or molecules of malignant cells, leaving normal cells unharmed, and thus has less side effects and wider therapeutic windows than chemotherapy. Monoclonal antibodies (mAb) can target against malignant cells by several mechanisms, such as, 1). Making the cancer cell more visible to the immune system (Villaruz, L. C. et al, 2014, Transl Lung Cancer Res, 3, 2-14; Camacho, L. H. 2015 Cancer Med 4, 661-72); 2). Blocking growth signals (Dillman, R. O. 2011, Cancer Biother Radiopharm, 26, 1-64; Ferris, R. L. et al 2010, J Clin Oncol, 28, 4390-9); 3). Stopping new blood vessels from forming (Arrillaga-Romany, I., et al, 2014, Expert Opin Investig Drugs, 23, 199-210); 4). Delivering radiation to cancer cells (Chapuy, B. et al, 2007, Biotechnol J. 2, 1435-43); 5). Delivering chemotherapy drug to cancer cells (Chari R. J. 2008 Acc Chem Res. 41, 98-107; Mullard A. 2013, Nature Reviews Drug Discovery 12, 329-32; Zhao, R. J. 2012, J. Med. Chem., 55, 766-82); and 6). Delivering enzyme to cancer cells (Francis R. J. et al, 2002, Br. J. Cancer 87, 600-7). One of these above strategies, delivering chemotherapy to cancer cells called antibody-drug conjugates (ADCs), which enables to target and deliver drugs to cancer cells leaving normal cells largely unaffected by the exquisite targeting ability of antibodies, has undergone intense exploitation in the last two decades. Currently there are more than 50 ADC drugs in the clinic trials according to www.clinictrails.gov.

The first-generation ADCs, including Kadcyla and Adcetris, are produced through nonselective conjugation of native lysine amines or inter chain cysteine thiols on an antibody respectively to a cytotoxic drug. Since there are over 50 surface-exposed lysines and 8 hinge cysteine residues in IgG1 antibodies, this nonselective conjugation results in randomly cross-linkage of cytotoxic drugs to practically all areas of the antibody molecule, particularly having a diverse population of ADCs with a wide distribution of drugs per antibody (DAR) (Wang, L., et al. 2005 Protein Sci. 14, 2436; Hamblett, K. J., et al. 2004 Clin. Cancer Res. 10, 7063). Thus some of the undesired ADC subpopulation could lead to shorter circulation half-life, lower efficacy, potentially increased off-target toxicity and a wide range of in vivo pharmacokinetic (PK) properties (Hamblett, K. J. et al, Clin. Cancer Res. 2004, 10, 7063-70; Adem, Y. T. et al, Bioconjugate Chem. 2014, 25, 656-664; Boylan, N. J. Bioconjugate Chem., 2013, 24, 1008-1016; Strop, P., et al 2013 Chem. Biol. 20, 161-67). In addition, with this classical conjugation, the batch-to-batch consistency in ADC production can be challenging and may require diligent manufacturing capabilities (Wakankar, A. mAbs, 2011, 3, 161-172).

Therefore, biotechnology companies and academic institutions are highly focusing on establishing novel reliable methods for site-specific ADC conjugation. So far, there are several approaches developed in recent years for site selective ADC preparation (Panowski, S, 2014, mAbs 6, 34). They include incorporation of unpaired cysteines, e.g. engineered reactive cysteine residues, called THIOMAB from Genentech (Junutula, J. R., et al 2010 Clin. Cancer Res. 16, 4769; Junutula, J. R., et al 2008 Nat Biotechnol. 26, 925-32; U.S. Pat. Nos. 8,309,300; 7,855,275; 7,521,541; 7,723,485, WO2008/141044), genetically introduced glutamine tag with *Streptoverticillium mobaraense* transglutaminase (mTG) (Strop, P., Bioconjugate Chem., 2014, 25, 855-862; Strop, P., et al., 2013, Chem. Biol. 20, 161-167; U.S. Pat. No. 8,871,908 for Rinat-Pfizer) or with Microbial transglutaminase (MTGase) (Dennler, P., et al, 2014, Bioconjug. Chem. 25, 569-578. US pat appl 20130189287 for Innate Pharma; U.S. Pat. No. 7,893,019 for Bio-Ker S.r.l. (IT)), incorporation of thiolfucose (Okeley, N. M., et al 2013 Bioconjugate Chem. 24, 1650), incorporation of unnatural amino acids through mutagenesis (Axup, J. Y., et al., 2012, Proc. Natl. Acad. Sci. 109, 16101-16106; Zimmerman, E. S., et al., 2014, Bioconjug. Chem. 25, 351-361; Wu, P., et al, 2009 Proc. Natl. Acad. Sci. 106, 3000-5; Rabuka, D., et al, 2012 Nat. Protoc. 7, 1052-67; U.S. Pat. No. 8,778,631 and US Pat Appl. 20100184135, WO2010/081110 for Sutro Biopharma; WO2006/069246, 2007/059312, U.S. Pat. Nos. 7,332,571, 7,696,312, and 7,638,299 for Ambrx; WO2007/130453, U.S. Pat. Nos. 7,632,492 and 7,829,659 for Allozyne), Incorporation of selenocysteine into antibodies (Hofer, T., et al 2009, Biochemistry 48, 12047-12057; U.S. Pat. No. 8,916,159 for US National Cancer Institute), Conversion of cysteines located in the CXPXR consensus sequence to formylglycine (FGly) with formylglycine generating enzyme (FGE) (Drake, P. M., et al., 2014, Bioconjug. Chem. 25, 1331-1341. Carrico, I. S. et al U.S. Pat. Nos. 7,985,783; 8,097,701; 8,349,910, and US Pat Appl 20140141025, 20100210543 for Redwood Bioscience), and through glycoengineeringly introduction of sialic acid with the use of galactosyl- and sialytransferases (Zhou, Q., et al 2014, Bioconjug. Chem., 25, 510-520, US Pat Appl 20140294867 for Sanofi-Genzyme). These above methods have produced nearly homogeneous product profiles, but they are required antibody-engineering processes and reoptimization of cell culture conditions. Moreover, expression yields for genetic encoding of an unnatural amino acid were typically not promisingly high enough (Tian, F., et al, 2014, Proc. Natl. Acad. Sci. U.S.A 111, 1766-71) which has significant impact on the cost of goods of the ADC. In addition, it has been known that ADCs obtained by conjugation to cysteine side chains often display limited stability in circulation, leading to premature disconnection of the cytotoxic payload before the tumor site is reached (Junutula, J. R., et al 2008, Nat. Biotechnol. 26, 925-32).

The disulfide bond structures of the four subclasses of IgG antibodies were known in the 1960s (Milstein C. Biochem J 1966, 101: 338-51; Pink J R, Milstein C. Nature 1967, 214: 92-4; Frangione B, Milstein C. Nature 1967, 216: 939-41; Pink J R, Milstein C. Nature 1967, 216: 941-42; Frangione B, et al. Biochem J. 1968, 106, 15-21; Frangione B, Milstein C. J Mol Biol 1968, 33: 893-906; Edelman G M, et al. Proc Natl Acad Sci USA 1969; 63: 78-85; Frangione B, et al. Nature 196, 221: 145-8, Spiegelberg, H. L. et al Biochemistry, 1975, 10, 2157-63). Disulfide bond structure is critical for the structure, stability, and biological functions of IgG molecules. Among the four subclasses of IgG antibodies, $IgG_1$, $IgG_2$, $IgG_3$ and $IgG_4$, each IgG contains a total of 12 intra-chain disulfide bonds; each disulfide bond is associated with an individual IgG domain. The two heavy chains are connected in the hinge region by a variable number of disulfide bonds: 2 for $IgG_1$ and $IgG_4$, 4 for $IgG_2$ and 11 for $IgG_3$. The light chain of the $IgG_1$ is connected to the heavy chain by a disulfide bond between the last cysteine residue of the light chain and the fifth cysteine residue of the heavy chain. But, for $IgG_2$, $IgG_3$ and $IgG_4$, the light chain is linked to the heavy chain by a disulfide bond between the last cysteine residue of the light chain and the third cysteine residue of the heavy chain (Liu, H. and May, K., 2012, mAbs 4, 17-23). On the ranks of the susceptibility of disulfide bonds in human IgG1 antibodies by experimental reduction, differential alkylation, and LC-MS analysis (Liu, H, et al, Anal. Chem., 2010, 82, 5219-26), inter chain disulfide bonds are more susceptible to reduction than intra chain disulfide bonds, and the disulfide bonds between the light chain and heavy chain were more susceptible than disulfide bonds between the two heavy chains. The upper disulfide bond of the two inter heavy chain disulfide bonds was more susceptible than the lower one. Furthermore, disulfide bonds in the CH2 domain were the most susceptible to reduction. Disulfide bonds in VL, CL, VH, and CH1 domains had similar and moderate susceptibility, while disulfide bonds in the CH3 domain were the least susceptible to reduction (Liu, H, et al Anal. Chem., 2010, 82, 5219-5226).

Based on the greater susceptibility of inter chain vs. intra chain disulfide bonds in human IgG1 antibodies, several institutions and companies adopted the chemically specific conjugation strategy through rebridging reduced inter chain disulfide bonds of a native antibody, such as, using bromo or dibromo-maleimides, called next generation maleimides (NGMs) (Schumacher, F. F., et al 2014, Org. Biomol. Chem. 12, 7261-69; UCL Cancer Institute), applying bis-alkylating reagents via a three-carbon bridge (Badescu, G., et al., 2014, Bioconjug. Chem. 25, 1124-1136, WO2013/190272, WO2014/064424 for PolyTherics Ltd), with disubstituted heteroaryl bridge (US Pat Appl. 2015/0105539 for Concortis Biosystem), or through di-maleimide as a bridge (WO2014/114207). We have also used bromo maleimide and dibromomaleimide linkers to conjugate both drugs and antibodies for a quite while (WO2014/009774, PCT/IB2012/053554). However, these above bridge linkers were designed in the way to conjugate only one cytotoxic agents to a pair of disulfide bonds, and therefore at most of time they only produced ADCs at DAR less than 2 (drugs per antibody), due to limited numbers (about two pairs) of reduced disulfide bonds are more accessible for conjugation.

As one of the major issues for ADCs is the limited numbers or amount of cytotoxic compound that ultimately reaches the tumor, and thus the favorable DAR over 3 is much important factor for improvement of ADC therapeutical index (Epenetos, A. A. et al, Cancer Res., 1986, 46, 3183-91; Chari, R. V. Acc. Chem. Res., 2008, 41, 98-107, Zhao, R. Y. et al, 2011, J. Med. Chem. 54, 3606-23), we therefore disclosed novel disulfur bridge linkers (PCT/IB2015) that not only are able to conjugate two or more drugs per linker for achieving higher DARs (≥4), but also can selectively rebridge pairs of reduced inter chain disulfide bonds on surface of antibody, which are generated by overloaded TCEP or DTT reduction agents. And the over reduced pairs of thiol groups that are inaccessibly reached by the bridge linkers can be recoupled (regenerated) by an oxide, e.g. dehydroascorbic acid (DHAA) or Cu(II), to form back disulfide bonds at the end of conjugation. In principal, this rebridging back of reduced disulfide bonds results in more stable or longer half-life of ADCs in comparison with traditional thiol linked ADCs.

It has been reported that the "ring-opened" succinimide ring linker bearing mono-thioether bond has improved in vitro stability, improved PK exposure, and improved efficacy as compared to the mono-thiol-maleimide-conjugated ADCs (Tumey, L. N, et al, 2014, Bioconjug. Chem. 25, 1871-80; Lyon, R. P, et al. 2014, Nat. Biotechnol. 32, 1059-62), due to the latter is prone to payload loss via a retro-Michael type reaction of the maleimide conjugation (Shen, B. Q, et al, 2012, Nat Biotechnol. 30, 184-9; Tumey, L. N, et al, 2014 Bioconjug Chem. 25, 1871-80). In this patent application, we extend the scopes of our earlier patent application. The bridge linkers of this invention containing a 2,3-disubstituted succinic group, or 2-monosubstituted, or 2,3-disubstituted fumaric or maleic (trans (E)- or cis (Z)-butenedioic) group, or acetylenedicarboxyl group have less payload loss as compared to their nonhydrolyzed bromo or dibromo-maleimide linkers which were tested in our lab. In other words, the methods of this invention can be used for the immunoconjugates that carry a combination of drugs and functional molecules such as PEGs, which can be used to shield the hydrolysis of conjugated drugs by hydrolases in the blood circulation as well as inhibit the degradation of the antibody by proteinases. Thus the major advantages of this patent for immunoconjugates include: prolonged the half lives of the conjugates during the targeted delivery; conjugated in steps of two or more different function molecules/drugs that act in different phases of the cell cycle to increase the number of target cells exposed to the particular pharmaceutical drugs or effectors; minimized exposure to non-target cells, tissues or organs through conjugation of the function molecules; precisely controlled over drug payloads and drug ratios at the specific sites leading to homogenous final products. In short, the bridge linkers of the invention can stabilize ADCs as well as make homogeneous production of ADCs in a simple manner.

SUMMARY OF THE INVENTION

The present invention provides linkers containing a 2,3-disubstituted succinic group, or 2-monosubstituted, or 2,3-disubstituted fumaric or maleic (trans (E)- or cis (Z)-butenedioic) group, or acetylenedicarboxyl group to link a drug and/or a function molecule to a cell-binding agent (e.g., an antibody). The preferred formula of the cell-binding molecule-linker-drug conjugates can be represented as:

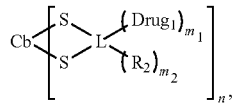

wherein Cb is a cell-binding agent, L is a linker containing succinic, fumaric or maleic group; Drug1 is a drug molecule; $m_1$, $m_2$ and n are an integer from 1 to 30; and two S (sulfur) elements from Cb bridgely link to L, which covalently connects a drug, $Drug_1$ and a function molecule, $R_2$, which is for stabilizing the conjugated "Drug1" during the circulation. The advantages in applying the linker in the cell molecule-drug conjugate are: a). Retaining the stability of the conjugates by covalently cross-linking (rebridging) the pairs of reduced disulfur atoms of the cell-binding agents, particularly of antibodies; b). Enabling conjugation of the cytotoxic agents/drugs to specific sites of a cell-binding molecule, e.g. the inter chain disulfide bond sites of IgG antibodies, resulting in homogeneous production of ADCs.

In one aspect of the present invention the linker is represented by Formula (I)

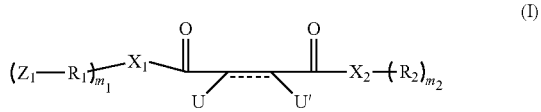

Wherein

— represents an optional single bond.

═══ represents either a single bond, or a double bond, or a triple bond.

It provided that when ═══ represents a single bond, both U and U' are not H; when ═══ represents a double bond, either U or U' can be H, but they are not H at the same time; when ═══ represents a triple bond, both U and U' can be absent.

U and U' represent the same or different leaving group that can be substituted by a thiol. Such leaving groups are, but are not limited to, a halide (e.g., fluoride, chloride, bromide, and iodide), methanesulfonyl (mesyl), toluenesulfonyl (tosyl), trifluoromethyl-sulfonyl (triflate), trifluoromethyl-sulfonate, nitrophenoxyl, N-succinimidyloxyl (NHS), phenoxyl; dinitrophenoxyl; pentafluorophenoxyl, tetrafluorophenoxyl, trifluorophenoxyl, difluorophenoxyl, monofluorophenoxyl, pentachlorophenoxyl, 1H-imidazole-1-yl, chlorophenoxyl, dichlorophenoxyl, trichlorophenoxyl, tetrachlorophenoxyl, N-(benzotriazol-yl)oxyl, 2-ethyl-5-phenylisoxazolium-yl, phenyloxadiazol-yl (ODA), oxadiazol-yl, or an intermediate molecule generated with a condensation reagent for Mitsunobu reactions.

$Z_1$ is a function group that enables to react with a cytotoxic drug, to form a disulfide, ether, ester, thioether, thioester, peptide, hydrazone, carbamate, carbonate, amine (secondary, tertiary, or quarter), imine, cycloheteroalkyane, heteroaromatic, alkyloxime or amide bond; $R_1$ can be absent, or can be selected from $C_1$-$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 carbon atoms of esters, ether, or amide; or polyethyleneoxy unit of formula $(OCH_2CH_2)_p$ or $(OCH_2CH(CH_3))_p$, wherein p is an integer from 0 to about 1000, or combination of above groups thereof.

Additionally $R_1$ is a chain of atoms selected from C, N, O, S, Si, and P, preferably having 0~500 atoms, which covalently connects to $X_1$ and $Z_1$. The atoms used in forming the $R_1$ may be combined in all chemically relevant ways, such as forming alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, peptides, acyloxylamines, hydroxamic acids, or combination above thereof.

$X_1$ and $X_2$ are independently selected from NH; NHNH; $N(R_3)$; $N(R_3)N(R_{3'})$; O; S; $C_1$-$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1~8 amino acids; Wherein $R_3$ and $R_{3'}$ are independently H; $C_1$-$C_8$ of alkyl; $C_2$-$C_8$ of hetero-alkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 carbon atoms of esters, ether, or amide; or polyethyleneoxy unit of formula $(OCH_2CH_2)_p$ or $(OCH_2CH(CH_3))_p$, wherein p is an integer from 0 to about 1000, or combination above thereof.

$R_2$ is independently selected from OH, H, $NH_2$, SH, $NHNH_2$, $N(R_3)(R_{3'})$, $N(R_3)NH(R_{3'})$, polyethyleneoxy unit of formula $(OCH_2CH_2)_pOR_3$, or $(OCH_2CH(CH_3))_pOR_3$, or $NH(CH_2CH_2O)_pR_3$, or $NH(CH_2CH(CH_3)O)_pR_3$, or $N[(CH_2CH_2O)_pR_3][(CH_2CH_2O)_{p'}R_{3'}]$, or $(OCH_2CH_2)_pCOOR_3$, or $CH_2CH_2(OCH_2CH_2)_pCOOR_3$, wherein p and p' are independently an integer selected from 0 to about 1000, or combination thereof, $C_1$-$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; Wherein $R_3$ and $R_{3'}$ are independently H; $C_1$-$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 carbon atoms of esters, ether, or amide; or 1~8 amino acids; or polyethyleneoxy unit of formula $(OCH_2CH_2)_p$ or $(OCH_2CH(CH_3))_p$, wherein p is an integer from 0 to about 1000, or combination above thereof.

$m_1$ and $m_2$ are independently an integer from 1 to 30, preferably from 1 to 10.

In another aspect, this invention provides a cell-binding agent-drug conjugate of Formula (II), in which the cell-binding agent, Cb, and the drug, Drug1, has reacted at the ends of the bridge linker:

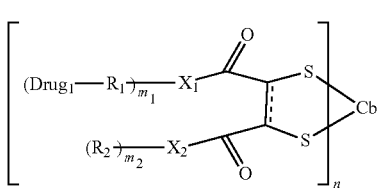
(II)

Wherein:

Cb represents a cell-binding agent, preferably an antibody;

Inside the bracket (square parentheses) are the linker-drug components that are conjugated to pairs of thiols of the cell-binding agent/molecule. The thiols are preferred pairs of sulfur atoms reduced from the inter chain disulfide bonds of the cell-binding agent by a reduction agent selected from dithiothreitol (DTT), dithioerythritol (DTE), L-glutathione (GSH), tris (2-carboxyethyl) phosphine (TCEP), 2-mercaptoethylamine (β-MEA), or/and beta mercaptoethanol (β-ME, 2-ME).

$Drug_1$ represents a cytotoxic agent or a drug, which is linked to the cell-binding agent via the bridge linker of the patent through $R_1$ that can be containing an $C_1$-$C_8$ of alkane; $C_2$-$C_8$ of alkylene, alkenylene, alkynylene, aromatic, ether, polyoxyalkylene, ester, amine, imine, polyamine, hydrazine, hydrazone, amide, urea, semicarbazide, carbazide, alkoxyamine, urethanes, amino acid, peptide, acyloxylamine, hydroxamic acid, disulfide, thioether, thioester, carbamate, carbonate, heterocyclic ring, heteroalkyl, heteroaromatic, or alkoxime; or combination above thereof.

═══ represents either single bond or double bond.

Inside the square bracket are agents that are conjugated to a cell-binding molecule through a pair of sulfur atoms on the cell-binding molecule.

n is 1~30; $R_1$, $R_2$, $m_1$, $m_2$, $X_1$ and $X_2$ are described the same previously in Formula (I).

In a further aspect, the present invention provides a modified cell-binding agent of Formula (III), in which the cell-binding agent, Cb, through its pair of thiols generated with reduction of disulfide bonds, has reacted with the bridge linker, which has $Z_1$, the function groups capable of reacting with a drug:

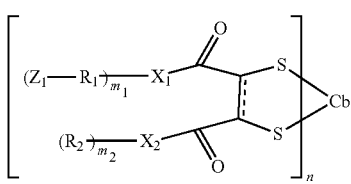
(III)

Wherein "———", $Z_1$, $Z_2$, n, $R_1$, $R_2$, $m_1$, $m_2$, $X_1$, and $X_2$ are defined the same as in Formula (I). ═══ and Cb are defined the same as in Formula (II).

In an even further aspect, the present invention provides a modified drug of Formula (IV), in which the drug, $Drug_1$, has reacted with the linker of Formula (I), which still has the 2,3-disubstituted succinic group, or 2-monosubstituted, or 2,3-disubstituted fumaric or maleic (trans (E)- or cis (Z)-butenedioic) group, or acetylenedicarboxyl group capable of reacting with a pair of thiols of the cell-binding agent:

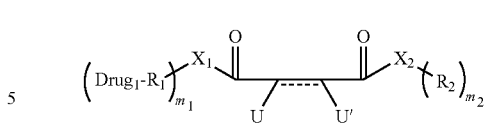
(IV)

Wherein "———", "═══", U, U', $R_1$, $R_2$, $m_1$, $m_2$, $X_1$, and $X_2$ are defined the same as in Formula (I). $Drug_1$ and Cb are defined the same as in Formula (II).

The present invention further relates to a method of making a cell-binding molecule-drug conjugate of Formula (II), wherein the drugs, "$Drug_1$" is linked to a cell-binding agent via the bridge linker.

The present invention also relates to a method of making a modified cell-binding molecule of Formula (III), wherein the cell-binding molecule is reacted with the bridge linker of Formula (I).

The present invention also relates to a method of making a modified drug of formula (IV), wherein the drug is reacted with the bridge linker of Formula (I).

DETAILED DESCRIPTION OF THE INVENTION

Definitions

Figure 1:
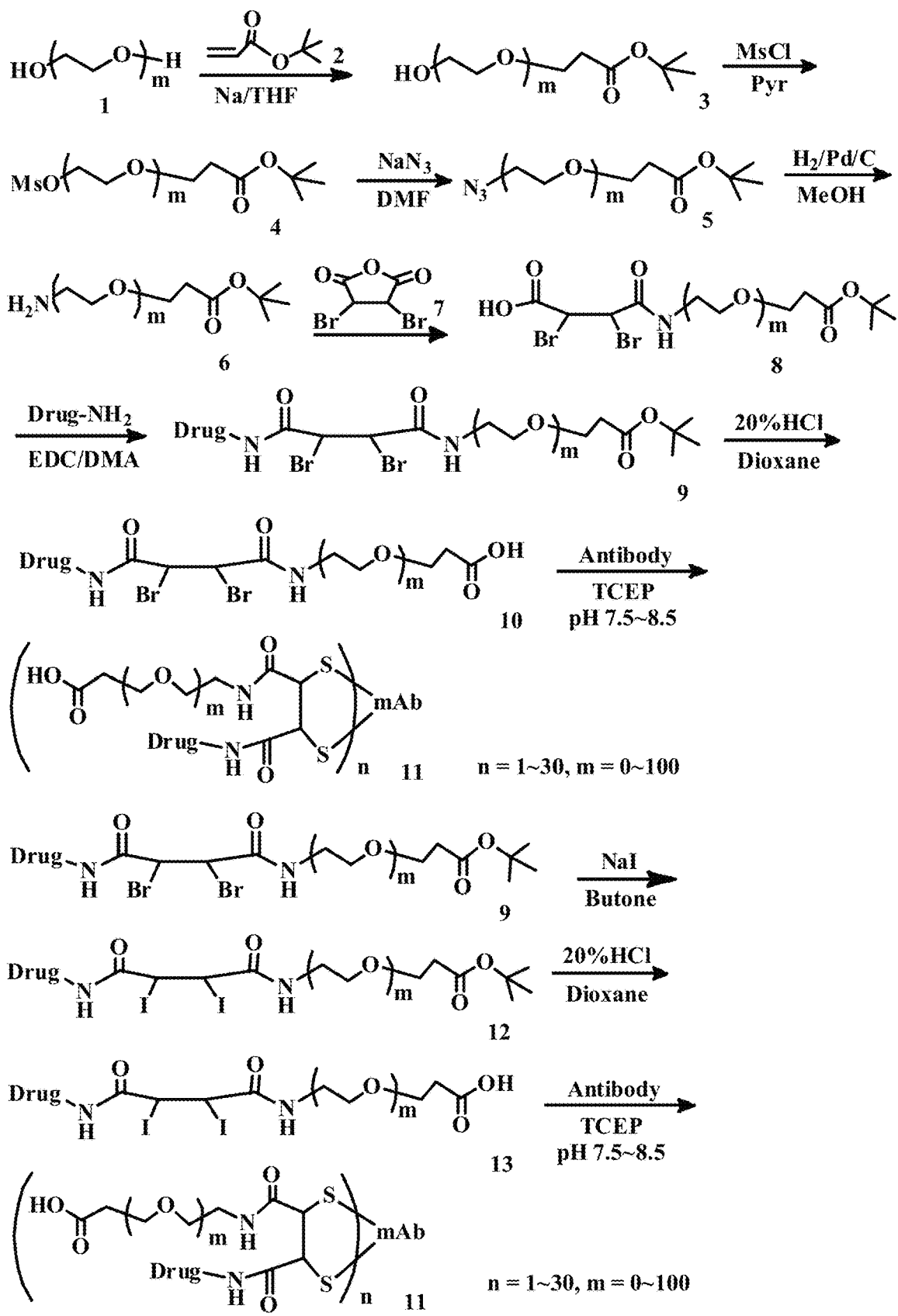
FIG. 1 shows the synthesis of a bridge linker containing a drug and a polyethylene glycol, and the application of this linker in the conjugation of the two different molecules to an antibody via amide bonds.
Figure 2:
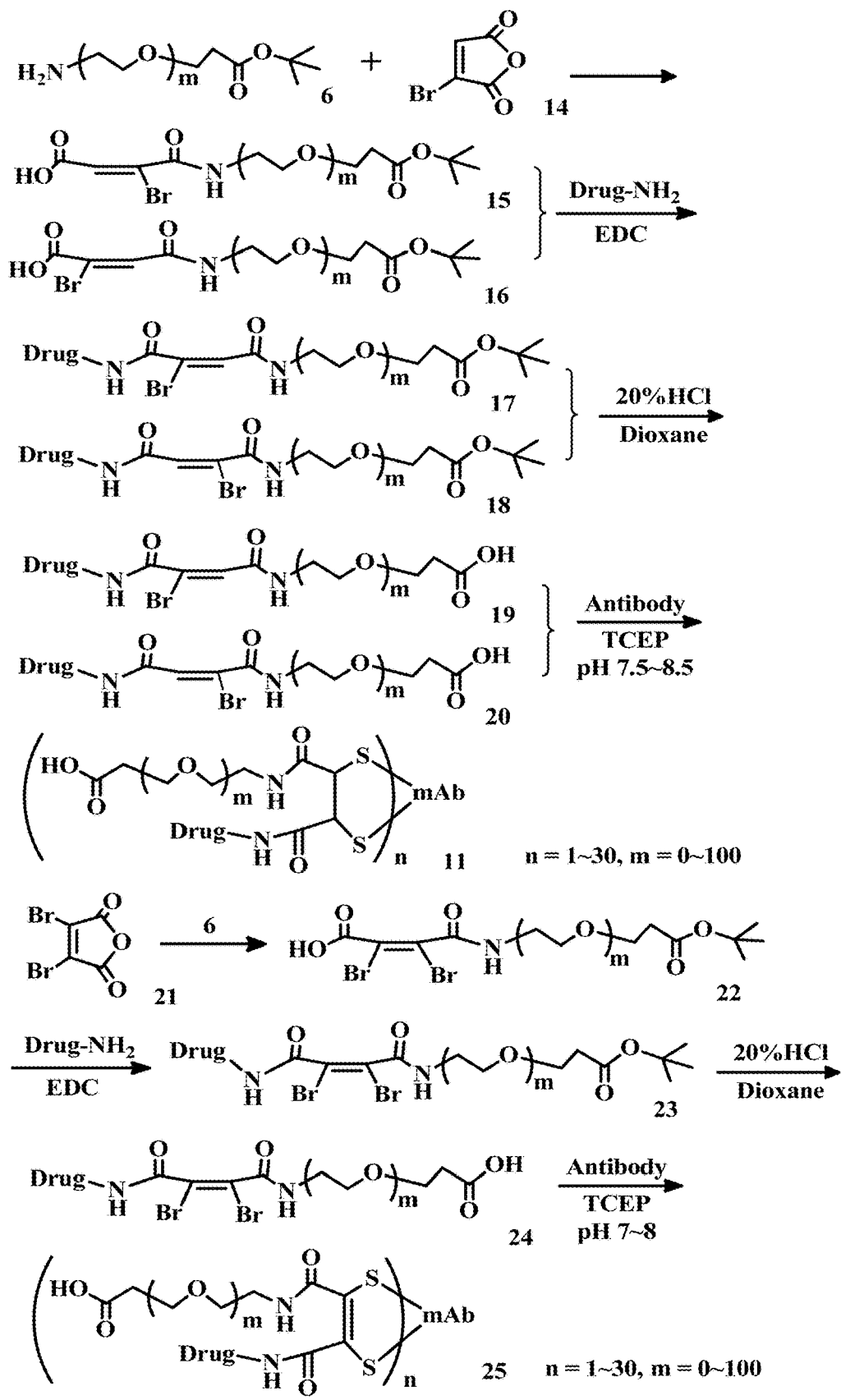
FIG. 2 shows the synthesis of bridge linkers containing a drug and a polyethylene glycol, and the application of the linkers in the conjugation of the two different molecules to an antibody via amide bonds.
Figure 3:
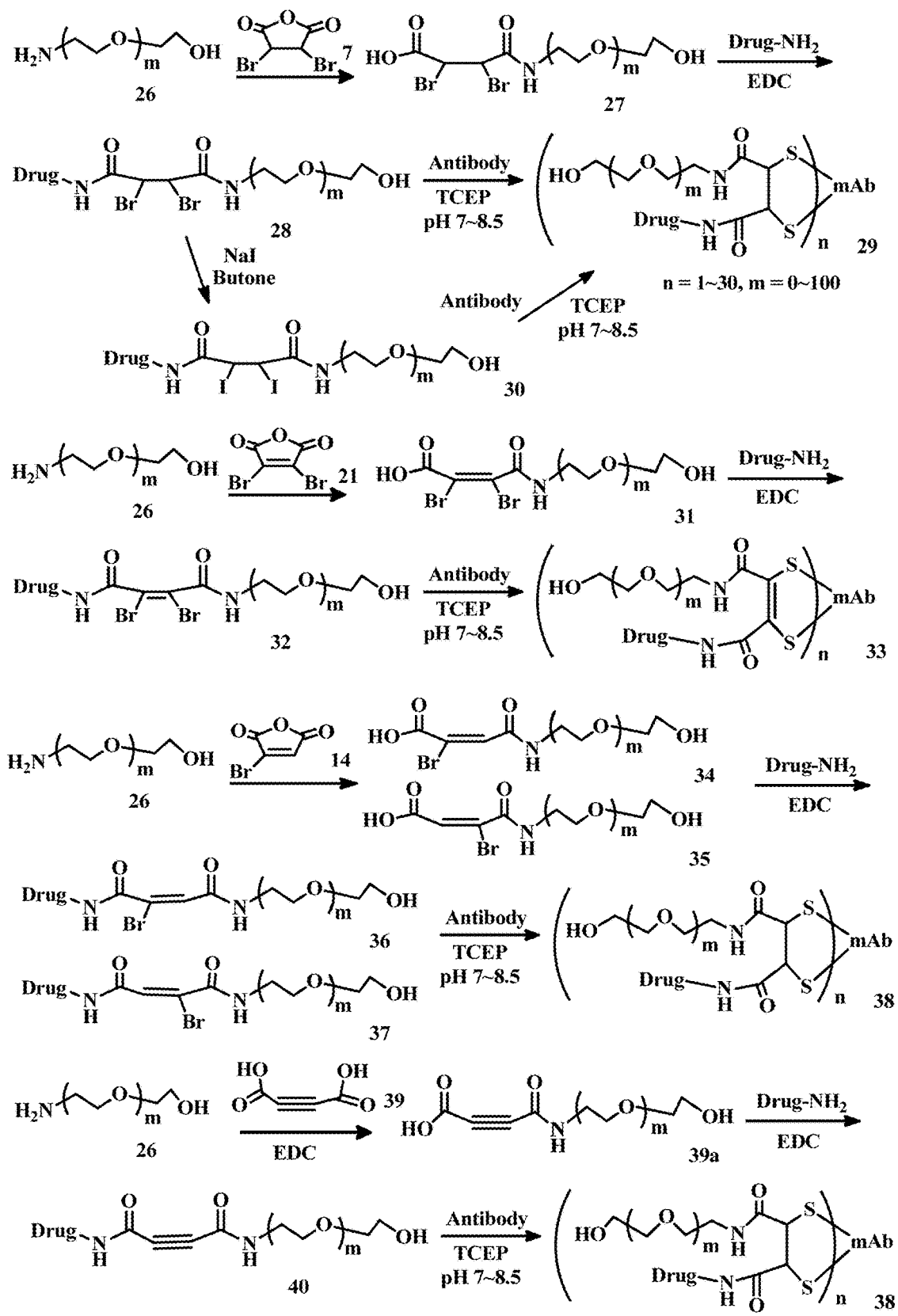
FIG. 3 shows the synthesis of bridge linkers containing a drug and a polyethylene glycol, and the application of the linkers in the conjugation of the two different molecules to an antibody via amide bonds.
Figure 4:
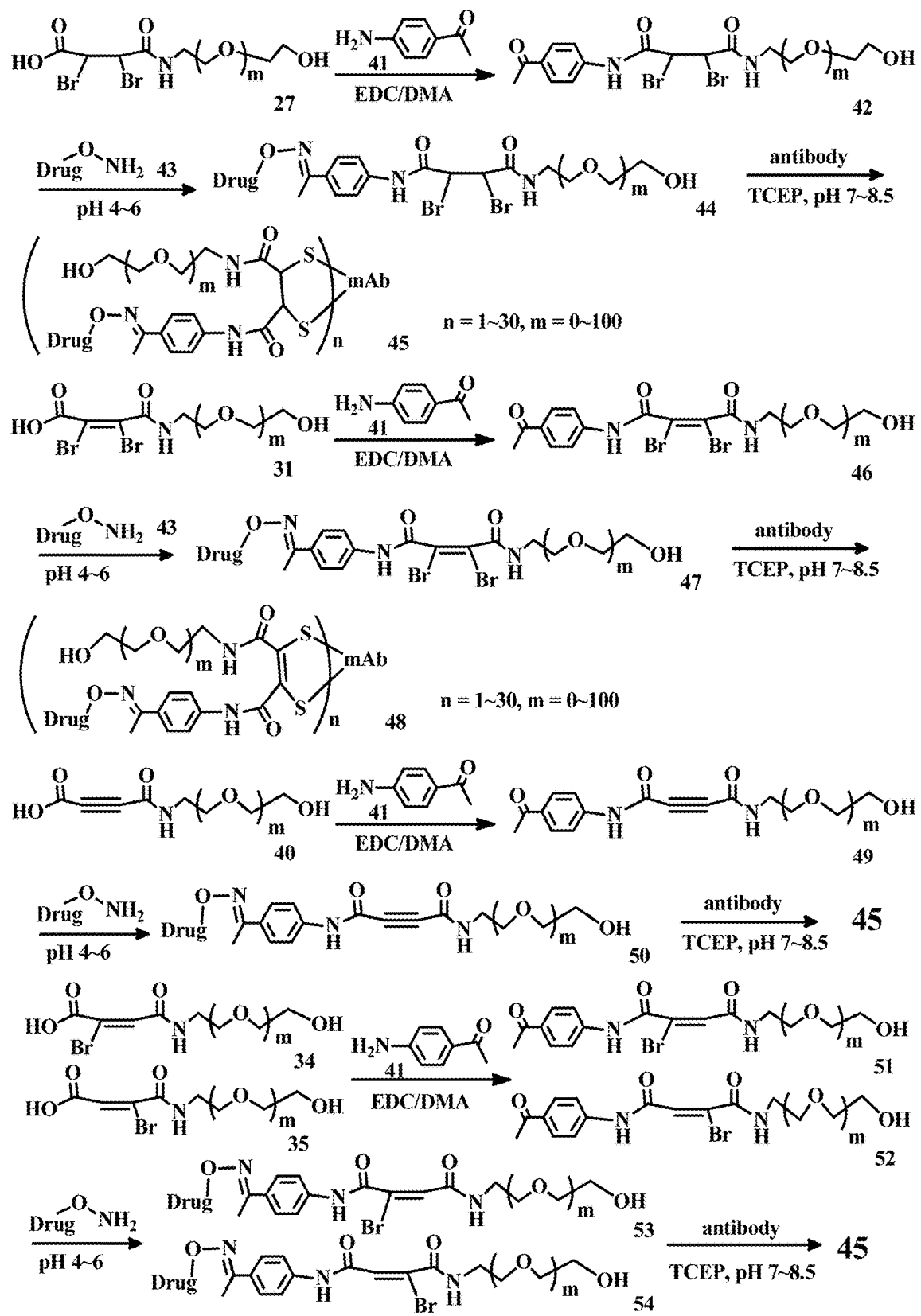
FIG. 4 shows the synthesis of bridge linkers containing a drug and a polyethylene glycol, and the application of the linkers in the conjugation of the two different molecules to an antibody via oxime linkage.
Figure 5:
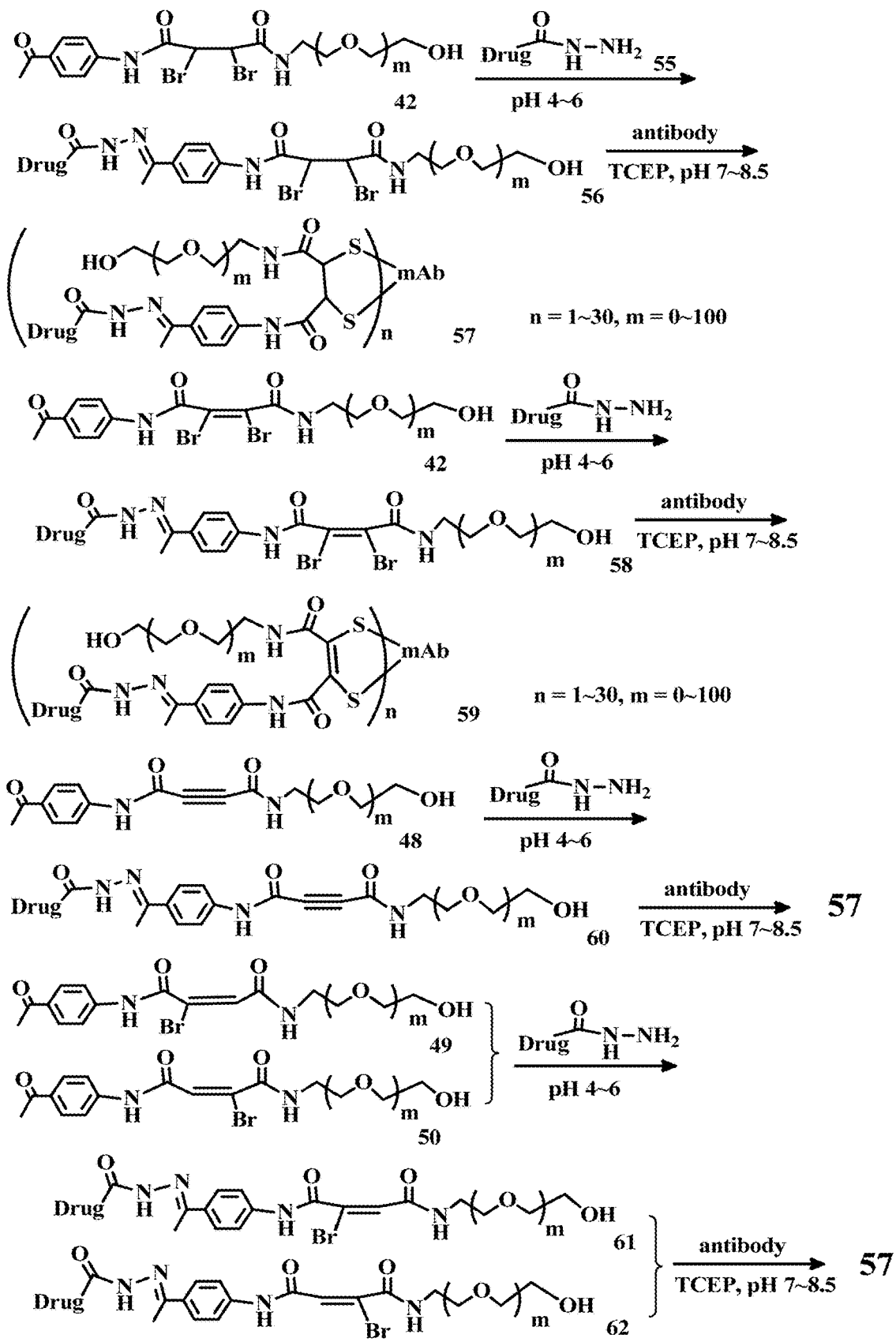
FIG. 5 shows the synthesis of bridge linkers containing a drug and a polyethylene glycol, and the application of the linkers in the conjugation of the two different molecules to an antibody via hydrazone linkage.
Figure 6:
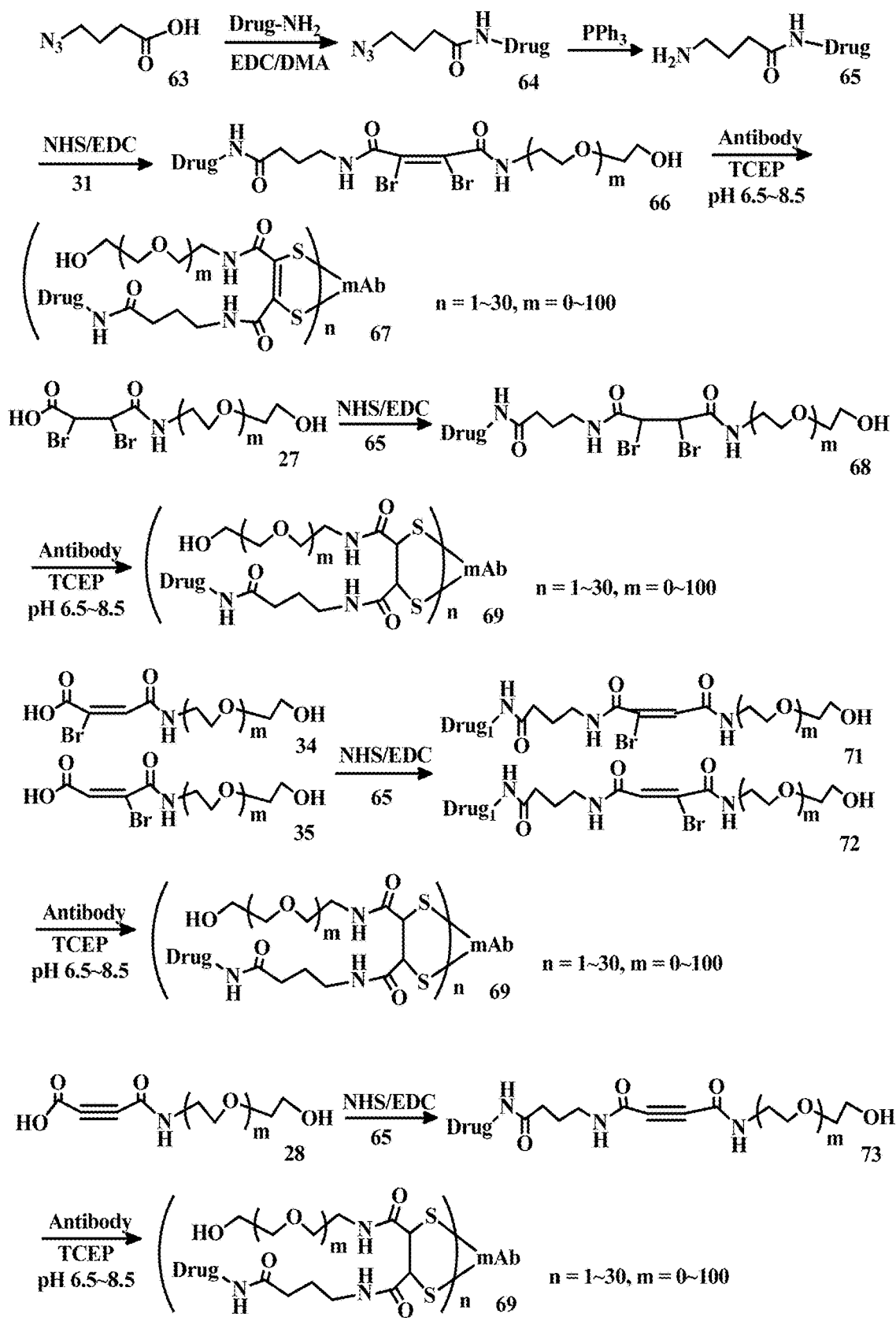
FIG. 6 shows the synthesis of bridge linkers containing a drug and a polyethylene glycol, and the application of the linkers in the conjugation of the two different molecules to an antibody via amide bonds.
Figure 7:
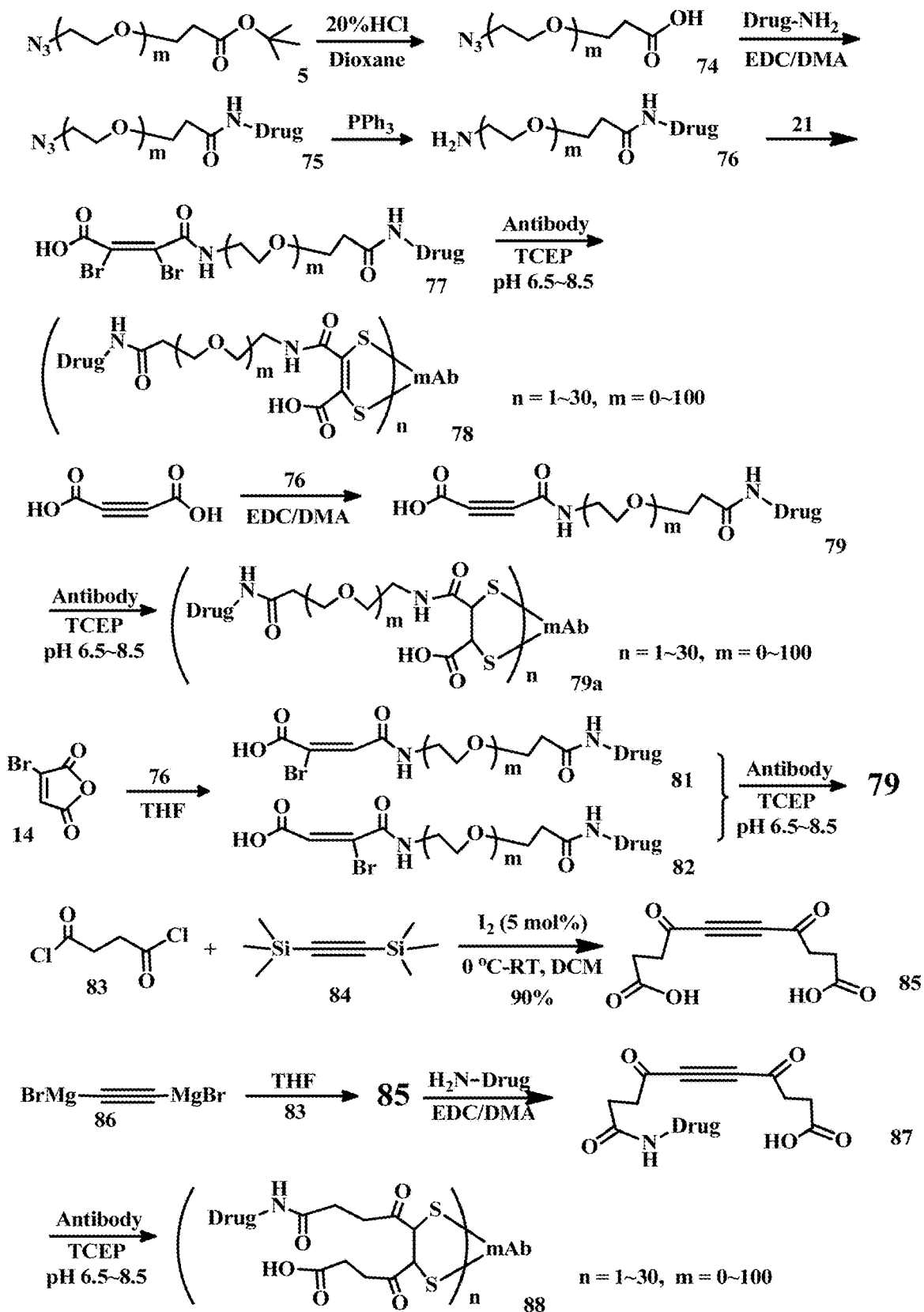
FIG. 7 shows the synthesis of bridge linkers containing a drug, a polyethylene glycol or short alkyl acid, and the conjugation of the drug via these linkers to an antibody.
Figure 8:
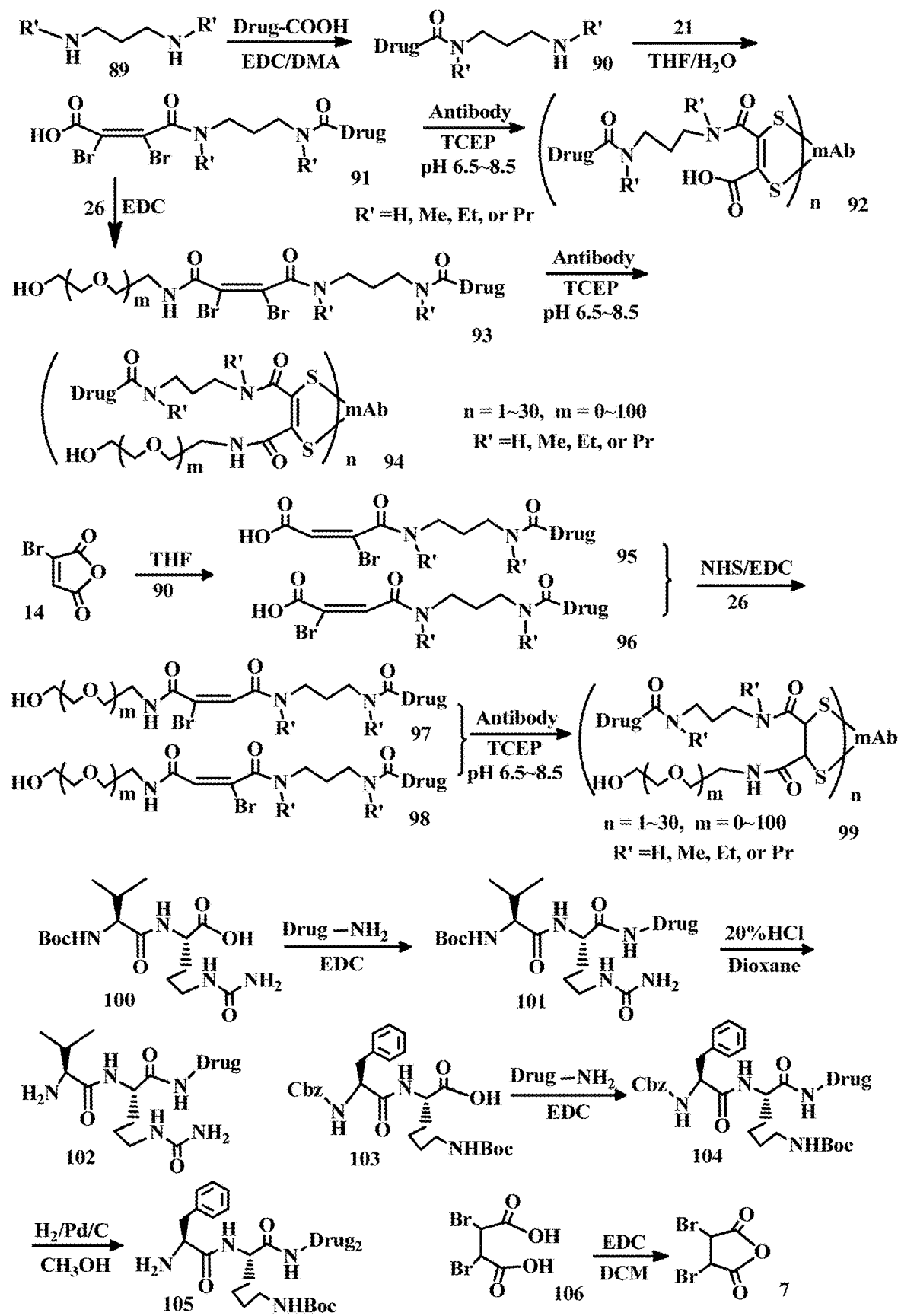
FIG. 8 shows the synthesis of bridge linkers containing a drug, a polyethylene glycol or peptides, and the application in the conjugation of the bridge linker-drug molecules to an antibody via hinder amide linkage.
Figure 9:
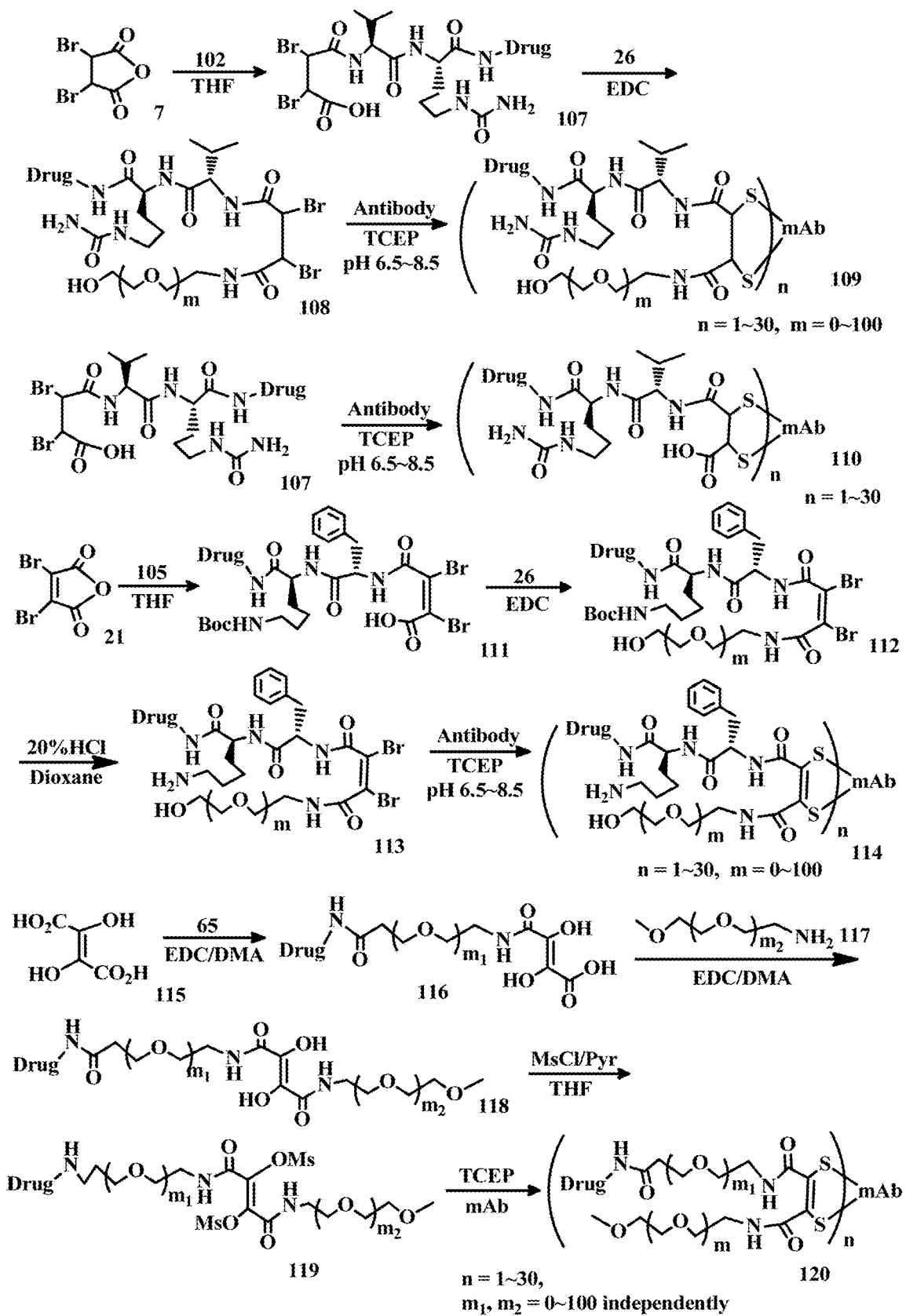
FIG. 9 shows the synthesis of bridge linkers containing peptides or polyethylene glycols, and the application of these linkers in the conjugation of the bridge linker-drug molecules to an antibody via amide linkage.
Figure 10:
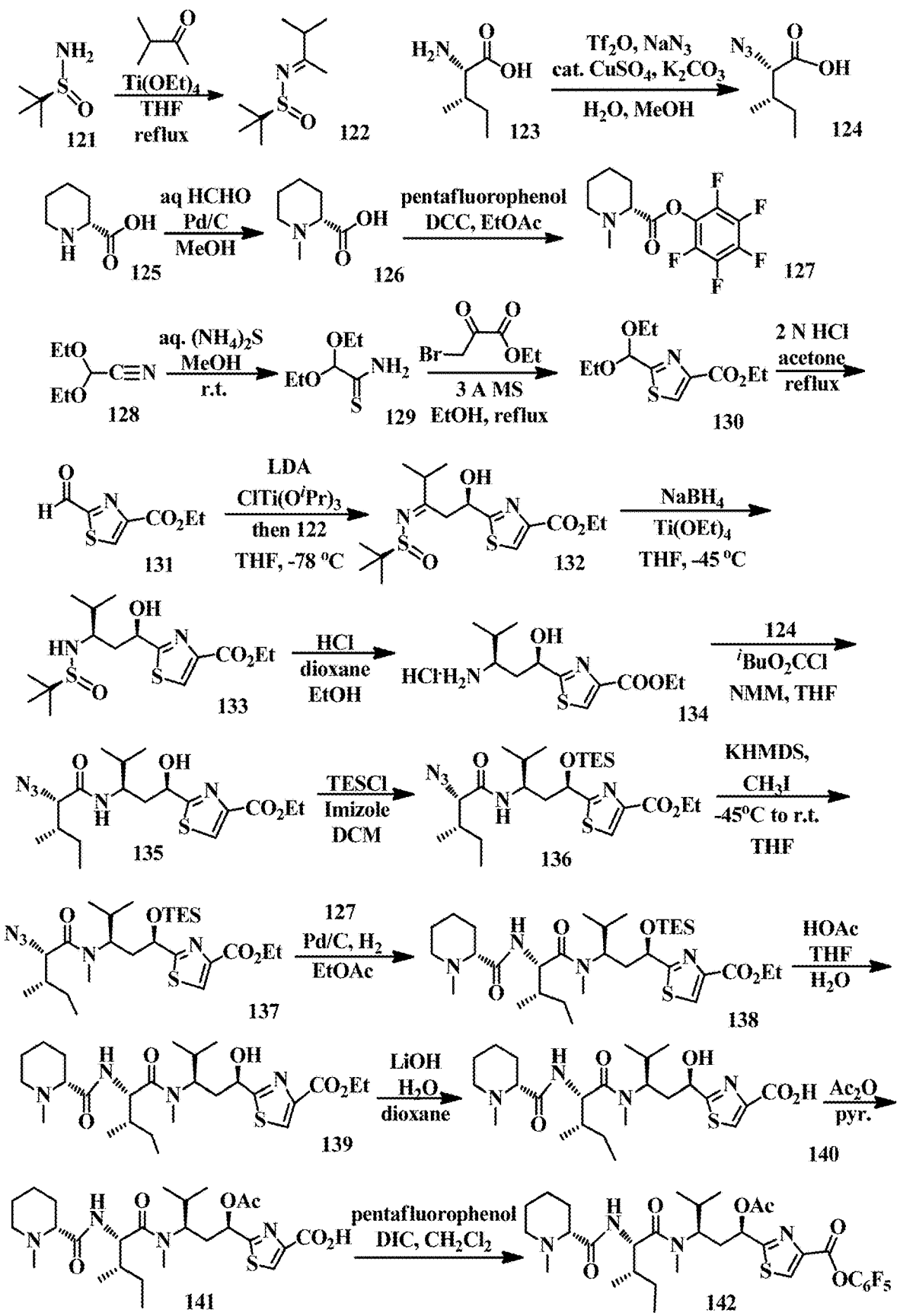
FIG. 10 shows the synthesis of the components of Tubulysin analogs.
Figure 11:
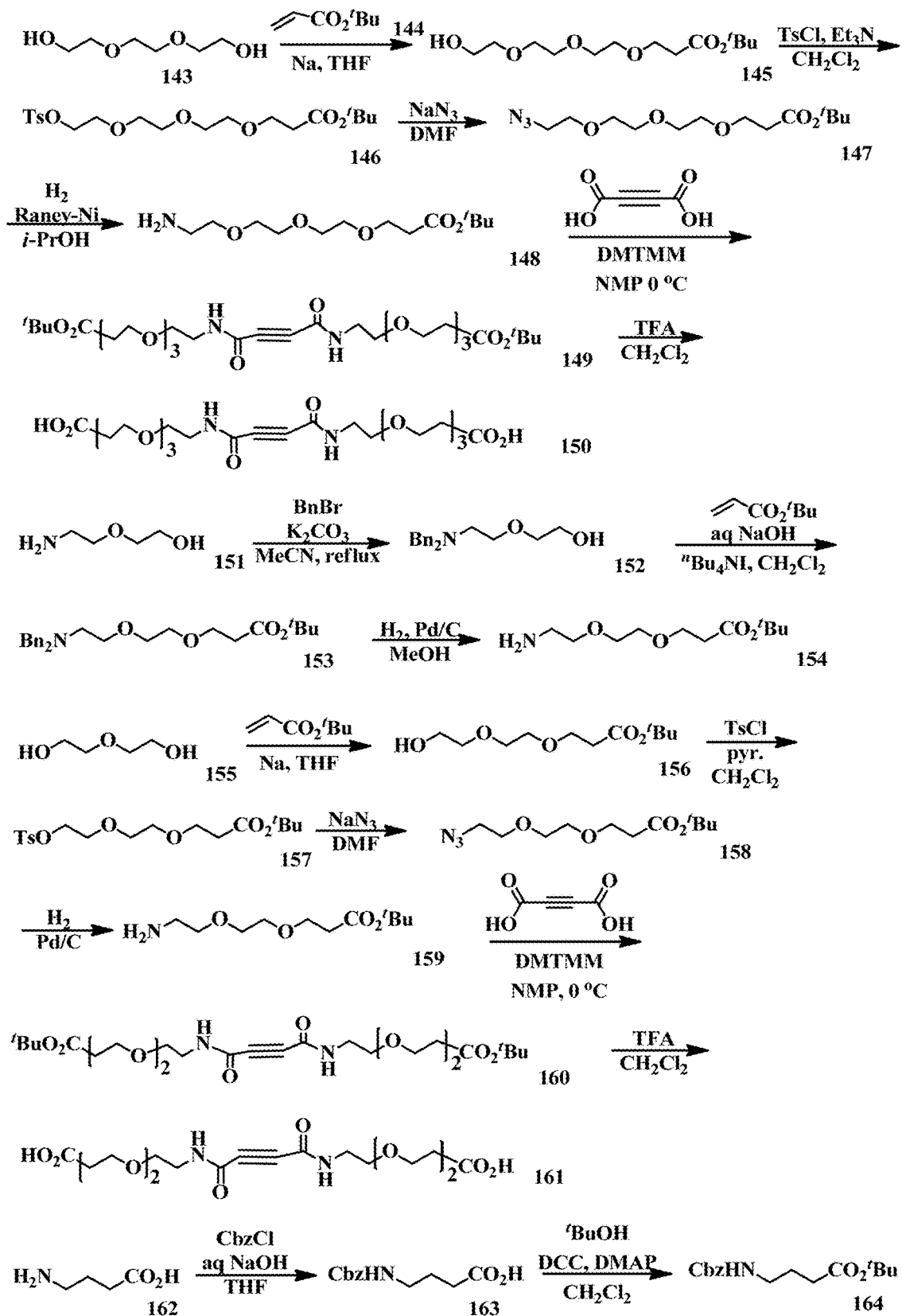
FIG. 11 shows the synthesis of the components of bridge linkers containing polyethylene glycol.
Figure 12:
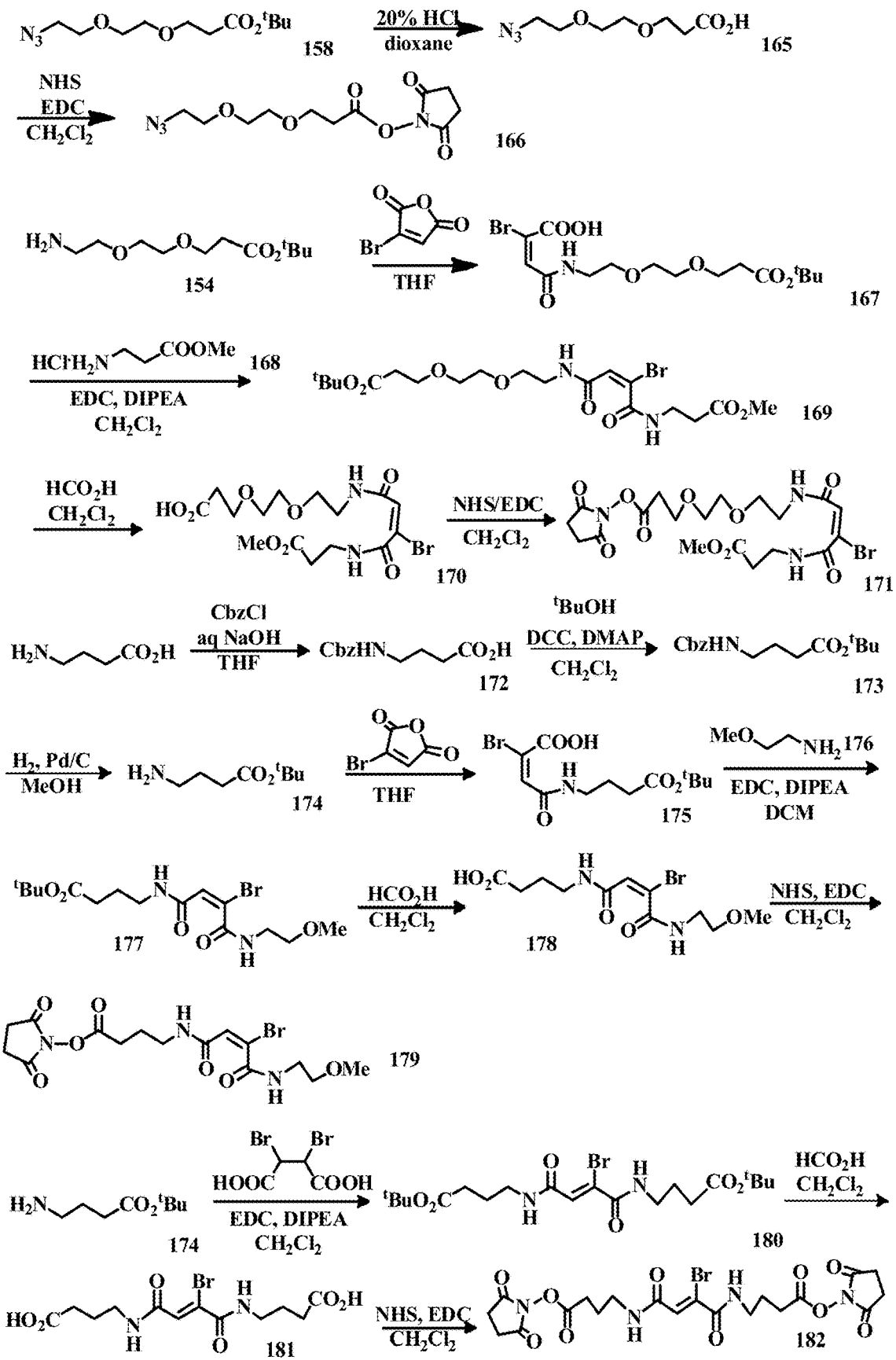
FIG. 12 shows the synthesis of the linkers of this patent application.
Figure 13:
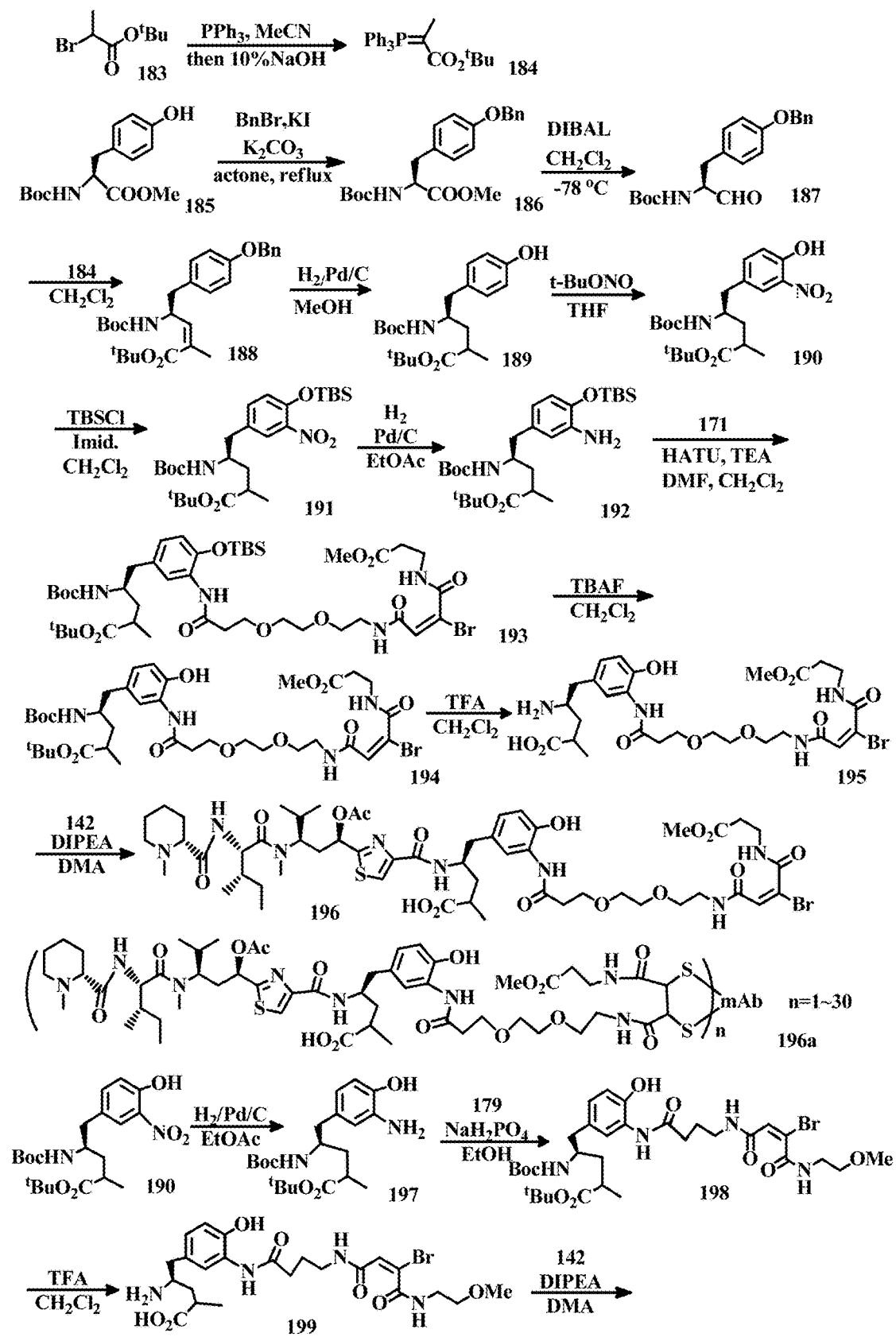
FIG. 13 shows the synthesis the conjugates of antibody-tubulysin analogs via a bridge linker of this patent application.
Figure 14:
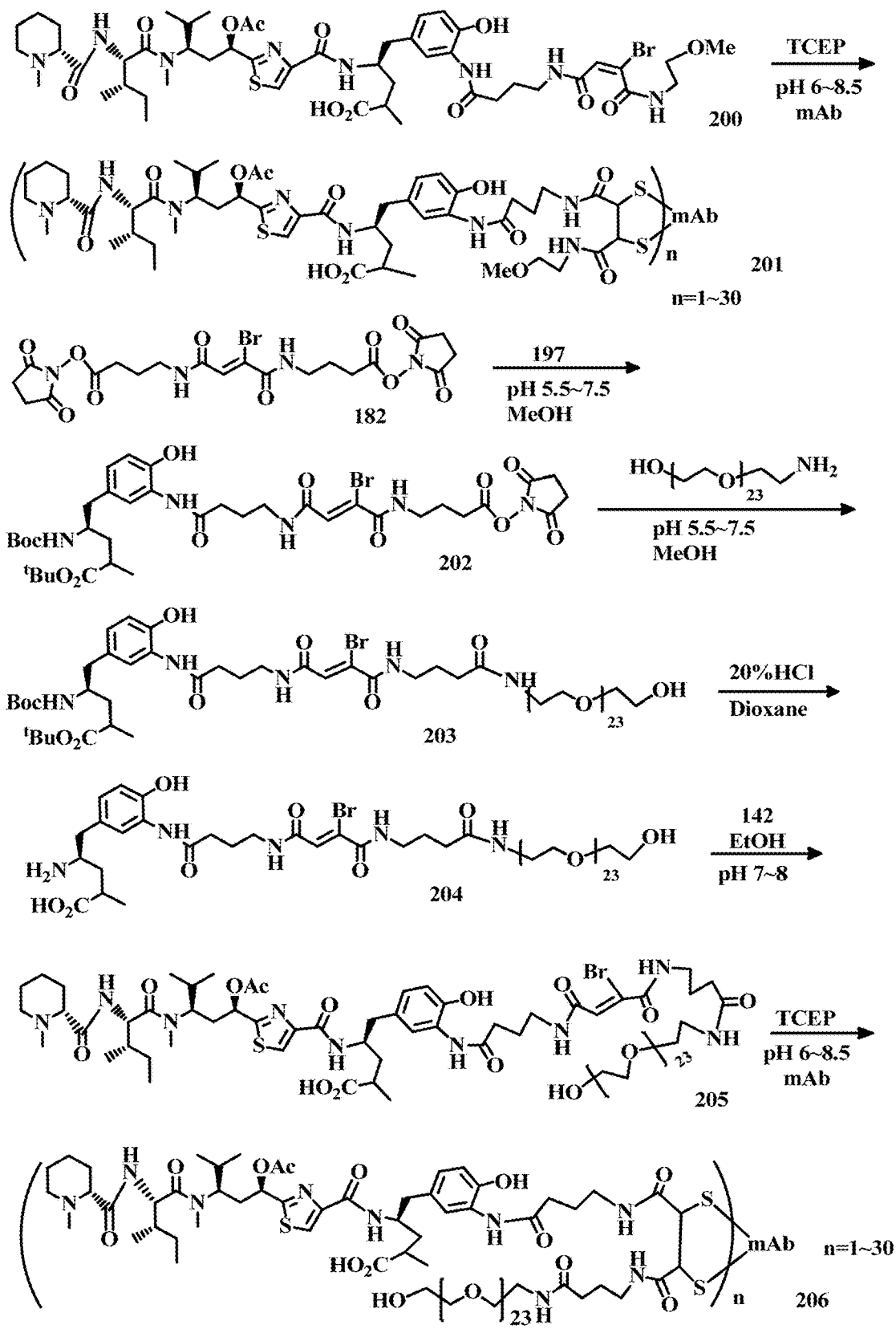
FIG. 14 shows the synthesis the conjugates of antibody-tubulysin analogs via a bridge-linker of this patent application.
Figure 15:
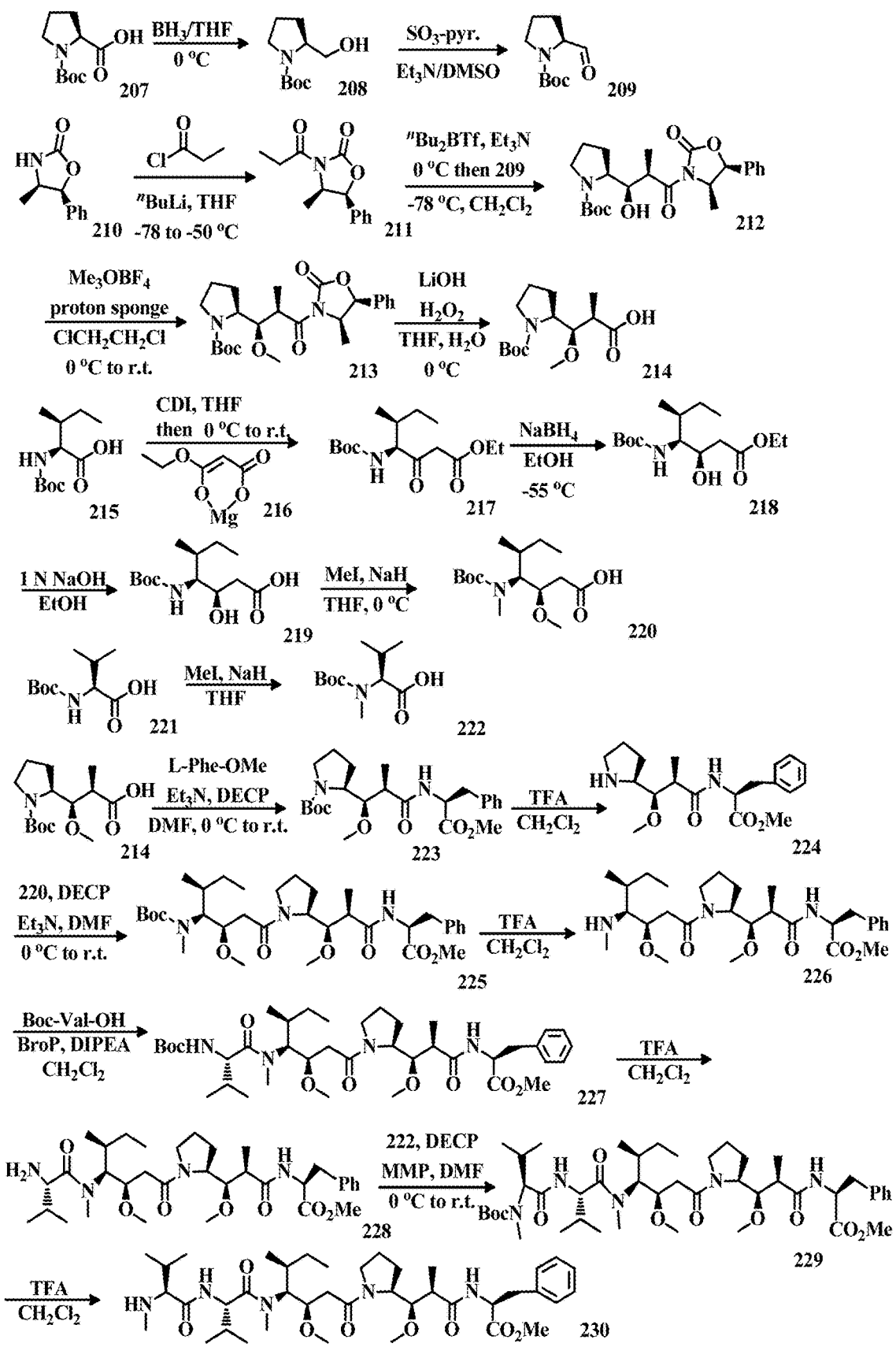
FIG. 15 shows the synthesis of the components of MMAF analogs.
Figure 16:
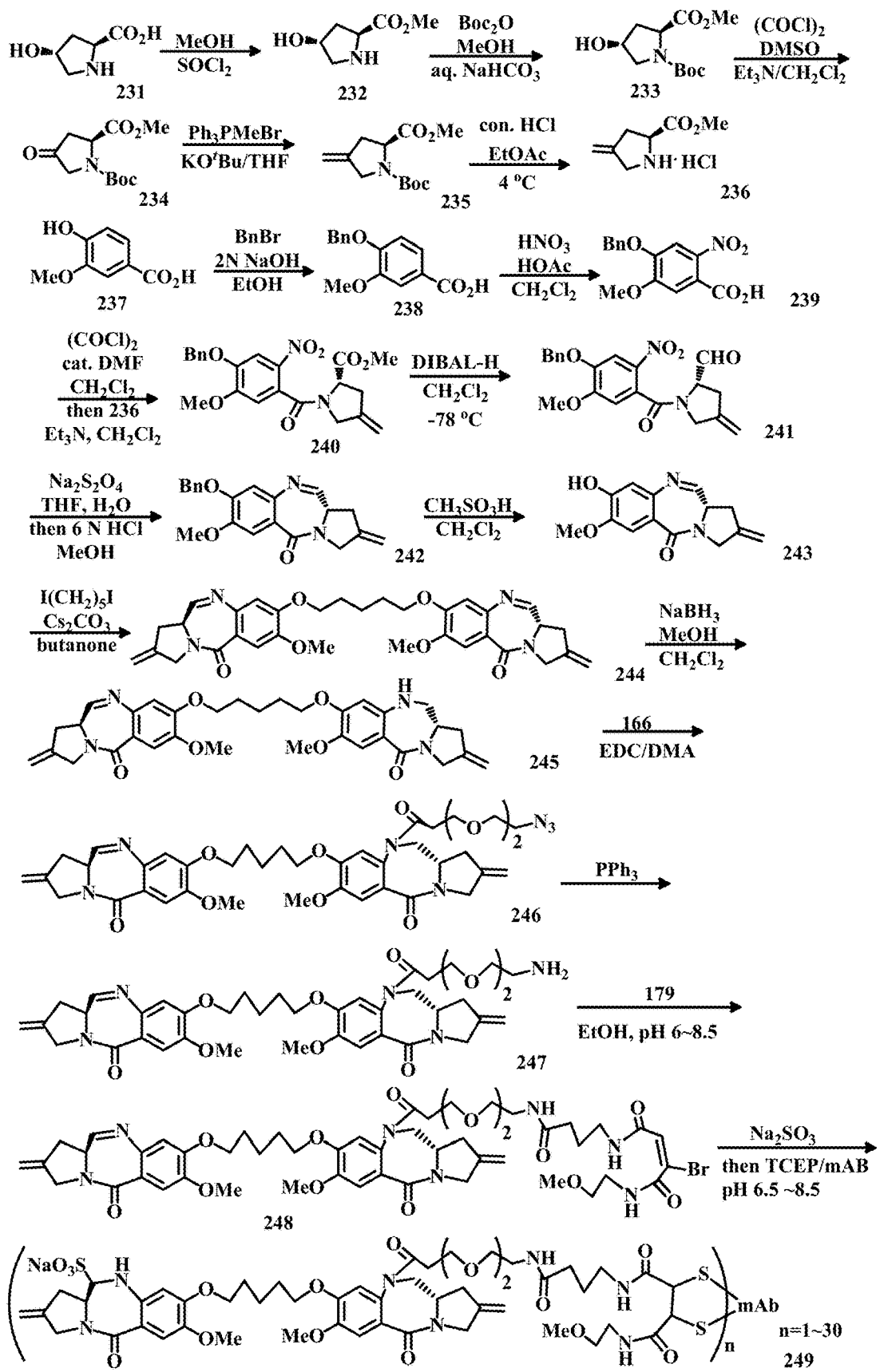
FIG. 16 shows the synthesis of a conjugate of antibody-PBD dimer analog via the bridge-linker.
Figure 17:
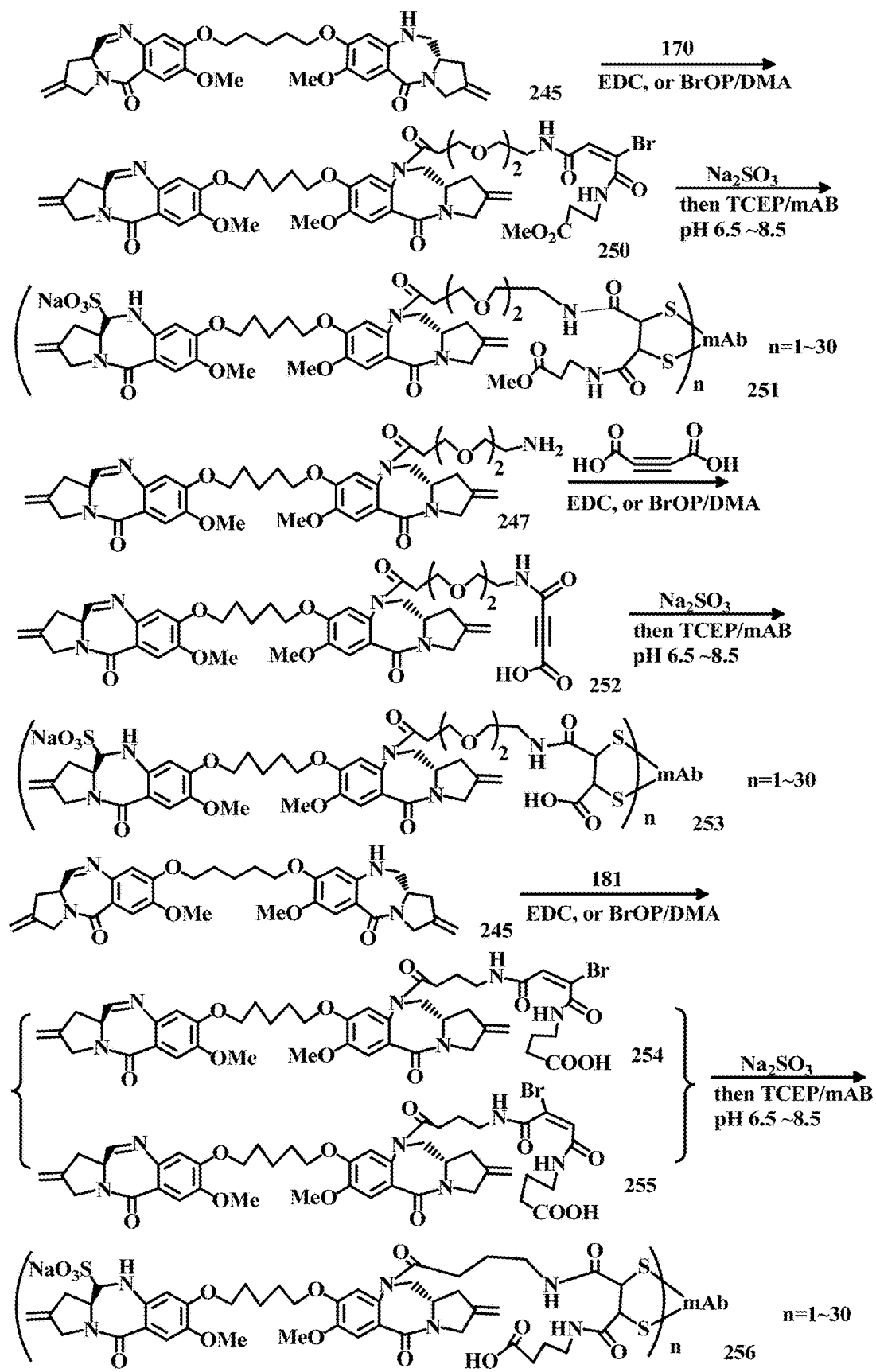
FIG. 17 shows the synthesis of conjugates of antibody-PBD dimer analogs via the bridge-linkers of this patent application.
Figure 18:
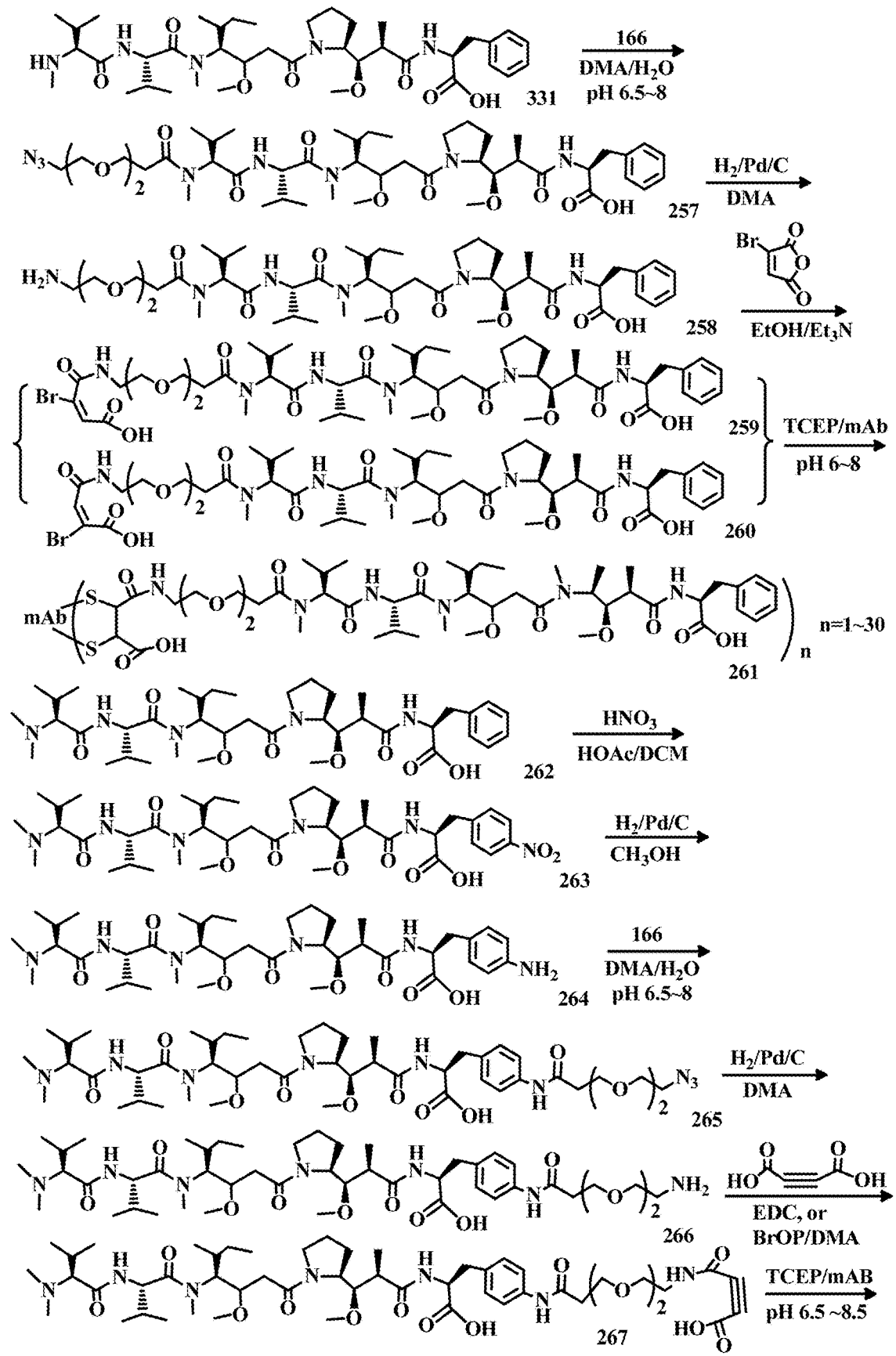
FIG. 18 shows the synthesis of conjugates of antibody-MMAF analogs via the bridge linkers of this patent application.
Figure 19:
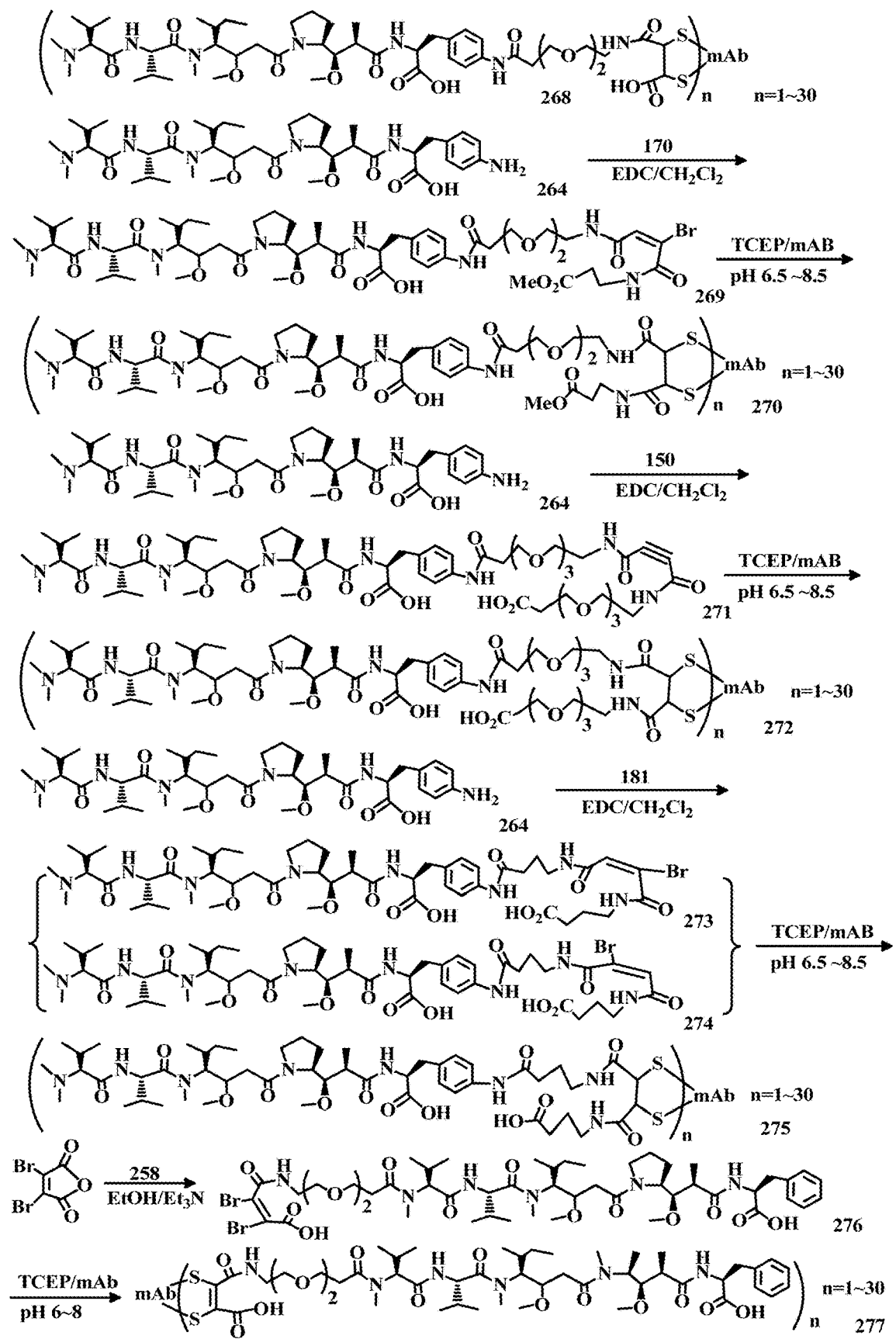
FIG. 19 shows the synthesis of conjugates of antibody-MMAF analogs via the bridge linkers of this patent application.
Figure 20:
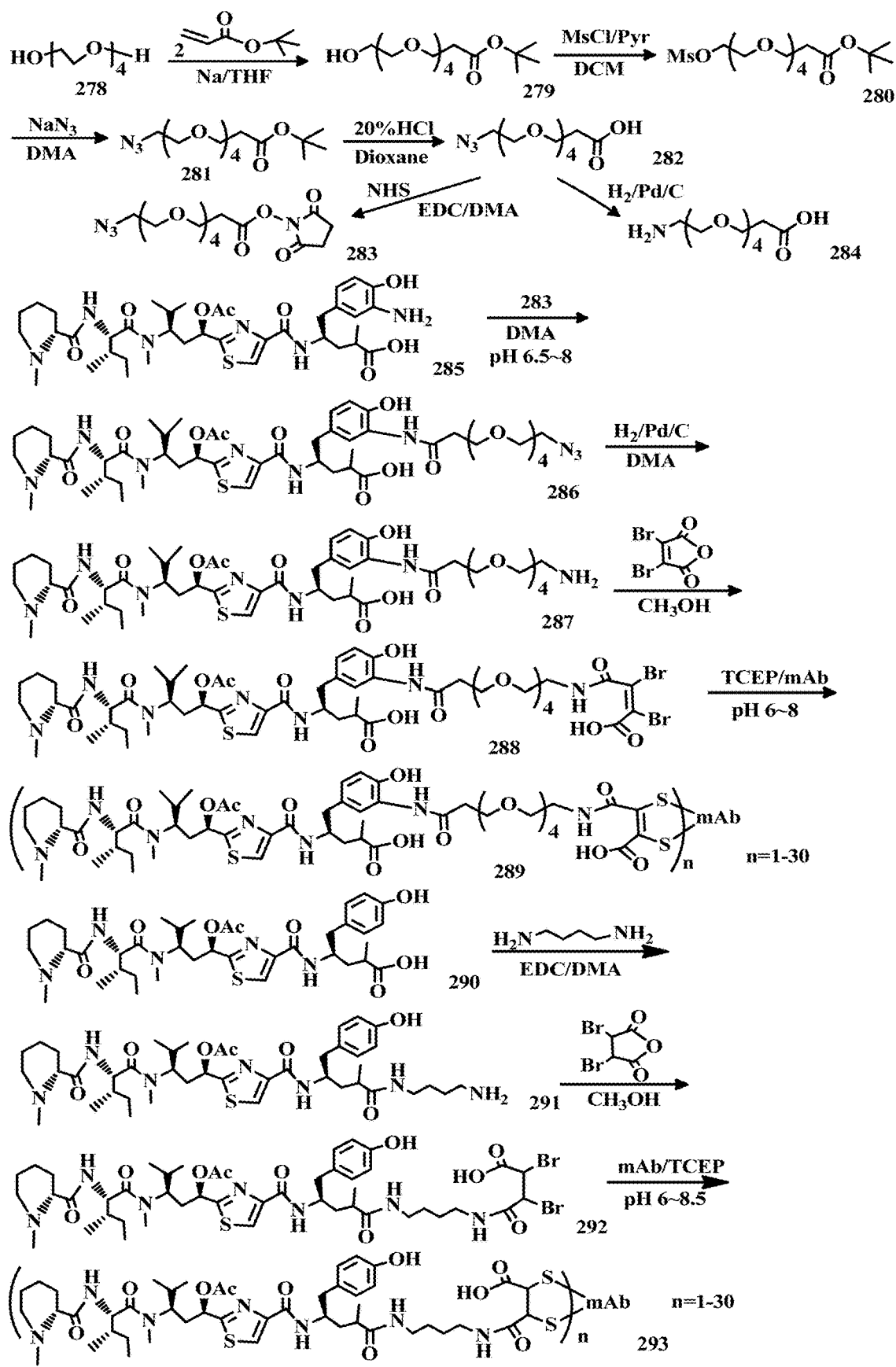
FIG. 20 shows the synthesis of conjugates of antibody-tubulysin analogs via the bridge linkers of this patent application.
Figure 21:
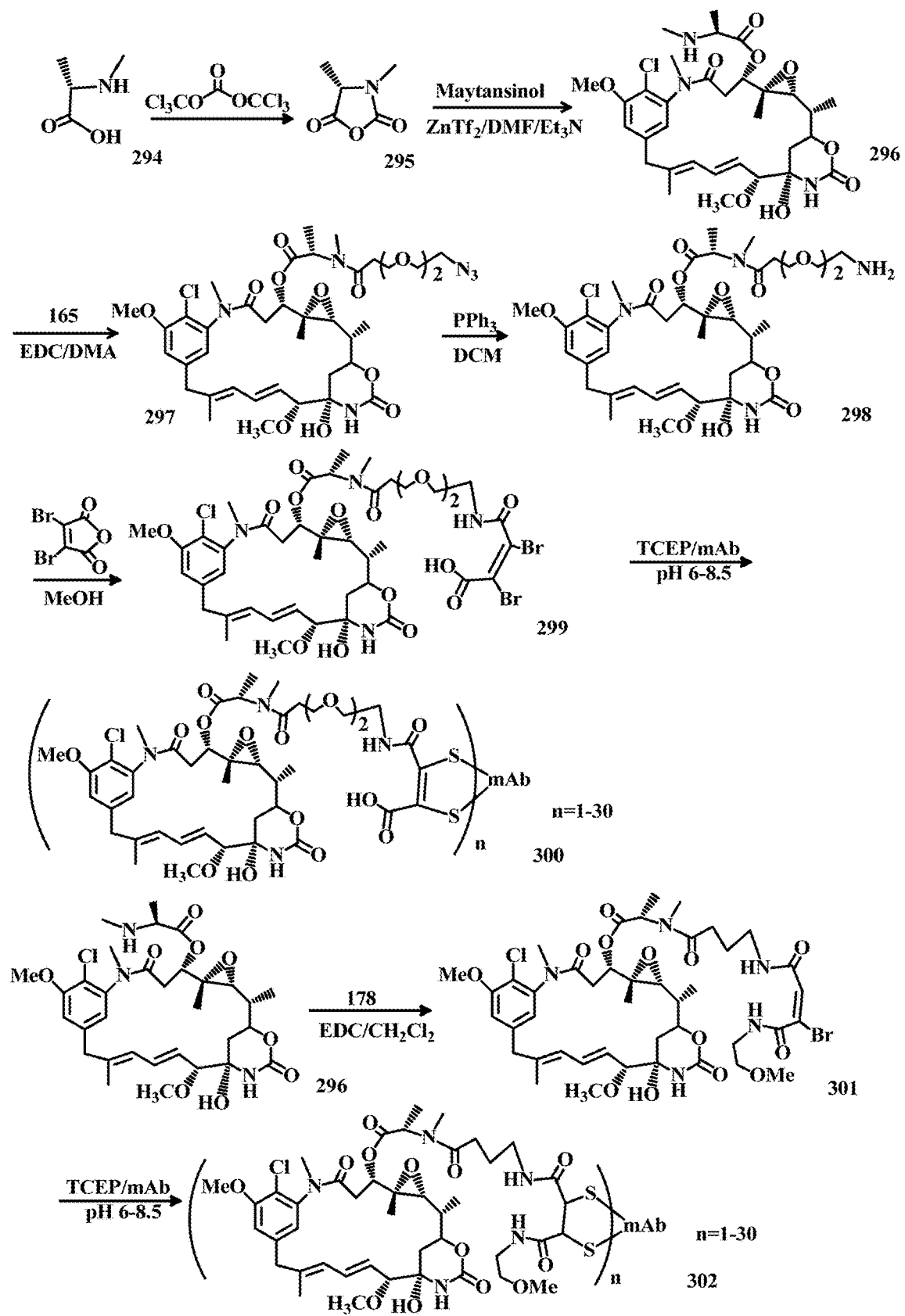
FIG. 21 shows the synthesis of the conjugates of Maytansinoid analogs via the bridge linkers of this patent application.
Figure 22:
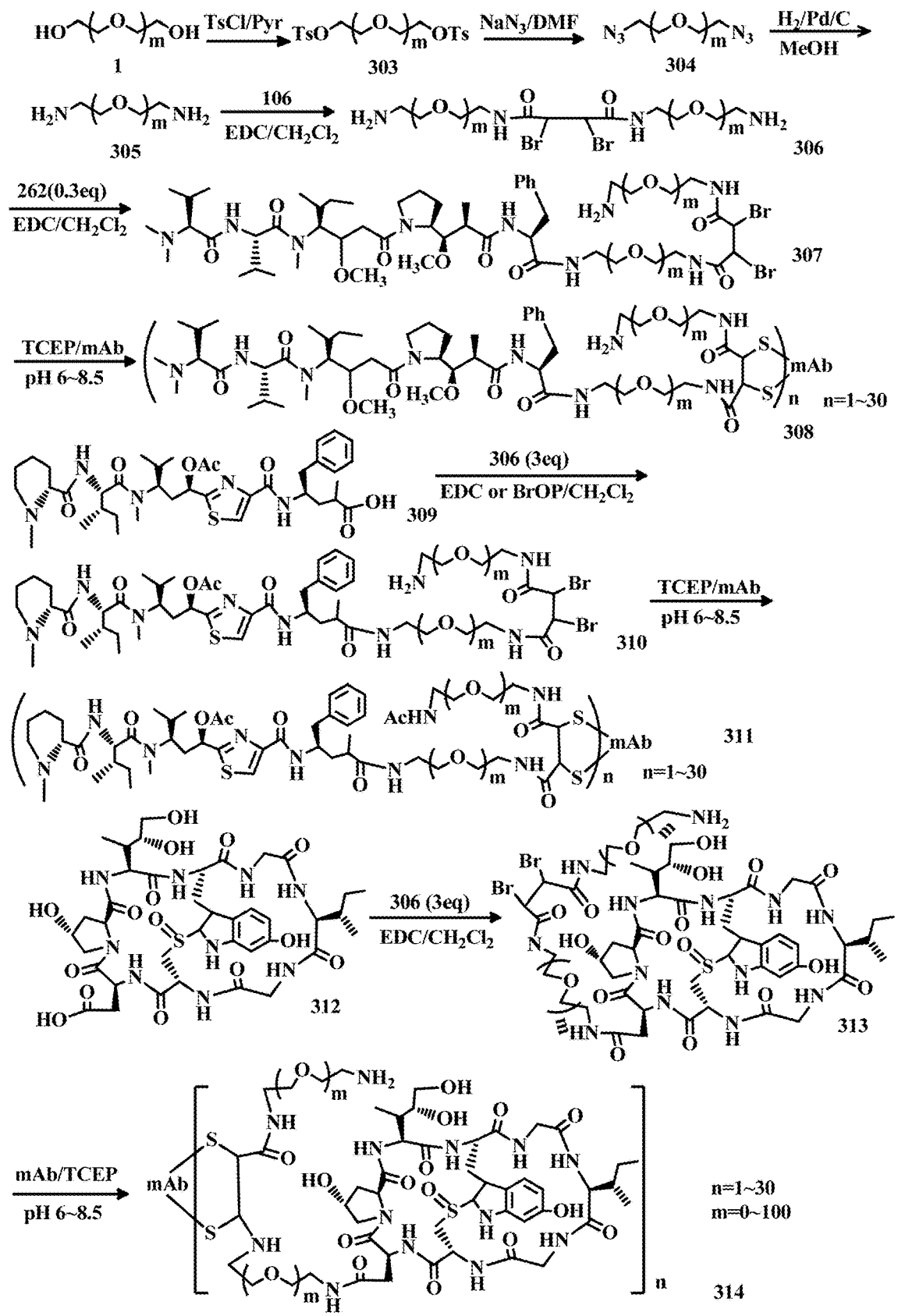
FIG. 22 shows the synthesis of the conjugates of MMAF analogs, tubulysin analogs and amatoxin analogs via the bridge linkers of this patent application.
Figure 23:
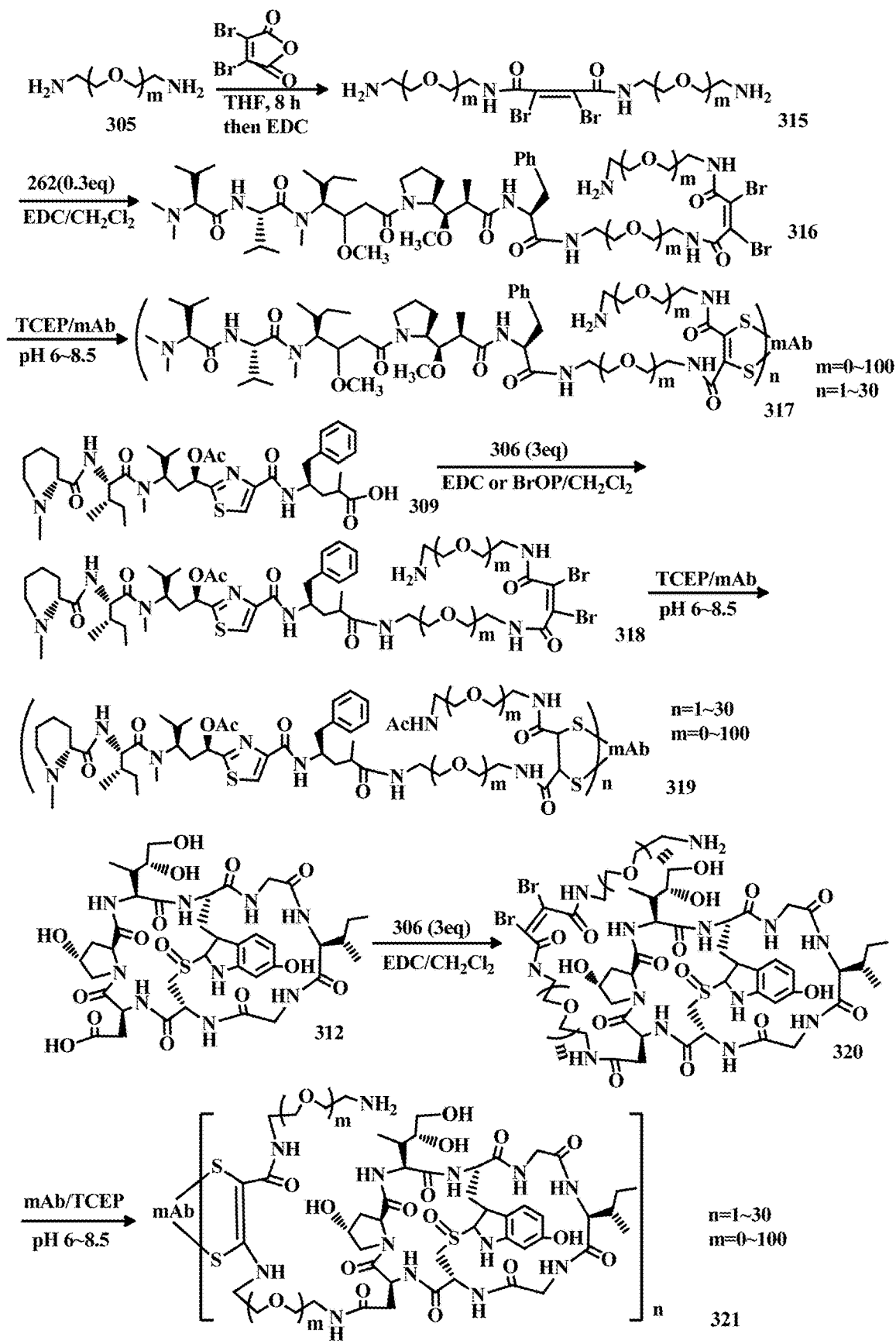
FIG. 23 shows the synthesis of the conjugates of MMAF analogs, tubulysin analogs and amatoxin analogs via the bridge linkers of this patent application.
Figure 24:
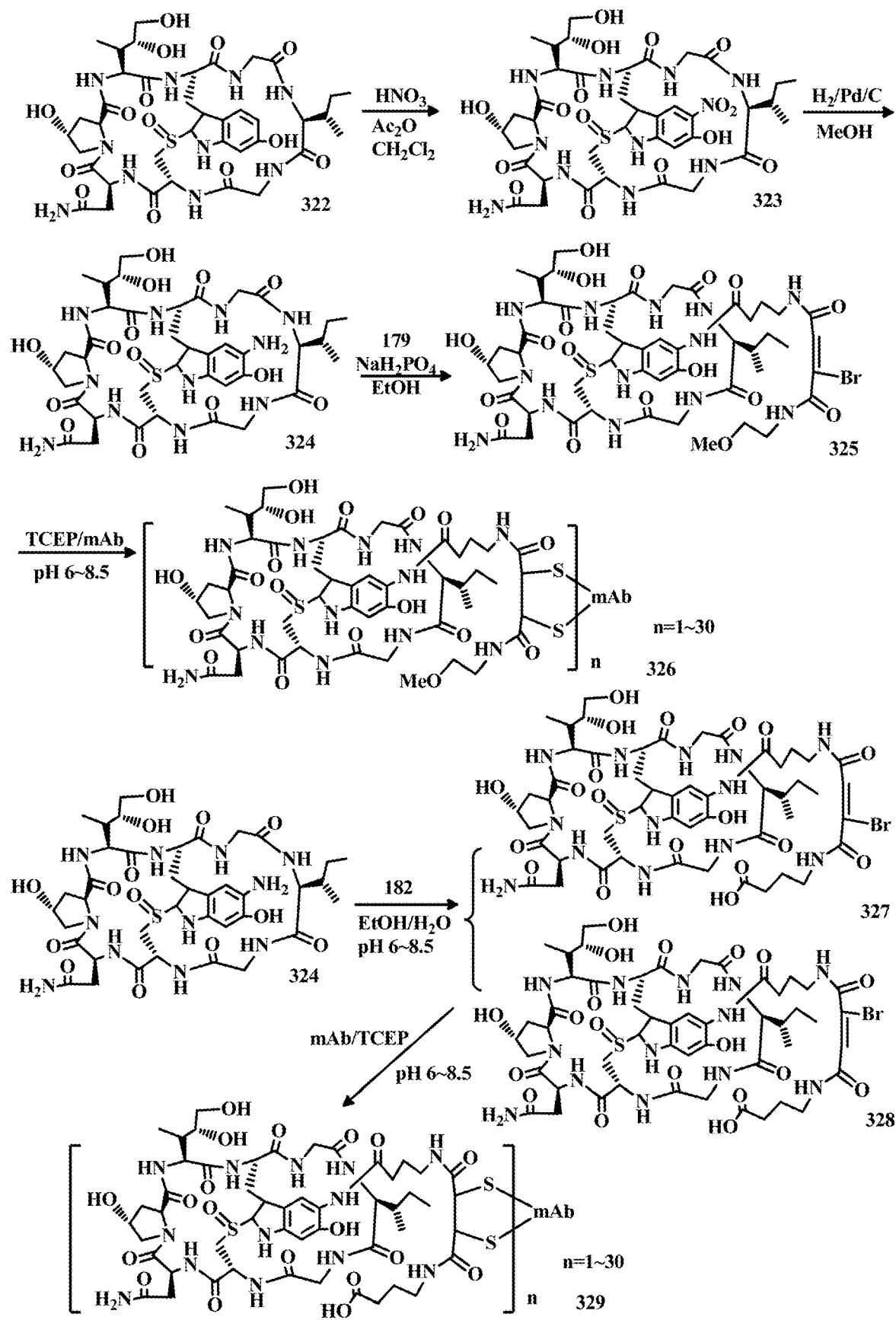
FIG. 24 shows the synthesis of the conjugates of amatoxin analogs via the bridge linkers of this patent application.
Figure 25:
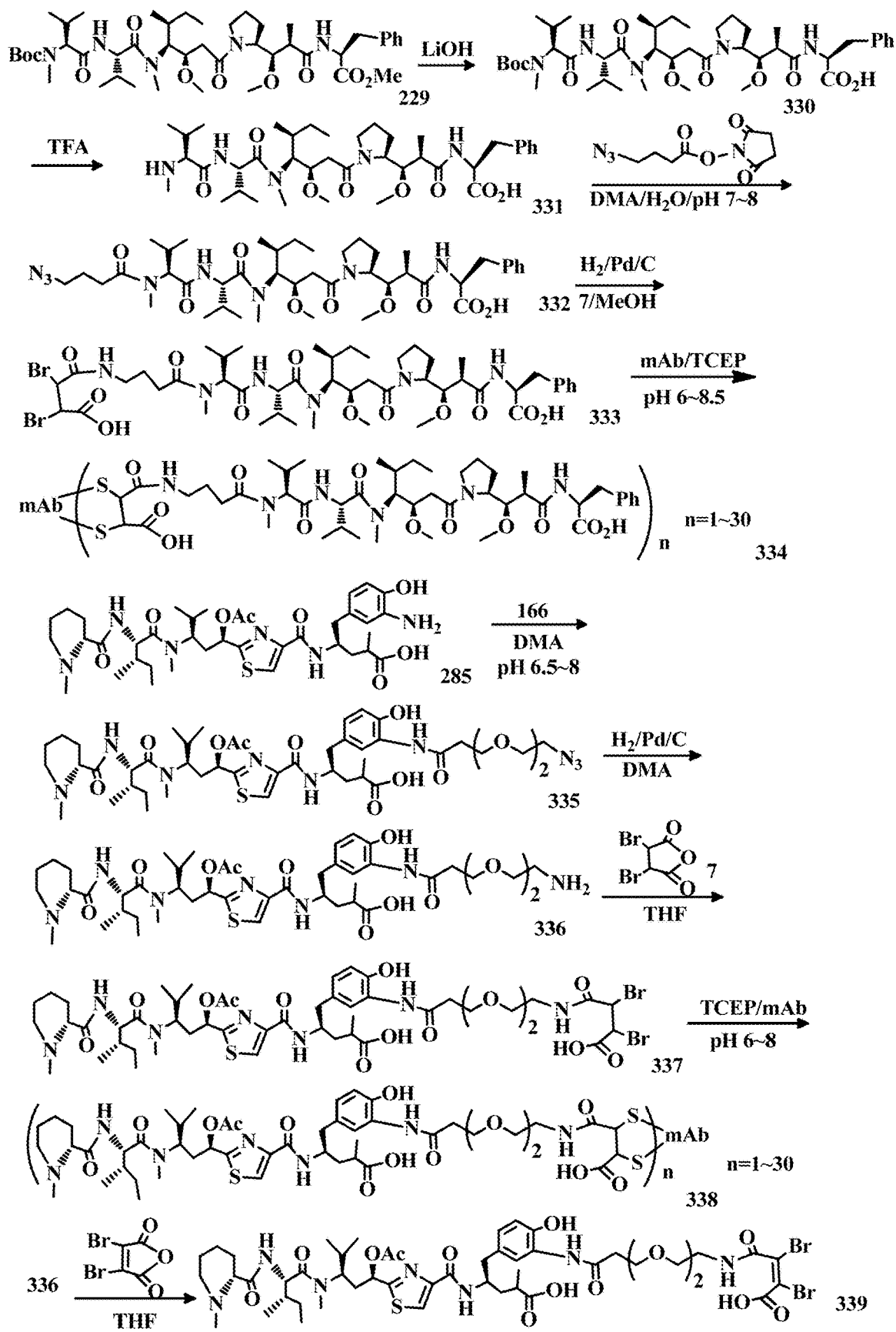
FIG. 25 shows the synthesis of the conjugates of MMAF analogs and tubulysin analogs via the bridge linkers of this patent application.
Figure 26:
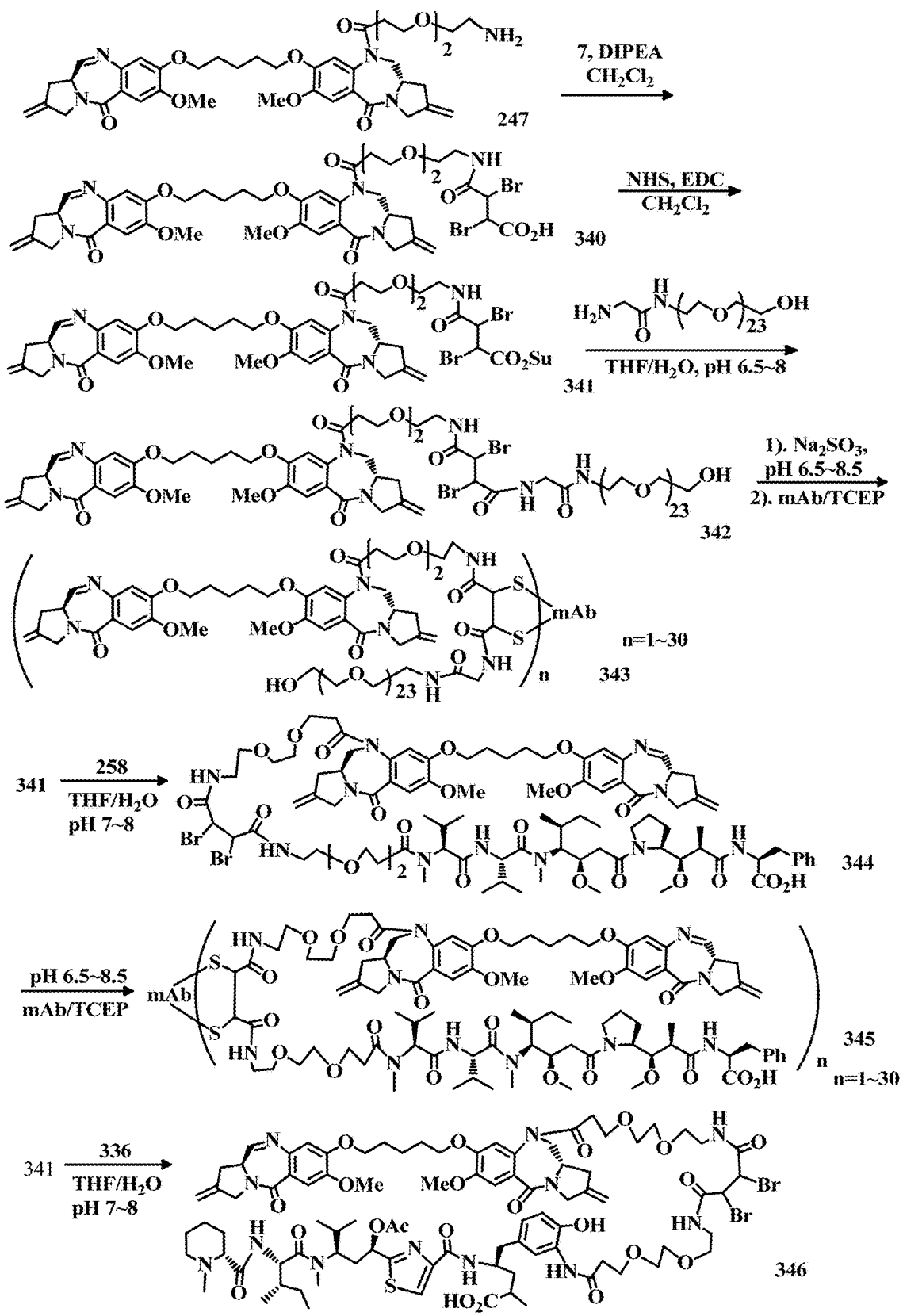
FIG. 26 shows the synthesis of the conjugates containing both PBD dimer analogs and polyethylene glycols, both PBD dimer analogs and MMAF analogs, and both PBD dimer analog and Tubulysin analogs, to an antibody via the bridge linkers of this patent.
Figure 27:
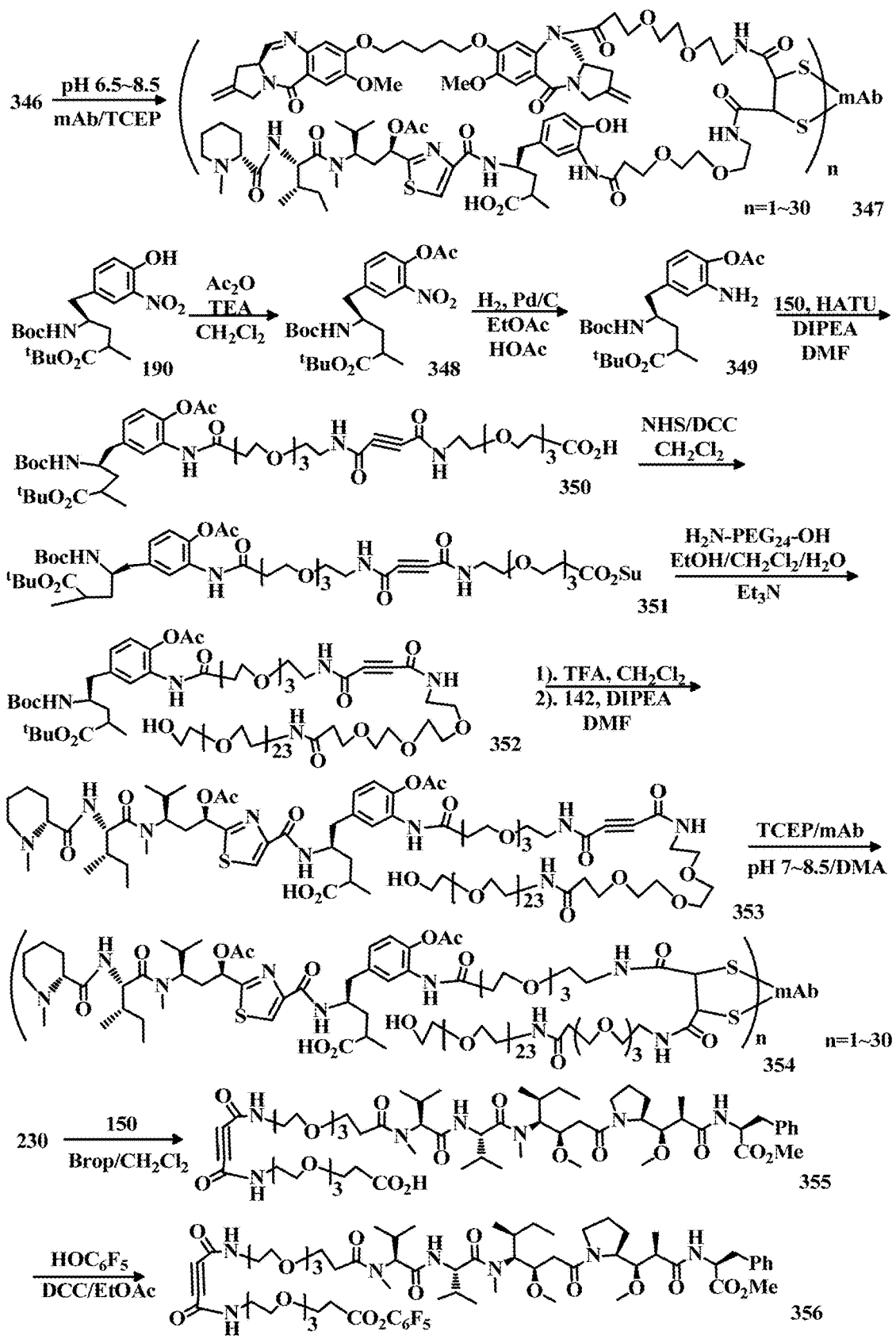
FIG. 27 shows the synthesis of the conjugates containing both PBD dimer analogs and Tubulysin analogs, both Tubulysin analogs and polyethylene glycols, and both MMAF analogs and polyethylene glycols, to an antibody via the bridge linkers of this patent application.
Figure 28:
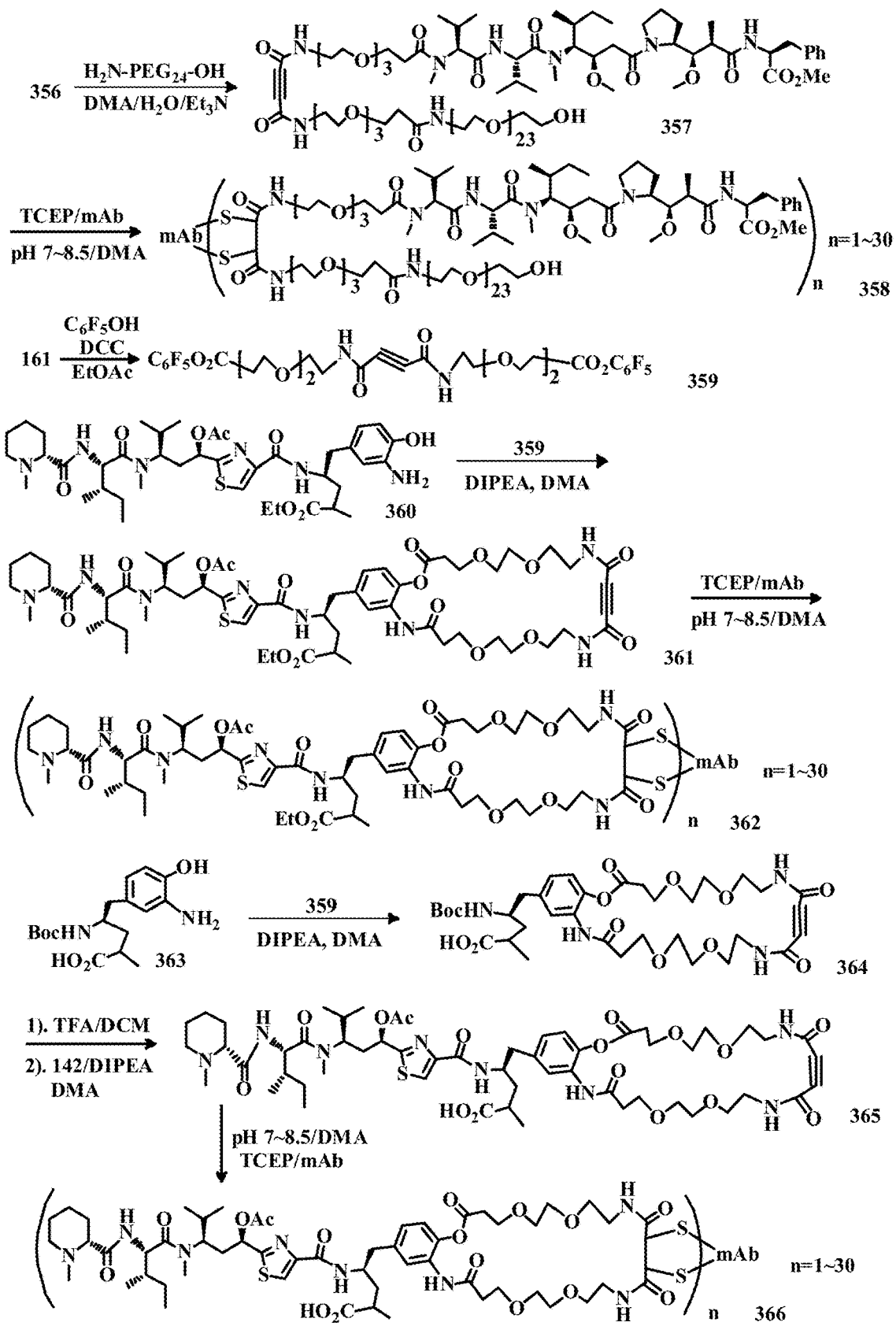
FIG. 28 shows the synthesis of the conjugates containing both MMAF analogs and polyethylene glycols, and Tubulysin B analogs via cyclic linkage of the bridge linkers of this patent application.
Figure 29:
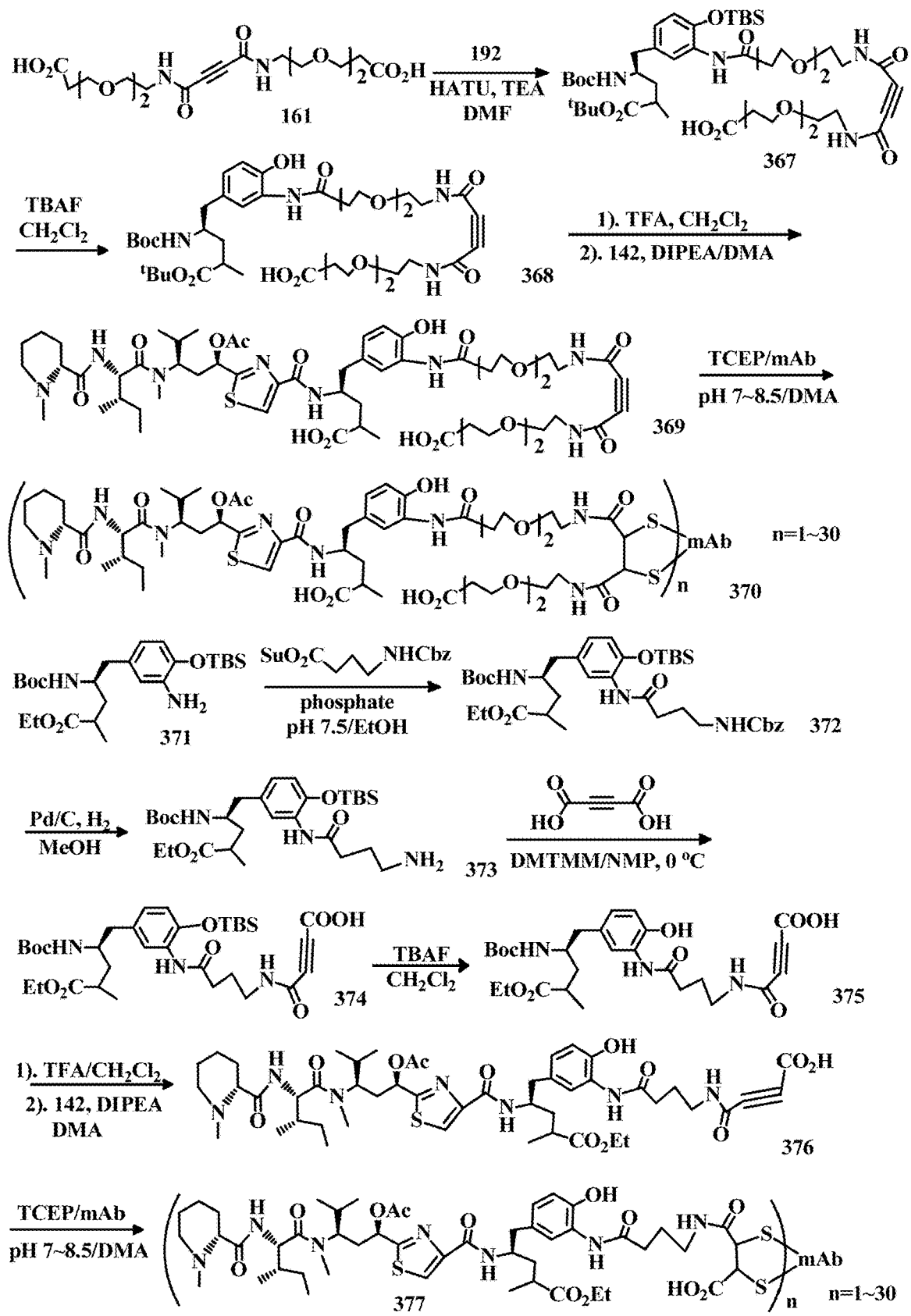
FIG. 29 shows the synthesis of the conjugates of tubulysin analogs via the bridge linkers of this patent application.
Figure 30:
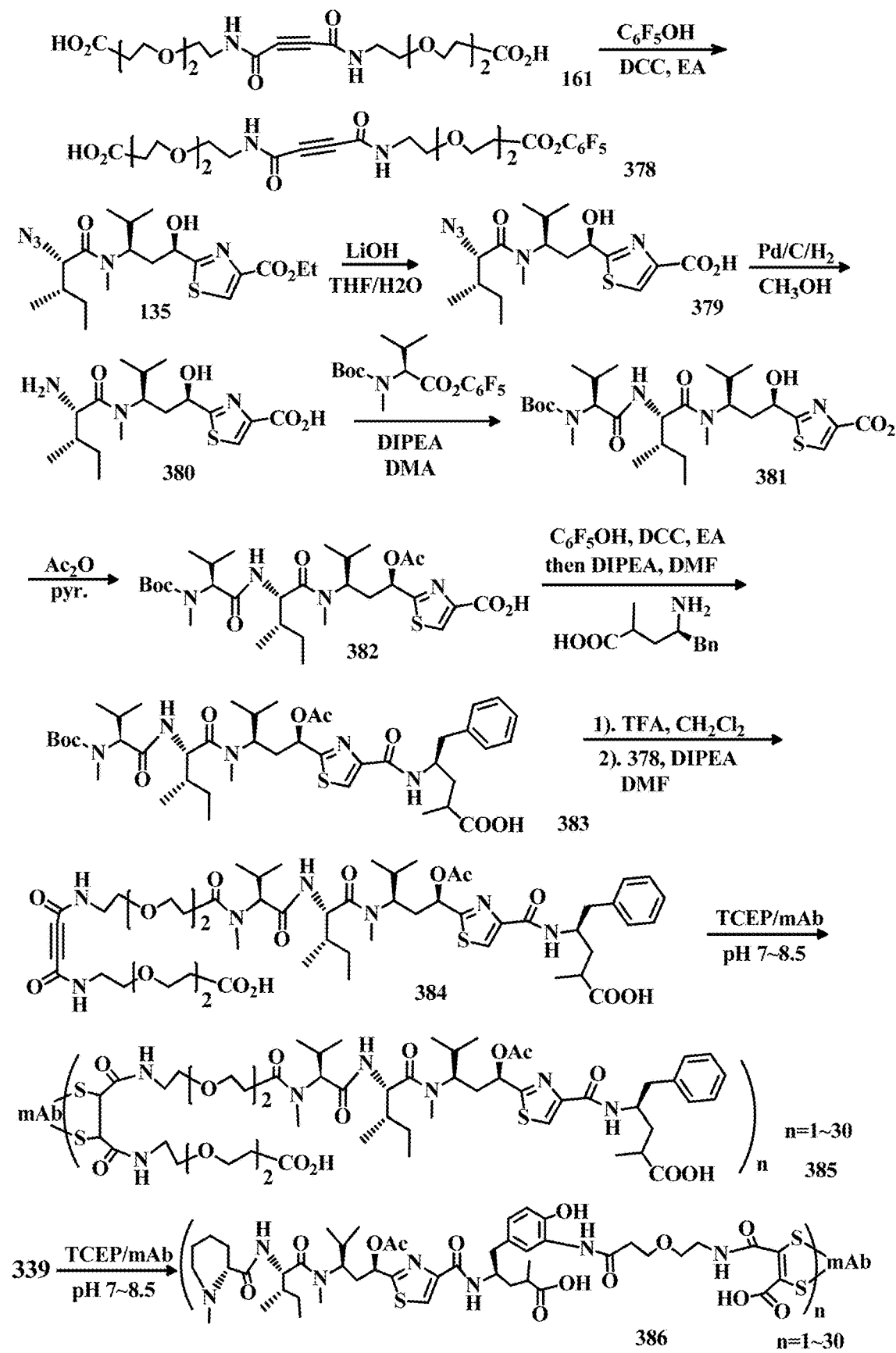
FIG. 30 shows the synthesis of the conjugates of tubulysin analogs via the bridge linkers of this patent application.
Figure 31:
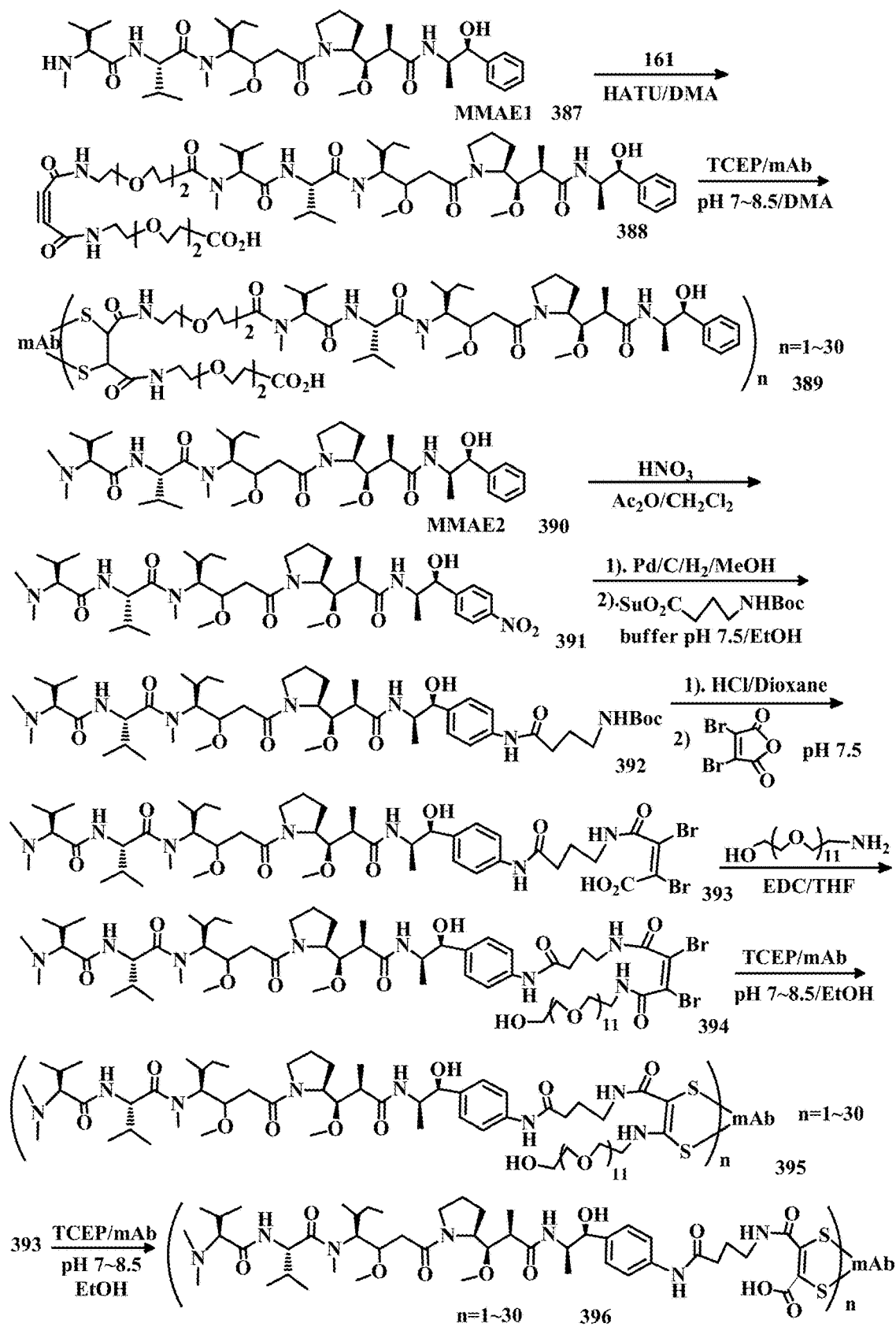
FIG. 31 shows the synthesis of the conjugates of MMAE analogs via the bridge linkers of this patent application.
Figure 32:
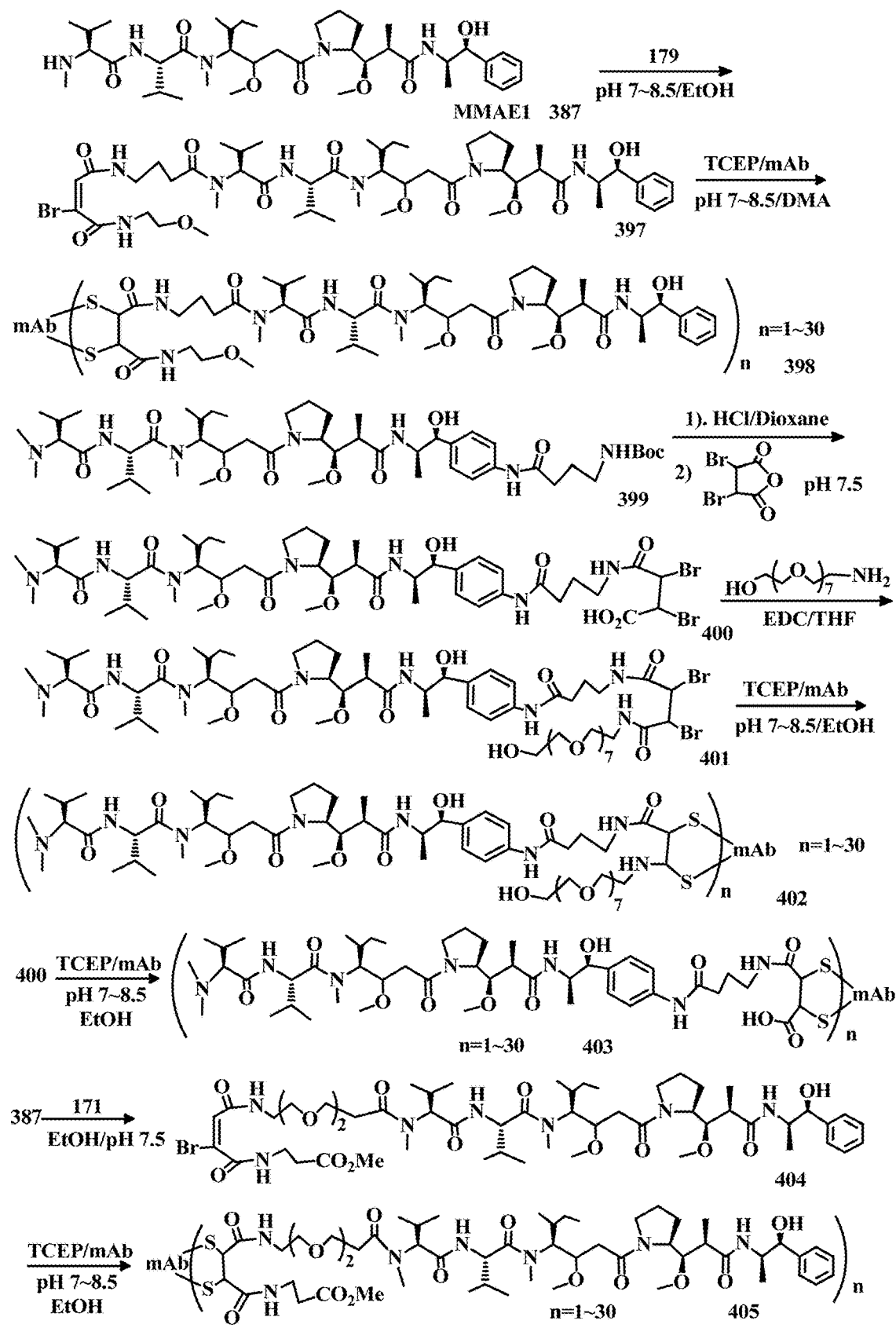
FIG. 32 shows the synthesis of the conjugates of MMAE analogs via the bridge linkers of this patent application.
Figure 33:
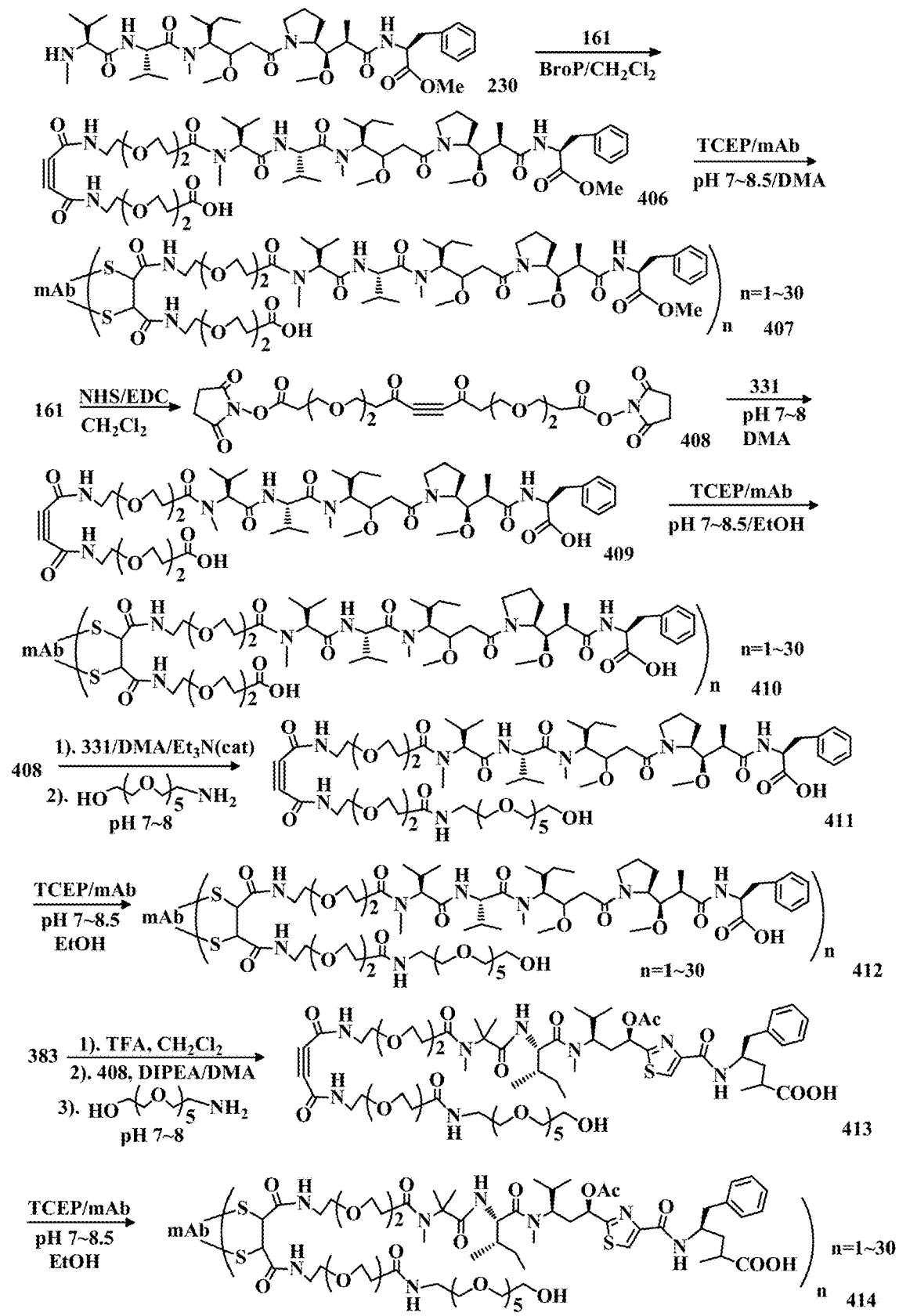
FIG. 33 shows the synthesis of the conjugates of MMAF analogs and tubulysin analogs via the bridge linkers of this patent application.
Figure 34:
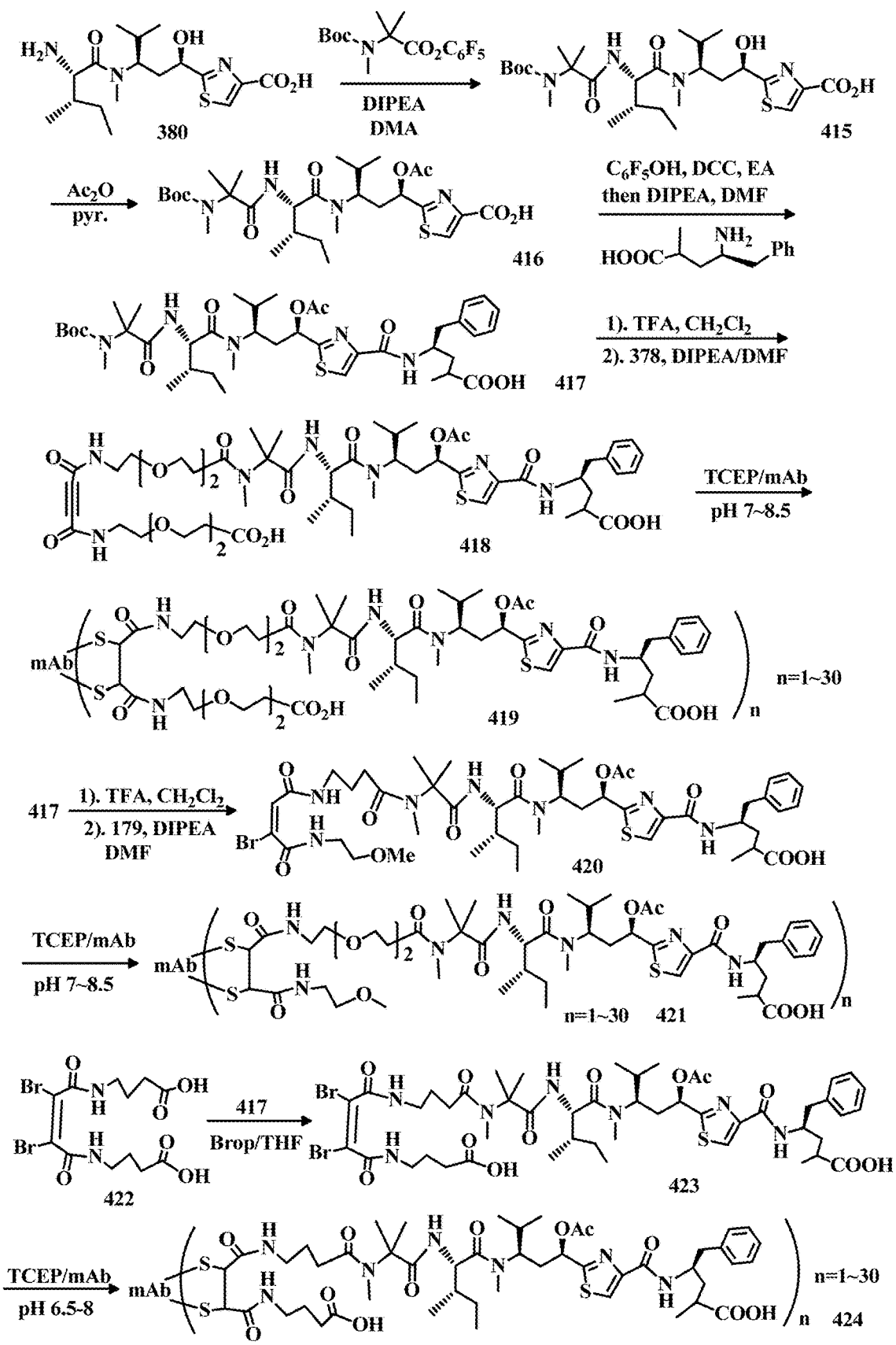
FIG. 34 shows the synthesis of the conjugates of tubulysin analogs via the bridge linkers of this patent application.
Figure 35:
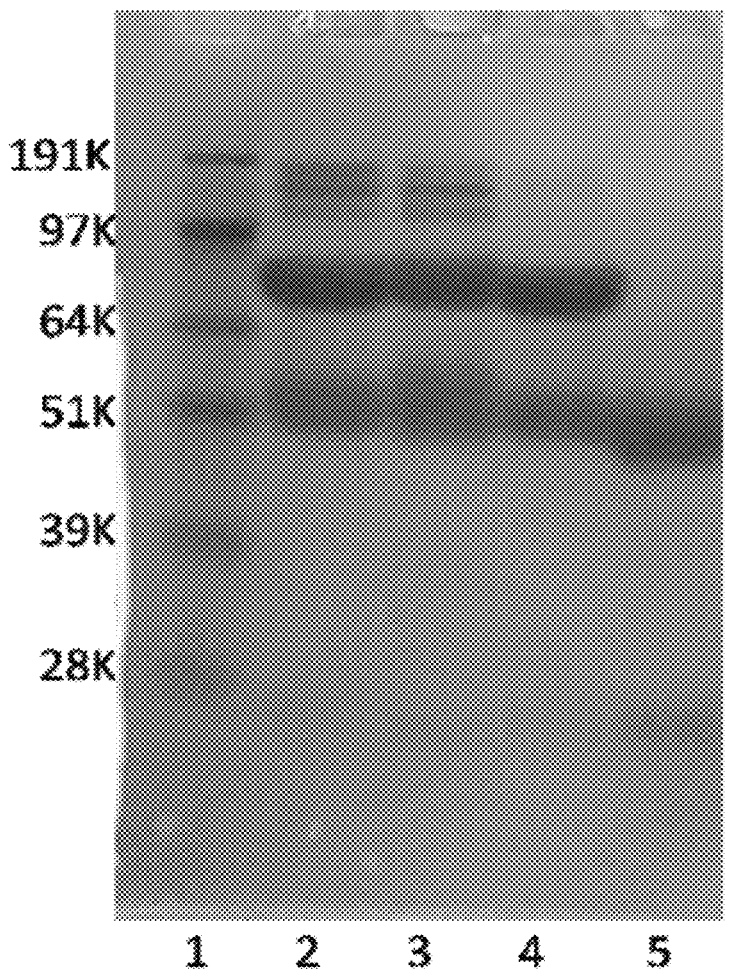
FIG. 35 shows the SDS-PAGE gel containing reduce agent DTT in the development. Lane 1 is biomarker, Lane 2 is conjugate 201, Lane 3 is conjugate 206, Lane 4 is conjugate 354, Lane 5 is Tubulysin analog conjugate through the traditional maleimidopropanoyl linker that we disclosed previously (Huang Y. et al, Med Chem. #44, 249th ACS National Meeting, Denver, CO, Mar. 22~26, 2015; WO2014009774). The conjugates 201, 206 and 354 via the bridge linkers of this patent application have the major band of 75 KD which indicates that the heavy chain and the light chain of the mAb were crossly linked with the bridge linkers. In comparison, the traditional maleimido linker has no 75 KD band and the 50 KD band is the single heavy chain of the antibody.

"Alkyl" refers to an aliphatic hydrocarbon group or univalent groups derived from alkane by removal of one or two hydrogen atoms from carbon atoms. It may be straight or branched having 1 to 8 carbon atoms in the chain. "Branched" means that one or more lower C numbers of alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl, cyclopentyl, cyclohexyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$, —NHC(O)R', —SR', —S(O)$_2$R', —S(O)R', —OH, -halogen, —N$_3$, —NH$_2$, —NH(R'), —N(R')$_2$ and —CN; where each R' is independently selected from —$C_1$-$C_8$ alkyl and aryl.

"Halogen" refers to fluorine, chlorine, bromine or iodine atom; preferably fluorine and chlorine atom.

"Heteroalkyl" refers to $C_2$-$C_8$ alkyl in which one to four carbon atoms are independently replaced with a heteroatom from the group consisting of O, S and N.

"Carbocycle" refers to a saturated or unsaturated ring having 3 to 8 carbon atoms as a monocycle or 7 to 13 carbon atoms as a bicycle. Monocyclic carbocycles have 3 to 6 ring atoms, more typically 5 or 6 ring atoms. Bicyclic carbocycles have 7 to 12 ring atoms, arranged as a bicycle [4,5], [5,5], [5,6] or [6,6] system, or 9 or 10 ring atoms arranged as a bicycle [5,6] or [6,6] system. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl.

A "$C_3$-$C_8$ carbocycle" refers to a 3-, 4-, 5-, 6-, 7- or 8-membered saturated or unsaturated nonaromatic carbocyclic ring. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$, —NHC(O)R', —SR', —S(O)R', —S(O)$_2$R', —OH, -halogen, —$N_3$, —$NH_2$, —NH(R'), —N(R')$_2$ and —CN; where each R' is independently selected from —$C_1$-$C_8$ alkyl and aryl.

"Alkenyl" refers to an aliphatic hydrocarbon group containing a carbon-carbon double bond which may be straight or branched having 2 to 8 carbon atoms in the chain. Exemplary alkenyl groups include ethenyl, propenyl, n-butenyl, i-butenyl, 3-methylbut-2-enyl, n-pentenyl, hexylenyl, heptenyl, octenyl.

"Alkynyl" refers to an aliphatic hydrocarbon group containing a carbon-carbon triple bond which may be straight or branched having 2 to 8 carbon atoms in the chain. Exemplary alkynyl groups include ethynyl, propynyl, n-butynyl, 2-butynyl, 3-methylbutynyl, 5-pentynyl, n-pentynyl, hexylynyl, heptynyl, and octynyl.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—), 1,2-ethyl (—$CH_2CH_2$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene, propargyl and 4-pentynyl.

"Aryl" or Ar refers to an aromatic or hetero aromatic group, composed of one or several rings, comprising three to fourteen carbon atoms, preferentially six to ten carbon atoms. The term of "hetero aromatic group" refers one or several carbon on aromatic group, preferentially one, two, three or four carbon atoms are replaced by O, N, Si, Se, P or S, preferentially by O, S, and N. The term aryl or Ar also refers to an aromatic group, wherein one or several H atoms are replaced independently by —R', -halogen, —OR', or —SR', —NR'R", —N=NR', —N=R', —NR'R", —$NO_2$, —S(O)R', —S(O)$_2$R', —S(O)$_2$OR', —OS(O)$_2$OR', —PR'R", —P(O)R'R", —P(OR')(OR"), —P(O)(OR')(OR") or —OP(O)(OR')(OR") wherein R', R" are independently H, alkyl, alkenyl, alkynyl, heteroalkyl, aryl, arylalkyl, carbonyl, or pharmaceutical salts.

"Heterocycle" refers to a ring system in which one to four of the ring carbon atoms are independently replaced with a heteroatom from the group of O, N, S, Se, B, Si and P. Preferable heteroatoms are O, N and S. Heterocycles are also described in The Handbook of Chemistry and Physics, 78th Edition, CRC Press, Inc., 1997-1998, p. 225 to 226, the disclosure of which is hereby incorporated by reference.

Preferred nonaromatic heterocyclic include, but are not limited to epoxy, aziridinyl, thiiranyl, pyrrolidinyl, pyrazolidinyl, imidazolidinyl, oxiranyl, tetrahydrofuranyl, dioxolanyl, tetrahydropyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydropyridyl, dihydropyridyl, tetrahydropyrimidinyl, dihydrothiopyranyl, azepanyl, as well as the fused systems resulting from the condensation with a phenyl group.

The term "heteroaryl" or aromatic heterocycles refers to a 3 to 14, preferably 5 to 10 membered aromatic hetero, mono-, bi-, or multi-cyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazolyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group.

"Alkyl", "cycloalkyl", "alkenyl", "alkynyl", "aryl", "heteroaryl", "heterocyclic" and the like refer also to the corresponding "alkylene", "cycloalkylene", "alkenylene", "alkynylene", "arylene", "heteroarylene", "heterocyclene" and the likes which are formed by the removal of two hydrogen atoms.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

"Heteroarylalkyl" refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl and the like.

Examples of a "hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triethylsilyl ether, triisopropylsilyl ether, t-butyldimethylsilyl ether, triphenylmethylsilyl ether, acetate ester, substituted acetate esters, pivaloate, benzoate, methanesulfonate and p-toluenesulfonate.

"Leaving group" refers to a functional group that can be substituted by another functional group. Such leaving groups are well known in the art, and examples include, but are not limited to, a halide (e.g., chloride, bromide, and iodide), methanesulfonyl (mesyl), p-toluenesulfonyl (tosyl), trifluoromethylsulfonyl (triflate), and trifluoromethylsulfonate.

The following abbreviations may be used herein and have the indicated definitions: Boc, tert-butoxy carbonyl; BroP, bromotrispyrrolidinophosphonium hexafluorophosphate; CDI, 1,1'-carbonyldiimidazole; DCC, dicyclohexylcarbodiimide; DCE, dichloroethane; DCM, dichloromethane; DIAD, diisopropylazodicarboxylate; DIBAL-H, diisobutylaluminium hydride; DIPEA, diisopropylethylamine; DEPC, diethyl phosphorocyanidate; DMA, N,N-dimethyl acetamide; DMAP, 4-(N, N-dimethylamino)pyridine; DMF, N,N-dimethylformamide; DMSO, dimethylsulfoxide; DTT, dithiothreitol; EDC, 1-(3-dimethylaminopropyl)-3-ethylcarbodiimide hydrochloride; ESI-MS, electrospray mass spectrometry; HATU, 0-(7-azabenzotriazol-1-yl)-N,N,N',N'-tetramethyluronium hexafluorophosphate; HOBt, 1-hydroxybenzotriazole; HPLC, high pressure liquid chromatography; NHS, N-Hydroxysuccinimide; MMP, 4-methylmorpholine; PAB, p-aminobenzyl; PBS, phosphate-buffered saline (pH 7.0~7.5); PEG, polyethylene glycol; SEC, size-exclusion chromatography; TCEP, tris(2-carboxyethyl) phosphine; TFA, trifluoroacetic acid; THF, tetrahydrofuran; Val, valine.

The "amino acid(s)" can be natural and/or unnatural amino acids, preferably alpha-amino acids. Natural amino acids are those encoded by the genetic code, which are alanine, arginine, asparagine, aspartic acid, cysteine, glutamic acid, glutamine, glycine, histidine, isoleucine, leucine, lysine, methionine, phenylalanine, proline, serine, threonine, tyrosine. tryptophan and valine. The unnatural amino acids are derived forms of proteinogenic amino acids. Examples include hydroxyproline, lanthionine, 2-aminoisobutyric acid, dehydroalanine, gamma-aminobutyric acid (the neurotransmitter), orithine, citrulline, beta alanine (3-aminopropanoic acid), gamma-carboxyglutamate, selenocysteine (present in many noneukaryotes as well as most eukaryotes, but not coded directly by DNA), pyrrolysine (found only in some archaea and one bacterium), N-formylmethionine (which is often the initial amino acid of proteins in bacteria, mitochondria, and chloroplasts), 5-hydroxytryptophan, L-dihydroxyphenylalanine, triiodothyronine, L-3,4-dihydroxyphenylalanine (DOPA), and O-phosphoserine. The term amino acid also includes amino acid analogs and mimetics. Analogs are compounds having the same general $H_2N(R)CHCO_2H$ structure of a natural amino acid, except that the R group is not one found among the natural amino acids. Examples of analogs include homoserine, norleucine, methionine-sulfoxide, and methionine methyl sulfonium. Preferably, an amino acid mimetic is a compound that has a structure different from the general chemical structure of an alpha-amino acid but functions in a manner similar to one. The term "unnatural amino acid" is intended to represent the "D" stereochemical form, the natural amino acids being of the "L" form. When 1~8 amino acids are used in this patent application, amino acid sequence is then preferably a cleavage recognition sequence for a protease. Many cleavage recognition sequences are known in the art. See, e.g., Matayoshi et al. Science 247: 954 (1990); Dunn et al. Meth. Enzymol. 241: 254 (1994); Seidah et al. Meth. Enzymol. 244: 175 (1994); Thornberry, Meth. Enzymol. 244: 615 (1994); Weber et al. Meth. Enzymol. 244: 595 (1994); Smith et al. Meth. Enzymol. 244: 412 (1994); and Bouvier et al. Meth. Enzymol. 248: 614 (1995); the disclosures of which are incorporated herein by reference. In particular, the sequence is selected from the group consisting of Val-Cit, Ala-Val, Val-Ala-Val, Lys-Lys, Ala-Asn-Val, Val-Leu-Lys, Cit-Cit, Val-Lys, Ala-Ala-Asn, Lys, Cit, Ser, and Glu.

"Pharmaceutically" or "pharmaceutically acceptable" refer to molecular entities and compositions that do not produce an adverse, allergic or other untoward reaction when administered to an animal, or a human, as appropriate.

"Pharmaceutically acceptable solvate" or "solvate" refer to an association of one or more solvent molecules and a disclosed compound. Examples of solvents that form pharmaceutically acceptable solvates include, but are not limited to, water, isopropanol, ethanol, methanol, DMSO, ethyl acetate, acetic acid and ethanolamine.

"Pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions as suitable therapeutic combinations.

As used herein, "pharmaceutical salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucuronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutical salts of the present invention can be synthesized from the parent compound which contains a basic or acidic moiety by conventional chemical methods. Generally, such salts can be prepared via reaction the free acidic or basic forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in Remington's Pharmaceutical Sciences, $17^{th}$ ed., Mack Publishing Company, Easton, PA, 1985, p. 1418, the disclosure of which is hereby incorporated by reference.

"Administering" or "administration" refers to any mode of transferring, delivering, introducing or transporting a pharmaceutical drug or other agent to a subject. Such modes include oral administration, topical contact, intravenous, intraperitoneal, intramuscular, intralesional, intranasal, subcutaneous or intrathecal administration. Also contemplated by the present invention is utilization of a device or instrument in administering an agent. Such device may utilize active or passive transport and may be slow-release or fast-release delivery device.

The novel conjugates disclosed herein use the bridge linkers. Examples of some suitable linkers and their synthesis are shown in FIGS. 1 to 34.

The Bridge Linkers

The synthetic routes to produce bridge linkers as well as the preparation of the conjugates of drugs to a cell binding molecules of the present invention are shown in FIGS. 1-34. The bridge linkers possess two elements: a) A Substituent that is a 2,3-disubstituted succinic group; or 2-monosubstituted, or 2,3-disubstituted fumaric group; or 2-monosubstituted, or 2,3-disubstituted maleic group; or acetylenedicarboxyl group, which can react to a pair of thiols to form covalent thioether bonds, and b) A group, such as but not limited to, a disulfide, maleimide, haloacetyl, aldehyde, ketone, azide, amine, alkoxyamine, hydrazide, ethenesulfonyl, acyl halide (acid halide), acryl (acryloyl), and/or acid anhydride group, capable of reaction with a drug. The bridge substituents of 2,3-disubstituted succinic group; or 2-monosubstituted, or 2,3-disubstituted fumaric group; or 2-monosubstituted, or 2,3-disubstituted maleic group; or acetylenedicarboxyl group; can be introduced by direct condensation of these 2,3-disubstituted succinic acid, or 2-monosubstituted or 2,3-disubstituted fumaric or maleic, or acetylenedicarboxyl groups with an amine, an alcohol, or a thiol group to form amide, ester or thioester bonds. The synthesis of these bridge linkers and their application for antibody conjugation are exampled in the FIGS. 1-34.

Preferably, the bridge linkers are compounds of the Formula (I) below:

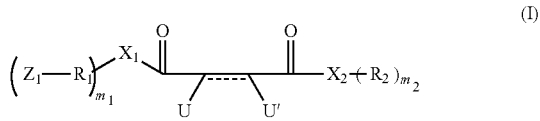

Wherein

"——" represents an optional single bond;

"===" represents either a single bond, or a double bond, or a triple bond.

It provided that when === represents a single bond, both U and U' are not H; when === represents a double bond, either U or U' can be H, but are not H at the same time; when === represents a triple bond, both U and U' can be absent.

Wherein the component:

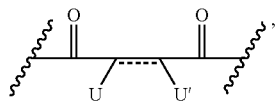

which is 2,3-disubstituted succinic group, or 2-monosubstituted or 2,3-disubstituted fumaric group, or 2-monosubstituted or 2,3-disubstituted maleic group, or acetylenedicarboxyl group, is capable of reacting with a pair of thiols of the cell-binding agent; The pair of thiols are preferred pairs of sulfur atoms reduced from the inter chain disulfide bonds of the cell-binding agent by a reducing agent, such as dithiothreitol (DTT), dithioerythritol (DTE), L-glutathione (GSH), tris (2-carboxyethyl) phosphine (TCEP), 2-mercaptoethylamine (β-MEA), or/and beta mercaptoethanol (β-ME, 2-ME).

U and U' represent the same or different leaving group that can be substituted by a thiol. Such leaving groups are, but are not limited to, a halide (e.g., fluoride, chloride, bromide, and iodide), methanesulfonyl (mesyl), toluenesulfonyl (tosyl), trifluoromethyl-sulfonyl (triflate), trifluoromethylsulfonate, nitrophenoxyl, N-succinimidyloxyl (NHS), phenoxyl; dinitrophenoxyl; pentafluorophenoxyl, tetrafluorophenoxyl, trifluorophenoxyl, difluorophenoxyl, monofluorophenoxyl, pentachlorophenoxyl, 1H-imidazole-1-yl, chlorophenoxyl, dichlorophenoxyl, trichlorophenoxyl, tetrachlorophenoxyl, N-(benzotriazol-yl)oxyl, 2-ethyl-5-phenylisoxazolium-3'-sulfonyl, phenyloxadiazolesulfonyl (-sulfone-ODA), oxadiazol-yl, or an intermediate molecule generated with a condensation reagent for Mitsunobu reactions.

$Z_1$ and $Z_2$ are the same or different a function group that enables to react with a cytotoxic drug, to form a disulfide, thioether, thioester, peptide, hydrazone, ether, ester, carbamate, carbonate, amine (secondary, tertiary, or quarter), imine, cycloheteroalkyane, heteroaromatic, alkoxime or amide bond;

$R_1$ can be absent, or can be selected from $C_1$-$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 carbon atoms of esters, ether, or amide; or polyethyleneoxy unit of formula $(OCH_2CH_2)_p$ or $(OCH_2CH(CH_3))_p$, wherein p is an integer from 0 to about 1000, or combination thereof.

Additionally $R_1$ is a chain of atoms selected from C, N, O, S, Si, and P, preferably having 0~500 atoms, which covalently connects to $X_1$ and $Z_1$. The atoms used in forming the $R_1$ may be combined in all chemically relevant ways, such as forming alkane, alkenylene, alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, peptides, acyloxylamines, hydroxamic acids, or combination thereof.

$X_1$ and $X_2$ are independently selected from NH; NHNH; $N(R_3)$; $N(R_3)N(R_{3'})$; O; S; $B(R_3)$; $Si(R_3)N(R_{3'})$; $P(O)(R_3)$; $C_1$-$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 amino acids; Wherein $R_3$ and $R_{3'}$ are independently H; $C_1$-$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 carbon atoms of esters, ether, or amide; or polyethyleneoxy unit of formula $(OCH_2CH_2)_p$ or $(OCH_2CH(CH_3))_p$, wherein p is an integer from 0 to about 1000, or combination thereof. In addition, $X_1$ and $X_2$ can be independently absent.

$R_2$ is independently selected from OH, H, $NH_2$, SH, $NHNH_2$, $N(R_3)(R_{3'})$; $N(R_3)NH(R_{3'})$; polyethyleneoxy unit of formula $(OCH_2CH_2)_pOR_3$, or $(OCH_2CH(CH_3))_pOR_3$, or $NH(CH_2CH_2O)_pR_3$, or $NH(CH_2CH(CH_3)O)_pR_3$, or $N[(CH_2CH_2O)_pR_3][(CH_2CH_2O)_{p'}R_{3'}]$, or $(OCH_2CH_2)_pCOOR_3$, or $CH_2CH_2(OCH_2CH_2)_pCOOR_3$, wherein p and p' are independently an integer selected from 0 to about 1000, or combination thereof, $C_1$-$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; Wherein $R_3$ and $R_{3'}$ are independently H; $C_1$-$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 carbon atoms of esters, ether, or amide; or 1~8 amino acids; or polyethyleneoxy unit of formula $(OCH_2CH_2)_p$ or $(OCH_2CH(CH_3))_p$, wherein p is an integer from 0 to about 1000, or combination thereof.

$m_1$ and $m_2$ are independently an integer from 1 to 30, preferably from 1 to 10.

In another embodiment, $R_1$, $R_3$ and $R_{3'}$, can be respectively a chain of atoms selected from C, N, O, S, Si, and P which covalently connects the cell-surface binding molecule and/or the conjugated drug. The atoms used in forming the bridge linker may be combined in all chemically relevant ways, such as forming alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, acyloxylamines, hydroxamic acids, and many others. In addition, it is to be understood that the atoms forming the linker (L) may be either saturated or unsaturated, or may be radicals, or may be cyclized upon each other to form divalent cyclic structures, including cycloalkanes, cyclic ethers, cyclic amines, arylenes, heteroarylenes, and the like in the linker.

Examples of the functional group, $Z_1$, which enables linkage of a cytotoxic drug, include groups that enable linkage via a disulfide, thioether, thioester, peptide, hydrazone, ester, carbamate, carbonate, alkoxime or an amide bond. Such functional groups include, but are not limited to, thiol, disulfide, amino, carboxyl, aldehydes, ketone, maleimido, haloacetyl, hydrazines, alkoxyamino, and/or hydroxy.

Examples of the functional group, $Z_1$, that enables reaction with the terminal of amine of a drug/cytotoxic agent, can be, but not limited to, N-hydroxysuccinimide esters, p-nitrophenyl esters, dinitrophenyl esters, pentafluorophenyl esters, carboxylic acid chlorides or carboxylic acid anhydride; With the terminal of thiol, can be, as but not limited to, pyridyldisulfides, nitropyridyldisulfides, maleimides, haloacetates, methylsulfonephenyloxadiazole (ODA), carboxylic acid chlorides and carboxylic acid anhydride; With the terminal of ketone or aldehyde, can be, as but not limited to, amines, alkoxyamines, hydrazines, acyloxylamine, or hydrazide; With the terminal of azide, can be, as but not limited to, alkyne. Examples of these function groups are displayed below:

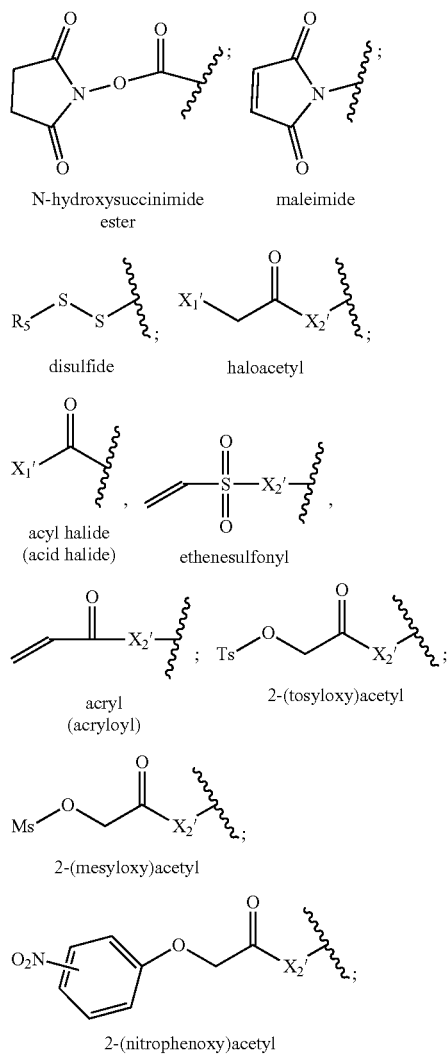
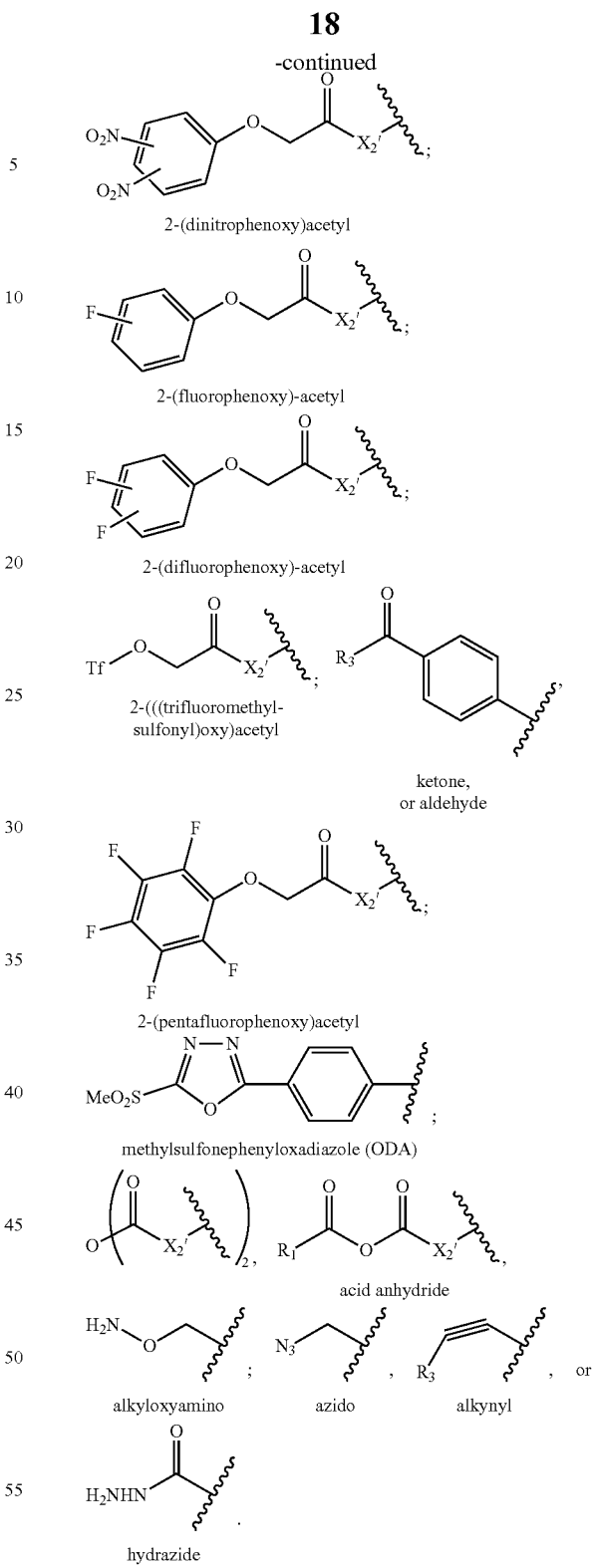

Wherein $X_1'$ is F, Cl, Br, I or $Lv_3$; $X_2'$ is O, NH, $N(R_1)$, or $CH_2$; $R_3$ and $R_5$ are independently H, $R_1$, aromatic, heteroaromatic, or aromatic group wherein one or several H atoms are replaced independently by $-R_1$, -halogen, $-OR_1$, $-SR_1$, $-NR_1R_2$, $-NO_2$, $-S(O)R_1$, $-S(O)_2R_1$, or $-COOR_1$; $Lv_3$ is a leaving group selected from nitrophenol; N-hydroxysuccinimide (NHS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate, anhydrides formed its self, or formed with the other anhydride, e.g. acetyl anhydride, formyl anhydride; or an intermediate molecule generated with a condensation reagent for peptide coupling reactions or for Mitsunobu reactions.

In preferred embodiments, $R_1$, $R_2$, $R_3$ and $R_{3'}$, are linear alkyl having from 1-6 carbon atoms, or polyethyleneoxy unit of formula $(OCH_2CH_2)_p$, $p=1{\sim}100$.

The key step of synthesis of the bridge linker containing 2,3-disubstituted succinic group, or 2-monosubstituted or 2,3-disubstituted fumaric group, or 2-monosubstituted or 2,3-disubstituted maleic group, or acetylenedicarboxyl group, is the condensation of the 2,3-disubstituted succinic acid, or 2-monosubstituted or 2,3-disubstituted fumaric acid, or 2-monosubstituted or 2,3-disubstituted maleic acid, or acetylenedicarboxyl group, or their acid derivatives, with the other components containing an amine (1° or 2° amines), alcohol, or thiol on their terminal, as shown in the following scheme (Ia) and (Ib):

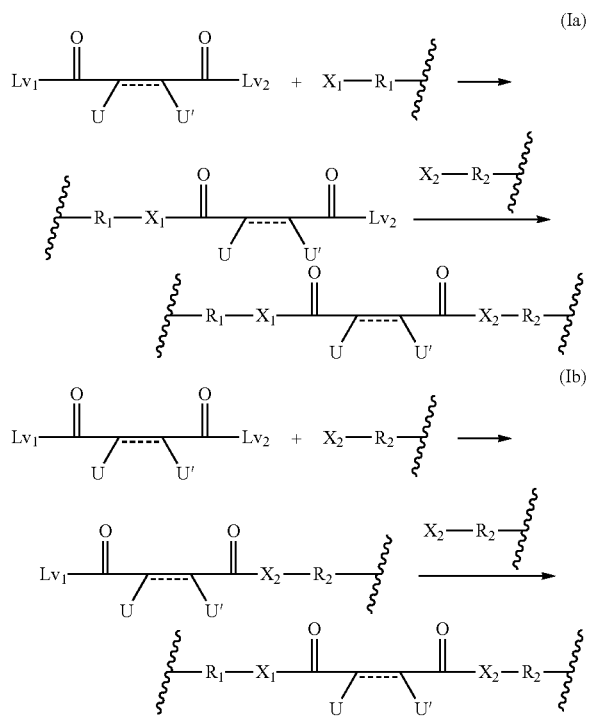

Wherein "≡", $X_1$, $X_2$, $R_1$, and $R_2$ are described the same in Formula (I).

$Lv_1$ and $Lv_2$ are the same or independently OH; F; Cl; Br; I; nitrophenol; N-hydroxysucci-nimide (NHS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate, anhydrides formed its self, or formed with the other anhydride, e.g. acetyl anhydride, formyl anhydride; or an intermediate molecule generated with a condensation reagent for peptide coupling reactions, or for Mitsunobu reactions, e.g. condensation reagents are: EDC (N-(3-Dimethylaminopropyl)-N'-ethylcarbodiimide), DCC (Dicyclohexyl-carbodiimide), N,N'-Diisopropylcarbodiimide (DIC), N-Cyclohexyl-N'-(2-morpholino-ethyl)carbodiimide metho-p-toluenesulfonate (CMC, or CME-CDI), 1,1'-Carbonyldiimi-dazole (CDI), TBTU (O-(Benzotriazol-1-yl)-N,N,N',N'-tetramethyluronium tetrafluoroborate), N,N,N',N'-Tetramethyl-O-(1H-benzotriazol-1-yl)uronium hexafluorophosphate (HBTU), (Benzotriazol-1-yloxy)tris(dimethylamino)phosphonium hexafluorophosphate (BOP), (Benzotriazol-1-yloxy)tripyrrolidinophosphonium hexafluorophosphate (PyBOP), Diethyl cyanophosphonate (DEPC), Chloro-N,N,N',N'-tetramethylformamidiniumhexafluorophosphate, 1-[Bis(dimethylamino)methylene]-1H-1,2,3-triazolo[4,5-b]pyridinium 3-oxide hexafluorophos-phate (HATU), 1-[(Dimethylami-no)(morpholino)methylene]-1H-[1,2,3]triazolo[4,5-b]pyridine-1-ium 3-oxide hexafluorophosphate (HDMA), 2-Chloro-1,3-dimethyl-imidazolidinium hexafluorophosphate (CIP), Chlorotripyrrolidinophosphonium hexafluorophosphate (PyCloP), Fluoro-N,N,N',N'-bis(tetramethylene)formamidinium hexafluorophosphate (BTFFH), N,N,N',N'-Tetramethyl-S-(1-oxido-2-pyridyl)thiuronium hexafluorophosphate, 0-(2-Oxo-1(2H)pyridyl)-N,N,N',N'-tetramethyluronium tetrafluoroborate (TPTU), S-(1-Oxido-2-pyridyl)-N,N,N',N'-tetramethylthiuronium tetrafluoroborate, O-[(Ethoxycarbonyl)-cyanomethylenamino]-N,N,N',N'-tetramethyluronium hexafluorophosphate (HOTU), (1-Cyano-2-ethoxy-2-oxoethylidenaminooxy) dimethylamino-morpholino-carbenium hexafluorophosphate (COMU), O-(Benzotriazol-1-yl)-N,N,N',N'-bis(tetramethylene)uronium hexafluorophosphate (HBPyU), N-Benzyl-N'-cyclo-hexyl-carbodiimide (with, or without polymer-bound), Dipyrrolidino (N-succinimidyl-oxy)carbenium hexafluorophosphate (HSPyU), Chlorodipyrrolidinocarbenium hexafluorophosphate (PyClU), 2-Chloro-1,3-dimethylimi-dazolidinium tetrafluoroborate (CIB), (Benzotriazol-1-yloxy)dipiperidino-carbenium hexafluorophosphate (HBPipU), 0-(6-Chlorobenzotriazol-1-yl)-N,N,N',N'-tetramethyluronium tetrafluoroborate (TCTU), Bromotris(dimethylamino)-phosphonium hexafluorophosphate (BroP), Propylphosphonic anhydride (PPACA, T3P®), 2-Morpholinoethyl isocyanide (MEI), N,N,N',N'-Tetramethyl-O—(N-succinimidyl)uronium hexafluorophosphate (HSTU), 2-Bromo-1-ethyl-pyridinium tetrafluoroborate (BEP), O-[(Ethoxycarbonyl)cyano-methylenamino]-N,N,N',N'-tetra-methyluronium tetrafluoroborate (TOTU), 4-(4,6-Dimethoxy-1,3,5-triazin-2-yl)-4-methylmorpholiniumchloride (MMTM, DMTMM), N,N,N',N'-Tetramethyl-O—(N-succinimidyl)uronium tetrafluoroborate (TSTU), 0-(3,4-Dihydro-4-oxo-1,2,3-benzotriazin-3-yl)-N,N,N',N'-tetramethyluronium tetrafluoro-borate (TDBTU), 1,1'-(Azodicarbonyl)-dipiperidine (ADD), Di-(4-chlorobenzyl) azodicarboxylate (DCAD), Di-tert-butyl azodicarboxylate (DBAD), Diisopropyl azodicarboxylate (DIAD), Diethyl azodicarboxylate (DEAD). In addition, $Lv_1$ and $Lv_2$ can be an anhydride, formed by acid themselves or formed with other $C_1$-$C_8$ acid anhydrides.

The detail examples of the synthesis of the bridge linkers are shown in the FIGS. 1-33. Normally the bridge substituents of 2,3-disubstituted succinic group, or 2-monosubstituted or 2,3-disubstituted fumaric group, or 2-monosubstituted or 2,3-disubstituted maleic group, or acetylenedicarboxyl group, can be condensated with linker components containing function groups capable to react to drugs of desired conjugation.

Cell-Binding Agent-Drug Conjugates

The conjugates of the present invention can be represented by the following formula,

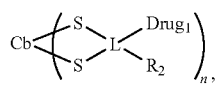

wherein Cb is a cell-binding agent, L is linker containing succinic, fumaric or maleic group, or acetylenedicarboxyl group, Drug₁ is a drug molecule, n is an integer from 1 to 30, and two S (sulfur) elements from Cb bridgely link to L, which covalently connects a drug and a functional molecule $R_2$.

The bridge linker L may be composed of one or more linker components. Exemplary linker components include 6-maleimidocaproyl ("MC"), maleimidopropanoyl ("MP"), valine-citrulline ("val-cit" or "vc"), alanine-phenylalanine ("ala-phe" or "af"), p-aminobenzyloxycarbonyl ("PAB"), 4-thiopentanoate ("SPP"), 4-(N-maleimidomethyl)-cyclohexane-1 carboxylate ("MCC"), (4-acetyl)aminobenzoate ("SIAB"), 4-thio-butyrate (SPDB), 4-thio-2-hydroxysulfonyl-butyrate (2-Sulfo-SPDB), ethyleneoxy —CH₂CH₂O— as one or more repeating units ("EO" or "PEO"). Additional linker components are known in the art and some are described herein.

Example structures of these components containing linkers are:

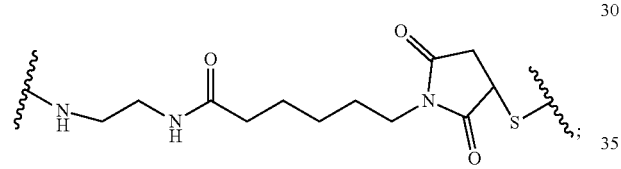

(MC, 6-maleimidocaproyl containing)

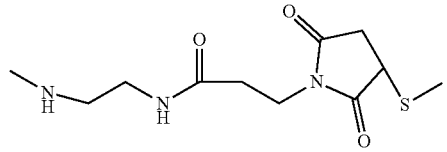

(MP, maleimidopropanoyl containing)

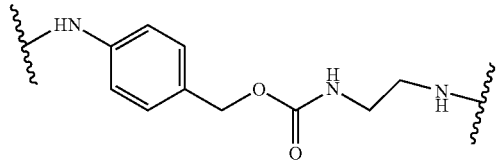

(PAB, p-aminobenzyloxycarbonyl containing)

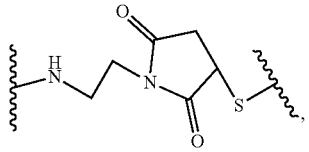

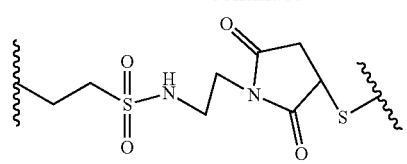

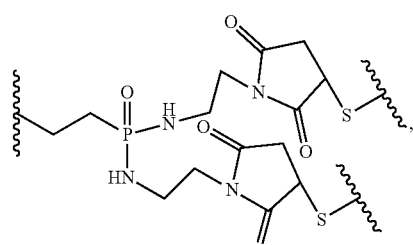

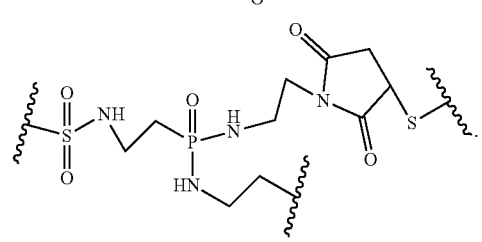

(ME, maleimidoethyl containing)

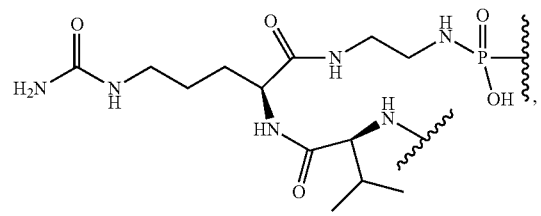

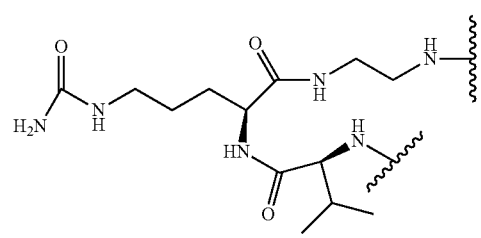

(valine-citrulline containing)

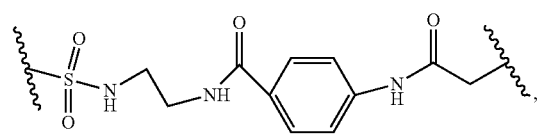

(MCC, 4-(N-maleimidomethyl)cyclohexane-1 carboxylate containing)

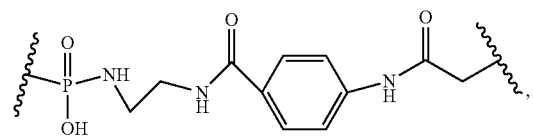

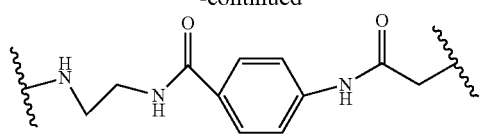

((4-acetyl)aminobenzoate containing)

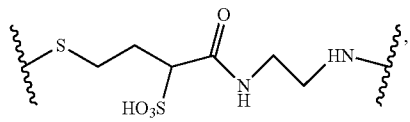

(4-thio-2-hydroxysulfonyl-butyrate,
2-sulfo-SPDB),
(PAB)

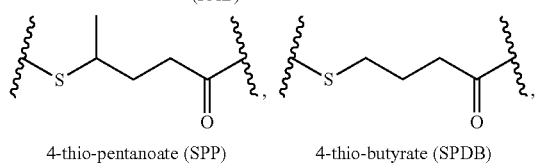

4-thio-pentanoate (SPP)   4-thio-butyrate (SPDB)

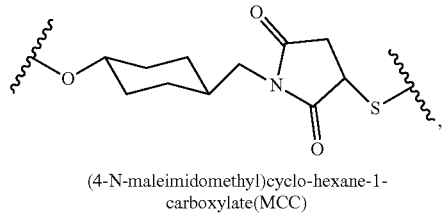

(4-N-maleimidomethyl)cyclo-hexane-1-carboxylate(MCC)

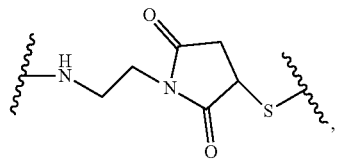

maleimidoethyl
(ME)

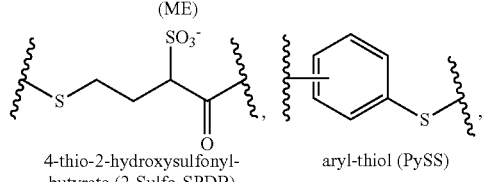

4-thio-2-hydroxysulfonyl-butyrate (2-Sulfo-SPDB)   aryl-thiol (PySS)

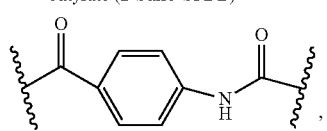

(4-acetyl)amino-benzoate
(SIAB)

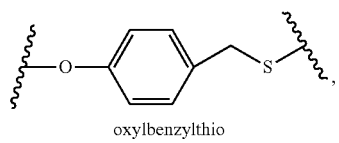

oxylbenzylthio

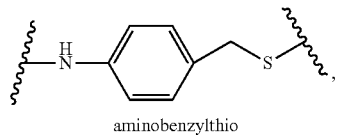

aminobenzylthio

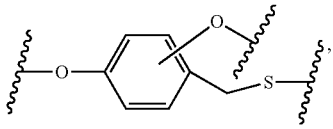

dioxylbenzylthio

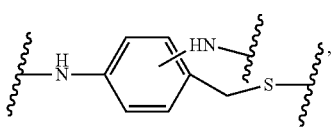

diaminobenzylthio

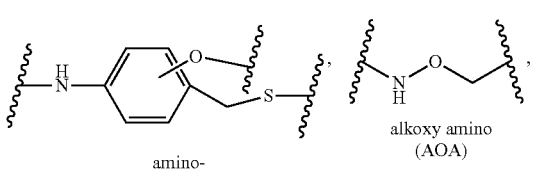

amino-oxylbenzylthio   alkoxy amino (AOA)

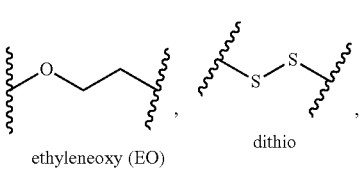

ethyleneoxy (EO)   dithio

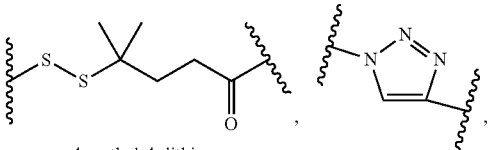

4-methyl-4-dithio-pentanoic (MPDP)   triazole

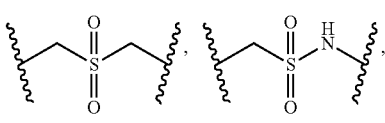

alkylsulfonyl   alkylsulfonamide

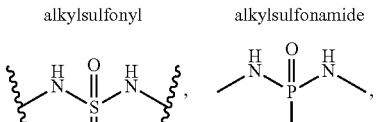

sulfon-bisamide   Phosphondiamide

alkylphosphonamide   phosphinic acid

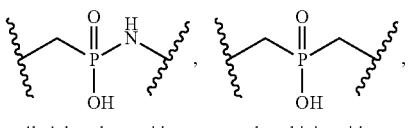

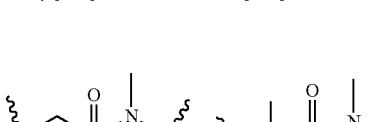
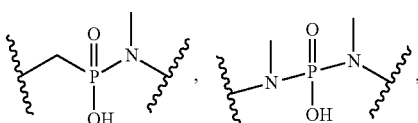

N-methylphosphonamidic acid   N,N'-dimethyl-phosphonamidic acid

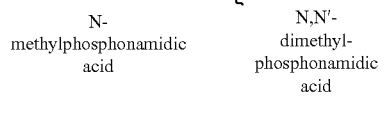

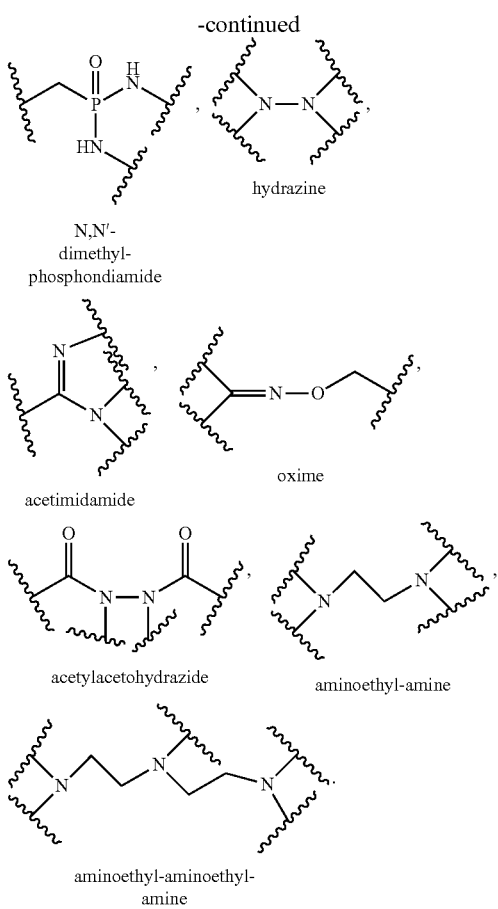

Preferably, the conjugates have the following Formula (II):

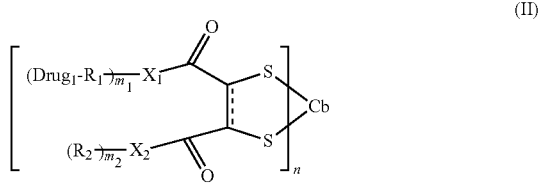

Wherein:

Cb represents a cell-binding agent, preferably an antibody, which conjugates to a Drug, $Drug_1$ and a function molecule, $R_2$, via a pair of sulfur atoms (thiols).

Inside the bracket (square parentheses) are the linker-drug components that are conjugated to pairs of thiols of the cell-binding agent/molecule. The thiols are preferred pairs of sulfur atoms reduced from the inter chain disulfide bonds of the cell-binding agent by a reduction agent selected from dithiothreitol (DTT), dithioerythritol (DTE), L-glutathione (GSH), tris (2-carboxyethyl) phosphine (TCEP), 2-mercaptoethylamine (β-MEA), or/and beta mercaptoethanol (j-ME, 2-ME).

$Drug_1$ represents a cytotoxic agent, linked to a cell-binding agent via the bridge linker of this patent through an alkyl, alkylene, alkenylene, alkynylene, ether, polyoxyalkylene, ester, amine, imine, polyamine, hydrazine, hydrazone, amide, urea, semicarbazide, carbazide, alkoxyamine, urethanes, amino acid, peptide, acyloxylamine, hydroxamic acid, disulfide, thioether, thioester, carbamate, carbonate, heterocyclic ring, heteroalkyl, heteroaromatic, or alkoxime bond, or combination above thereof.

"═" represents either single bond or double bond.

n is 1~30; $R_1$, $R_2$, $m_1$, $m_2$, $X_1$ and $X_2$ are described the same previously in Formula (I).

As described in more detail below, $Drug_1$ can be any of many small molecule drugs, including, but not limited to, tubulysins, calicheamicins, auristatins, maytansinoids, CC-1065 analogs, morpholinos doxorubicins, taxanes, cryptophycins, amatoxins (amanitins), epothilones, geldanamycins, duocarmycins, daunomycins, methotrexates, vindesines, vincristines, and benzodiazepine dimers (e.g., dimmers of pyrrolobenzodiazepine (PBD) or tomaymycin), indolinobenzodiazepines, imidazobenzothiadiazepines, or oxazolidinobenzodiazepines).

To synthesize the conjugate, the cell-binding agent can be first modified with the bridge linkers of the present invention through reduction of disulfide bonds of the cell-binding molecule.

The yielded a pair of free thiols can react to the bridge linker of Formula (I) at pH 5~9 aqueous media with or without addition of 0~30% of water mixable (miscible) organic solvents, such as DMA, DMF, ethanol, methanol, acetone, acetonitrile, THF, isopropanol, dioxane, propylene glycol, or ethylene diol, to introduce the reactive group of $Z_1$ containing disulfide, maleimido, haloacetyl, azide, 1-yne, ketone, aldehyde, alkoxyamino, or hydrazide groups, as well a function molecule group $R_2$, which is preferably a polyethylene glycol, carboxylic acid, or carboxylic amide, or ester, or other derivatives. Then a reactive group of a cytotoxic agent reacts to the modified cell-binding molecule accordingly. For example, synthesis of the cell-binding agent-drug conjugates linked via disulfide bonds is achieved by a disulfide exchange between the disulfide bond in the modified cell-binding agent and a drug containing a free thiol group. Synthesis of the cell-binding agent-drug conjugates linked via thioether is achieved by reaction of the maleimido or haloacetyl or ethylsulfonyl modified cell-binding agent and a drug containing a free thiol group. Synthesis of conjugates bearing an acid labile hydrazone can be achieved by reaction of a carbonyl group with the hydrazide moiety in the linker, by methods known in the art (see, for example, P. Hamann et al., Cancer Res. 53, 3336-34, 1993; B. Laguzza et al., J. Med. Chem., 32; 548-55, 1959; P. Trail et al., Cancer Res., 57; 100-5, 1997). Synthesis of conjugates bearing triazole linkage can be achieved by reaction of a 1-yne group of the drug with the azido moiety in the linker, through the click chemistry (Huisgen cycloaddition) (Lutz, J-F. et al, 2008, Adv. Drug Del. Rev. 60, 958-70; Sletten, E. M. et al 2011, AccChen. Research 44, 666-76).

Alternatively, the drug can react with the bridge linkers of the present invention that have conjugated to a cell-binding molecule to give a modified cell-binding molecule linker of Formula (III) bearing functionalities. For example, a thiol-containing drug can react with the modified cell-binding molecule bridge linker of Formula (III) bearing a maleimido, or a haloacetyl, or an ethylsulfonyl substituent at pH 5.5~9.0 in aqueous buffer to give a cell-binding molecule-drug conjugate via a thioether linkage. A thiol-containing drug can undergo disulfide exchange with a modified bridge linker of Formula (III) bearing a pyridyldithio moiety to give a conjugate a disulfide bond linkage. A drug bearing a hydroxyl group or a thiol group can be reacted with a modified bridge linker of Formula (III) bearing a halogen, particularly the alpha halide of carboxylates, in the presence of a mild base, e.g. pH 8.0~9.5, to give a modified drug bearing an ether or thiol ether link. A hydroxyl group containing drug can be condensed with a bridge cross linker of Formula (I) bearing a carboxyl group, in the presence of a dehydrating agent, such as EDC or DCC, to give ester linkage, then the subject drug modified bridge linker undergoes the conjugation with a cell-binding molecule. A drug containing an amino group can condensate with a carboxyl ester of NHS, imidazole, nitrophenol; N-hydroxysuccinimide (NHS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxyben-zotriazole; tosylate; mesylate; 2-ethyl-5-phenylisoxazolium-3'-sulfonate on the cell-binding molecule-bridge linker of Formula (III) to give a conjugate via amide bond linkage.

The conjugate may be purified by standard biochemical means, such as gel filtration on a Sephadex G25 or Sephacryl S300 column, adsorption chromatography, and ion exchange or by dialysis. In some cases, a small molecule as a cell-binding agent (e.g. folic acid, melanocyte stimulating hormone, EGF etc) conjugated with a small molecular drugs can be purified by chromatography such as by HPLC, medium pressure column chromatography or ion exchange chromatography.

Modified Cell-Binding Agents/Molecules

The cell-binding agent modified by reaction with linkers of the present invention is preferably represented by the Formula (III):

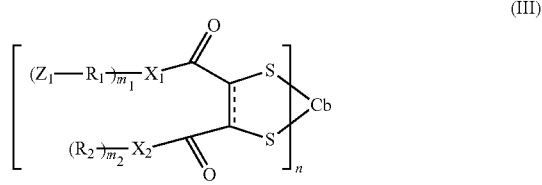

Wherein === represents either a single bond, or a double bond.

Cb, $Z_1$, $Z_2$, n, $R_1$, $R_2$, $m_1$, $m_2$, $X_1$, and $X_2$ are defined the same as in Formula (I) and (II).

In preferred embodiments, $Z_1$ is a disulfide substituent, maleimido, haloacetyl, alkoxyamine, azido, ketone, aldehyde, hydrazine, alkyne, an N-hydroxysuccinimide ester, or a carboxyl ester formed with phenol; dinitrophenol; pentafluorophenol; tetrafluoro-phenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxa-zolium-3'-sulfonate. $Z_1$ can then react with a cytotoxic agent through disulfide, thioether, hydrazone, amide, alkoxime, carbamate, ester, ether bond or hetero-aromatic ring. The modified cell-binding agent can be prepared via a reaction of the cell-binding agent with the bridge linkers of Formula (I) as described in Formula (II) above.

In order to achieve a higher conjugation reaction yield of 2,3-disubstituted succinic group, or 2-monosubstituted or 2,3-disubstituted fumaric group, or 2-monosubstituted or 2,3-disubstituted maleic group, or acetylenedicarboxyl group, on the bridge linkers of the Formula (I) with a pair of free thiols on the cell-binding molecule, preferably on an antibody, a small percentage of organic co-solvent may be required to add to the reaction mixture, as well in the solution after the reaction to maintain solubility of the Formula (III) in aqueous solution. To modify the cell-binding agents, the cross-linking reagent (bridge linker) of Formula (I) can be first dissolved in a polar organic solvent that is miscible with water, for example different alcohols, such as methanol, ethanol, and propanol, acetone, acetonitrile, tetrahydrofuran (THF), 1,4-dioxane, dimethyl formamide (DMF), dimethyl acetamide (DMA), or dimethylsulfoxide (DMSO) at a high concentration, for example 1-500 mM. Meanwhile, the cell-binding molecule, such as antibody dissolved in an aqueous buffer pH 5~9.5, preferably pH 6-8.5, at 1~35 mg/ml concentration was treated with 1~20 equivalent of TCEP or DTT for 20 min to 48 hour. After the reduction, DTT can be removed by SEC chromatographic purification. TCEP can be optionally removed by SEC chromatography too, or staying in the reaction mixture for the next step reaction without purification. Furthermore, the reduction of antibodies or the other cell-binding agents with TCEP can be performed with a bridge linker of Formula (I), for which the cross-linking conjugation for the cell-binding molecules can be achieved simultaneously along with the TCEP reduction.

The aqueous solutions for the modification of cell-binding agents are buffered between pH 6 and 9, preferably between 6.5 and 7.5 and can contain any non-nucleophilic buffer salts useful for these pH ranges. Typical buffers include phosphate, triethanolamine HCl, HEPES, and MOPS buffers, which can contain additional components, such as cyclodextrins, sucrose and salts, for examples, NaCl and KCl. After the addition of the bridge linker of Formula (I) into the solution containing the reduced cell-binding molecules, the reaction mixture is incubated at a temperature of from 4° C. to 45° C., preferably at ambient temperature. The progress of the reaction can be monitored by measuring the decrease in the absorption at a certain UV wavelength, such as at 254 nm, or increase in the absorption at a certain UV wavelength, such as 280 nm, or the other appropriate wavelength. After the reaction is complete, isolation of the modified cell-binding agent can be performed in a routine way, using for example gel filtration chromatography, or adsorptive chromatography.

The extent of modification can be assessed by measuring the absorbance of the nitropyridine thione, dinitropyridine dithione, pyridine thione, carboxylamidopyridine dithione and dicarboxyl-amidopyridine dithione group released via UV spectra. For the conjugation without a chromophore group, the modification or conjugation reaction can be monitored by LC-MS, preferably by UPLC-QTOF mass spectrometry, or Capilary electrophoresis-mass spectrometry (CE-MS). The bridge cross-linkers described herein have diverse functional groups that can react with any drugs, preferably cytotoxic agents that possess a suitable substituent. For examples, the modified cell-binding molecules bearing an amino or hydroxyl substituent can react with drugs bearing an N-hydroxysuccinimide (NHS) ester, the modified cell-binding molecules bearing a thiol substituent can react with drugs bearing a maleimido or haloacetyl group. Additionally, the modified cell-binding molecules bearing a carbonyl (ketone or aldehyde) substituent can react with drugs bearing a hydrazide or an alkoxyamine. One skilled in the art can readily determine which linker to use based on the known reactivity of the available functional group on the linkers.

Modified Cytotoxic Drugs

The cytotoxic drugs modified by reaction with cross-linkers of the present invention are preferably represented by the Formula (IV):

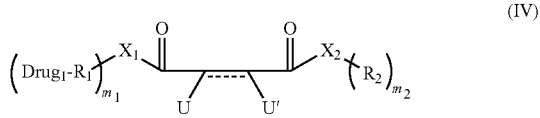

(IV)

Wherein "≡" represents either a single bond, or a double bond, or a triple bond.

"——", U, U', Drug$_1$, Drug$_2$, R$_1$, R$_2$, m$_1$, m$_2$, X$_1$, and X$_2$ are defined the same as in Formula (I) and (II).

The modified drugs can be prepared via reaction of the drug with the linkers of the Formula (I) to give a modified drug of Formula (IV) bearing functionality of an 2,3-disubstituted succinic group, or 2-monosubstituted or 2,3-disubstituted fumaric group, or 2-monosubstituted or 2,3-disubstituted maleic group, or acetylenedicarboxyl group. But for drugs containing a thiol, or the drugs undergoing to conjugation of a cell-binding molecule via the bridge linkers through thioether, thioester or disulfide bond, it is therefore preferred that the Drug$_1$ may be synthesized to connect to R$_1$ in a piece of components via the linkage of thioether, thioester or disulfide bond first. Then the synthesized R$_1$-Drug$_1$ component is assembled to 2,3-disubstituted succinic acid, or 2-monosubstituted or 2,3-disubstituted fumaric acid, or 2-monosubstituted or 2,3-disubstituted maleic acid, or acetylenedicarboxyl group, to form the bridge linker modified drugs of Formula (IV).

For examples of the synthesis, a thiol-containing drug can be reacted with the linker of components R$_1$ bearing a maleimido substituent at neutral pH in aqueous buffer to give a R$_1$-Drug$_1$ compartment bearing thioether linkage, and following by condensation with either 2,3-disubstituted succinic acid, or 2-monosubstituted or 2,3-disubstituted fumaric acid, or 2-monosubstituted or 2,3-disubstituted maleic acid, or acetylenedicarboxyl group, to give a modified drug of Formula (IV) bearing thioether linkage. A drug bearing a hydroxyl group can be reacted with a linker component R$_1$ bearing a halogen, or a tosylate, or a mesylate, in the presence of a mild base, to give a R$_1$-Drug$_1$ compartment bearing ether linkage, and following by condensation with 2,3-disubstituted succinic acid, or 2-monosubstituted or 2,3-disubstituted fumaric acid, or 2-monosubstituted or 2,3-disubstituted maleic acid, or acetylenedicarboxyl group, to give a modified drug of Formula (IV) bearing thioether linkage. A hydroxyl group containing drug can be condensed with a linker of Formula (I) bearing a carboxyl group, in the presence of a dehydrating agent, such as EDC or dicyclohexylcarbodiimide (DCC), to give a modified drug of Formula (IV) via ester linkage. A drug bearing a thiol group can also react the linker of components R$_1$ bearing a maleimido or a vinylsulfonyl, or a haloacetyl group, give a R$_1$-Drug$_1$ compartment bearing thioether linkage, and following by condensation with a compartment of 2,3-disubstituted succinic acid, or 2-monosubstituted or 2,3-disubstituted fumaric acid, or 2-monosubstituted or 2,3-disubstituted maleic acid, or acetylenedicarboxyl group, to give a modified drug of Formula (IV) bearing thioether linkage. An amino group containing drug can similarly undergo condensation with a carboxyl group on the bridge linker of Formula (I) to give a modified drug of Formula (IV) bearing amide bonds. The modified drug can be purified by standard methods such as column chromatography over silica gel or alumina, crystallization, preparatory thin layer chromatography, ion exchange chromatography, or HPLC.

Cell-Binding Agents

The cell-binding molecule, Cb, that comprises the conjugates and the modified cell-binding agents of the present invention may be of any kind presently known, or that become known, molecule that binds to, complexes with, or reacts with a moiety of a cell population sought to be therapeutically or otherwise biologically modified.

The cell binding agents include, but are not limited to, large molecular weight proteins such as, for example, full-length antibodies (polyclonal antibodies, monoclonal antibodies, dimers, multimers, multispecific antibodies (e.g., bispecific antibodies); single chain antibodies; fragments of antibodies such as Fab, Fab', F(ab')$_2$, F$_v$, [Parham, J. Immunol. 131, 2895-902 (1983)], fragments produced by a Fab expression library, anti-idiotypic (anti-Id) antibodies, CDR's, diabody, triabody, tetrabody, miniantibody, small immune proteins (SIP), and epitope-binding fragments of any of the above which immuno-specifically bind to cancer cell antigens, viral antigens, microbial antigens or a protein generated by the immune system that is capable of recognizing, binding to a specific antigen or exhibiting the desired biological activity (Miller et al (2003) J. of Immunology 170: 4854-61); interferons (such as type I, II, III); peptides; lymphokines such as IL-2, IL-3, IL-4, IL-5, IL-6, IL-10, GM-CSF, interferon-gamma (IFN-γ); hormones such as insulin, TRH (thyrotropin releasing hormones), MSH (melanocyte-stimulating hormone), steroid hormones, such as androgens and estrogens, melanocyte-stimulating hormone (MSH); growth factors and colony-stimulating factors such as epidermal growth factors (EGF), granulocyte-macrophage colony-stimulating factor (GM-CSF), transforming growth factors (TGF), such as TGFα, TGFβ, insulin and insulin like growth factors (IGF-I, IGF-II) G-CSF, M-CSF and GM-CSF [Burgess, Immunology Today, 5, 155-8 (1984)]; vaccinia growth factors (VGF); fibroblast growth factors (FGFs); smaller molecular weight proteins, polypeptide, peptides and peptide hormones, such as bombesin, gastrin, gastrin-releasing peptide; platelet-derived growth factors; interleukin and cytokines, such as interleukin-2 (IL-2), interleukin-6 (IL-6), leukemia inhibitory factors, granulocyte-macrophage colony-stimulating factor (GM-CSF); vitamins, such as folate; apoproteins and glycoproteins, such as transferrin [O'Keefe et al, 260 J. Biol. Chem. 932-7 (1985)]; sugar-binding proteins or lipoproteins, such as lectins; cell nutrient-transport molecules; and small molecular inhibitors, such as prostate-specific membrane antigen (PSMA) inhibitors and small molecular tyrosine kinase inhibitors (TKI), non-peptides or any other cell binding molecule or substance, such as bioactive polymers (Dhar, et al, Proc. Natl. Acad. Sci. 2008, 105, 17356-61); bioactive dendrimers (Lee, et al, Nat. Biotechnol. 2005, 23, 1517-26; Almutairi, et al; Proc. Natl. Acad. Sci. 2009, 106, 685-90); nanoparticles (Liong, et al, ACS Nano, 2008, 2, 1309-12; Medarova, et al, Nat. Med. 2007, 13, 372-7; Javier, et al, Bioconjugate Chem. 2008, 19, 1309-12); liposomes (Medinai, et al, Curr. Phar. Des. 2004, 10, 2981-9); viral capsides (Flenniken, et al, Viruses Nanotechnol. 2009, 327, 71-93).

In general, a monoclonal antibody is preferred as a cell-surface binding agent if an appropriate one is available. And the antibody may be murine, human, humanized, chimeric, or derived from other species.

Production of antibodies used in the present invention involves in vivo or in vitro procedures or combinations thereof. Methods for producing polyclonal anti-receptor peptide antibodies are well-known in the art, such as in U.S. Pat. No. 4,493,795 (to Nestor et al). A monoclonal antibody is typically made by fusing myeloma cells with the spleen cells from a mouse that has been immunized with the desired antigen (Kohler, G.; Milstein, C. (1975). Nature 256: 495-7). The detailed procedures are described in "Antibodies-A Laboratory Manual", Harlow and Lane, eds., Cold Spring Harbor Laboratory Press, New York (1988), which is incorporated herein by reference. Particularly monoclonal antibodies are produced by immunizing mice, rats, hamsters or any other mammal with the antigen of interest such as the intact target cell, antigens isolated from the target cell, whole virus, attenuated whole virus, and viral proteins. Splenocytes are typically fused with myeloma cells using polyethylene glycol (PEG) 6000. Fused hybrids are selected by their sensitivity to HAT (hypoxanthine-aminopterin-thymine). Hybridomas producing a monoclonal antibody useful in practicing this invention are identified by their ability to immunoreact specified receptors or inhibit receptor activity on target cells.

A monoclonal antibody used in the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques, such as using protein-A affinity chromatography; anion, cation, hydrophobic, or size exclusive chromatographies (particularly by affinity for the specific antigen after protein A, and sizing column chromatography); centrifugation, differential solubility, or by any other standard technique for the purification of proteins.

Media useful for the preparation of these compositions are both well-known in the art and commercially available and include synthetic culture media. An exemplary synthetic medium is Dulbecco's minimal essential medium (DMEM; Dulbecco et al., Virol. 8, 396 (1959)) supplemented with 4.5 gm/l glucose, 0~20 mM glutamine, 0~20% fetal calf serum, several ppm amount of heavy metals, such as Cu, Mn, Fe, or Zn, etc, or/and the other heavy metals added in their salt forms, and with an anti-foaming agent, such as polyoxyethylene-polyoxypropylene block copolymer.

In addition, antibody-producing cell lines can also be created by techniques other than fusion, such as direct transformation of B lymphocytes with oncogenic DNA, or transfection with an oncovirus, such as Epstein-Barr virus (EBV, also called human herpesvirus 4 (HHV-4)) or Kaposi's sarcoma-associated herpesvirus (KSHV). See, U.S. Pat. Nos. 4,341,761; 4,399,121; 4,427,783; 4,444,887; 4,451,570; 4,466,917; 4,472,500; 4,491,632; 4,493,890. A monoclonal antibody may also be produced via an anti-receptor peptide or peptides containing the carboxyl terminal as described well-known in the art. See Niman et al., Proc. Natl. Acad. Sci. USA, 80: 4949-53 (1983); Geysen et al., Proc. Natl. Acad. Sci. USA, 82: 178-82 (1985); Lei et al. Biochemistry 34(20): 6675-88, (1995). Typically, the anti-receptor peptide or a peptide analog is used either alone or conjugated to an immunogenic carrier, as the immunogen for producing anti-receptor peptide monoclonal antibodies.

There are also a number of other well-known techniques for making monoclonal antibodies as binding molecules in this invention. Particularly useful are methods of making fully human antibodies. One method is phage display technology which can be used to select a range of human antibodies binding specifically to the antigen using methods of affinity enrichment. Phage display has been thoroughly described in the literature and the construction and screening of phage display libraries are well known in the art, see, e.g., Dente et al, Gene. 148(1):7-13 (1994); Little et al, Biotechnol Adv. 12(3): 539-55 (1994); Clackson et al., Nature 352: 264-8 (1991); Huse et al., Science 246: 1275-81 (1989).

Monoclonal antibodies derived by hybridoma technique from another species than human, such as mouse, can be humanized to avoid human anti-mouse antibodies when infused into humans. Among the more common methods of humanization of antibodies are complementarity-determining region grafting and resurfacing. These methods have been extensively described, see e.g. U.S. Pat. Nos. 5,859, 205 and 6,797,492; Liu et al, Immunol Rev. 222: 9-27 (2008); Almagro et al, Front Biosci. 13: 1619-33 (2008); Lazar et al, Mol Immunol. 44(8): 1986-98 (2007); Li et al, Proc. Natl. Acad. Sci. USA. 103(10): 3557-62 (2006) each incorporated herein by reference. Fully human antibodies can also be prepared by immunizing transgenic mice, rabbits, monkeys, or other mammals, carrying large portions of the human immunoglobulin heavy and light chains, with an immunogen. Examples of such mice are: the Xenomouse. (Abgenix/Amgen), the HuMAb-Mouse (Medarex/BMS), the VelociMouse (Regeneron), see also U.S. Pat. Nos. 6,596, 541, 6,207,418, 6,150,584, 6,111,166, 6,075,181, 5,922,545, 5,661,016, 5,545,806, 5,436,149 and 5,569,825. In human therapy, murine variable regions and human constant regions can also be fused to construct called "chimeric antibodies" that are considerably less immunogenic in man than murine mAbs (Kipriyanov et al, Mol Biotechnol. 26: 39-60 (2004); Houdebine, Curr Opin Biotechnol. 13: 625-9 (2002) each incorporated herein by reference). In addition, site-directed mutagenesis in the variable region of an antibody can result in an antibody with higher affinity and specificity for its antigen (Brannigan et al, Nat Rev Mol Cell Biol. 3: 964-70, (2002)); Adams et al, J Immunol Methods. 231: 249-60 (1999)) and exchanging constant regions of a mAb can improve its ability to mediate effector functions of binding and cytotoxicity.

Antibodies immunospecific for a malignant cell antigen can also be obtained commercially or produced by any method known to one of skill in the art such as, e.g., chemical synthesis or recombinant expression techniques. The nucleotide sequence encoding antibodies immune-specific for a malignant cell antigen can be obtained commercially, e.g., from the GenBank database or a database like it, the literature publications, or by routine cloning and sequencing.

Apart from an antibody, a peptide or protein that bind/block/target or in some other way interact with the epitopes or corresponding receptors on a targeted cell can be used as a binding molecule. These peptides or proteins could be any random peptide or proteins that have an affinity for the epitopes or corresponding receptors and they don't necessarily have to be of the immune-globulin family. These peptides can be isolated by similar techniques as for phage display antibodies (Szardenings, J Recept Signal Transduct Res. 2003, 23(4): 307-49). The use of peptides from such random peptide libraries can be similar to antibodies and antibody fragments. The binding molecules of peptides or proteins may be conjugated on or linked to a large molecules or materials, such as, but is not limited, an albumin, a polymer, a liposome, a nano particle, a dendrimer, as long as such attachment permits the peptide or protein to retain its antigen binding specificity.

Examples of antibodies used for conjugation of drugs via the bridge linkers of this prevention for treating cancer, autoimmune disease, and/or infectious disease include, but are not limited to, 3F8 (anti-GD2), Abagovomab (anti CA-125), Abciximab (anti CD41 (integrin alpha-IIb), Adalimumab (anti-TNF-α), Adecatumumab (anti-EpCAM, CD326), Afelimomab (anti-TNF-α); Afutuzumab (anti-CD20), Alacizumab pegol (anti-VEGFR2), ALD518 (anti-IL-6), Alemtuzumab (Campath, MabCampath, anti-CD52), Altumomab (anti-CEA), Anatumomab (anti-TAG-72), Anrukinzumab (IMA-638, anti-IL-13), Apolizumab (anti-HLA-DR), Arcitumomab (anti-CEA), Aselizumab (anti-L-selectin (CD62L), Atlizumab (tocilizumab, Actemra, RoActemra, anti-IL-6 receptor), Atorolimumab (anti-Rhesus factor), Bapineuzumab (anti-beta amyloid), Basiliximab (Simulect, antiCD25 (a chain of IL-2 receptor), Bavituximab (anti-phosphatidylserine), Bectumomab (LymphoScan, anti-CD22), Belimumab (Benlysta, LymphoStat-B, anti-BAFF), Benralizumab (anti-CD125), Bertilimumab (anti-CCL11 (eotaxin-1)), Besilesomab (Scintimun, anti-CEA-related antigen), Bevacizumab (Avastin, anti-VEGF-A), Biciromab (FibriScint, anti-fibrin II beta chain), Bivatuzumab (anti-CD44 v6), Blinatumomab (BiTE, anti-CD19), Brentuximab (cAC10, anti-CD30 TNFRSF8), Briakinumab (anti-IL-12, IL-23) Canakinumab (Ilaris, anti-IL-1), Cantuzumab (C242, anti-CanAg), Capromab, Catumaxomab (Removab, anti-EpCAM, anti-CD3), CC49 (anti-TAG-72), Cedelizumab (anti-CD4), Certolizumab pegol (Cimzia anti-TNF-α), Cetuximab (Erbitux, IMC-C225, anti-EGFR), Citatuzumab bogatox (anti-EpCAM), Cixutumumab (anti-IGF-1), Clenoliximab (anti-CD4), Clivatuzumab (anti-MUC1), Conatumumab (anti-TRAIL-R2), CR6261 (anti-Influenza A hemagglutinin), Dacetuzumab (anti-CD40), Daclizumab (Zenapax, anti-CD25 (a chain of IL-2 receptor)), Daratumumab (anti-CD38 (cyclic ADP ribose hydrolase), Denosumab (Prolia, anti-RANKL), Detumomab (anti-B-lymphoma cell), Dorlimomab, Dorlixizumab, Ecromeximab (anti-GD3 ganglioside), Eculizumab (Soliris, anti-C5), Edobacomab (anti-endotoxin), Edrecolomab (Panorex, MAbT7-TA, anti-EpCAM), Efalizumab (Raptiva, anti-LFA-1 (CD11a), Efungumab (Mycograb, anti-Hsp90), Elotuzumab (anti-SLAMF7), Elsilimomab (anti-IL-6), Enlimomab pegol (anti-ICAM-1 (CD54)), Epitumomab (anti-episialin), Epratuzumab (anti-CD22), Erlizumab (anti-ITGB2 (CD18)), Ertumaxomab (Rexomun, anti-HER2/neu, CD3), Etaracizumab (Abegrin, anti-integrin $\alpha_v\beta_3$), Exbivirumab (anti-hepatitis B surface antigen), Fanolesomab (NeutroSpec, anti-CD15), Faralimomab (anti-interferon receptor), Farletuzumab (anti-folate receptor 1), Felvizumab (anti-respiratory syncytial virus), Fezakinumab (anti-IL-22), Figitumumab (anti-IGF-1 receptor), Fontolizumab (anti-IFN-γ), Foravirumab (anti-rabies virus glycoprotein), Fresolimumab (anti-TGF-β), Galiximab (anti-CD80), Gantenerumab (anti-beta amyloid), Gavilimomab (anti-CD147 (basigin)), Gemtuzumab (anti-CD33), Girentuximab (anti-carbonic anhydrase 9), Glembatumumab (CR011, anti-GPNMB), Golimumab (Simponi, anti-TNF-α), Gomiliximab (anti-CD23 (IgE receptor)), Ibalizumab (anti-CD4), Ibritumomab (anti-CD20), Igovomab (Indimacis-125, anti-CA-125), Imciromab (Myoscint, anti-cardiac myosin), Infliximab (Remicade, anti-TNF-α), Intetumumab (anti-CD51), Inolimomab (anti-CD25 (a chain of IL-2 receptor)), Inotuzumab (anti-CD22), Ipilimumab (anti-CD152), Iratumumab (anti-CD30 (TNFRSF8)), Keliximab (anti-CD4), Labetuzumab (CEA-Cide, anti-CEA), Lebrikizumab (anti-IL-13), Lemalesomab (anti-NCA-90 (granulocyte antigen)), Lerdelimumab (anti-TGF beta 2), Lexatumumab (anti-TRAIL-R2), Libivirumab (anti-hepatitis B surface antigen), Lintuzumab (anti-CD33), Lucatumumab (anti-CD40), Lumiliximab (anti-CD23 (IgE receptor), Mapatumumab (anti-TRAIL-R1), Maslimomab (anti-T-cell receptor), Matuzumab (anti-EGFR), Mepolizumab (Bosatria, anti-IL-5), Metelimumab (anti-TGF beta 1), Milatuzumab (anti-CD74), Minretumomab (anti-TAG-72), Mitumomab (BEC-2, anti-GD3 ganglioside), Morolimumab (anti-Rhesus factor), Motavizumab (Numax, anti-respiratory syncytial virus), Muromonab-CD3 (Orthoclone OKT3, anti-CD3), Nacolomab (anti-C242), Naptumomab (anti-5T4), Natalizumab (Tysabri, anti-integrin $\alpha_4$), Nebacumab (anti-endotoxin), Necitumumab (anti-EGFR), Nerelimomab (anti-TNF-α), Nimotuzumab (Theracim, Theraloc, anti-EGFR), Nofetumomab, Ocrelizumab (anti-CD20), Odulimomab (Afolimomab, anti-LFA-1 (CDTTa)), Ofatumumab (Arzerra, anti-CD20), Olaratumab (anti-PDGF-R a), Omalizumab (Xolair, anti-IgE Fc region), Oportuzumab (anti-EpCAM), Oregovomab (OvaRex, anti-CA-125), Otelixizumab (anti-CD3), Pagibaximab (anti-lipoteichoic acid), Palivizumab (Synagis, Abbosynagis, anti-respiratory syncytial virus), Panitumumab (Vectibix, ABX-EGF, anti-EGFR), Panobacumab (anti-*Pseudomonas aeruginosa*), Pascolizumab (anti-IL-4), Pemtumomab (Theragyn, anti-MUC1), Pertuzumab (Omnitarg, 2C4, anti-HER2/neu), Pexelizumab (anti-C5), Pintumomab (anti-adenocarcinoma antigen), Priliximab (anti-CD4), Pritumumab (anti-vimentin), PRO 140 (anti-CCR5), Racotumomab (1E10, anti-(N-glycolylneuraminic acid (NeuGc, NGNA)-gangliosides GM3)), Rafivirumab (anti-rabies virus glycoprotein), Ramucirumab (anti-VEGFR2), Ranibizumab (Lucentis, anti-VEGF-A), Raxibacumab (anti-anthrax toxin, protective antigen), Regavirumab (anti-cytomegalovirus glycoprotein B), Reslizumab (anti-IL-5), Rilotumumab (anti-HGF), Rituximab (MabThera, Rituxanmab, anti-CD20), Robatumumab (anti-IGF-1 receptor), Rontalizumab (anti-IFN-α), Rovelizumab (LeukArrest, anti-CD11, CD18), Ruplizumab (Antova, anti-CD154 (CD40L)), Satumomab (anti-TAG-72), Sevirumab (anti-cytomegalovirus), Sibrotuzumab (anti-FAP), Sifalimumab (anti-IFN-α), Siltuximab (anti-IL-6), Siplizumab (anti-CD2), (Smart) MI95 (anti-CD33), Solanezumab (anti-beta amyloid), Sonepcizumab (anti-sphingosine-1-phosphate), Sontuzumab (anti-episialin), Stamulumab (anti-myostatin), Sulesomab (LeukoScan, (anti-NCA-90 (granulocyte antigen), Tacatuzumab (anti-alpha-fetoprotein), Tadocizumab (anti-integrin $\alpha_{IIb}\beta_3$), Talizumab (anti-IgE), Tanezumab (anti-NGF), Taplitumomab (anti-CD19), Tefibazumab (Aurexis, (anti-clumping factor A), Telimomab, Tenatumomab (anti-tenascin C), Teneliximab (anti-CD40), Teplizumab (anti-CD3), TGN1412 (anti-CD28), Ticilimumab (Tremelimumab, (anti-CTLA-4), Tigatuzumab (anti-TRAIL-R2), TNX-650 (anti-IL-13), Tocilizumab (Atlizumab, Actemra, RoActemra, (anti-IL-6 receptor), Toralizumab (anti-CD154 (CD40L)), Tositumomab (anti-CD20), Trastuzumab (Herceptin, (anti-HER2/neu), Tremelimumab (anti-CTLA-4), Tucotuzumab celmoleukin (anti-EpCAM), Tuvirumab (anti-hepatitis B virus), Urtoxazumab (anti-*Escherichia coli*), Ustekinumab (Stelara, anti-IL-12, IL-23), Vapaliximab (anti-AOC3 (VAP-1)), Vedolizumab, (anti-integrin $\alpha_4\beta_7$), Veltuzumab (anti-CD20), Vepalimomab (anti-AOC3 (VAP-1), Visilizumab (Nuvion, anti-CD3), Vitaxin (anti-vascular integrin avb3), Volociximab (anti-integrin $\alpha_5\beta_1$), Votumumab (HumaSPECT, anti-tumor antigen CTAA16.88), Zalutumumab (HuMax-EGFr, (anti-EGFR), Zanolimumab (HuMax-CD4, anti-CD4), Ziralimumab (anti-CD147 (basigin)), Zolimomab (anti-CD5), Etanercept (Enbrel®), Alefacept (Amevive®), Abatacept (Orencia®), Rilonacept (Arcalyst), 14F7 [anti-IRP-2 (Iron Regulatory Protein 2)], 14G2a (anti-GD2 ganglioside, from Nat. Cancer Inst. for melanoma and solid tumors), J591 (anti-PSMA, Weill Cornell Medical School for prostate cancers), 225.28S [anti-HMW-MAA (High molecular weight-melanoma-associated antigen), Sorin Radiofarmaci S.R.L. (Milan, Italy) for melanoma], COL-1 (anti-CEACAM3, CGM1, from Nat. Cancer Inst. USA for colorectal and gastric cancers), CYT-356 (Oncoltad®, for prostate cancers), HNK20 (OraVax Inc. for respiratory syncytial virus), ImmuRAIT (from Immunomedics for NHL), Lym-1 (anti-HLA-DR10, Peregrine Pharm. for Cancers), MAK-195F [anti-TNF (tumor necrosis factor; TNFA, TNF-alpha; TNFSF2), from Abbott/Knoll for Sepsis toxic shock], MEDI-500 [T10B9, anti-CD3, TRap (T cell receptor alpha/beta), complex, from MedImmune Inc for Graft-versus-host disease], RING SCAN [anti-TAG 72 (tumour associated glycoprotein 72), from Neoprobe Corp. for Breast, Colon and Rectal cancers], Avicidin (anti-EPCAM (epithelial cell adhesion molecule), anti-TACSTD1 (Tumor-associated calcium signal transducer 1), anti-GA733-2 (gastrointestinal tumor-associated protein 2), anti-EGP-2 (epithelial glycoprotein 2); anti-KSA; KS1/4 antigen; M4S; tumor antigen 17-1A; CD326, fromNeoRx Corp. for Colon, Ovarian, Prostate cancers and NHL]; LymphoCide (Immunomedics, NJ), Smart ID10 (Protein Design Labs), Oncolym (Techniclone Inc, CA), Allomune (BioTransplant, CA), anti-VEGF (Genentech, CA); CEAcide (Immunomedics, NJ), IMC-1C11 (ImClone, NJ) and Cetuximab (ImClone, NJ).

Other antibodies as cell binding molecules/ligands include, but are not limited to, are antibodies against the following antigens: Aminopeptidase N (CD13), Annexin A1, B7-H3 (CD276, various cancers), CA125 (ovarian), CA15-3 (carcinomas), CA19-9 (carcinomas), L6 (carcinomas), Lewis Y (carcinomas), Lewis X (carcinomas), alpha fetoprotein (carcinomas), CA242 (colorectal), placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (Metastatic melanoma, sarcoma), CD52 (leukemia), CD56 (small cell lung cancers, ovarian cancer, Merkel cell carcinoma, and the liquid tumor, multiple myeloma), CD66e (cancers), CD70 (metastatic renal cell carcinoma and non-Hodgkin lymphoma), CD74 (multiple myeloma), CD80 (lymphoma), CD98 (cancers), mucin (carcinomas), CD221 (solid tumors), CD227 (breast, ovarian cancers), CD262 (NSCLC and other cancers), CD309 (ovarian cancers), CD326 (solid tumors), CEACAM3 (colorectal, gastric cancers), CEACAM5 (carcinoembryonic antigen; CEA, CD66e) (breast, colorectal and lung cancers), DLL4 (delta-like-4), EGFR (Epidermal Growth Factor Receptor, various cancers), CTLA4 (melanoma), CXCR4 (CD184, Heme-oncology, solid tumors), Endoglin (CD105, solid tumors), EPCAM (epithelial cell adhesion molecule, bladder, head, neck, colon, NHL prostate, and ovarian cancers), ERBB2 (Epidermal Growth Factor Receptor 2; lung, breast, prostate cancers), FCGR1 (autoimmune diseases), FOLR (folate receptor, ovarian cancers), GD2 ganglioside (cancers), G-28 (a cell surface antigen glyvolipid, melanoma), GD3 idiotype (cancers), Heat shock proteins (cancers), HER1 (lung, stomach cancers), HER2 (breast, lung and ovarian cancers), HLA-DR10 (NHL), HLA-DRB (NHL, B cell leukemia), human chorionic gonadotropin (carcinoma), IGF1R (insulin-like growth factor 1 receptor, solid tumors, blood cancers), IL-2 receptor (interleukin 2 receptor, T-cell leukemia and lymphomas), IL-6R (interleukin 6 receptor, multiple myeloma, RA, Castleman's disease, IL6 dependent tumors), Integrins ($\alpha v \beta 3$, $\alpha 5 \beta 1$, $\alpha 6 \beta 4$, $\alpha 11 \beta 3$, $\alpha 5 \beta 5$, $\alpha v \beta 5$, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 or MUC1-KLH (breast, ovarian, cervix, bronchus and gastrointestinal cancer), MUC16 (CA125) (Ovarian cancers), CEA (colorectal), gp100 (melanoma), MART1 (melanoma), MPG (melanoma), MS4A1 (membrane-spanning 4-domains subfamily A, small cell lung cancers, NHL), Nucleolin, Neu oncogene product (carcinomas), P21 (carcinomas), Paratope of anti-(N-glycolyl-neuraminic acid, Breast, Melanoma cancers), PLAP-like testicular alkaline phosphatase (ovarian, testicular cancers), PSMA (prostate tumors), PSA (prostate), ROBO4, TAG 72 (tumour associated glycoprotein 72, AML, gastric, colorectal, ovarian cancers), T cell transmembrane protein (cancers), Tie (CD202b), TNFRSF10B (tumor necrosis factor receptor superfamily member 10B, cancers), TNFRSF13B (tumor necrosis factor receptor superfamily member 13B, multiple myeloma, NHL, other cancers, RA and SLE), TPBG (trophoblast glycoprotein, Renal cell carcinoma), TRAIL-R1 (Tumor necrosis apoprosis Inducing ligand Receptor 1, lymphoma, NHL, colorectal, lung cancers), VCAM-1 (CD106, Melanoma), VEGF, VEGF-A, VEGF-2 (CD309) (various cancers). Some other tumor associated antigens recognized by antibodies have been reviewed (Gerber, et al, mAbs 1:3, 247-53 (2009); Novellino et al, Cancer Immunol Immunother. 54(3), 187-207 (2005). Franke, et al, Cancer Biother Radiopharm. 2000, 15, 459-76).

The cell-binding agents, more preferred antibodies, can be any agents that are able to against tumor cells, virus infected cells, microorganism infected cells, parasite infected cells, autoimmune cells, activated cells, myeloid cells, activated T-cells, B cells, or melanocytes. More specifically the cell binding agents can be any agent/molecule that is able to against any one of the following antigens or receptors: CD3, CD4, CD5, CD6, CD7, CD8, CD9, CD10, CD11a, CD11b, CD11c, CD12w, CD14, CD15, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49b, CD49c, CD51, CD52, CD53, CD54, CD55, CD56, CD58, CD59, CD61, CD62E, CD62L, CD62P, CD63, CD66, CD68, CD69, CD70, CD72, CD74, CD79, CD79a, CD79b, CD80, CD81, CD82, CD83, CD86, CD87, CD88, CD89, CD90, CD91, CD95, CD96, CD98, CD100, CD103, CD105, CD106, CD109, CD117, CD120, CD125, CD126, CD127, CD133, CD134, CD135, CD137, CD138, CD141, CD142, CD143, CD144, CD147, CD151, CD147, CD152, CD154, CD156, CD158, CD163, CD166, CD168, CD174, CD180, CD184, CDw186, CD194, CD195, CD200, CD200a, CD200b, CD209, CD221, CD227, CD235a, CD240, CD262, CD271, CD274, CD276 (B7-H3), CD303, CD304, CD309, CD326, 4-1BB, 5AC, 5T4 (Trophoblast glycoprotein, TPBG, 5T4, Wnt-Activated Inhibitory Factor 1 or WAIF1), Adenocarcinomaantigen, AGS-5, AGS-22M6, Activin receptor-like kinase 1, AFP, AKAP-4, ALK, Alpha intergrin, Alpha v beta6, Amino-peptidase N, Amyloid beta, Androgen receptor, Angiopoietin 2, Angiopoietin 3, Annexin A1, Anthrax toxin-protective antigen, Anti-transferrin receptor, AOC3 (VAP-1), B7-H3, *Bacillus* anthracisanthrax, BAFF (B-cell activating factor), B-lymphoma cell, bcr-abl, Bombesin, BORIS, C5, C242 antigen, CA125 (carbohydrate antigen 125, MUC16), CA-IX (or CAIX, carbonic anhydrase 9), CALLA, CanAg, *Canis lupus familiaris* IL31, Carbonic anhydrase IX, Cardiac myosin, CCL11 (C—C motif chemokine 11), CCR4 (C—C chemokine receptor type 4, CD194), CCR5, CD3E (epsilon), CEA (Carcinoembryonic antigen), CEACAM3, CEACAM5 (carcinoembryonic antigen), CFD (Factor D), Ch4D5, Cholecystokinin 2 (CCK2R), CLDN18 (Claudin-18), Clumping factor A, CRIPTO, FCSF1R (Colony stimulating factor 1 receptor, CD115), CSF2 (colony stimulating factor 2, Granulocyte-macrophage colony-stimulating factor (GM-CSF)), CTLA4 (cytotoxic T-lymphocyte associated protein 4), CTAA16.88 tumor antigen, CXCR4 (CD184), C—X—C chemokine receptor type 4, cyclic ADP ribose hydrolase, Cyclin B1, CYPIB1, Cytomegalovirus, Cytomegalovirus glycoprotein B, Dabigatran, DLL4 (delta-like-ligand 4), DPP4 (Dipeptidyl-peptidase 4), DR5 (Death receptor 5), *E. coli* shiga toxintype-1, *E. coli* shiga toxintype-2, ED-B, EGFL7 (EGF-like domain-containing protein 7), EGFR, EGFRII, EGFRvIII, Endoglin (CD105), Endothelin B receptor, Endotoxin, EpCAM (epithelial cell adhesion molecule), EphA2, Episialin, ERBB2 (Epidermal Growth Factor Receptor 2), ERBB3, ERG (TMPRSS2 ETS fusion gene), *Escherichia coli*, ETV6-AML, FAP (Fibroblast activation proteinalpha), FCGR1, alpha-Fetoprotein, Fibrin II, beta chain, Fibronectin extra domain-B, FOLR (folate receptor), Folate receptor alpha, Folate hydrolase, Fos-related antigen 1, F protein of respiratory syncytial virus, Frizzled receptor, Fucosyl GM1, GD2 ganglioside, G-28 (a cell surface antigen glyvolipid), GD3 idiotype, GloboH, Glypican 3, N-glycolylneuraminic acid, GM3, GMCSF receptor α-chain, Growth differentiation factor 8, GP100, GPNMB (Transmembrane glycoprotein NMB), GUCY2C (Guanylate cyclase 2C, guanylyl cyclase C (GC-C), intestinal Guanylate cyclase, Guanylate cyclase-C receptor, Heat-stable enterotoxin receptor (hSTAR)), Heat shock proteins, Hemagglutinin, Hepatitis B surface antigen, Hepatitis B virus, HER1 (human epidermal growth factor receptor 1), HER2, HER2/neu, HER3 (ERBB-3), IgG4, HGF/SF (Hepatocyte growth factor/scatter factor), HHGFR, HIV-1, Histone complex, HLA-DR (human leukocyte antigen), HLA-DR10, HLA-DRB, HMWMAA, Human chorionic gonadotropin, HNGF, Human scatter factor receptor kinase, HPV E6/E7, Hsp90, hTERT, ICAM-1 (Intercellular Adhesion Molecule 1), Idiotype, IGF1R (IGF-1, insulin-like growth factor 1 receptor), IGHE, IFN-γ, Influeza hemag-glutinin, IgE, IgE Fc region, IGHE, IL-1, IL-2 receptor (interleukin 2 receptor), IL-4, IL-5, IL-6, IL-6R (interleukin 6 receptor), IL-9, IL-10, IL-12, IL-13, IL-17, IL-17A, IL-20, IL-22, IL-23, IL31RA, ILGF2 (Insulin-like growth factor 2), Integrins (α4, $α_{IIb}β3$, αvβ3, $α_4β_7$, α5β1, α6β4, α7β7, α11β3, α5β5, αvβ5), Interferon gamma-induced protein, ITGA2, ITGB2, KIR2D, LCK, Le, Legumain, Lewis-Y antigen, LFA-1 (Lymphocyte function-associated antigen 1, CD11a), LHRH, LINGO-1, Lipoteichoic acid, LIVIA, LMP2, LTA, MAD-CT-1, MAD-CT-2, MAGE-1, MAGE-2, MAGE-3, MAGE A1, MAGE A3, MAGE 4, MART1, MCP-1, MIF (Macrophage migration inhibitory factor, or glycosylation-inhibiting factor (GIF)), MS4A1 (membrane-spanning 4-domains subfamily A member 1), MSLN (meso-thelin), MUC1 (Mucin 1, cell surface associated (MUC1) or polymorphic epithelial mucin (PEM)), MUC1-KLH, MUC16 (CA125), MCP1 (monocyte chemotactic protein 1), MelanA/MART1, ML-IAP, MPG, MS4A1 (membrane-spanning 4-domains subfamily A), MYCN, Myelin-associated glycoprotein, Myostatin, NA17, NARP-1, NCA-90 (granulocyte antigen), Nectin-4 (ASG-22ME), NGF, Neural apoptosis-regulated proteinase 1, NOGO-A, Notch receptor, Nucleolin, Neu oncogene product, NY-BR-1, NY-ESO-1, OX-40, OxLDL (Oxidized low-density lipoprotein), OY-TES1, P21, $p^{53}$ nonmutant, P97, Page 4, PAP, Paratope of anti-(N-glycolylneuraminic acid), PAX3, PAX5, PCSK9, PDCD1 (PD-1, Programmed cell death protein 1, CD279), PDGF-Ra (Alpha-type platelet-derived growth factor receptor), PDGFR-0, PDL-1, PLAC1, PLAP-like testicular alkaline phosphatase, Platelet-derived growth factor receptor beta, Phosphate-sodium co-transporter, PMEL 17, Polysialic acid, Proteinase3 (PR1), Prostatic carcinoma, PS (Phos-phatidylserine), Prostatic carcinoma cells, *Pseudomonas aeruginosa*, PSMA, PSA, PSCA, Rabies virus glycoprotein, RHD (Rh polypeptide 1 (RhPI), CD240), Rhesus factor, RANKL, RhoC, Ras mutant, RGS5, ROBO4, Respiratory syncytial virus, RON, Sarcoma translocation breakpoints, SART3, Sclerostin, SLAMF7 (SLAM family member 7), Selectin P, SDC1 (Syndecan 1), sLe(a), Somatomedin C, SIP (Sphingosine-1-phosphate), Somatostatin, Sperm protein 17, SSX2, STEAP1 (six-transmembrane epithelial antigen of the prostate 1), STEAP2, STn, TAG-72 (tumor associated glycoprotein 72), Survivin, T-cell receptor, T cell transmembrane protein, TEM1 (Tumor endothelial marker 1), TENB2, Tenascin C (TN-C), TGF-α, TGF-β (Transforming growth factor beta), TGF-β1, TGF-β2 (Transforming growth factor-beta 2), Tie (CD202b), Tie2, TIM-1 (CDX-014), Tn, TNF, TNF-α, TNFRSF8, TNFRS-FIOB (tumor necrosis factor receptor superfamily member 10B), TNFRSF13B (tumor necrosis factor receptor superfamily member 13B), TPBG (trophoblast glycoprotein), TRAIL-R1 (Tumor necrosis apoprosis Inducing ligand Receptor 1), TRAILR2 (Death receptor 5 (DR5)), tumor-associated calcium signal transducer 2, tumor specific glycosylation ofMUC1, TWEAK receptor, TYRP1 (glycoprotein 75), TRP-2, Tyrosinase, VCAM-1 (CD106), VEGF, VEGF-A, VEGF-2 (CD309), VEGFR-1, VEGFR2, or vimentin, WTi, XAGE 1, or cells expressing any insulin growth factor receptors, or any epidermal growth factor receptors.

In another specific embodiment, the cell-binding ligand-drug conjugates via the bridge linkers of this invention are used for the targeted treatment of cancers. The targeted cancers include, but are not limited, Adrenocortical Carcinoma, Anal Cancer, Bladder Cancer, Brain Tumor (Adult, Brain Stem Glioma, Childhood, Cerebellar Astrocytoma, Cerebral Astrocytoma, Ependymoma, Medulloblastoma, Supratentorial Primitive Neuroectodermal and Pineal Tumors, Visual Pathway and Hypothalamic Glioma), Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Eye Cancer, Intraocular Melanoma, Gallbladder Cancer, Gastric Cancer (Stomach), Germ Cell Tumor, Extragonadal, Gestational Trophoblastic Tumor, Head and Neck Cancer, Hypopharyngeal Cancer, Islet Cell Carcinoma, Kidney Cancer (renal cell cancer), Laryngeal Cancer, Leukemia (Acute Lymphoblastic, Acute Myeloid, Chronic Lymphocytic, Chronic Myelogenous, Hairy Cell), Lip and Oral Cavity Cancer, Liver Cancer, Lung Cancer (Non-Small Cell, Small Cell, Lymphoma (AIDS-Related, Central Nervous System, Cutaneous T-Cell, Hodgkin's Disease, Non-Hodgkin's Disease, Malignant Mesothelioma, Melanoma, Merkel Cell Carcinoma, Metasatic Squamous Neck Cancer with Occult Primary, Multiple Myeloma, and Other Plasma Cell Neoplasms, Mycosis Fungoides, Myelodysplastic Syndrome, Myeloproli-ferative Disorders, Nasopharyngeal Cancer, Neuroblastoma, Oral Cancer, Oropharyngeal Cancer, Osteosarcoma, Ovarian Cancer (Epithelial, Germ Cell Tumor, Low Malignant Potential Tumor), Pancreatic Cancer (Exocrine, Islet Cell Carcinoma), Paranasal Sinus and Nasal Cavity Cancer, Parathyroid Cancer, Penile Cancer, Pheochromocytoma Cancer, Pituitary Cancer, Plasma Cell Neoplasm, Prostate Cancer Rhabdomyosarcoma, Rectal Cancer, Renal Cell Cancer (kidney cancer), Renal Pelvis and Ureter (Transitional Cell), Salivary Gland Cancer, Sezary Syndrome, Skin Cancer, Skin Cancer (Cutaneous T-Cell Lymphoma, Kaposi's Sarcoma, Melanoma), Small Intestine Cancer, Soft Tissue Sarcoma, Stomach Cancer, Testicular Cancer, Thymoma (Malignant), Thyroid Cancer, Urethral Cancer, Uterine Cancer (Sarcoma), Unusual Cancer of Childhood, Vaginal Cancer, Vulvar Cancer, Wilms' Tumor.

In another specific embodiment, the cell-binding-drug conjugates via the bridge linkers of this invention are used in accordance with the compositions and methods for the treatment or prevention of an autoimmune disease. The autoimmune diseases include, but are not limited, Achlorhydra Autoimmune Active Chronic Hepatitis, Acute Disseminated Encephalomyelitis, Acute hemorrhagic leukoencephalitis, Addison's Disease, Agammaglobulinemia, Alopecia areata, Amyotrophic Lateral Sclerosis, Ankylosing Spondylitis, Anti-GBM/TBM Nephritis, Antiphospholipid syndrome, Antisynthetase syndrome, Arthritis, Atopic allergy, Atopic Dermatitis, Autoimmune Aplastic Anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome Types I, II, & III, Autoimmune progesterone dermatitis, Autoimmune thrombocytopenic purpura, Autoimmune uveitis, Balo disease/Balo concentric sclerosis, Bechets Syndrome, Berger's disease, Bickerstaffs encephalitis, Blau syndrome, Bullous Pemphigoid, Castleman's disease, Chagas disease, Chronic Fatigue Immune Dysfunction Syndrome, Chronic inflammatory demyelinating polyneuropathy, Chronic recurrent multifocal ostomyelitis, Chronic lyme disease, Chronic obstructive pulmonary disease, Churg-Strauss syndrome, Cicatricial Pemphigoid, Coeliac Disease, Cogan syndrome, Cold agglutinin disease, Complement component 2 deficiency, Cranial arteritis, CREST syndrome, Crohns Disease (a type of idiopathic inflammatory bowel diseases), Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Discoid lupus erythematosus, Eczema, Endometriosis, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressiva, Fibromyalgia, Fibromyositis, Fibrosing aveolitis, Gastritis, Gastrointestinal pemphigoid, Giant cell arteritis, Glomerulonephritis, Goodpasture's syndrome, Graves' disease, Guillain-Barre syndrome, Hashimoto's encephalitis, Hashimoto's thyroiditis, Haemolytic anaemia, Henoch-Schonlein purpura, Herpes gestationis, Hidradenitis suppurativa, Hughes syndrome (See Antiphospholipid syndrome), Hypogammaglobulinemia, Idiopathic Inflammatory Demyelinating Diseases, Idiopathic pulmonary fibrosis, Idiopathic thrombocytopenic purpura (See Autoimmune thrombocytopenic purpura), IgA nephropathy (Also Berger's disease), Inclusion body myositis, Inflammatory demyelinating polyneuopathy, Interstitial cystitis, Irritable Bowel Syndrome, Juvenile idiopathic arthritis, Juvenile rheumatoid arthritis, Kawasaki's Disease, Lambert-Eaton myasthenic syndrome, Leukocytoclastic vasculitis, Lichen planus, Lichen sclerosus, Linear IgA disease (LAD), Lou Gehrig's Disease (Also Amyotrophic lateral sclerosis), Lupoid hepatitis, Lupus erythematosus, Majeed syndrome, Meniere's disease, Microscopic polyangiitis, Miller-Fisher syndrome, Mixed Connective Tissue Disease, Morphea, Mucha-Habermann disease, Muckle-Wells syndrome, Multiple Myeloma, Multiple Sclerosis, Myasthenia gravis, Myositis, Narcolepsy, Neuromyelitis optica (Devic's Disease), Neuromyotonia, Occular cicatricial pemphigoid, Opsoclonus myoclonus syndrome, Ord thyroiditis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria, Parry Romberg syndrome, Parsonnage-Turner syndrome, Pars planitis, Pemphigus, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic Arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatoid fever, Sarcoidosis, Schizophrenia, Schmidt syndrome, Schnitzler syndrome, Scleritis, Scleroderma, Sjögren's syndrome, Spondyloarthropathy, Sticky blood syndrome, Still's Disease, Stiff person syndrome, Subacute bacterial endocarditis, Susac's syndrome, Sweet syndrome, Sydenham Chorea, Sympathetic ophthalmia, Takayasu's arteritis, Temporal arteritis (giant cell arteritis), Tolosa-Hunt syndrome, Transverse Myelitis, Ulcerative Colitis (a type of idiopathic inflammatory bowel diseases), Undifferentiated connective tissue disease, Undifferentiated spondyloarthropathy, Vasculitis, Vitiligo, Wegener's granulomatosis, Wilson's syndrome, Wiskott-Aldrich syndrome In another specific embodiment, a binding molecule used for the conjugate via the bridge linkers of this invention for the treatment or prevention of an autoimmune disease can be, but are not limited to, anti-elastin antibody; Abys against epithelial cells antibody; Anti-Basement Membrane Collagen Type IV Protein antibody; Anti-Nuclear Antibody; Anti ds DNA; Anti ss DNA, Anti Cardiolipin Antibody IgM, IgG; anti-celiac antibody; Anti Phospholipid Antibody IgK, IgG; Anti SM Antibody; Anti Mitochondrial Antibody; Thyroid Antibody; Microsomal Antibody, T-cells antibody; Thyroglobulin Antibody, Anti SCL-70; Anti-Jo; Anti-U.sub.1RNP; Anti-La/SSB; Anti SSA; Anti SSB; Anti Perital Cells Antibody; Anti Histones; Anti RNP; C-ANCA; P-ANCA; Anti centromere; Anti-Fibrillarin, and Anti GBM Antibody, Anti-ganglioside antibody; Anti-Desmogein 3 antibody; Anti-p62 antibody; Anti-sp100 antibody; Anti-Mitochondrial (M2) antibody; Rheumatoid factor antibody; Anti-MCV antibody; Anti-topoisomerase antibody; Anti-neutrophil cytoplasmic (cANCA) antibody.

In certain preferred embodiments, the binding molecule for the conjugate in the present invention, can bind to both a receptor and a receptor complex expressed on an activated lymphocyte which is associated with an autoimmune disease. The receptor or receptor complex can comprise an immunoglobulin gene superfamily member (e.g. CD2, CD3, CD4, CD8, CD19, CD20, CD22, CD28, CD30, CD33, CD37, CD38, CD56, CD70, CD79, CD79b, CD90, CD125, CD137, CD138, CD147, CD152/CTLA-4, PD-1, or ICOS), a TNF receptor superfamily member (e.g. CD27, CD40, CD95/Fas, CD134/OX40, CD137/4-1BB, INF-$R_1$, TNFR-2, RANK, TACI, BCMA, osteoprotegerin, Apo2/TRAIL-$R_1$, TRAIL-$R_2$, TRAIL-$R_3$, TRAIL-$R_4$, and APO-3), an integrin, a cytokine receptor, a chemokine receptor, a major histocompatibility protein, a lectin (C-type, S-type, or I-type), or a complement control protein.

In another specific embodiment, useful cell binding ligands that are immunospecific for a viral or a microbial antigen are humanized or human monoclonal antibodies. As used herein, the term "viral antigen" includes, but is not limited to, any viral peptide, polypeptide protein (e.g. HIV gp120, HIV nef, RSV F glycoprotein, influenza virus neuramimi-dase, influenza virus hemagglutinin, HTLV tax, herpes simplex virus glycoprotein (e.g. gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacteria, fungi, pathogenic protozoa, or yeast polypeptides including, e.g., LPS and capsular polysaccharide 5/8) that is capable of eliciting an immune response. Examples of antibodies available 1 for the viral or microbial infection include, but are not limited to, Palivizumab which is a humanized anti-respiratory syncytial virus monoclonal antibody for the treatment of RSV infection; PR0542 which is a CD4 fusion antibody for the treatment of HIV infection; Ostavir which is a human antibody for the treatment of hepatitis B virus; PROTVIR which is a humanized IgG.sub.1 antibody for the treatment of cytomegalovirus; and anti-LPS antibodies.

The cell binding molecules-drug conjugates via the bridge linkers of this invention can be used in the treatment of infectious diseases. These infectious diseases include, but are not limited to, *Acinetobacter* infections, Actinomycosis, African sleeping sickness (African trypanosomiasis), AIDS (Acquired immune deficiency syndrome), Amebiasis, Anaplasmosis, Anthrax, Arcano-bacterium *haemolyticum* infection, Argentine hemorrhagic fever, Ascariasis, Aspergillosis, Astrovirus infection, Babesiosis, *Bacillus cereus* infection, Bacterial pneumonia, Bacterial vaginosis, *Bacteroides* infection, Balantidiasis, *Baylisascaris* infection, BK virus infection, Black *piedra*, *Blastocystis hominis* infection, Blastomycosis, Bolivian hemorrhagic fever, *Borrelia* infection, Botulism (and Infant botulism), Brazilian hemorrhagic fever, Brucellosis, *Burkholderia* infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, *Chlamydia*, *Chlamydophila pneumoniae* infection, Cholera, Chromoblastomycosis, Clonorchiasis, *Clostridium difficile* infection, Coccidioido-mycosis, Colorado tick fever, Common cold (Acute viral rhinopharyngitis; Acute coryza), Creutzfeldt-Jakob disease, Crimean-Congo hemorrhagic fever, Cryptococcosis, Cryptosporidiosis, Cutaneous larva migrans, Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem *subitum*, Fasciolopsiasis, Fasciolosis, Fatal familial insomnia, Filariasis, Food poisoning by *Clostridium perfringens*, Free-living amebic infection, *Fusobacterium* infection, Gas gangrene (Clostridial myonecrosis), Geotrichosis, Gerstmann-Straussler-Scheinker syndrome, Giardiasis, Glanders, Gnathosto-miasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome, *Helicobacter pylori* infection, Hemolytic-uremic syndrome, Hemorrhagic fever with renal syndrome, Hepatitis A, Hepatitis B, Hepatitis C, Hepatitis D, Hepatitis E, Herpes simplex, Histoplasmosis, Hookworm infection, Human bocavirus infection, Human *ewingii* ehrlichiosis, Human granulocytic anaplasmosis, Human metapneumovirus infection, Human monocytic ehrlichiosis, Human papillomavirus infection, Human parainfluenza virus infection, Hymenolepiasis, Epstein-Barr Virus Infectious Mononucleosis (Mono), Influenza, Isosporiasis, Kawasaki disease, Keratitis, *Kingella kingae* infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever, Measles, Melioidosis (Whitmore's disease), Meningitis, Meningococcal disease, Metagonimiasis, Microsporidiosis, Molluscum *contagiosum*, Mumps, Murine typhus (Endemic typhus), *Mycoplasma* pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease, Pertussis (Whooping cough), Plague, Pneumococcal infection, *Pneumocystis* pneumonia, Pneumonia, Poliomyelitis, *Prevotella* infection, Primary amoebic meningoencephalitis, Progressive multifocal leukoencephalopathy, Psittacosis, Q fever, Rabies, Rat-bite fever, Respiratory syncytial virus infection, Rhinosporidiosis, Rhinovirus infection, Rickettsial infection, Rickettsial-pox, Rift Valley fever, Rocky mountain spotted fever, Rotavirus infection, Rubella, *Salmonellosis*, SARS (Severe Acute Respiratory Syndrome), Scabies, Schistosomiasis, Sepsis, Shigellosis (Bacillary dysentery), Shingles (Herpes zoster), Smallpox (*Variola*), Sporotrichosis, Staphylococcal food poisoning, Staphylococcal infection, Strongyloidiasis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea *versicolor* (*Pityriasis versicolor*), Toxocariasis (Ocular Larva Migrans), Toxocariasis (Visceral Larva Migrans), Toxoplasmosis, Trichinellosis, Trichomoniasis, Trichuriasis (Whipworm infection), Tuberculosis, Tularemia, *Ureaplasma urealyticum* infection, Venezuelan equine encephalitis, Venezuelan hemorrhagic fever, Viral pneumonia, West Nile Fever, White *piedra* (Tinea blanca), *Yersinia* pseudotuberculosis infection, Yersiniosis, Yellow fever, Zygomycosis.

The cell binding molecule, which is more preferred to be an antibody described in this patent that are against pathogenic strains include, but are not limit, *Acinetobacter baumannii, Actinomyces israelii, Actinomyces gerencseriae* and *Propionibacterium propionicus, Trypanosoma brucei*, HIV (Human immunodeficiency virus), *Entamoeba histolytica, Anaplasma genus, Bacillus anthracis, Arcanobacterium haemolyticum, Junin virus, Ascaris lumbricoides, Aspergillus* genus, Astroviridae family, *Babesia* genus, *Bacillus cereus*, multiple bacteria, *Bacteroides* genus, *Balantidium coli, Baylisascaris* genus, BK virus, *Piedraia hortae, Blastocystis hominis, Blastomyces* dermatidites, Machupo virus,

*Borrelia* genus, *Clostridium botulinum*, Sabia, *Brucella* genus, usually *Burkholderia cepacia* and other *Burkholderia* species, *Mycobacterium ulcerans*, Caliciviridae family, *Campylobacter* genus, usually *Candida albicans* and other *Candida* species, *Bartonella henselae*, Group A *Streptococcus* and *Staphylococcus*, *Trypanosoma cruzi*, *Haemophilus ducreyi*, Varicella zoster virus (VZV), *Chlamydia trachomatis*, *Chlamydophila pneumoniae*, *Vibrio cholerae*, *Fonsecaea pedrosoi*, *Clonorchis sinensis*, *Clostridium difficile*, *Coccidioides immitis* and *Coccidioides posadasii*, Colorado tick fever virus, rhinoviruses, coronaviruses, CJD prion, Crimean-Congo hemorrhagic fever virus, *Cryptococcus neoformans*, *Cryptosporidium* genus, *Ancylostoma braziliense*; multiple parasites, *Cyclospora cayetanensis*, *Taenia solium*, Cytomegalovirus, Dengue viruses (DEN-1, DEN-2, DEN-3 and DEN-4)—Flaviviruses, *Dientamoeba fragilis*, *Corynebacterium diphtheriae*, *Diphyllobothrium*, *Dracunculus medinensis*, Ebolavirus, *Echinococcus* genus, *Ehrlichia* genus, *Enterobius vermicularis*, *Enterococcus* genus, Enterovirus genus, *Rickettsia prowazekii*, Parvovirus B19, Human herpesvirus 6 and Human herpesvirus 7, *Fasciolopsis buski*, *Fasciola hepatica* and *Fasciola gigantica*, FFI prion, Filarioidea superfamily, *Clostridium perfringens*, *Fusobacterium* genus, *Clostridium perfringens*; other *Clostridium* species, *Geotrichum candidum*, GSS prion, *Giardia intestinalis*, *Burkholderia mallei*, *Gnathostoma spinigerum* and *Gnathostoma hispidum*, *Neisseria gonorrhoeae*, *Klebsiella granulomatis*, *Streptococcus pyogenes*, *Streptococcus agalactiae*, *Haemophilus influenzae*, Enteroviruses, mainly Coxsackie A virus and Enterovirus 71, Sin Nombre virus, *Helicobacter pylon*, *Escherichia coli* O157: H7, Bunyaviridae family, Hepatitis A Virus, Hepatitis B Virus, Hepatitis C Virus, Hepatitis D Virus, Hepatitis E Virus, Herpes simplex virus 1, Herpes simplex virus 2, *Histoplasma capsulatum*, *Ancylostoma duodenale* and *Necator americanus*, *Hemophilus influenzae*, Human bocavirus, *Ehrlichia ewingii*, *Anaplasma phagocytophilum*, Human metapneumovirus, *Ehrlichia chaffeensis*, Human papillomavirus, Human parainfluenza viruses, *Hymenolepis nana* and *Hymenolepis diminuta*, Epstein-Barr Virus, Orthomy-xoviridae family, *Isospora belli*, *Kingella kingae*, *Klebsiella pneumoniae*, *Klebsiella ozaenas*, *Klebsiella* rhinoscleromotis, Kuru prion, Lassa virus, *Legionella pneumophila*, *Legionella pneumophila*, *Leishmania* genus, *Mycobacterium leprae* and *Mycobacterium* lepromatosis, *Leptospira* genus, *Listeria monocytogenes*, *Borrelia burgdorferi* and other *Borrelia* species, *Wuchereria bancrofti* and *Brugia malayi*, Lymphocytic choriomeningitis virus (LCMV), *Plasmodium* genus, Marburg virus, Measles virus, *Burkholderia pseudomallei*, *Neisseria meningitides*, *Metagonimus yokagawai*, Microsporidia phylum, Molluscum *contagiosum* virus (MCV), Mumps virus, *Rickettsia typhi*, *Mycoplasma pneumoniae*, numerous species of bacteria (Actinomycetoma) and fungi (Eumycetoma), parasitic dipterous fly larvae, *Chlamydia trachomatis* and *Neisseria gonorrhoeae*, vCJD prion, *Nocardia asteroides* and other *Nocardia* species, *Onchocerca volvulus*, *Paracoccidioides brasiliensis*, *Paragonimus westermani* and other *Paragonimus* species, *Pasteurella* genus, *Pediculus humanus capitis*, *Pediculus humanus* corporis, *Phthirus pubis*, *Bordetella pertussis*, *Yersinia pestis*, *Streptococcus pneumoniae*, *Pneumocystis jirovecii*, Poliovirus, *Prevotella* genus, *Naegleria fowleri*, JC virus, *Chlamydophila psittaci*, *Coxiella burnetii*, Rabies virus, *Streptobacillus moniliformis* and *Spirillum minus*, Respiratory syncytial virus, *Rhinosporidium seeberi*, Rhinovirus, *Rickettsia* genus, *Rickettsia akari*, Rift Valley fever virus, *Rickettsia rickettsii*, Rotavirus, Rubella virus, *Salmonella* genus, SARS coronavirus, *Sarcoptes scabiei*, *Schistosoma* genus, *Shigella* genus, Varicella zoster virus, *Variola major* or *Variola minor*, *Sporothrix schenckii*, *Staphylococcus* genus, *Staphylococcus* genus, *Staphylococcus aureus*, *Streptococcus pyogenes*, *Strongyloides stercoralis*, *Treponema pallidum*, *Taenia* genus, *Clostridium tetani*, *Trichophyton* genus, *Trichophyton tonsurans*, *Trichophyton* genus, *Epidermophyton floccosum*, *Trichophyton rubrum*, and *Trichophyton mentagrophytes*, *Trichophyton rubrum*, *Hortaea werneckii*, *Trichophyton* genus, *Malassezia* genus, *Toxocara canis* or *Toxocara cati*, *Toxoplasma gondii*, *Trichinella spiralis*, *Trichomonas vaginalis*, *Trichuris trichiura*, *Mycobacterium tuberculosis*, *Francisella tularensis*, *Ureaplasma urealyticum*, Venezuelan equine encephalitis virus, *Vibrio* colerae, Guanarito virus, West Nile virus, *Trichosporon beigelii*, *Yersinia pseudotuberculosis*, *Yersinia enterocolitica*, Yellow fever virus, Mucorales order (Mucormycosis) and Entomophthorales order (*Entomophthoramycosis*), *Pseudomonas aeruginosa*, *Campylobacter* (*Vibrio*) *fetus*, *Aeromonas hydrophila*, *Edwardsiella tarda*, *Yersinia pestis*, *Shigella dysenteriae*, *Shigella flexneri*, *Shigella sonnei*, *Salmonella typhimurium*, *Treponema pertenue*, *Treponema carateneum*, *Borrelia vincentii*, *Borrelia burgdorferi*, *Leptospira icterohemorrhagiae*, *Pneumocystis carinii*, *Brucella abortus*, *Brucella suis*, *Brucella melitensis*, *Mycoplasma* spp., *Rickettsia prowazeki*, *Rickettsia tsutsugumushi*, *Clamydia* spp.; pathogenic fungi (*Aspergillus fumigatus*, *Candida albicans*, *Histoplasma capsulatum*); protozoa (*Entomoeba histolytica*, *Trichomonas tenas*, *Trichomonas hominis*, *Tryoanosoma gambiense*, *Trypanosoma rhodesiense*, *Leishmania donovani*, *Leishmania tropica*, *Leishmania braziliensis*, *Pneumocystis pneumonia*, *Plasmodium vivax*, *Plasmodium falciparum*, *Plasmodium malaria*); or Helminiths (*Schistosoma japonicum*, *Schistosoma mansoni*, *Schistosoma haematobium*, and hookworms).

Other antibodies as cell binding ligands used in this invention for treatment of viral disease include, but are not limited to, antibodies against antigens of pathogenic viruses, including as examples and not by limitation: Poxyiridae, Herpesviridae, Adenoviridae, Papovaviridae, Enteroviridae, Picomaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Non-A/Non-B Hepatitis virus, Rhinoviridae, Coronaviridae, Rotoviridae, Oncovirus [such as, HBV (Hepatocellular carcinoma), HPV (Cervical cancer, Anal cancer), Kaposi's sarcoma-associated herpesvirus (Kaposi's sarcoma), Epstein-Barr virus (Nasopharyngeal carcinoma, Burkitt's lymphoma, Primary central nervous system lymphoma), MCPyV (Merkel cell cancer), SV40 (Simian virus 40), HCV (Hepatocellular carcinoma), HTLV-I (Adult T-cell leukemia/lymphoma)], Immune disorders caused virus: [such as Human Immunodeficiency Virus (AIDS)]; Central nervous system virus: [such as, JCV (Progressive multifocal leukoencephalopathy), MeV (Subacute sclerosing panencephalitis), LCV (Lymphocytic choriomeningitis), Arbovirus encephalitis, Orthomyxoviridae (probable) (Encephalitis lethargica), RV (Rabies), Chandipura virus, Herpesviral meningitis, Ramsay Hunt syndrome type II; Poliovirus (Poliomyelitis, Post-polio syndrome), HTLV-I (Tropical spastic paraparesis)]; Cytomegalovirus (Cytomegalovirus retinitis, HSV (Herpetic keratitis)); Cardiovascular virus [such as CBV (Pericarditis, Myocarditis)]; Respiratory system/acute viral nasopharyngitis/viral pneumonia: [Epstein-Barr virus (EBV infection/Infectious mononucleosis), Cytomegalovirus; SARS coronavirus (Severe acute respiratory syndrome) Orthomyxoviridae: Influenzavirus A/B/C (Influenza/Avian influenza), Paramyxovirus: Human parainfluenza viruses (Parainfluenza), RSV (Human respiratory syncytialvirus), hMPV]; Digestive system virus [MuV (Mumps), Cytomegalovirus (Cytomegalovirus esophagitis); Adenovirus (Adenovirus infection); Rotavirus, Norovirus, Astrovirus, Coronavirus; HBV (Hepatitis B virus), CBV, HAV (Hepatitis A virus), HCV (Hepatitis C virus), HDV (Hepatitis D virus), HEV (Hepatitis E virus), HGV (Hepatitis G virus)]; Urogenital virus [such as, BK virus, MuV (Mumps)].

According to a further object, the present invention also concerns pharmaceutical compositions comprising the conjugate via the bridge linkers of the invention together with a pharmaceutically acceptable carrier, diluent, or excipient for treatment of cancers, infections or autoimmune disorders. The method for treatment of cancers, infections and autoimmune disorders can be practiced in vitro, in vivo, or ex vivo. Examples of in vitro uses include treatments of cell cultures in order to kill all cells except for desired variants that do not express the target antigen; or to kill variants that express undesired antigen. Examples of ex vivo uses include treatments of hematopoietic stem cells (HSC) prior to the performance of the transplantation (HSCT) into the same patient in order to kill diseased or malignant cells. For instance, clinical ex vivo treatment to remove tumour cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent graft-versus-host disease, can be carried out as follows. Bone marrow is harvested from the patient or other individual and then incubated in medium containing serum to which is added the conjugate of the invention, concentrations range from about 1 pM to 0.1 mM, for about 30 minutes to about 48 hours at about 37° C. The exact conditions of concentration and time of incubation (=dose) are readily determined by the skilled clinicians. After incubation, the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the conjugate via the linkers of the invention will be supplied as solutions or as a lyophilized solid that can be redissolved in sterile water for injection. Examples of suitable protocols of conjugate administration are as follows. Conjugates are given weekly for 8~20 weeks as an i.v. bolus. Bolus doses are given in 50 to 500 ml of normal saline to which human serum albumin (e.g. 0.5 to 1 mL of a concentrated solution of human serum albumin, 100 mg/mL) can be added. Dosages will be about 50 µg to 20 mg/kg of body weight per week, i.v. (range of 10 µg to 200 mg/kg per injection). 4~20 weeks after treatment, the patient may receive a second course of treatment. Specific clinical protocols with regard to route of administration, excipients, diluents, dosages, times, etc., can be determined by the skilled clinicians.

Examples of medical conditions that can be treated according to the in vivo or ex vivo methods of killing selected cell populations include malignancy of any types of cancer, autoimmune diseases, graft rejections, and infections (viral, bacterial or parasite).

The amount of a conjugate which is required to achieve the desired biological effect, will vary depending upon a number of factors, including the chemical characteristics, the potency, and the bioavailability of the conjugates, the type of disease, the species to which the patient belongs, the diseased state of the patient, the route of administration, all factors which dictate the required dose amounts, delivery and regimen to be administered.

In general terms, the conjugates via the linkers of this invention may be provided in an aqueous physiological buffer solution containing 0.1 to 10% w/v conjugates for parenteral administration. Typical dose ranges are from 1 µg/kg to 0.1 g/kg of body weight per day; a preferred dose range is from 0.01 mg/kg to 20 mg/kg of body weight per day, or per week, or an equivalent dose in a human child. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the conjugates by the chosen delivery route, and the speed (bolus or continuous infusion) and schedule of administrations (number of repetitions in a given period of time).

The conjugates via the linkers of the present invention are also capable of being administered in unit dose forms, wherein the term "unit dose" means a single dose which is capable of being administered to a patient, and which can be readily handled and packaged, remaining as a physically and chemically stable unit dose comprising either the active conjugate itself, or as a pharmaceutically acceptable composition, as described hereinafter. As such, typical total daily/weekly/biweekly/monthly dose ranges are from 0.01 to 100 mg/kg of body weight. By way of general guidance, unit doses for humans range from 1 mg to 3000 mg per day, or per week, per two weeks (biweekly) or per month. Preferably the unit dose range is from 1 to 500 mg administered one to four times a week, and even more preferably from 1 mg to 100 mg, once a week. Conjugates provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasal, particularly in the form of powders, nasal drops, or aerosols; or dermally, for example, topically in ointments, creams, lotions, gels or sprays, or via transdermal patches.

Drugs/Cytotoxic Agents

Drugs that can be conjugated to a cell-binding molecule in the present invention are small molecule drugs including cytotoxic agents, which can be linked to or after they are modified for linkage to the cell-binding agent. A "small molecule drug" is broadly used herein to refer to an organic, inorganic, or organometallic compound that may have a molecular weight of, for example, 100 to 2500, more suitably from 120 to 1500. Small molecule drugs are well characterized in the art, such as in WO05058367A2, and in U.S. Pat. No. 4,956,303, among others and are incorporated in their entirety by reference. The drugs include known drugs and those that may become known drugs.

Drugs that are known include, but not limited to,

1). Chemotherapeutic agents: a). Alkylating agents: such as Nitrogen mustards: chlorambucil, chlomaphazine, cyclophosphamide, dacarbazine, estramustine, ifosfamide, mechlorethamine, mechlorethamine oxide hydrochloride, mannomustine, mitobronitol, melphalan, mitolactol, pipobroman, novembichin, phenesterine, prednimustine, thiotepa, trofosfamide, uracil mustard; CC-1065 (including its adozelesin, carzelesin and bizelesin synthetic analogues); Duocarmycin (including the synthetic analogues, KW-2189 and CBI-TMI); Benzodiazepine dimers (e.g., dimmers of pyrrolobenzodiazepine (PBD) or tomaymycin, indolinobenzodiazepines, imidazobenzothiadiazepines, or oxazolidinobenzodiazepines); Nitrosoureas: (carmustine, lomustine, chlorozotocin, fotemustine, nimustine, ranimustine); Alkylsulphonates: (busulfan, treosulfan, improsulfan and piposulfan); Triazenes: (dacarbazine); Platinum containing compounds: (carboplatin, cisplatin, oxaliplatin); aziridines, such as benzodopa, carboquone, meturedopa, and uredopa; ethylenimines and methylamelamines including altretamine, triethylenemel-amine, trietylenephosphoramide, triethylenethiophosphaoramide and trimethylolomel-amine]; b). Plant Alkaloids: such as *Vinca* alkaloids: (vincristine, vinblastine, vindesine, vinorelbine, navelbin); Taxoids: (paclitaxel, docetaxol) and their analogs, Maytansinoids (DM1, DM2, DM3, DM4, maytansine and ansamitocins) and their analogs, cryptophycins (particularly cryptophycin 1 and cryptophycin 8); epothilones, eleutherobin, discodermolide, bryostatins, dolostatins, auristatins, tubulysins, cephalostatins; pancratistatin; a sarcodictyin; spongistatin; c). DNA Topoisomerase Inhibitors: such as [Epipodophyllins: (9-aminocamptothecin, camptothecin, crisnatol, daunomycin, etoposide, etoposide phosphate, irinotecan, mitoxantrone, novantrone, retinoic acids (retinols), teniposide, topotecan, 9-nitrocamptothecin (RFS 2000)); mitomycins: (mitomycin C)]; d). Anti-metabolites: such as {[Anti-folate: DHFR inhibitors: (methotrexate, trimetrexate, denopterin, pteropterin, aminopterin (4-aminopteroic acid) or the other folic acid analogues); IMP dehydrogenase Inhibitors: (mycophenolic acid, tiazofurin, ribavirin, EICAR); Ribonucleotide reductase Inhibitors: (hydroxyurea, deferoxamine)]; [Pyrimidine analogs: Uracil analogs: (ancitabine, azacitidine, 6-azauridine, capecitabine (Xeloda), carmofur, cytarabine, dideoxyuridine, doxifluridine, enocitabine, 5-Fluorouracil, floxuridine, ratitrexed (Tomudex)); Cytosine analogs: (cytarabine, cytosine arabinoside, fludarabine); Purine analogs: (azathioprine, fludarabine, mercaptopurine, thiamiprine, thioguanine)]; folic acid replenisher, such as frolinic acid}; e). Hormonal therapies: such as {Receptor antagonists: [Anti-estrogen: (megestrol, raloxifene, tamoxifen); LHRH agonists: (goscrclin, leuprolide acetate); Anti-androgens: (bicalutamide, flutamide, calusterone, dromostanolone propionate, epitiostanol, goserelin, leuprolide, mepitiostane, nilutamide, testolactone, trilostane and other androgens inhibitors)]; Retinoids/Deltoids: [Vitamin D3 analogs: (CB 1093, EB 1089 KH 1060, cholecalciferol, ergocalciferol); Photodynamic therapies: (verteporfin, phthalocyanine, photosensitizer Pc4, demethoxy-hypocrellin A); Cytokines: (Interferon-alpha, Interferon-gamma, tumor necrosis factor (TNFs), human proteins containing a TNF domain)]}; f). Kinase inhibitors, such as BIBW 2992 (anti-EGFR/Erb2), imatinib, gefitinib, pegaptanib, sorafenib, dasatinib, sunitinib, erlotinib, nilotinib, lapatinib, axitinib, pazopanib. vandetanib, E7080 (anti-VEGFR2), mubritinib, ponatinib (AP24534), bafetinib (INNO-406), bosutinib (SKI-606), cabozantinib, vismodegib, iniparib, ruxolitinib, CYT387, axitinib, tivozanib, sorafenib, bevacizumab, cetuximab, Trastuzumab, Ranibizumab, Panitumumab, ispinesib; g). antibiotics, such as the enediyne antibiotics (e.g. calicheamicins, especially calicheamicin γ1, δ1, α1 and β1, see, e.g., *J. Med. Chem.,* 39 (11), 2103-2117 (1996), Angew Chem Intl. Ed. Engl. 33:183-186 (1994); dynemicin, including dynemicin A and deoxydynemicin; esperamicin, kedarcidin, C-1027, maduropeptin, as well as neocarzinostatin chromophore and related chromoprotein enediyne antiobiotic chromomophores), aclacinomysins, actinomycin, authramycin, azaserine, bleomycins, cactinomycin, carabicin, carminomycin, carzinophilin; chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin and deoxydoxorubicin, epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; f). Others: such as Polyketides (acetogenins), especially bullatacin and bullatacinone; gemcitabine, epoxomicins (e. g. carfilzomib), bortezomib, thalidomide, lenalidomide, pomalidomide, tosedostat, zybrestat, PLX4032, STA-9090, Stimuvax, allovectin-7, Xegeva, Provenge, Yervoy, Isoprenylation inhibitors (such as Lovastatin), Dopaminergic neurotoxins (such as 1-methyl-4-phenylpyridinium ion), Cell cycle inhibitors (such as staurosporine), Actinomycins (such as Actinomycin D, dactinomycin), Bleomycins (such as bleomycin A2, bleomycin B2, peplomycin), Anthracyclines (such as daunorubicin, doxorubicin (adriamycin), idarubicin, epirubicin, pirarubicin, zorubicin, mtoxantrone, MDR inhibitors (such as verapamil), CaATPase inhibitors (such as thapsigargin), Histone deacetylase inhibitors (Vorinostat, Romidepsin, Panobinostat, Valproic acid, Mocetinostat (MGCD0103), Belinostat, PCI-24781, Entinostat, SB939, Resminostat, Givinostat, AR-42, CUDC-101, sulforaphane, Trichostatin A); Thapsigargin, Celecoxib, glitazones, epigallocatechin gallate, Disulfiram, Salinosporamide A; Antiadrenals, such as aminoglutethimide, mitotane, trilostane; aceglatone; aldophosphamide glycoside; aminolevulinic acid; amsacrine; arabinoside, bestrabucil; bisantrene; edatraxate; defofamine; demecolcine; diaziquone; eflomithine (DFMO), elfomithine; elliptinium acetate, etoglucid; gallium nitrate; gacytosine, hydroxyurea; ibandronate, lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2,2',2"-trichlorotriethylamine; trichothecenes (especially T-2 toxin, verrucarin A, roridin A and anguidine); urethane, siRNA, antisense drugs, and a nucleolytic enzyme.

2). An anti-autoimmune disease agent includes, but is not limited to, cyclosporine, cyclosporine A, aminocaproic acid, azathioprine, bromocriptine, chlorambucil, chloroquine, cyclophosphamide, corticosteroids (e.g. amcinonide, betamethasone, budesonide, hydrocortisone, flunisolide, fluticasone propionate, fluocortolone danazol, dexamethasone, Triamcinolone acetonide, beclometasone dipropionate), DHEA, enanercept, hydroxychloroquine, infliximab, meloxicam, methotrexate, mofetil, mycophenylate, prednisone, sirolimus, tacrolimus.

3). An anti-infectious disease agent includes, but is not limited to, a). Aminoglycosides: amikacin, astromicin, gentamicin (netilmicin, sisomicin, isepamicin), hygromycin B, kanamycin (amikacin, arbekacin, bekanamycin, dibekacin, tobramycin), neomycin (framycetin, paromomycin, ribostamycin), netilmicin, spectinomycin, streptomycin, tobramycin, verdamicin; b). Amphenicols: azidamfenicol, chloramphenicol, florfenicol, thiamphenicol; c). Ansamycins: geldanamycin, herbimycin; d). Carbapenems: biapenem, doripenem, ertapenem, imipenem/cilastatin, meropenem, panipenem; e). Cephems: carbacephem (loracarbef), cefacetrile, cefaclor, cefradine, cefadroxil, cefalonium, cefaloridine, cefalotin or cefalothin, cefalexin, cefaloglycin, cefamandole, cefapirin, cefatrizine, cefazaflur, cefazedone, cefazolin, cefbuperazone, cefcapene, cefdaloxime, cefepime, cefminox, cefoxitin, cefprozil, cefroxadine, ceftezole, cefuroxime, cefixime, cefdinir, cefditoren, cefepime, cefetamet, cefmenoxime, cefodizime, cefonicid, cefoperazone, ceforanide, cefotaxime, cefotiam, cefozopran, cephalexin, cefpimizole, cefpiramide, cefpirome, cefpodoxime, cefprozil, cefquinome, cefsulodin, ceftazidime, cefteram, ceftibuten, ceftiolene, ceftizoxime, ceftobiprole, ceftriaxone, cefuroxime, cefuzonam, cephamycin (cefoxitin, cefotetan, cefmetazole), oxacephem (flomoxef, latamoxef); f). Glycopeptides: bleomycin, vancomycin (oritavancin, telavancin), teicoplanin (dalbavancin), ramoplanin; g). Glycylcyclines: e. g. tigecycline; g). β-Lactamase inhibitors: penam (sulbactam, tazobactam), clavam (clavulanic acid); i). Lincosamides: clindamycin, lincomycin; j). Lipopeptides: daptomycin, A54145, calcium-dependent antibiotics (CDA); k). Macrolides: azithromycin, cethromycin, clarithromycin, dirithromycin, erythromycin, flurithromycin, josamycin, ketolide (telithromycin, cethromycin), midecamycin, miocamycin, oleandomycin, rifamycins (rifampicin, rifampin, rifabutin, rifapentine), rokitamycin, roxithromycin, spectinomycin, spiramycin, tacrolimus (FK506), troleandomycin, telithromycin; 1). Monobactams: aztreonam, tigemonam; m). Oxazolidinones: linezolid; n). Penicillins: amoxicillin, ampicillin (pivampicillin, hetacillin, bacampicillin, metampicillin, talampicillin), azidocillin, azlocillin, benzylpenicillin, benzathine benzylpenicillin, benzathine phenoxymethyl-penicillin, clometocillin, procaine benzylpenicillin, carbenicillin (carindacillin), cloxacillin, dicloxacillin, epicillin, flucloxacillin, mecillinam (pivmecillinam), mezlocillin, meticillin, nafcillin, oxacillin, penamecillin, penicillin, pheneticillin, phenoxymethylpenicillin, piperacillin, propicillin, sulbenicillin, temocillin, ticarcillin; o). Polypeptides: bacitracin, colistin, polymyxin B; p). Quinolones: alatrofloxacin, balofloxacin, ciprofloxacin, clinafloxacin, danofloxacin, difloxacin, enoxacin, enrofloxacin, floxin, garenoxacin, gatifloxacin, gemifloxacin, grepafloxacin, kano trovafloxacin, levofloxacin, lomefloxacin, marbofloxacin, moxifloxacin, nadifloxacin, norfloxacin, orbifloxacin, ofloxacin, pefloxacin, trovafloxacin, grepafloxacin, sitafloxacin, sparfloxacin, temafloxacin, tosufloxacin, trovafloxacin); q). Streptogramins: pristinamycin, quinupristin/dalfopristin); r). Sulfonamides: mafenide, prontosil, sulfacetamide, sulfamethizole, sulfanilimide, sulfasalazine, sulfisoxazole, trimethoprim, trimethoprim-sulfamethoxazole (co-trimoxazole); s). Steroid antibacterials: e.g. fusidic acid; t). Tetracyclines: doxycycline, chlortetracycline, clomocycline, demeclocycline, lymecycline, meclocycline, metacycline, minocycline, oxytetracycline, penimepicycline, rolitetracycline, tetracycline, glycylcyclines (e.g. tigecycline); u). Other types of antibiotics: annonacin, arsphenamine, bactoprenol inhibitors (Bacitracin), DADAL/AR inhibitors (cycloserine), dictyostatin, discodermolide, eleutherobin, epothilone, ethambutol, etoposide, faropenem, fusidic acid, furazolidone, isoniazid, laulimalide, metronidazole, mupirocin, mycolactone, NAM synthesis inhibitors (e. g. fosfomycin), nitrofurantoin, paclitaxel, platensimycin, pyrazinamide, quinupristin/dalfopristin, rifampicin (rifampin), tazobactam tinidazole, uvaricin;

4). Anti-viral drugs: a). Entry/fusion inhibitors: aplaviroc, maraviroc, vicriviroc, gp41 (enfuvirtide), PRO 140, CD4 (ibalizumab); b). Integrase inhibitors: raltegravir, elvitegravir, globoidnan A; c). Maturation inhibitors: bevirimat, vivecon; d). Neuraminidase inhibitors: oseltamivir, zanamivir, peramivir; e). Nucleosides & nucleotides: abacavir, aciclovir, adefovir, amdoxovir, apricitabine, brivudine, cidofovir, clevudine, dexelvucitabine, didanosine (ddI), elvucitabine, emtricitabine (FTC), entecavir, famciclovir, fluorouracil (5-FU), 3'-fluoro-substituted 2',3'-dideoxynucleoside analogues (e.g. 3'-fluoro-2',3'-dideoxythymidine (FLT) and 3'-fluoro-2',3'-dideoxyguanosine (FLG), fomivirsen, ganciclovir, idoxuridine, lamivudine (3TC), 1-nucleosides (e.g. β-1-thymidine and β-1-2'-deoxycytidine), penciclovir, racivir, ribavirin, stampidine, stavudine (d4T), taribavirin (viramidine), telbivudine, tenofovir, trifluridine valaciclovir, valganciclovir, zalcitabine (ddC), zidovudine (AZT); f). Non-nucleosides: amantadine, ateviridine, capravirine, diarylpyrimidines (etravirine, rilpivirine), delavirdine, docosanol, emivirine, efavirenz, foscamet (phosphonoformic acid), imiquimod, interferon alfa, loviride, lodenosine, methisazone, nevirapine, NOV-205, peginterferon alfa, podophyllotoxin, rifampicin, rimantadine, resiquimod (R-848), tromantadine; g). Protease inhibitors: amprenavir, atazanavir, boceprevir, darunavir, fosamprenavir, indinavir, lopinavir, nelfinavir, pleconaril, ritonavir, saquinavir, telaprevir (VX-950), tipranavir; h). Other types of anti-virus drugs: abzyme, arbidol, calanolide a, ceragenin, cyanovirin-n, diarylpyrimidines, epigallocatechin gallate (EGCG), foscamet, griffithsin, taribavirin (viramidine), hydroxyurea, KP-1461, miltefosine, pleconaril, portmanteau inhibitors, ribavirin, seliciclib.

5). The drugs used for conjugates via a bridge linker of the present invention also include radioisotopes. Examples of radioisotopes (radionuclides) are $^{3}H$, $^{11}C$, $^{14}C$, $^{18}F$, $^{32}P$, $^{35}S$, $^{64}Cu$, $^{68}Ga$, $^{86}Y$, $^{99}Tc$, $^{111}In$, $^{123}I$, $^{124}I$, $^{125}I$, $^{131}I$, $^{133}Xe$, $^{177}Lu$, $^{211}At$, or $^{213}Bi$. Radioisotope labeled antibodies are useful in receptor targeted imaging experiments or can be for targeted treatment such as with the antibody-drug conjugates of the invention (Wu et al (2005) Nature Biotechnology 23(9): 1137-46). The cell binding molecules, e.g. an antibody can be labeled with ligand reagents through the bridge linkers of the present patent that bind, chelate or otherwise complex a radioisotope metal, using the techniques described in Current Protocols in Immunology, Volumes 1 and 2, Coligen et al, Ed. Wiley-Interscience, New York, Pubs. (1991). Chelating ligands which may complex a metal ion include DOTA, DOTP, DOTMA, DTPA and TETA (Macrocyclics, Dallas, Tex. USA).

6). The pharmaceutically acceptable salts, acids or derivatives of any of the above drugs.

In another embodiment, the drug in the Formula (II) and/or (IV) can be a chromophore molecule, for which the conjugate can be used for detection, monitoring, or study the interaction of the cell binding molecule with a target cell. Chromophore molecules are a compound that have the ability to absorb a kind of light, such as UV light, florescent light, IR light, near IR light, visual light; A chromatophore molecule includes a class or subclass of xanthophores, erythrophores, iridophores, leucophores, melanophores, and cyanophores; a class or subclass of fluorophore molecules which are fluorescent chemical compounds re-emitting light upon light; a class or subclass of visual phototransduction molecules; a class or subclass of photophore molecules; a class or subclass of luminescence molecules; and a class or subclass of luciferin compounds.

The chromophore molecule can be selected from, but not limited, non-protein organic fluorophores, such as: Xanthene derivatives (fluorescein, rhodamine, Oregon green, eosin, and Texas red); Cyanine derivatives: (cyanine, indocarbocyanine, oxacarbocyanine, thiacarbocyanine, and merocyanine); Squaraine derivatives and ring-substituted squaraines, including Seta, SeTau, and Square dyes; Naphthalene derivatives (dansyl and prodan derivatives); Coumarin derivatives; Oxadiazole derivatives (pyridyloxazole, nitrobenzoxadiazole and benzoxadiazole); Anthracene derivatives (anthraquinones, including DRAQ5, DRAQ7 and CyTRAK Orange); Pyrene derivatives (cascade blue, etc); Oxazine derivatives (Nile red, Nile blue, cresyl violet, oxazine 170 etc). Acridine derivatives (proflavin, acridine orange, acridine yellow etc). Arylmethine derivatives (auramine, crystal violet, malachite green). Tetrapyrrole derivatives (porphin, phthalocyanine, bilirubin).

Or a chromophore molecule can be selected from any analogs and derivatives of the following fluorophore compounds: CF dye (Biotium), DRAQ and CyTRAK probes (BioStatus), BODIPY (Invitrogen), Alexa Fluor (Invitrogen), DyLight Fluor (Thermo Scientific, Pierce), Atto and Tracy (Sigma Aldrich), FluoProbes (Interchim), Abberior Dyes (Abberior), DY and MegaStokes Dyes (Dyomics), Sulfo Cy dyes (Cyandye), HiLyte Fluor (AnaSpec), Seta, SeTau and Square Dyes (SETA BioMedicals), Quasar and Cal Fluor dyes (Biosearch Technologies), SureLight Dyes (APC, RPEPerCP, Phycobilisomes)(Columbia Biosciences), APC, APCXL, RPE, BPE (Phyco-Biotech).

Examples of the widely used fluorophore compounds which are reactive or conjugatable with the linkers of the invention are: Allophycocyanin (APC), Aminocoumarin, APC-Cy7 conjugates, BODIPY-FL, Cascade Blue, Cy2, Cy3, Cy3.5, Cy3B, Cy5, Cy5.5, Cy7, Fluorescein, FluorX, Hydroxycoumarin, IR-783, Lissamine Rhodamine B, Lucifer yellow, Methoxycoumarin, NBD, Pacific Blue, Pacific Orange, PE-Cy5 conjugates, PE-Cy7 conjugates, PerCP, R-Phycoerythrin (PE), Red 613, Seta-555-Azide, Seta-555-DBCO, Seta-555-NHS, Seta-580-NHS, Seta-680-NHS, Seta-780-NHS, Seta-APC-780, Seta-PerCP-680, Seta-R-PE-670, SeTau-380-NHS, SeTau-405-Maleimide, SeTau-405-NHS, SeTau-425-NHS, SeTau-647-NHS, Texas Red, TRITC, TruRed, X-Rhodamine.

The fluorophore compounds that can be linked to the linkers of the invention for study of nucleic acids or proteins are selected from the following compounds or their derivatives: 7-AAD (7-aminoactinomycin D, CG-selective), Acridine Orange, Chromomycin A3, CyTRAK Orange (Biostatus, red excitation dark), DAPI, DRAQ5, DRAQ7, Ethidium Bromide, Hoechst33258, Hoechst33342, LDS 751, Mithramycin, PropidiumIodide (PI), SYTOX Blue, SYTOX Green, SYTOX Orange, Thiazole Orange, TO-PRO: Cyanine Monomer, TOTO-1, TO-PRO-1, TOTO-3, TO-PRO-3, YOSeta-1, YOYO-1. The fluorophore compounds that can be linked to the linkers of the invention for study cells are selected from the following compounds or their derivatives: DCFH (2'7' Dichorodihydro-fluorescein, oxidized form), DHR (Dihydrorhodamine 123, oxidized form, light catalyzes oxidation), Fluo-3 (AM ester. pH>6), Fluo-4 (AM ester. pH 7.2), Indo-1 (AM ester, low/high calcium (Ca2+)), and SNARF (pH 6/9). The preferred fluorophore compounds that can be linked to the linkers of the invention for study proteins/antibodies are selected from the following compounds or their derivatives: Allophycocyanin (APC), AmCyan1 (tetramer, Clontech), AsRed2 (tetramer, Clontech), Azami Green (monomer, MBL), Azurite, B-phycoerythrin (BPE), Cerulean, CyPet, DsRed monomer (Clontech), DsRed2 ("RFP", Clontech), EBFP, EBFP2, ECFP, EGFP (weak dimer, Clontech), Emerald (weak dimer, Invitrogen), EYFP (weak dimer, Clontech), GFP (S65A mutation), GFP (S65C mutation), GFP (S65L mutation), GFP (S65T mutation), GFP (Y66F mutation), GFP (Y66H mutation), GFP (Y66W mutation), GFPuv, HcRedl, J-Red, Katusha, Kusabira Orange (monomer, MBL), mCFP, mCherry, mCitrine, Midoriishi Cyan (dimer, MBL), mKate (TagFP635, monomer, Evrogen), mKeima-Red (monomer, MBL), mKO, mOrange, mPlum, mRaspberry, mRFP1 (monomer, Tsien lab), mStrawberry, mTFP1, mTurquoise2, P3 (phycobilisome complex), Peridinin Chlorophyll (PerCP), R-phycoerythrin (RPE), T-Sapphire, TagCFP (dimer, Evrogen), TagGFP (dimer, Evrogen), TagRFP (dimer, Evrogen), TagYFP (dimer, Evrogen), tdTomato (tandem dimer), Topaz, TurboFP602 (dimer, Evrogen), TurboFP635 (dimer, Evrogen), TurboGFP (dimer, Evrogen), TurboRFP (dimer, Evrogen), TurboYFP (dimer, Evrogen), Venus, Wild Type GFP, YPet, ZsGreenl (tetramer, Clontech), ZsYellowl (tetramer, Clontech).

The examples of the structure of the conjugates of the antibody-chromophore molecules via the bridge linker are as following Ac01, Ac02, Ac03, Ac04 and Ac05:

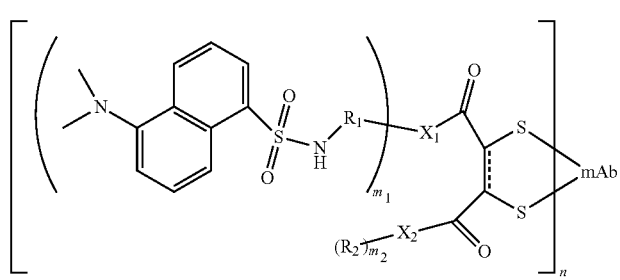

Ac01

-continued
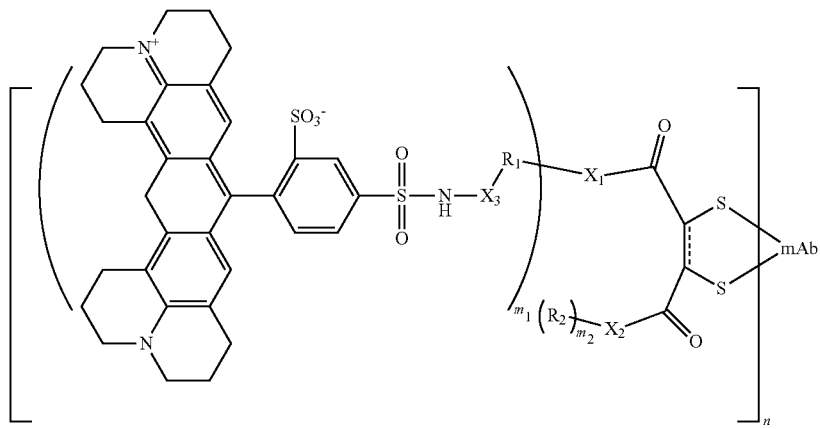
Ac02
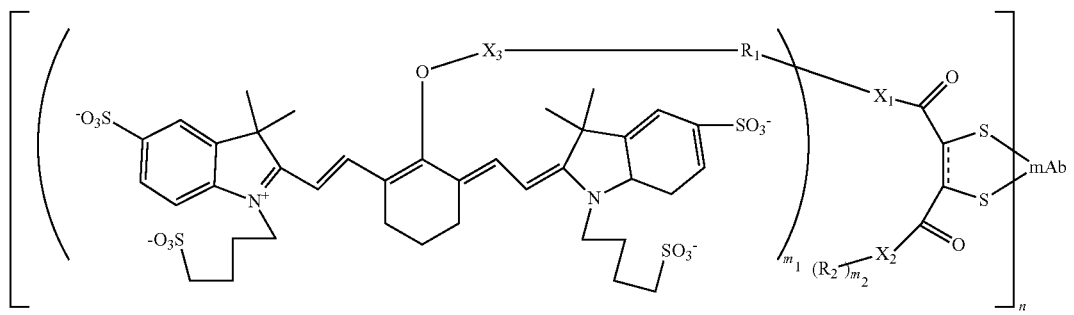
Ac03
(FNIR-774 conjugate)
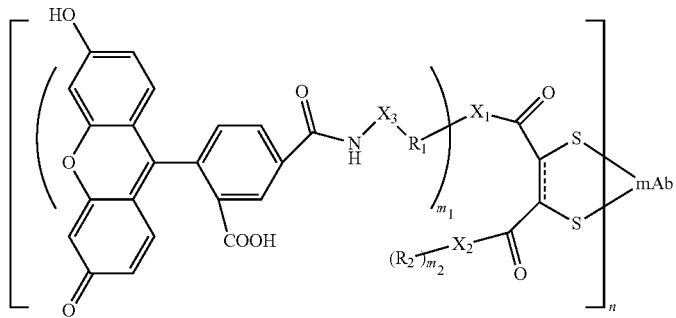
Ac04
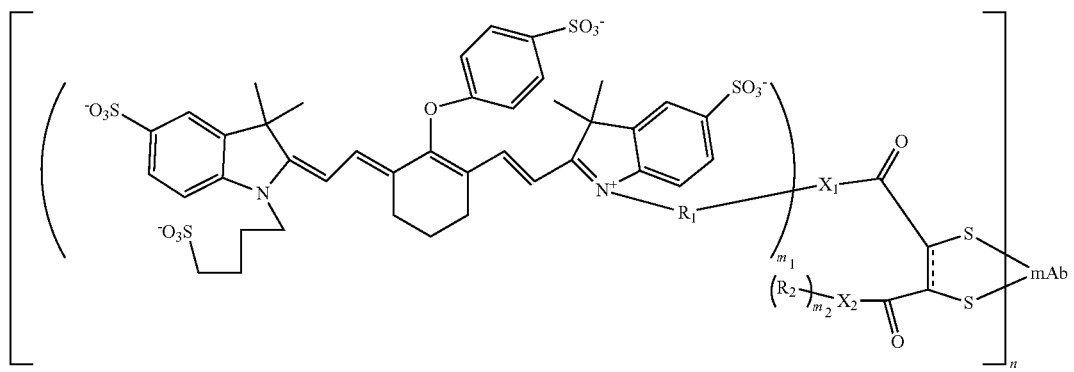
Ac05
(IR800CW conjugate)

Wherein "═" represents either single bond or double bond; mAb is antibody, preferably monoclonal antibody; n, $m_1$, $m_2$, $X_1$, $X_2$, $R_1$, $R_2$ and $R_3$ are the same defined in Formula (I) and (II).

In another embodiment, the drug in the Formula (II) and (IV) can be polyalkylene glycols that are used for extending the half-life of the cell-binding molecule when administered to a mammal. Polyalkylene glycols include, but are not limited to, poly(ethylene glycols) (PEGs), poly(propylene glycol) and copolymers of ethylene oxide and propylene oxide; particularly preferred are PEGs, and more particularly preferred are monofunctionally activated hydroxyPEGs (e.g., hydroxyl PEGs activated at a single terminus, including reactive esters of hydroxyPEG-monocarboxylic acids, hydroxyPEG-monoaldehydes, hydroxyPEG-monoamines, hydroxyPEG-monohydrazides, hydroxyPEG-monocarbazates, hydroxyl PEG-monoiodoacetamides, hydroxyl PEG-monomaleimides, hydroxyl PEG-monoorthopyridyl disulfides, hydroxyPEG-monooximes, hydroxyPEG-monophenyl carbonates, hydroxyl PEG-monophenyl glyoxals, hydroxyl PEG-monothiazolidine-2-thiones, hydroxyl PEG-monothioesters, hydroxyl PEG-monothiols, hydroxyl PEG-monotriazines and hydroxyl PEG-monovinylsulfones).

In certain such embodiments, the polyalkylene glycol has a molecular weight of from about Daltons to about 200 kDa, preferably about 88 Da to about 40 kDa; two branches each with a molecular weight of about 88 Da to about 40 kDa; and more preferably two branches, each of about 88 Da to about 20 kDa. In one particular embodiment, the polyalkylene glycol is poly(ethylene) glycol and has a molecular weight of about 10 kDa; about 20 kDa, or about 40 kDa. In specific embodiments, the PEG is a PEG 10 kDa (linear or branched), a PEG 20 kDa (linear or branched), or a PEG 40 kDa (linear or branched). A number of US patents have disclosed the preparation of linear or branched "non-antigenic" PEG polymers and derivatives or conjugates thereof, e.g., U.S. Pat. Nos. 5,428,128; 5,621,039; 5,622,986; 5,643,575; 5,728,560; 5,730,990; 5,738,846; 5,811,076; 5,824,701; 5,840,900; 5,880,131; 5,900,402; 5,902,588; 5,919,455; 5,951,974; 5,965,119; 5,965,566; 5,969,040; 5,981,709; 6,011,042; 6,042,822; 6,113,906; 6,127,355; 6,132,713; 6,177,087, and 6,180,095. The structure of the conjugates of the antibody-polyalkylene glycols via the bridge linker is as following Pg01:

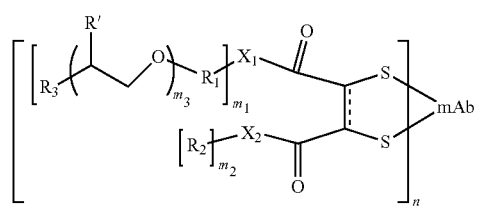

Pg01

Wherein mAb is an antibody; R' is H or $CH_3$; $m_3$ is an integer from 1 to 5000; $R_3$ is OH, H, or $R_1$; "═" represents either single bond or double bond; $m_1$, $m_2$, n, "——", $X_1$, $X_2$, $R_1$, and $R_2$ are the same defined in Formula (I) and (II). In addition, $R_1$ can be absent.

In yet another embodiment, the preferred cytotoxic agents that conjugated to a cell-binding molecule via a bridge linker of this patent are tubulysins, maytansinoids, taxanoids (taxanes), CC-1065 analogs, daunorubicin and doxorubicin compounds, amatoxins, benzodiazepine dimers (e.g., dimers of pyrrolobenzodiazepine (PBD), tomaymycin, anthramycin, indolinobenzodiazepines, imidazobenzothiadiazepines, or oxazolidinobenzodiazepines), calicheamicins and the enediyne antibiotics, actinomycin, azaserines, bleomycins, epirubicin, tamoxifen, idarubicin, dolastatins, auristatins (e.g. monomethyl auristatin E, MMAE, MMAF, auristatin PYE, auristatin TP, Auristatins 2-AQ, 6-AQ, EB (AEB), and EFP (AEFP)), duocarmycins, geldanamycins, methotrexates, thiotepa, vindesines, vincristines, hemiasterlins, nazumamides, microginins, radiosumins, alterobactins, microsclerodermins, theonellamides, esperamicins, PNU-159682, and their analogues and derivatives above thereof.

Tubulysins that are preferred for conjugation in the present invention are well known in the art and can be isolated from natural sources according to known methods or prepared synthetically according to known methods (e. g. Balasubramanian, R., et al. J. Med. Chem., 2009, 52, 238-40; Wipf, P., et al. Org. Lett., 2004, 6, 4057-60; Pando, O., et al. J. Am. Chem. Soc., 2011, 133, 7692-5; Reddy, J. A., et al. Mol. Pharmaceutics, 2009, 6, 1518-25; Raghavan, B., et al. J. Med. Chem., 2008, 51, 1530-33; Patterson, A. W., et al. J. Org. Chem., 2008, 73, 4362-9; Pando, O., et al. Org. Lett., 2009, 11 (24), 5567-9; Wipf, P., et al. Org. Lett., 2007, 9 (8), 1605-7; Friestad, G. K., Org. Lett., 2004, 6, 3249-52; Peltier, H. M., et al. J. Am. Chem. Soc., 2006, 128, 16018-9; Chandrasekhar, S., et al J. Org. Chem., 2009, 74, 9531-4; Liu, Y., et al. Mol. Pharmaceutics, 2012, 9, 168-75; Friestad, G. K., et al. Org. Lett., 2009, 11, 1095-8; Kubicek, K., et al., Angew Chem Int Ed Engl, 2010.49: 4809-12; Chai, Y., et al., Chem Biol, 2010, 17: 296-309; Ullrich, A., et al., Angew Chem Int Ed Engl, 2009, 48, 4422-5; Sani, M., et al. Angew Chem Int Ed Engl, 2007, 46, 3526-9; Domling, A., et al., Angew Chem Int Ed Engl, 2006, 45, 7235-9; Patent applications: Zanda, M., et al, Can. Pat. Appl. CA 2710693 (2011); Chai, Y., et al. Eur. Pat. Appl. 2174947 (2010), WO 2010034724; Leamon, C. et al, WO2010033733, WO 2009002993; Ellman, J., et al, PCT WO2009134279; WO 2009012958, US appl. 20110263650, 20110021568; Matschiner, G., et al, WO2009095447; Vlahov, I., et al, WO2009055562, WO 2008112873; Low, P., et al, WO2009026177; Richter, W., WO2008138561; Kjems, J., et al, WO 2008125116; Davis, M.; et al, WO2008076333; Diener, J.; et al, U.S. Pat. Appl. 20070041901, WO2006096754; Matschiner, G., et al, WO2006056464; Vaghefi, F., et al, WO2006033913; Doemling, A., Ger. Offen. DE102004030227, WO2004005327, WO2004005326, WO2004005269; Stanton, M., et al, U.S. Pat. Appl. Publ. 20040249130; Hoefle, G., et al, Ger. Offen. DE10254439, DE10241152, DE10008089; Leung, D., et al, WO2002077036; Reichenbach, H., et al, Ger. Offen. DE19638870; Wolfgang, R., US20120129779; Chen, H., US appl. 20110027274. The preferred structures of tubulysins for conjugation of cell binding molecules are described in the patent application of PCT/IB2012/053554.

Examples of the structures of the conjugates of the antibody-tubulysin analogs via the bridge linker are T01, T02, T03, T04, T05, T06 and T07 as following:

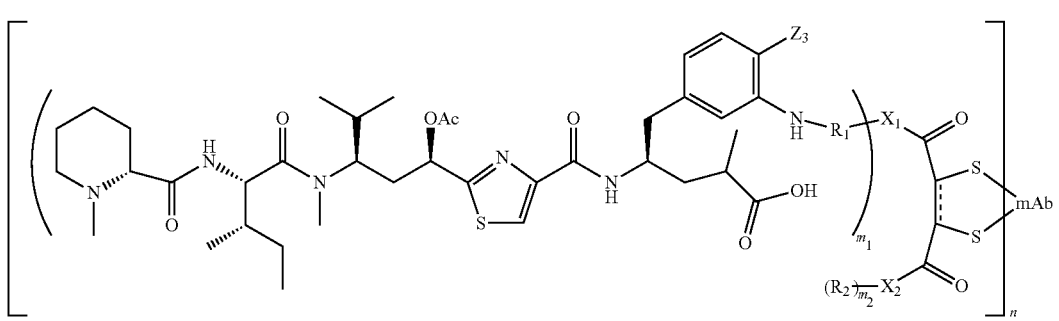
T01
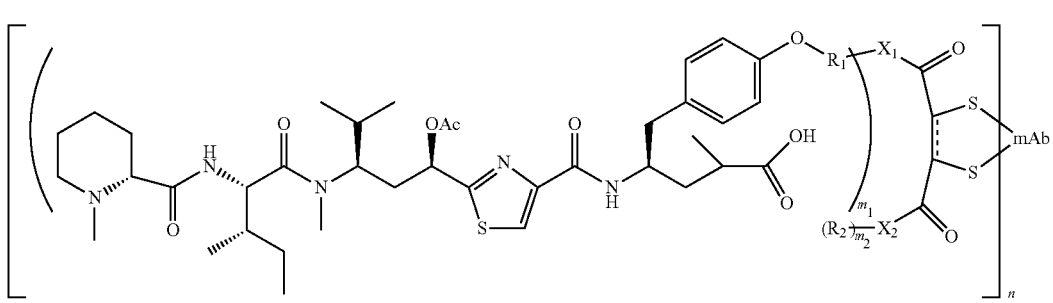
T02
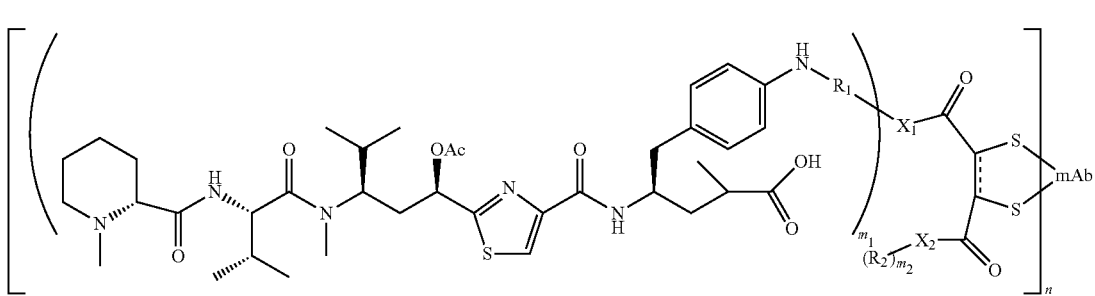
T03
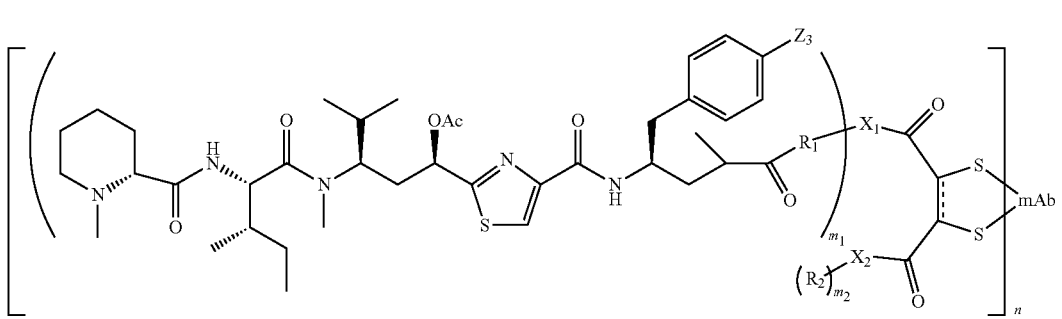
T04
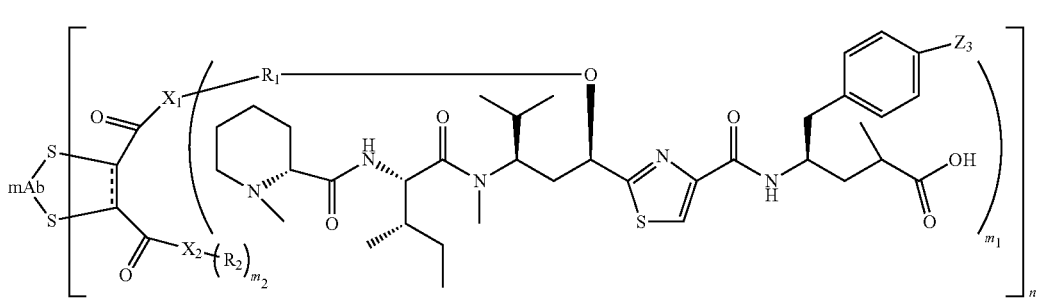
T05

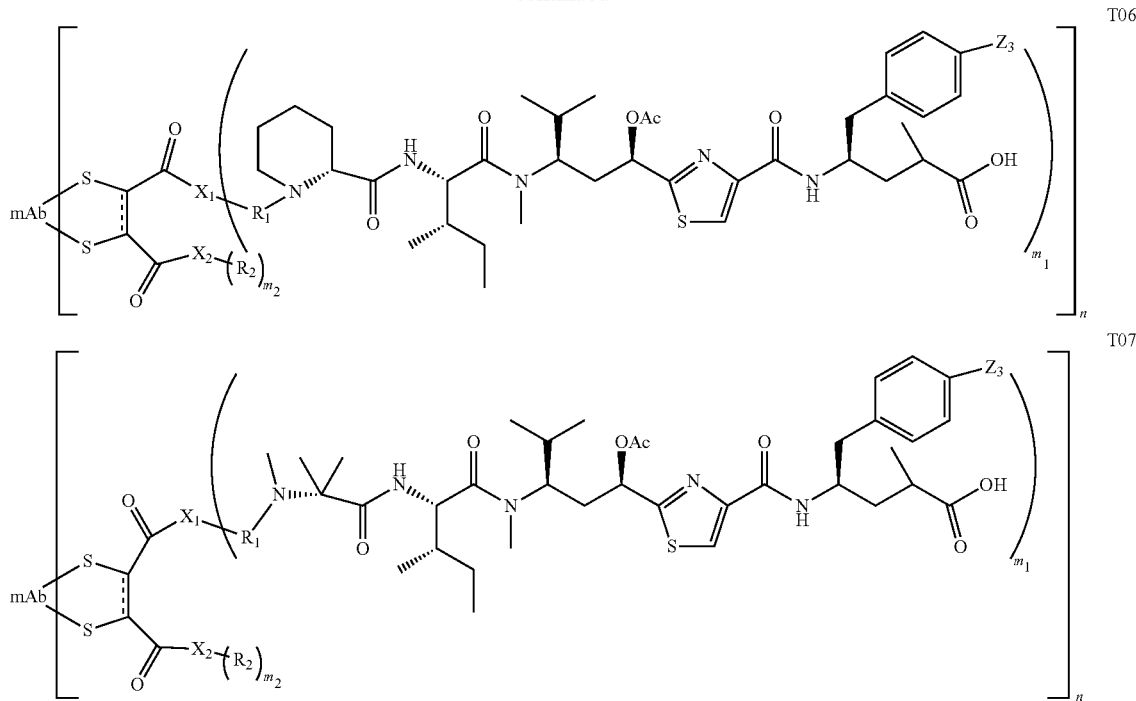

Wherein mAb is an antibody; $Z_3$ and $Z'_3$ are independently H, $OP(O)(OM_1)(OM_2)$, $OCH_2OP(O)(OM_1)(OM_2)$, $OSO_3M_1$, $R_1$, or O-glycoside (glucoside, galactoside, mannoside, giucuronoside, alloside, fructoside, etc), NH-glycoside, S-glycoside or $CH_2$-glycoside; $M_1$ and $M_2$ are independently H, Na, K, Ca, Mg, $NH_4$, $NR_1R_2R_3$; "═" represents either single bond or double bond; n, $m_1$, $m_2$, "──", $X_1$, $X_2$, $R_1$, $R_2$ and $R_3$ are the same defined in Formula (I) and (II).

Calicheamicins and their related enediyne antibiotics that are preferred for cell-binding molecule-drug conjugates of this patent are described in: Nicolaou, K. C. et al, Science 1992, 256, 1172-1178; Proc. Natl. Acad. Sci USA. 1993, 90, 5881-8), U.S. Pat. Nos. 4,970,198; 5,053,394; 5,108,912; 5,264,586; 5,384,412; 5,606,040; 5,712,374; 5,714,586; 5,739,116; 5,770,701; 5,770,710; 5,773,001; 5,877,296; 6,015,562; 6,124,310; 8,153,768. An Example of the structure of the conjugate of the antibody-Calicheamicin analog via the bridge linker is C01 as the following:

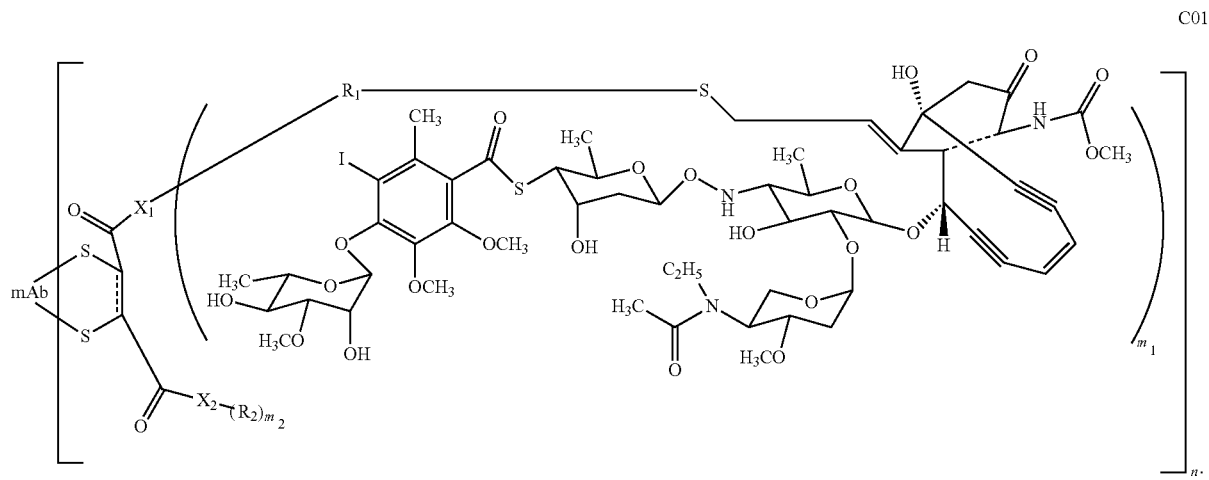

Wherein mAb is an antibody; "═" represents either single bond or double bond; n, $m_1$, $m_2$, "──", $X_1$, $X_2$, $R_1$, and $R_2$ are the same defined in Formula (I) and (II).

Maytansinoids that are preferred to be used in the present invention including maytansinol and its analogues are described in U.S. Pat. Nos. 4,256,746, 4,361,650, 4,307,016, 4,294,757, 4,294,757, 4,371,533, 4,424,219, 4,331,598, 4,450,254, 4,364,866, 4,313,946, 4,315,929 4,362,663, 4,322,348, 4,371,533, 4,424,219, 5,208,020, 5,416,064, 5,208,020; 5,416,064; 6,333.410; 6,441,163; 6,716,821, 7,276,497, 7,301,019, 7,303,749, 7,368,565, 7,411,063, 7,851,432, and 8,163,888. An example of the structure of the conjugate of the antibody-Maytansinoids via the bridge linker is as the following My01:

My01

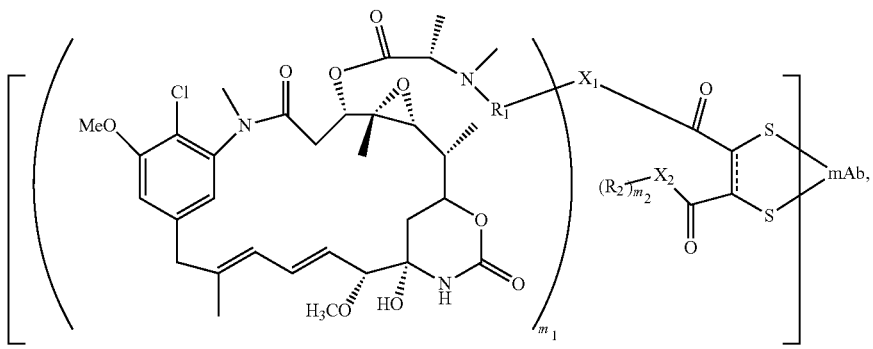

Wherein mAb is an antibody; n, $m_1$, $m_2$, "═" represents either single bond or double bond; n, $m_1$, $m_2$, "—", $X_1$, $X_2$, $R_1$, and $R_2$ are the same defined in Formula (I) and (II).

Taxanes, which includes Paclitaxel (Taxol), a cytotoxic natural product, and docetaxel (Taxotere), a semi-synthetic derivative, and their analogs which are preferred for conjugation via the bridge linkers of the present patent are exampled in: K C. Nicolaou et al., J. Am. Chem. Soc. 117, 2409-20, (1995); Ojima et al, J. Med. Chem. 39:3889-3896 (1996); 40:267-78 (1997); 45, 5620-3 (2002); Ojima et al., Proc. Natl. Acad. Sci., 96:4256-61 (1999); Kim et al., Bull. Korean Chem. Soc., 20, 1389-90 (1999); Miller, et al. J. Med. Chem., 47, 4802-5(2004); U.S. Pat. No. 5,475,011 5,728,849, 5,811,452; 6,340,701; 6,372,738; 6,391,913, 6.436,931; 6,589,979; 6,596,757; 6,706,708; 7,008,942; 7,186,851; 7,217,819; 7,276,499; 7,598,290; and 7,667,054.

Examples of the structures of the conjugate of the antibody-taxanes via the bridge linker are as the following Tx01, Tx02 and Tx03.

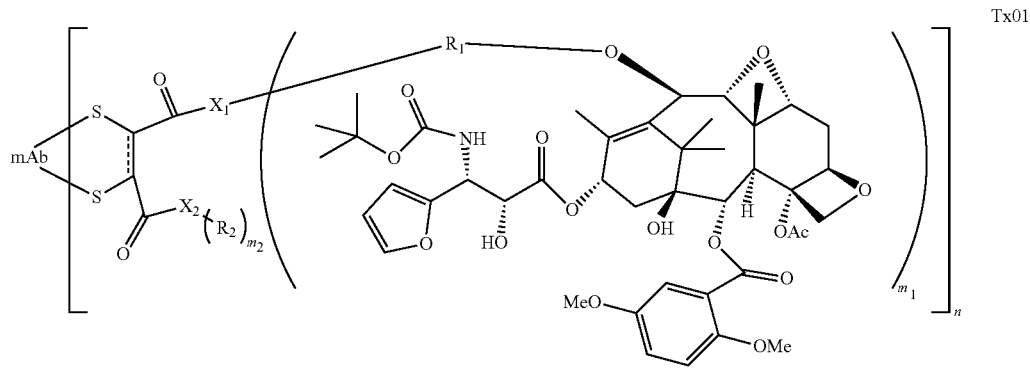

Tx01

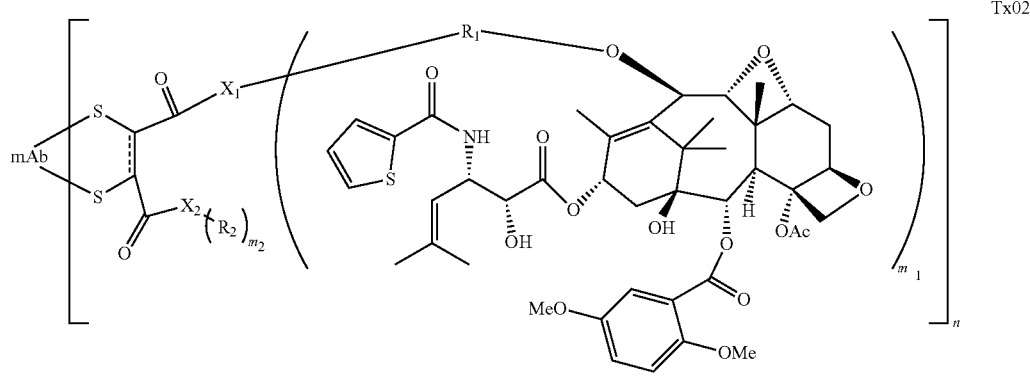

Tx02

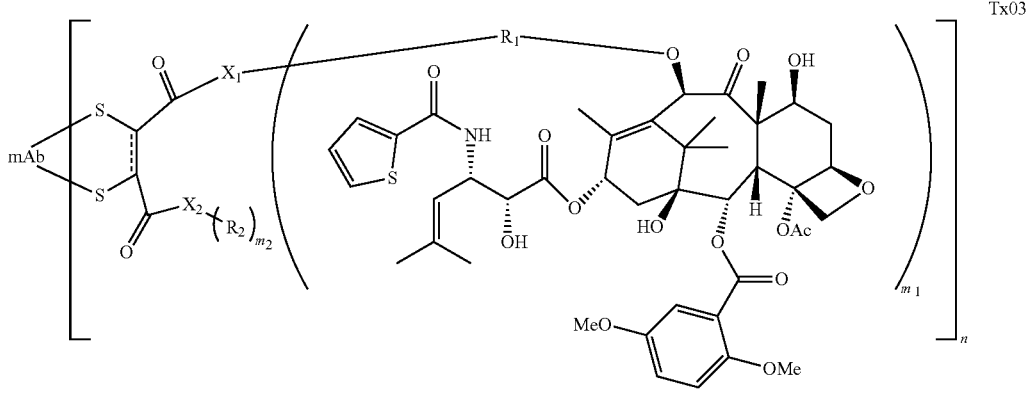

Tx03

Wherein mAb is an antibody; n, $m_1$, $m_2$, "===" represents either single bond or double bond; n, $m_1$, $m_2$, "—", $X_1$, $X_2$, $R_1$, and $R_2$ are the same defined in Formula (I) and (II).

CC-1065 analogues and duocarmycin analogs are also preferred to be used for a conjugate with the bridge linkers of the present patent. The examples of the CC-1065 analogues and duocarmycin analogs as well as their synthesis are described in: e.g. Warpehoski, et al, J. Med. Chem. 31:590-603 (1988); D. Boger et al., J. Org. Chem; 66; 6654-61, 2001; U.S. Pat. Nos. 4,169,888, 4,391,904, 4,671,958, 4,816,567, 4,912,227, 4,923,990, 4,952,394, 4,975,278, 4,978,757, 4,994,578, 5,037,993, 5,070,092, 5,084,468, 5,101,038, 5,117,006, 5,137,877, 5,138,059, 5,147,786, 5,187,186, 5,223,409, 5,225,539, 5,288,514, 5,324,483, 5,332,740, 5,332,837, 5,334,528, 5,403,484, 5,427,908, 5,475,092, 5,495,009, 5,530,101, 5,545,806, 5,547,667, 5,569,825, 5,571,698, 5,573,922, 5,580,717, 5,585,089, 5,585,499, 5,587,161, 5,595,499, 5,606,017, 5,622,929, 5,625,126, 5,629,430, 5,633,425, 5,641,780, 5,660,829, 5,661,016, 5,686,237, 5,693,762, 5,703,080, 5,712,374, 5,714,586, 5,739,116, 5,739,350, 5,770,429, 5,773,001, 5,773,435, 5,786,377 5,786,486, 5,789,650, 5,814,318, 5,846,545, 5,874,299, 5,877,296, 5,877,397, 5,885,793, 5,939,598, 5,962,216, 5,969,108, 5,985,908, 6,060,608, 6,066,742, 6,075,181, 6,103,236, 6,114,598, 6,130,237, 6,132,722, 6,143,901, 6,150,584, 6,162,963, 6,172,197, 6,180,370, 6,194,612, 6,214,345, 6,262,271, 6,281,354, 6,310,209, 6,329,497, 6,342,480, 6,486,326, 6,512,101, 6,521,404, 6,534,660, 6,544,731, 6,548,530, 6,555,313, 6,555,693, 6,566,336, 6,586,618, 6,593,081, 6,630,579, 6,756,397, 6,759,509, 6,762,179, 6,884,869, 6,897,034, 6,946,455, 7,049,316, 7,087,600, 7,091,186, 7,115,573, 7,129,261, 7,214,663, 7,223,837, 7,304,032, 7,329,507, 7,329,760, 7,388,026, 7,655,660, 7,655,661, 7,906,545, and 8,012,978. Examples of the structures of the conjugate of the antibody-CC-1065 analogs via the bridge linker are as the following CC01, CC02, and CC03.

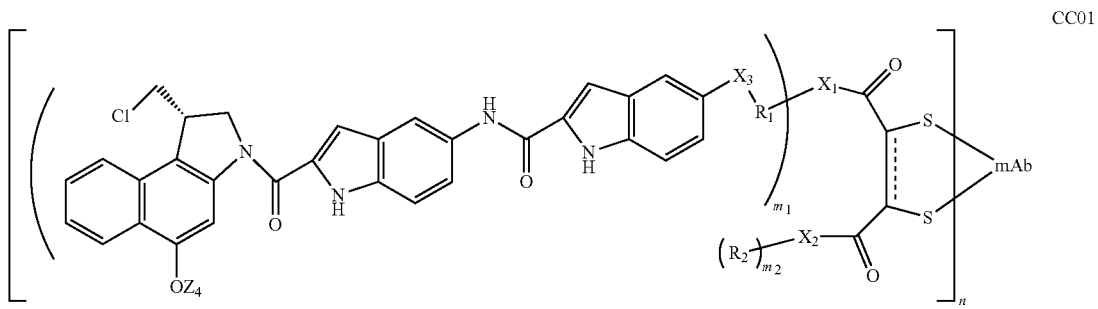

CC01

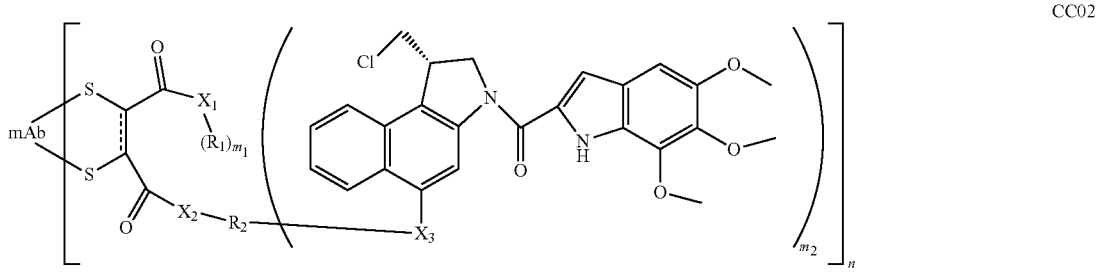

CC02

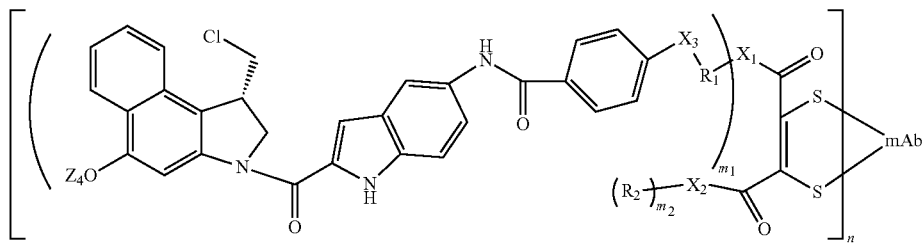

CC03

Wherein mAb is an antibody; $Z_4$ and $Z'_4$ are independently H, $PO(OM_1)(OM_2)$, $SO_3M_1$, $CH_2PO(OM_1)(OM_2)$, $CH_3N(CH_2CH_2)_2NC(O)$—, $O(CH_2CH_2)_2NC(O)$—, $R_1$, or glycoside; $X_3$ is O, NH, NHC(O), OC(O), —C(O)O, $R_1$, or absent; "═" represents either single bond or double bond; n, $m_1$, $m_2$, "—", $X_1$, $X_2$, $R_1$, $R_2$, $M_1$, and $M_2$ are the same defined in Formula (I) and (II).

Daunorubicin/Doxorubicin Analogues are also preferred for conjugation via the bridge linkers of the present patent. The preferred structures and their synthesis are exampled in: Hurwitz, E., et al., Cancer Res. 35, 1175-81 (1975). Yang, H. M., and Reisfeld, R. A., Proc. Natl. Acad. Sci. 85, 1189-93 (1988); Pietersz, C. A., E., et al., E., et al.," Cancer Res. 48, 926-311 (1988); Trouet, et al., 79, 626-29 (1982); Z. Brich et al., J. Controlled Release, 19, 245-58 (1992); Chen et al., Syn. Comm., 33, 2377-90, 2003; King et al., Bioconj. Chem., 10, 279-88, 1999; King et al., J. Med. Chem., 45, 4336-43, 2002; Kratz et al., J Med Chem. 45, 5523-33, 2002; Kratz et al., Biol Pharm Bull. January 21, 56-61, 1998; Lau et al., Bioorg. Med. Chem. 3, 1305-12, 1995; Scott et al., Bioorg. Med. Chem. Lett. 6, 1491-6, 1996; Watanabe et al., Tokai J. Experimental Clin. Med. 15, 327-34, 1990; Zhou et al., J. Am. Chem. Soc. 126, 15656-7, 2004; WO 01/38318; U.S. Pat. Nos. 5,106,951; 5,122,368; 5,146,064; 5,177,016; 5,208,323; 5,824,805; 6,146,658; 6,214,345; 7,569,358; 7,803,903; 8,084,586; 8,053,205. Examples of the structures of the conjugate of the antibody-CC-1065 analogs via the bridge linker are as the following Da01, Da02, Da03 and Da04.

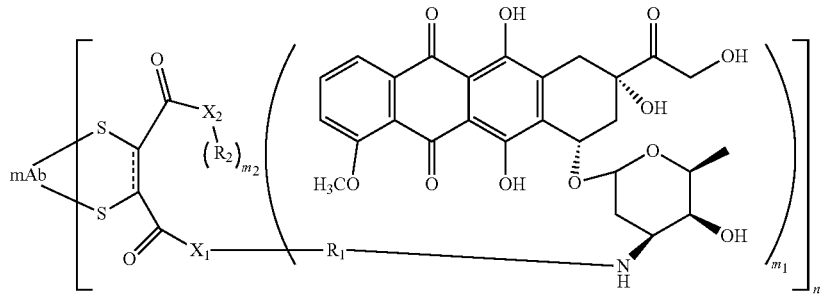

Da01

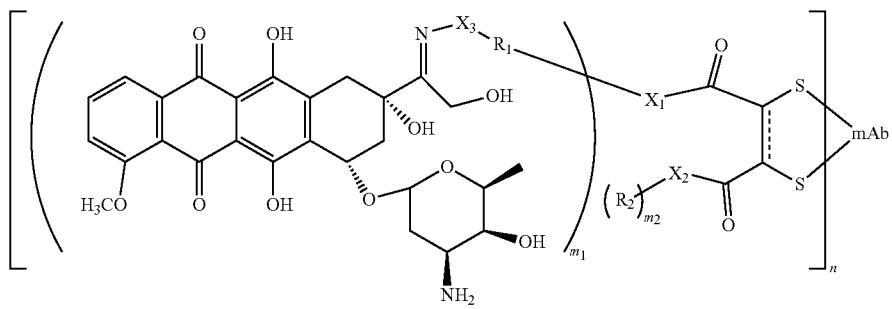

Da02

-continued

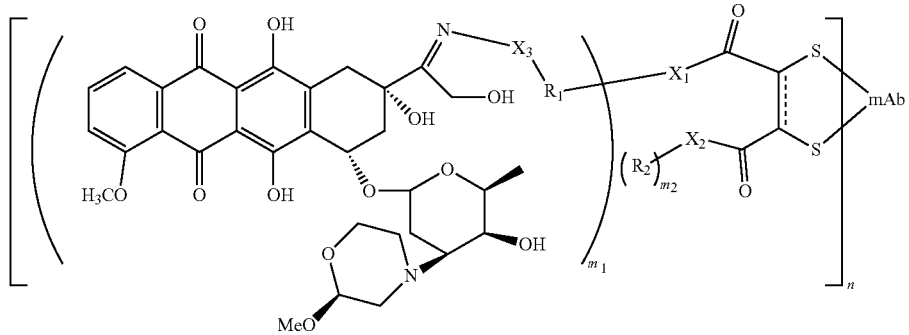

Da03

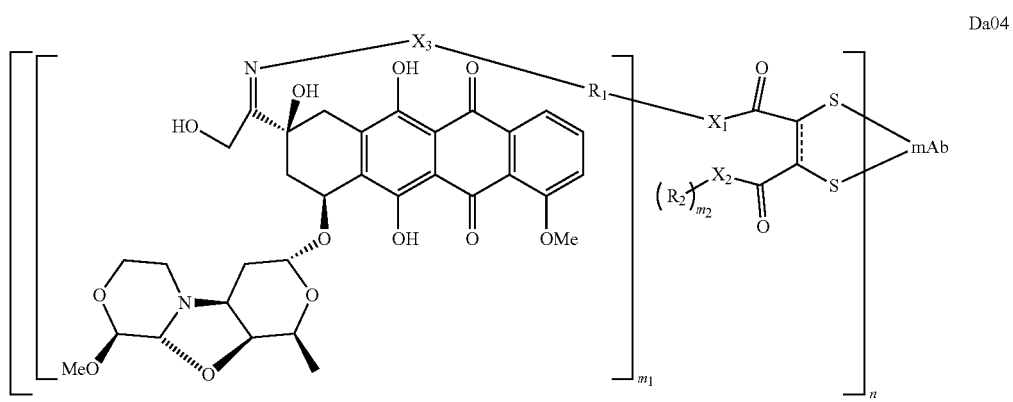

Da04

Wherein mAb is anantibody; $X_3$ is O, NH, NHC(O), NHC(O)NH, C(O), $R_1$, OC(O), or absent; "=" represents either single bond or double bond; n, $m_1$, $m_2$, "—", $X_1$, $X_2$, $R_1$, and $R_2$ are the same defined in Formula (I) and (II).

Auristatins and dolastatins are preferred in conjugation via the bridge linkers of this patent. The auristatins (e. g. auristatin E (AE) auristatin EB (AEB), auristatin EFP (AEFP), monomethyl auristatin E (MMAE), Monomethyl-auristatin (MMAF), Auristatin F phenylene diamine (AFP) and a phenylalanine variant of MMAE) which are synthetic analogs of dolastatins, are described in Int. J. Oncol. 15: 367-72 (1999); Molecular Cancer Therapeutics, vol. 3, No. 8, pp. 921-32 (2004); U.S. Pat. No. 11,134,826, 20060074008, 2006022925. U.S. Pat. Nos. 4,414,205, 4,753,894, 4,764,368, 4,816,444, 4,879,278, 4,943,628, 4,978,744, 5,122,368, 5,165,923, 5,169,774, 5,286,637, 5,410,024, 5,521,284, 5,530,097, 5,554,725, 5,585,089, 5,599,902, 5,629,197, 5,635,483, 5,654,399, 5,663,149, 5,665,860, 5,708,146, 5,714,586, 5,741,892, 5,767,236, 5,767,237, 5,780,588, 5,821,337, 5,840,699, 5,965,537, 6,004,934, 6,033,876, 6,034,065, 6,048,720, 6,054,297, 6,054,561, 6,124,431, 6,143,721, 6,162,930, 6,214,345, 6,239,104, 6,323,315, 6,342,219, 6,342,221, 6,407,213, 6,569,834, 6,620,911, 6,639,055, 6,884,869, 6,913,748, 7,090,843, 7,091,186, 7,097,840, 7,098,305, 7,098,308, 7,498,298, 7,375,078, 7,462,352, 7,553,816, 7,659,241, 7,662,387, 7,745,394, 7,754,681, 7,829,531, 7,837,980, 7,837,995, 7,902,338, 7,964,566, 7,964,567, 7,851,437, 7,994,135. Examples of the structures of the conjugate of the antibody-auristatins via the bridge linker are as the following Au01, Au02, Au03, Au04, and Au05.

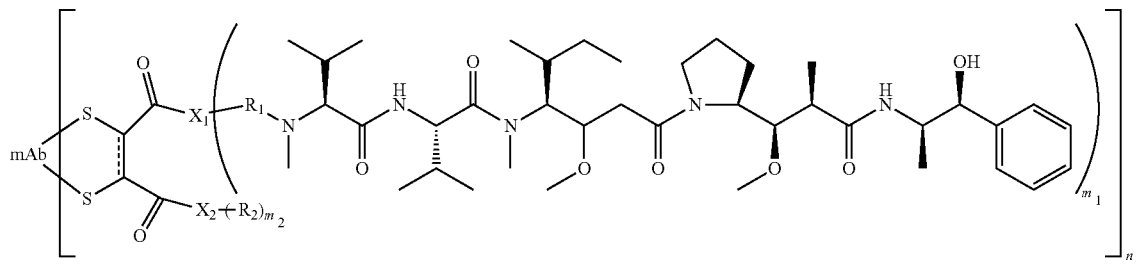

Au01

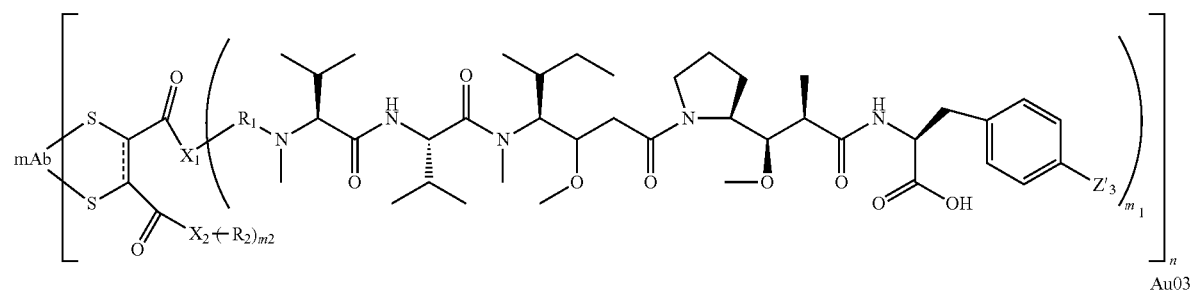

Au02

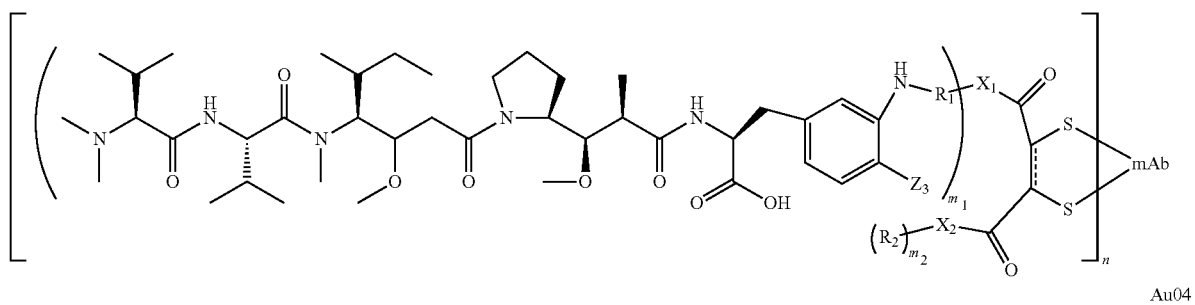

Au03

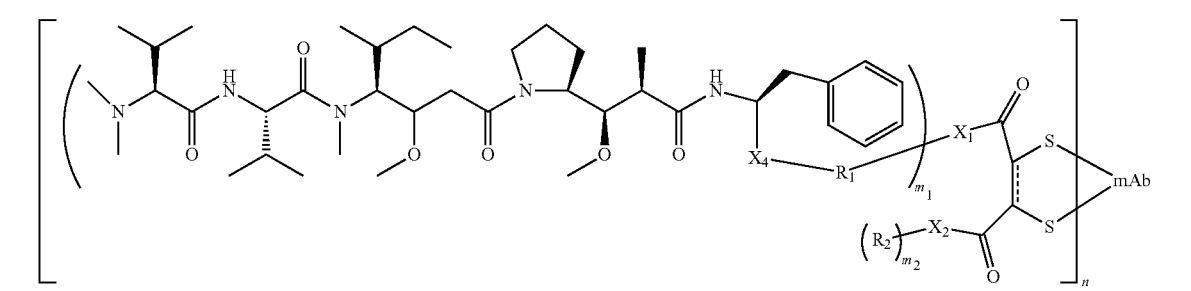

Au04

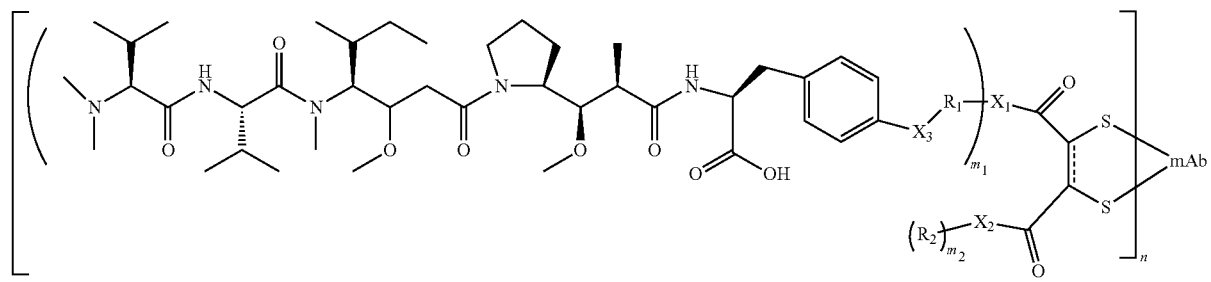

Au05

Wherein mAb is an antibody; $X_3$ is $CH_2$, O, NH, NHC(O), NHC(O)NH, C(O), OC(O) $R_1$, or absent; $X_4$ is $CH_2$, C(O), C(O)NH, C(O)N($R_1$), $R_1$, $NHR_1$, $NR_1$, C(O)$R_1$ or C(O)O; $Z_3$ is H, $R_1$, OP(O)(O$M_1$)(O$M_2$), $NHR_1$, $OCH_2OP(O)(OM_1)$ (O$M_2$), $OSO_3M_1$, or O-glycoside (glucoside, galactoside, mannoside, glucuronoside, alloside, fructoside), NH-glycoside, S-glycoside, or $CH_2$-glycoside; $M_1$ and $M_2$ are independently H, Na, K, Ca, Mg, $NH_4$, $NR_1R_2R_3$; "═══" represents either single bond or double bond; n, $m_1$, $m_2$, "——", $X_1$, $X_2$, $R_1$, $R_2$ and $R_3$ are the same defined in Formula (I) and (II). In addition, $R_1$ can be absent and $R_2$ can be H.

The benzodiazepine dimers (e. g. dimmers of pyrrolobenzodiazepine (PBD) or (tomaymycin), indolinobenzodiazepines, imidazobenzothiadiazepines, or oxazolidinobenzodiazepines) which are preferred cytotoxic agents according to the present invention are exampled in the art: U.S. Pat. Nos. 8,163,736; 8,153,627; 8,034,808; 7,834,005; 7,741,319; 7,704,924; 7,691,848; 7,678,787; 7,612,062; 7,608,615; 7,557,099; 7,528,128; 7,528,126; 7,511,032; 7,429,658; 7,407,951; 7,326,700; 7,312,210; 7,265,105; 7,202,239; 7,189,710; 7,173,026; 7,109,193; 7,067,511; 7,064,120; 7,056,913; 7,049,311; 7,022,699; 7,015,215; 6,979,684; 6,951,853; 6,884,799; 6,800,622; 6,747,144; 6,660,856; 6,608,192; 6,562,806; 6,977,254; 6,951,853; 6,909,006; 6,344,451; 5,880,122; 4,935,362; 4,764,616; 4,761,412; 4,723,007; 4,723,003; 4,683,230; 4,663,453; 4,508,647; 4,464,467; 4,427,587; 4,000,304; US patent appl. 20100203007, 20100316656, 20030195196. Examples of the structures of the conjugate of the antibody-benzodiazepine dimers via the bridge linker are as the following PB01, PB02, PB03, PB04, PB05, PB06, PB07, PB08, PB09, PB10 and PB11.

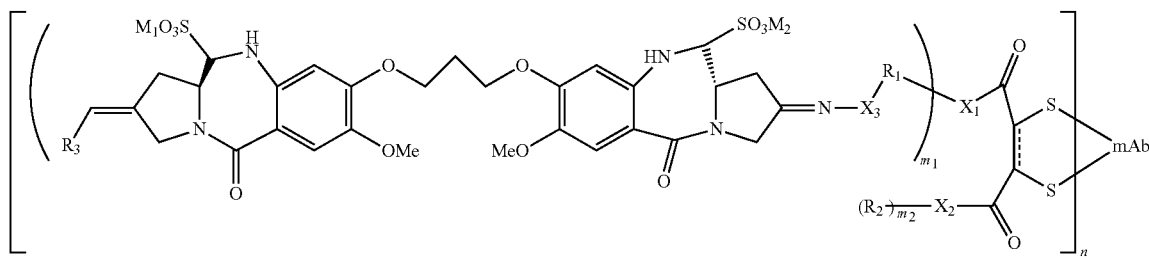
PB01
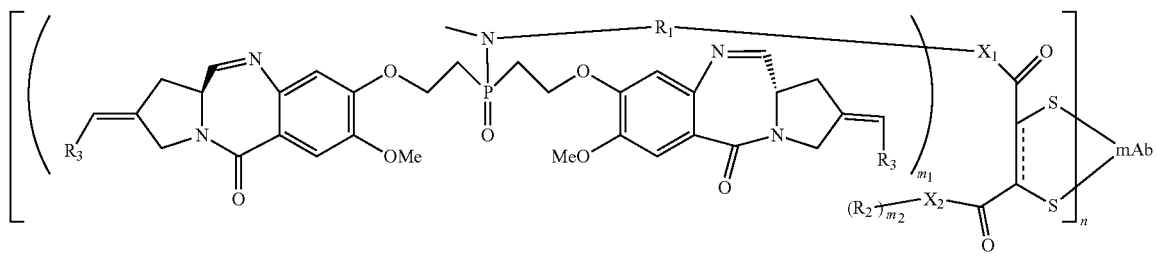
PB02
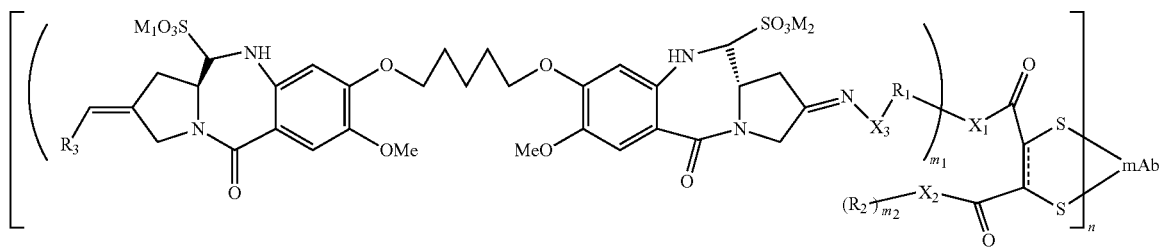
PB03
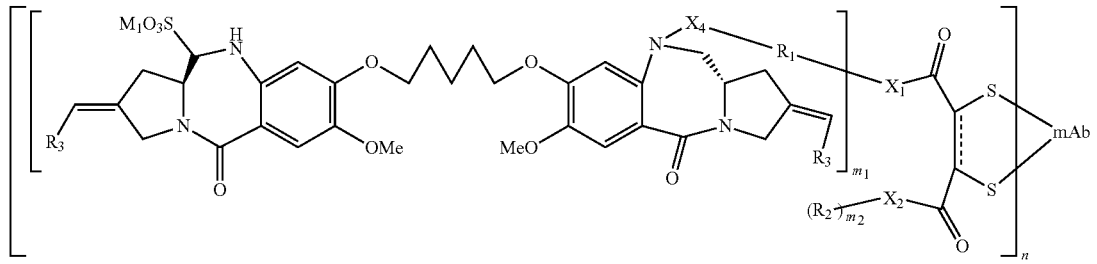
PB04
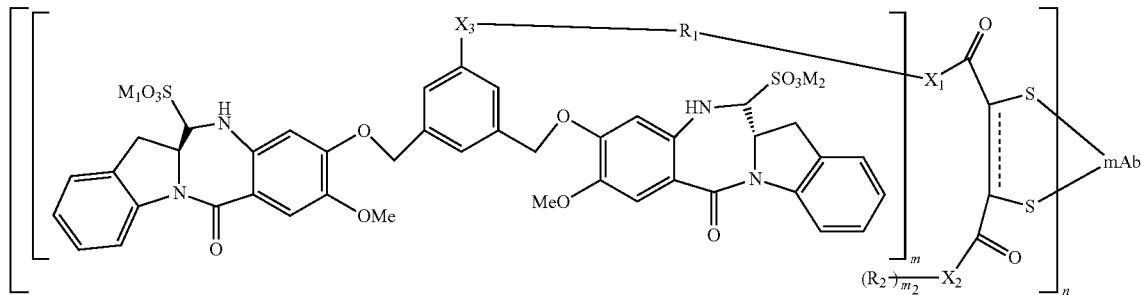
PB05

-continued
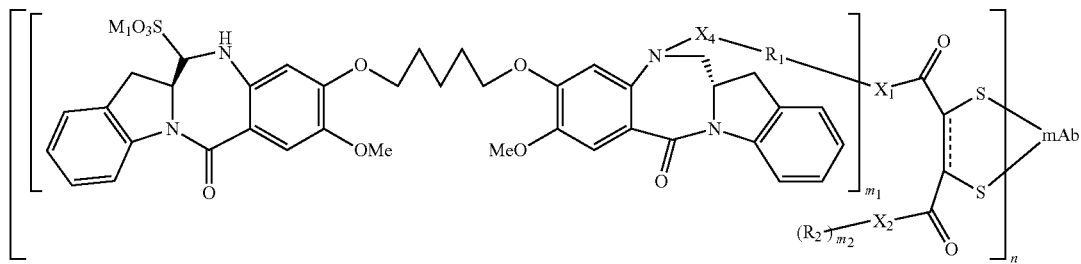
PB06
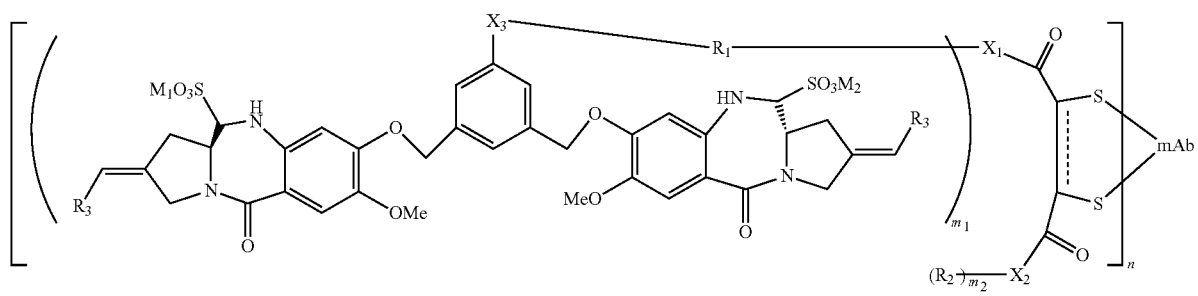
PB07
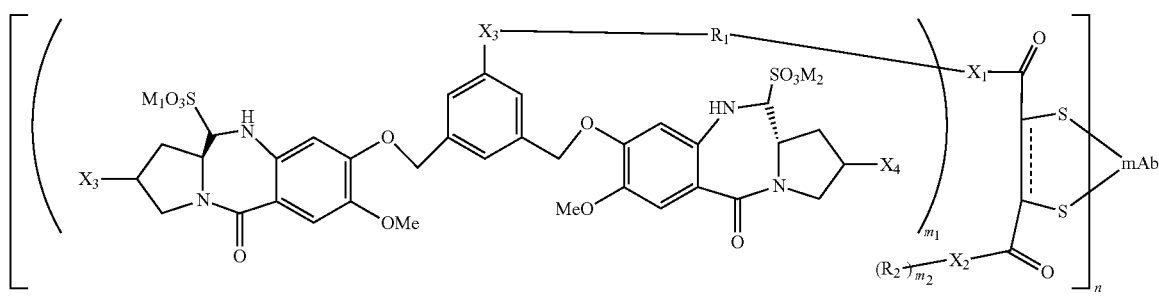
PB08
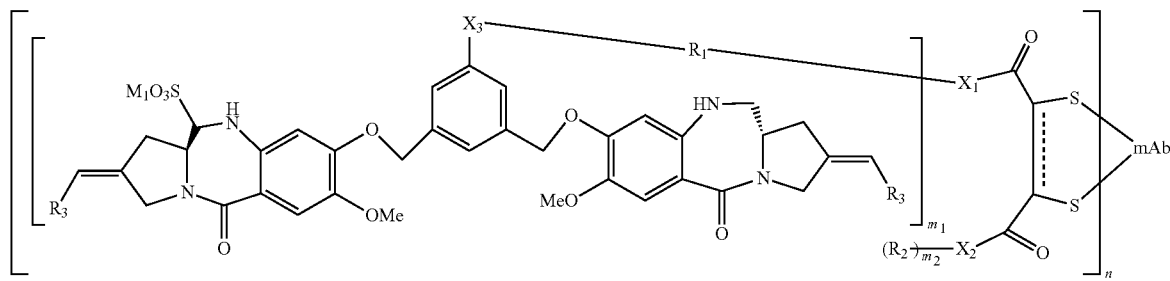
PB09
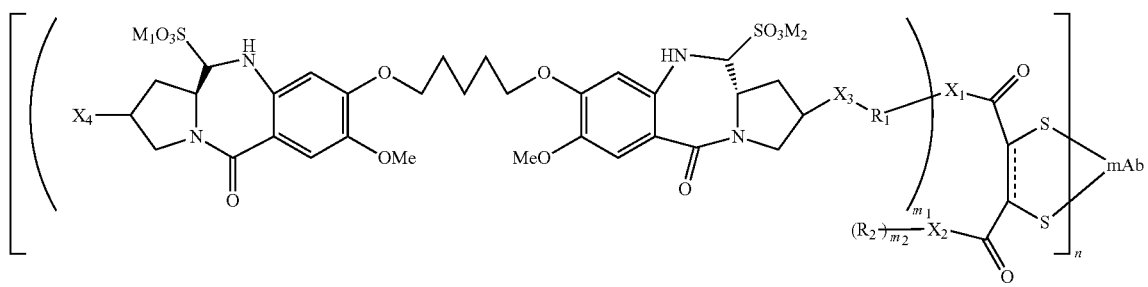
PB10

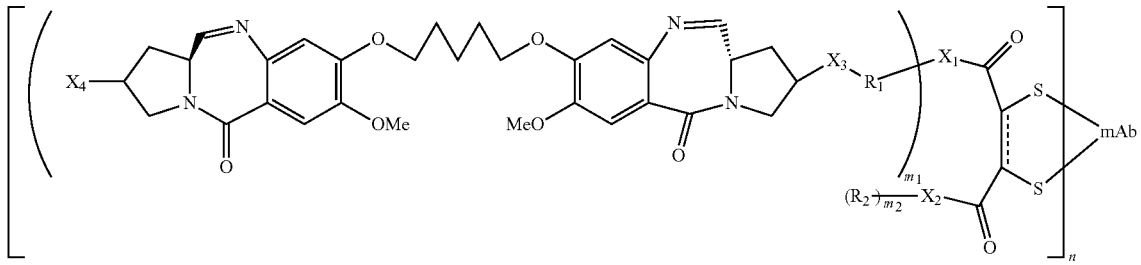

PB11

Wherein mAb is an antibody; $X_3$ is $CH_2$, O, NH, NHC(O), NHC(O)NH, C(O), OC(O), OC(O)(NR$_3$), $R_1$, NHR$_1$, NR$_1$, C(O)R$_1$ or absent; $X_4$ is $CH_2$, C(O), C(O)NH, C(O)N(R$_1$), $R_1$, NHR$_1$, NR$_1$, C(O)R$_1$ or C(O)O; $M_1$ and $M_2$ are independently H, Na, K, Ca, Mg, NH$_4$, NR$_1$R$_2$R$_3$; "═" represents either single bond or double bond; n, $m_1$, $m_2$, "—", $X_1$, $X_2$, $R_1$, $R_2$ and $R_3$ are the same defined in Formula (I) and (II). In addition, $R_1$ can be absent.

Amatoxins which are a subgroup of at least ten toxic compounds originally found in several genera of poisonous mushrooms, most notably *Amanita phalloides* and several other mushroom species, are also preferred for conjugation via the bridge linkers of the present patent. These ten amatoxins, named α-Amanitin, β-Amanitin, γ-Amanitin, ε-Amanitin, Amanullin, Amanullinic acid, Amaninamide, Amanin, Proamanullin, are rigid bicyclic peptides that are synthesized as 35-amino-acid proproteins, from which the final eight amino acids are cleaved by a prolyl oligopeptidase (Litten, W. 1975 Scientific American232 (3): 90-101; H. E. Hallen, et al 2007 Proc. Nat. Aca. Sci. USA 104, 19097-101; K. Baumann, et al, 1993 Biochemistry 32 (15): 4043-50; Karlson-Stiber C, Persson H. 2003, Toxicon 42 (4): 339-49; Horgen, P. A. et al. 1978 Arch. Microbio. 118 (3): 317-9). Amatoxins kill cells by inhibiting RNA polymerase II (Pol II), shutting down gene transcription and protein biosynthesis (Brodner, O. G. and Wieland, T. 1976 Biochemistry, 15(16): 3480-4; Fiume, L., Curr Probl Clin Biochem, 1977, 7: 23-8; Karlson-Stiber C, Persson H. 2003, Toxicon 42(4): 339-49; Chafin, D. R., Guo, H. & Price, D. H. 1995 J. Biol. Chem. 270 (32): 19114-19; Wieland (1983) Int. J. Pept. Protein Res. 22(3): 257-76). Amatoxins can be produced from collected *Amanita phalloides* mushrooms (Yocum, R. R. 1978 Biochemistry 17(18): 3786-9; Zhang, P. et al, 2005, FEMS Microbiol. Lett. 252(2), 223-8), or from fermentation using a basidiomycete (Muraoka, S. and Shinozawa T., 2000 J. Biosci. Bioeng. 89(1): 73-6) or from fermentation using A. fissa (Guo, X. W., et al, 2006 Wei Sheng Wu Xue Bao 46(3): 373-8), or from culturing *Galerina fasciculata* or *Galerina helvoliceps*, a strain belonging to the genus (WO/1990/009799, JP11137291). However the yields from these isolation and fermentation were quite low (less than 5 mg/L culture). Several preparations of amatoxins and their analogs have been reported in the past three decades (W. E. Savige, A. Fontana, Chem. Commun. 1976, 600-1; Zanotti, G., et al, Int J Pept Protein Res, 1981. 18(2): 162-8; Wieland, T., et al, Eur. J. Biochem. 1981, 117, 161-4; P. A. Bartlett, et al, Tetrahedron Lett. 1982, 23, 619-22; Zanotti, G., et al., Biochim Biophys Acta, 1986. 870(3): 454-62; Zanotti, G., et al., Int. J. Peptide Protein Res. 1987, 30, 323-9; Zanotti, G., et al., Int. J. Peptide Protein Res. 1987, 30, 450-9; Zanotti, G., et al., Int J Pept Protein Res, 1988. 32(1): 9-20; G. Zanotti, T. et al, Int. J. Peptide Protein Res. 1989, 34, 222-8; Zanotti, G., et al., Int J Pept Protein Res, 1990. 35(3): 263-70; Mullersman, J. E. and J. F. Preston, 3rd, Int J Pept Protein Res, 1991. 37(6): 544-51; Mullersman, J. E., et al, Int J Pept Protein Res, 1991. 38(5): 409-16; Zanotti, G., et al, Int J Pept Protein Res, 1992. 40(6): 551-8; Schmitt, W. et al, J. Am. Chem. Soc. 1996, 118, 4380-7; Anderson, M. O., et al, J. Org. Chem., 2005, 70(12): 4578-84; J. P. May, et al, J. Org. Chem. 2005, 70, 8424-30; F. Brueckner, P. Cramer, Nat. Struct. Mol. Biol. 2008, 15, 811-8; J. P. May, D. M. Perrin, Chem. Eur. J. 2008, 14, 3404-9; J. P. May, et al, Chem. Eur. J. 2008, 14, 3410-17; Q. Wang, et al, Eur. J. Org. Chem. 2002, 834-9; May, J. P. and D. M. Perrin, Biopolymers, 2007. 88(5): 714-24; May, J. P., et al., Chemistry, 2008. 14(11): 3410-7; S. De Lamo Marin, et al, Eur. J. Org. Chem. 2010, 3985-9; Pousse, G., et al., Org Lett, 2010. 12(16): 3582-5; Luo, H., et al., Chem Biol, 2014. 21(12): 1610-7; Zhao, L., et al., Chembiochem, 2015. 16(10): 1420-5) and most of these preparations were by partial synthesis. Because of their extreme potency and unique mechanism of cytotoxicity, amatoxins have been used as payloads for conjugations (Fiume, L., Lancet, 1969. 2 (7625): 853-4; Barbanti-Brodano, G. and L. Fiume, Nat New Biol, 1973. 243(130): 281-3; Bonetti, E., M. et al, Arch Toxicol, 1976. 35(1): p. 69-73; Davis, M. T., Preston, J. F. Science 1981, 213, 1385-1388; Preston, J. F., et al, Arch Biochem Biophys, 1981. 209(1): 63-71; H. Faulstich, et al, Biochemistry 1981, 20, 6498-504; Barak, L. S., et al., Proc Natl Acad Sci USA, 1981. 78(5): 3034-8; Faulstich, H. and L. Fiume, Methods Enzymol, 1985. 112: 225-37; Zhelev, Z., A. et al, Toxicon, 1987. 25(9): 981-7; Khalacheva, K., et al, Eksp Med Morfol, 1990. 29(3): 26-30; U. Bermbach, H. Faulstich, Biochemistry 1990, 29, 6839-45; Mullersman, J. E. and J. F. Preston, Int. J. Peptide Protein Res. 1991, 37, 544-51; Mullersman, J. E. and J. F. Preston, Biochem Cell Biol, 1991. 69(7): 418-27; J. Anderl, H. Echner, H. Faulstich, Beilstein J. Org. Chem. 2012, 8, 2072-84; Moldenhauer, G., et al, J. Natl. Cancer Inst. 2012, 104, 622-34; A. Moshnikova, et al; Biochemistry 2013, 52, 1171-8; Zhao, L., et al., Chembiochem, 2015. 16(10): 1420-5; Zhou, B., et al., Biosens Bioelectron, 2015. 68: 189-96; WO2014/043403, US20150218220, EP 1661584). We have been working on the conjugation of amatoxins for a while. Examples of the structures of the conjugate of the antibody-amatoxins via the bridge linker are preferred as the following structures of Am01, Am02, Am03, and Am04.

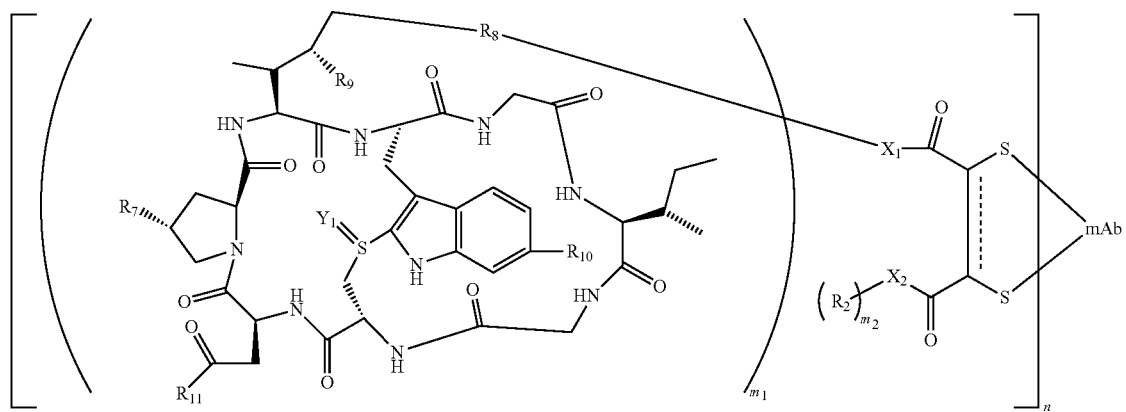
Am01
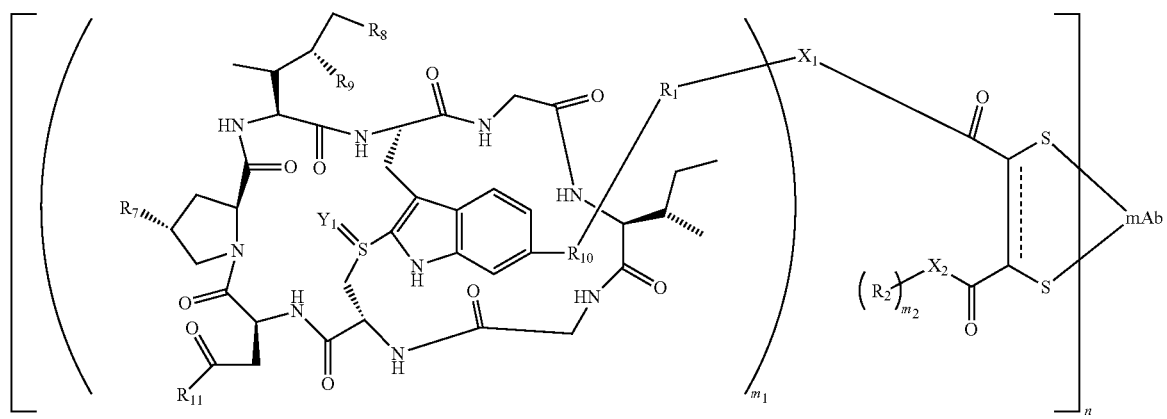
Am02
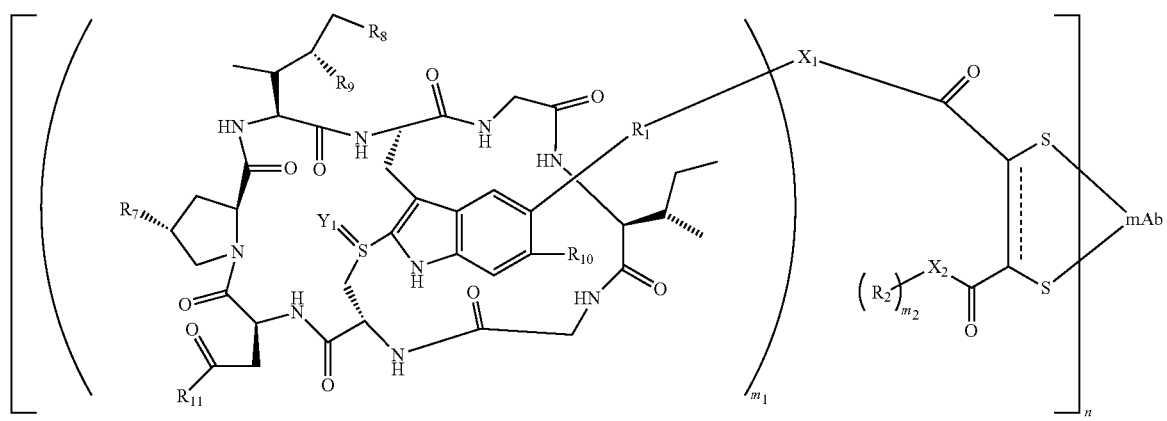
Am03

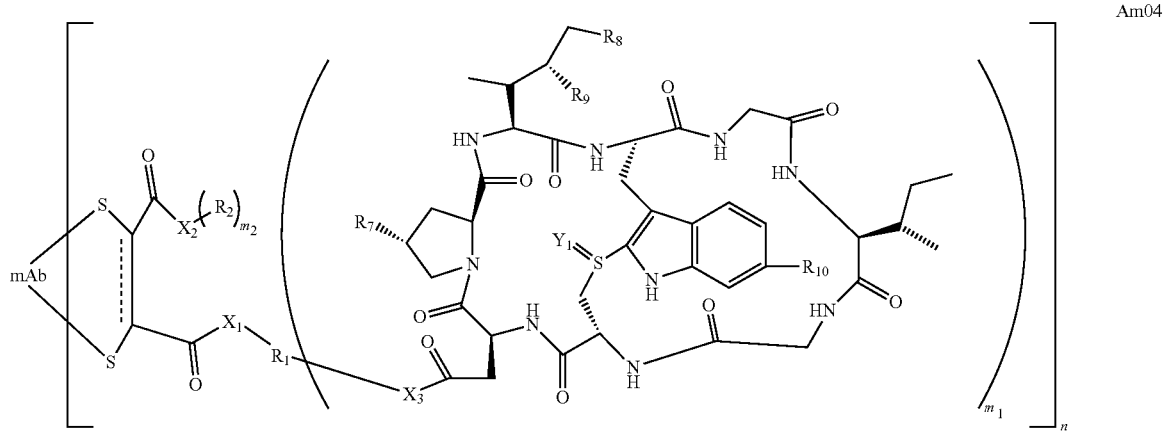

Am04

Wherein mAb is an antibody; $X_3$ is $CH_2$, O, NH, NHC(O), NHC(O)NH, C(O), OC(O), OC(O)(NR_3)$, $R_1$, $NHR_1$, $NR_1$, $C(O)R_1$ or absent; $R_7$, $R_8$, $R_9$, $R_{10}$ and $R_{11}$ are independently H, OH, $OR_1$, $NH_2$, $NHR_1$, $C_1$-$C_6$ alkyl, or absent; $Y_1$ is O, $O_2$, or absent; $X_1$, $X_2$, $R_1$, $R_2$ and $R_3$ are the same defined in Formula (I).

In yet another embodiment, two or more different cytotoxic agents are preferred conjugated to a cell-binding molecule via a bridge linker of this patent. The two or more different cytotoxic agents can be selected from any combinations of tubulysins, maytansinoids, taxanoids (taxanes), CC-1065 analogs, daunorubicin and doxorubicin compounds, benzodiazepine dimers (e.g., dimers of pyrrolobenzodiazepine (PBD), tomaymy cin, anthramycin, indolinobenzodiazepines, imidazobenzothiadiazepines, or oxazolidinobenzodiazepines), calicheamicins and the enediyne antibiotics, actinomycins, amanitins, azaserines, bleomycins, epirubicin, tamoxifen, idarubicin, dolastatins, auristatins (e.g. monomethyl auristatin E, MMAE, MMAF, auristatin PYE, auristatin TP, Auristatins 2-AQ, 6-AQ, EB (AEB), and EFP (AEFP)), duocarmycins, thiotepa, vincristines, hemiasterlins, nazumamides, microginins, radiosumins, alterobactins, microsclerodermins, theonellamides, esperamicins, PNU-159682, and their analogues and derivatives above thereof. Examples of the structures of the conjugates containing two or more different cytotoxic agents via the bridge linker are as the following Z01, Z02, Z02, Z04, Z05, Z06, Z07, Z08, Z09, Z10, Z12, Z13, Z14, Z15, Z16, Z17 and Z18.

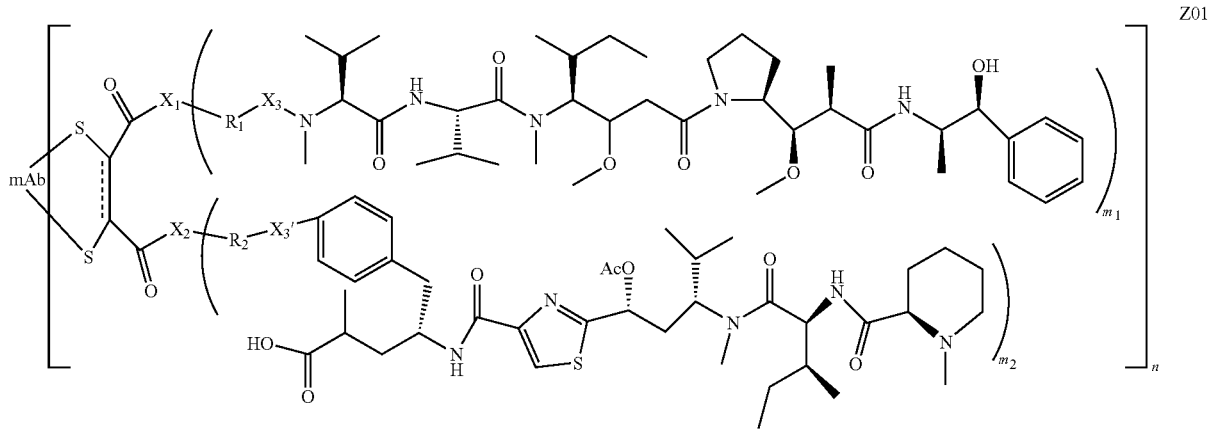

Z01

-continued
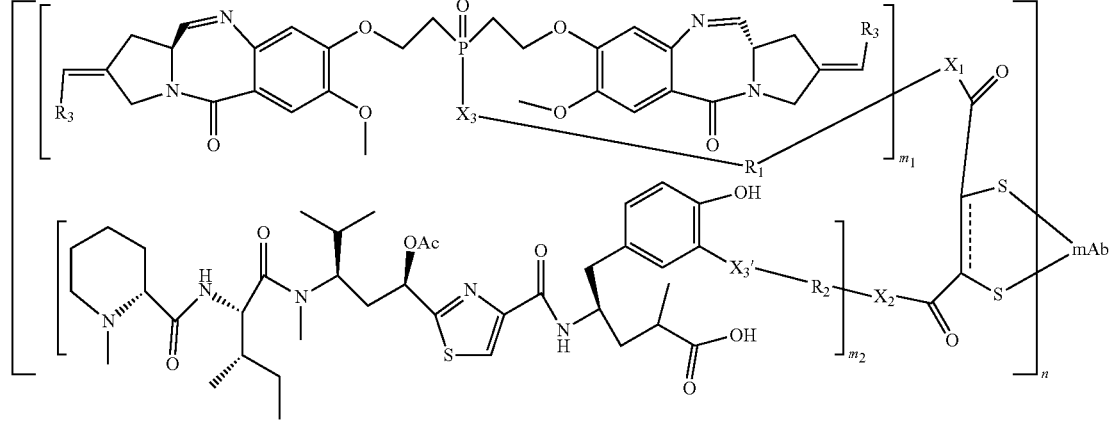
Z02
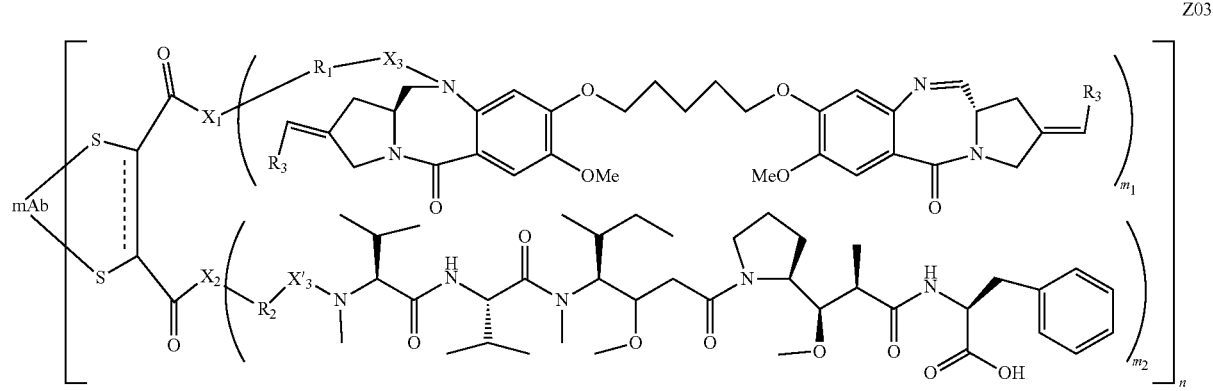
Z03
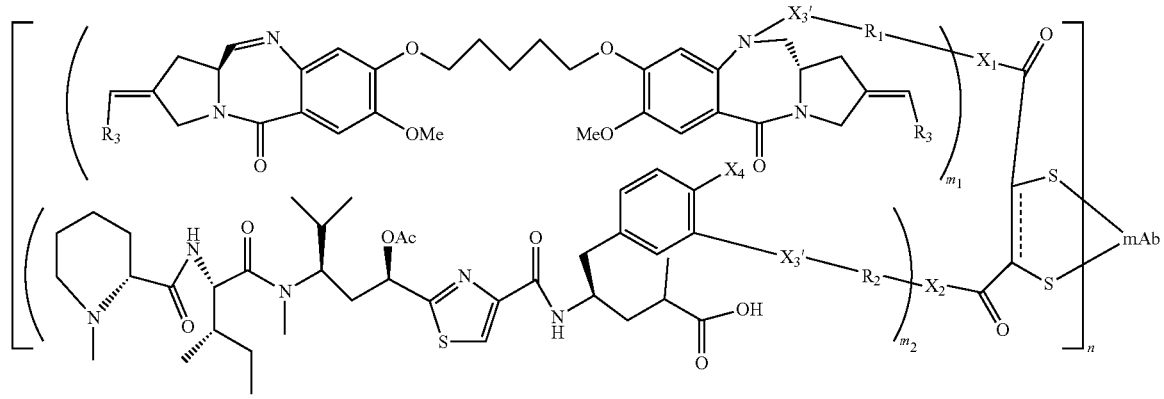
Z04
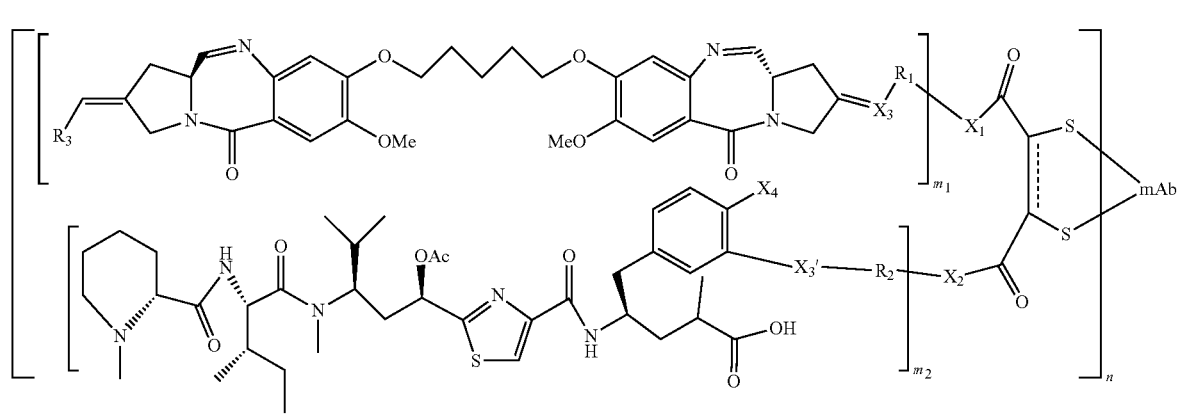
Z05

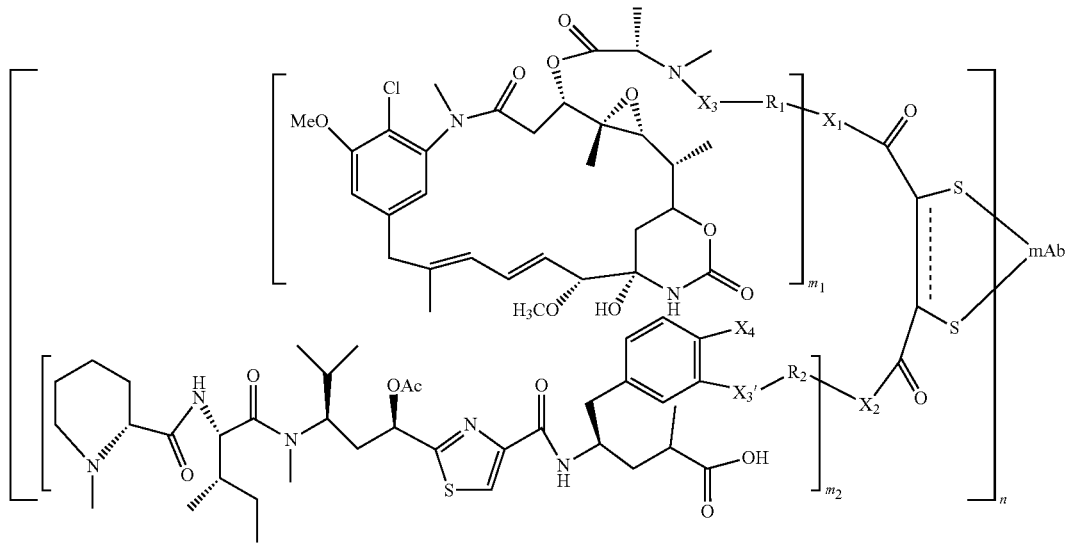
Z06
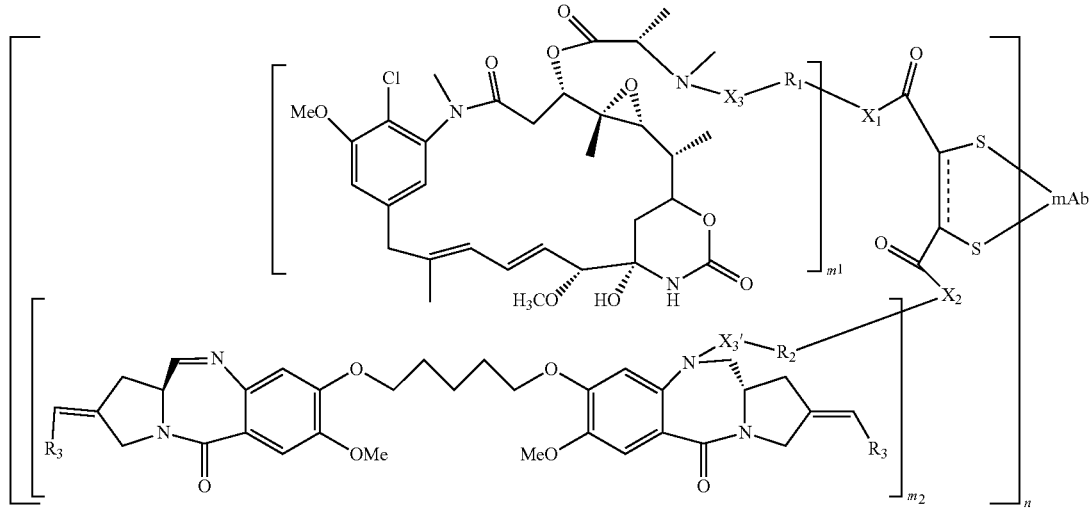
Z07
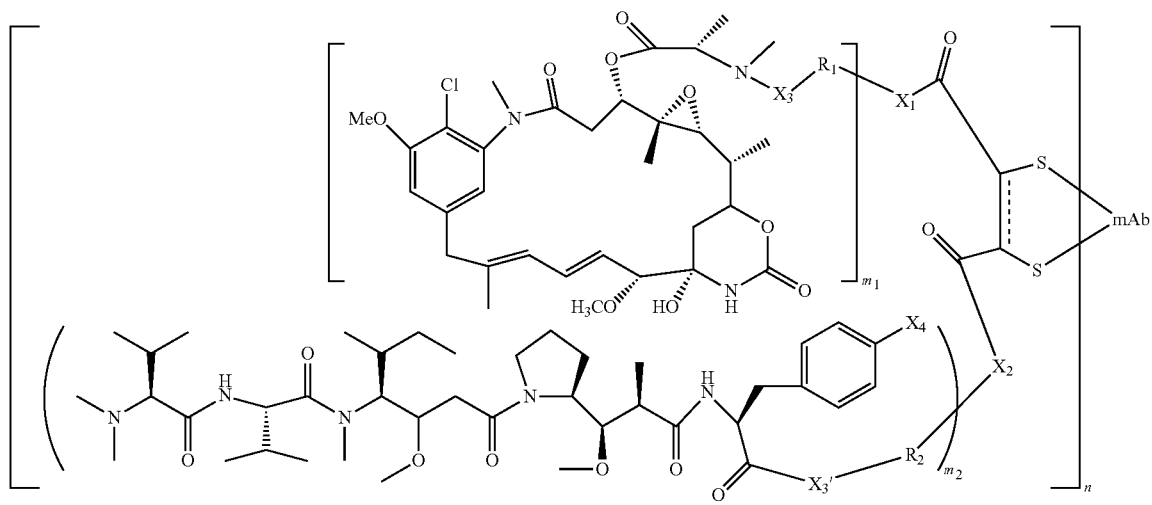
Z08

-continued
Z09
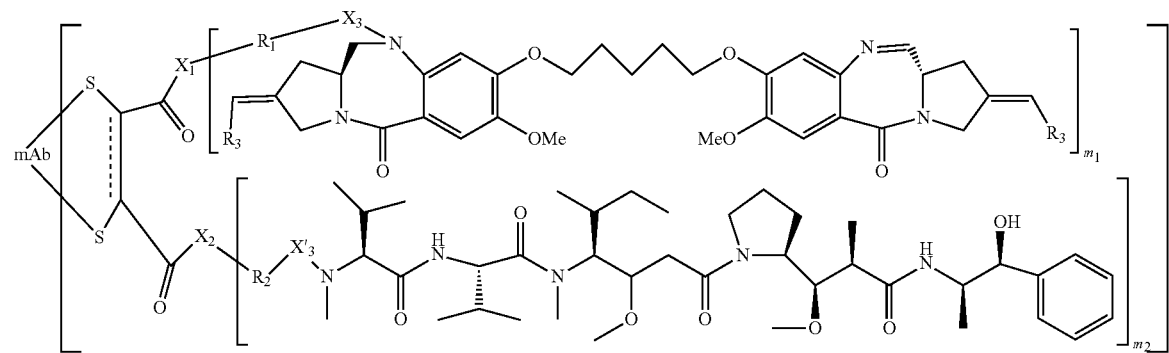
Z10
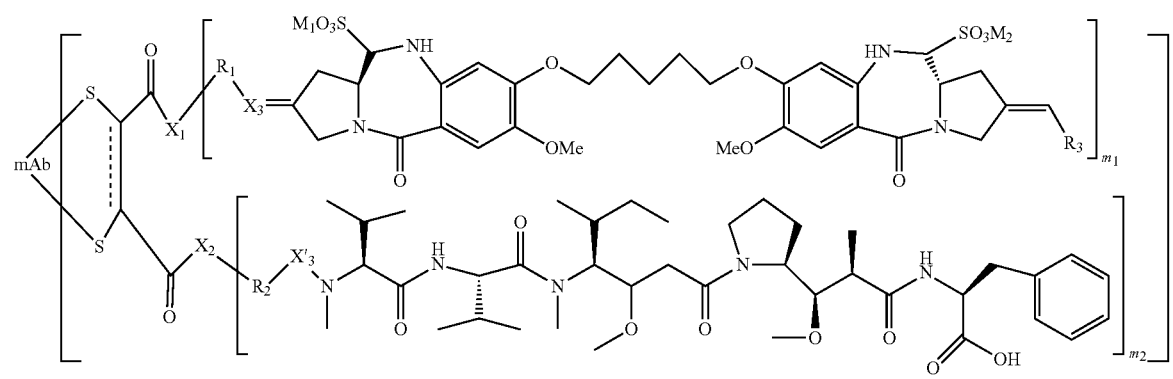
Z11
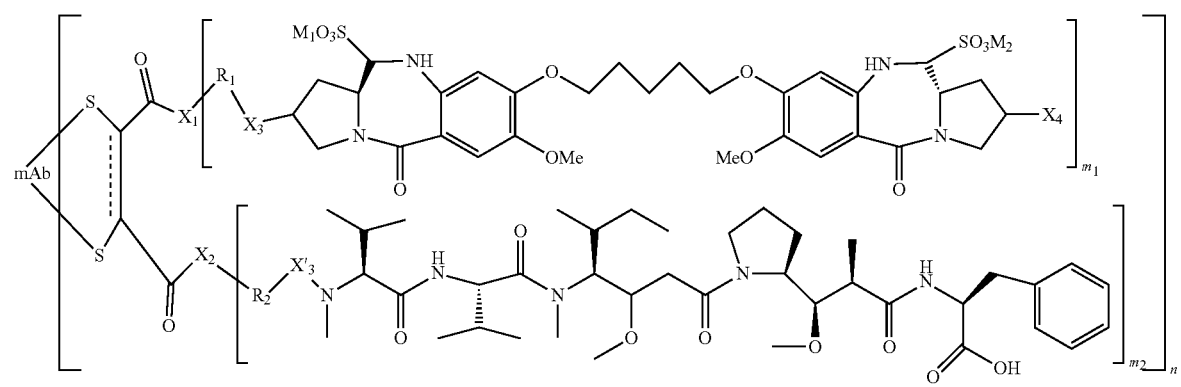
Z12
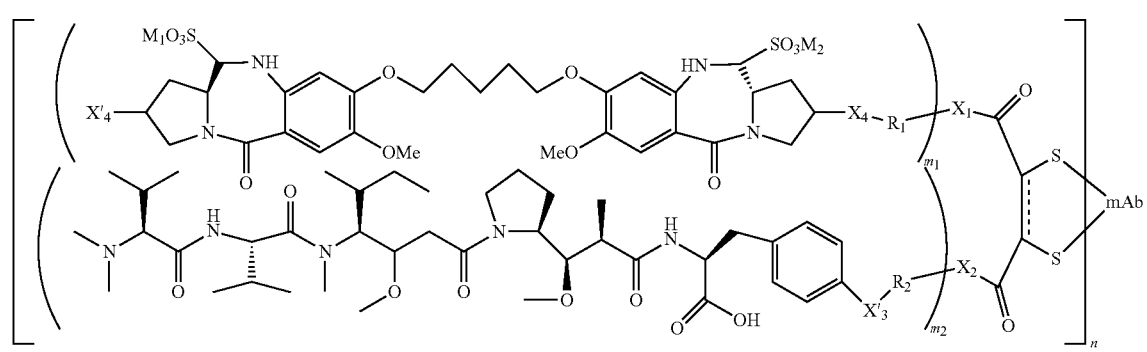

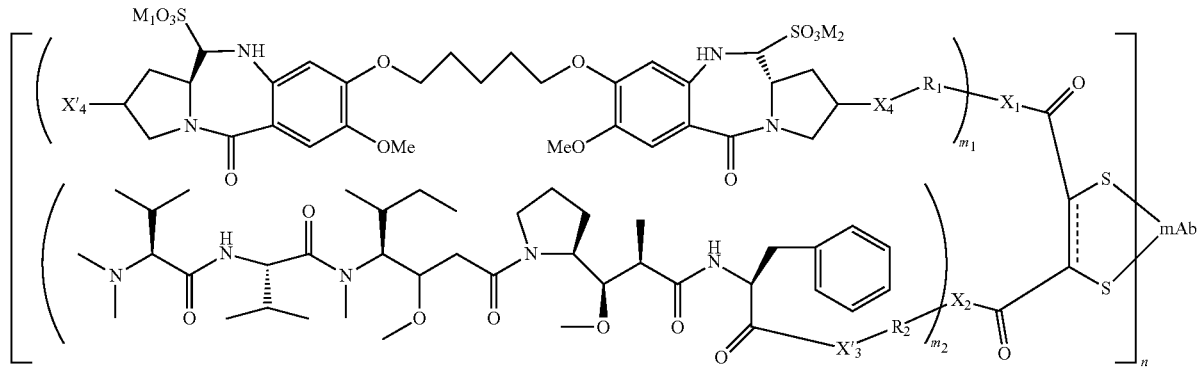
Z13
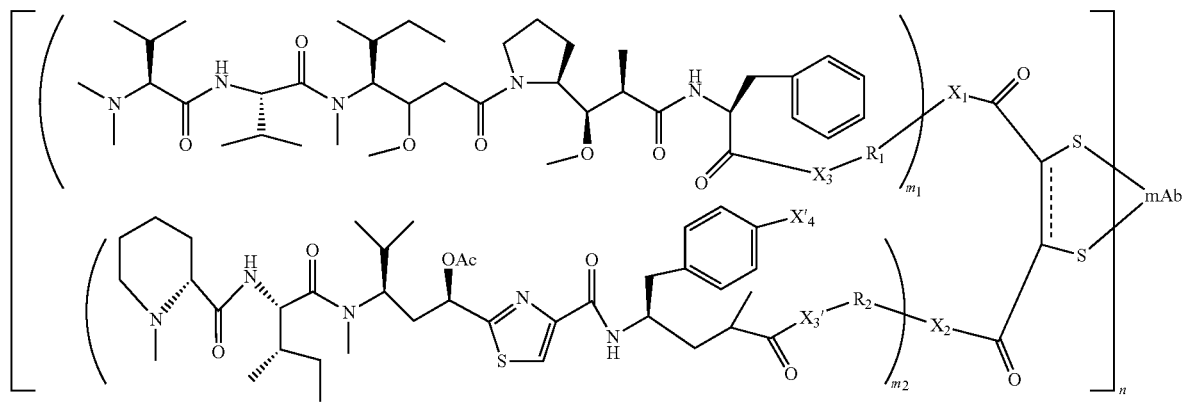
Z14
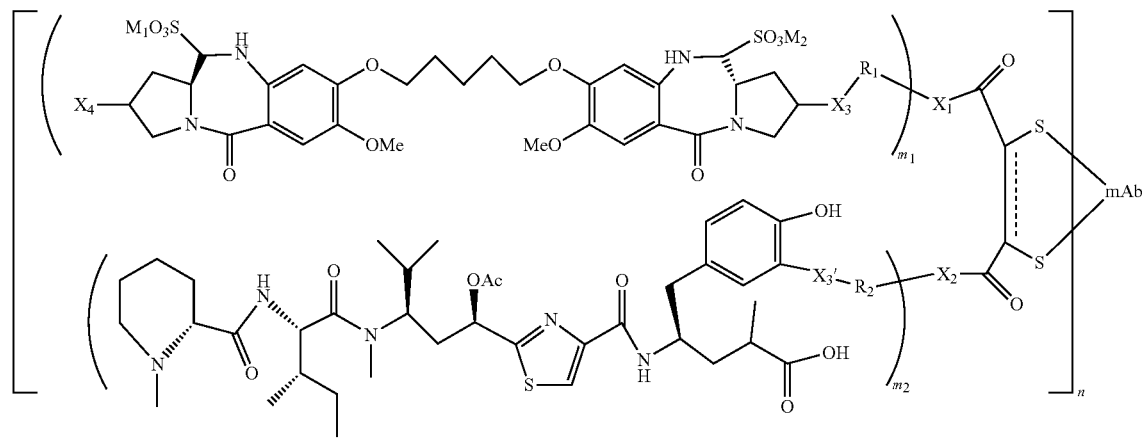
Z15

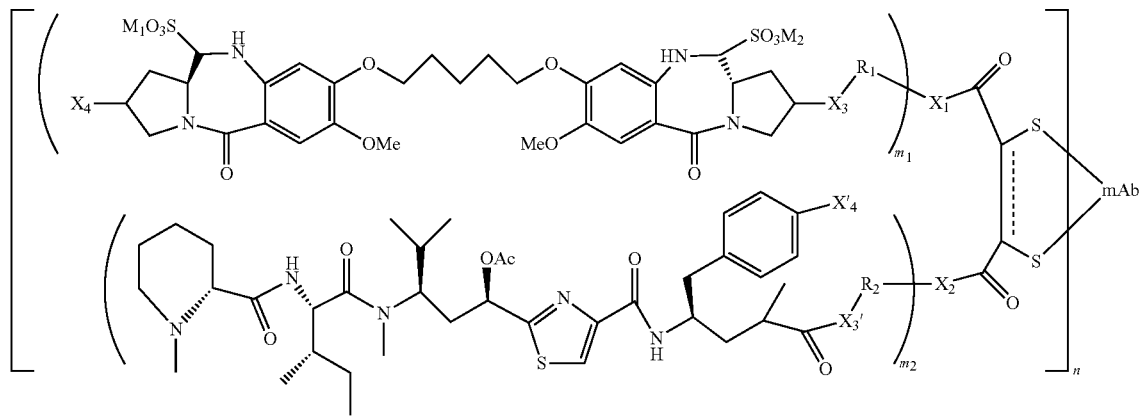
Z16
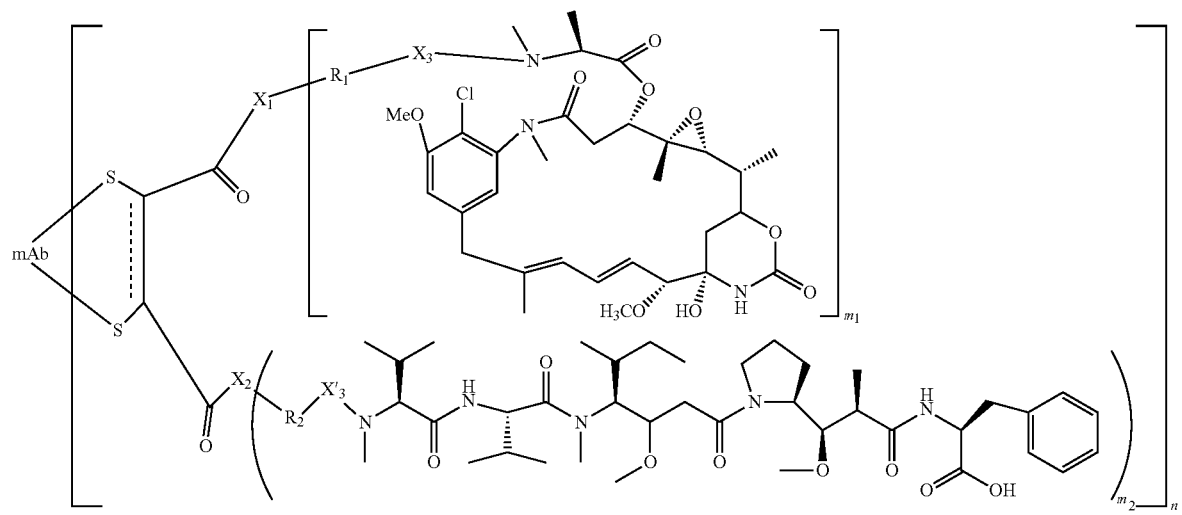
Z17
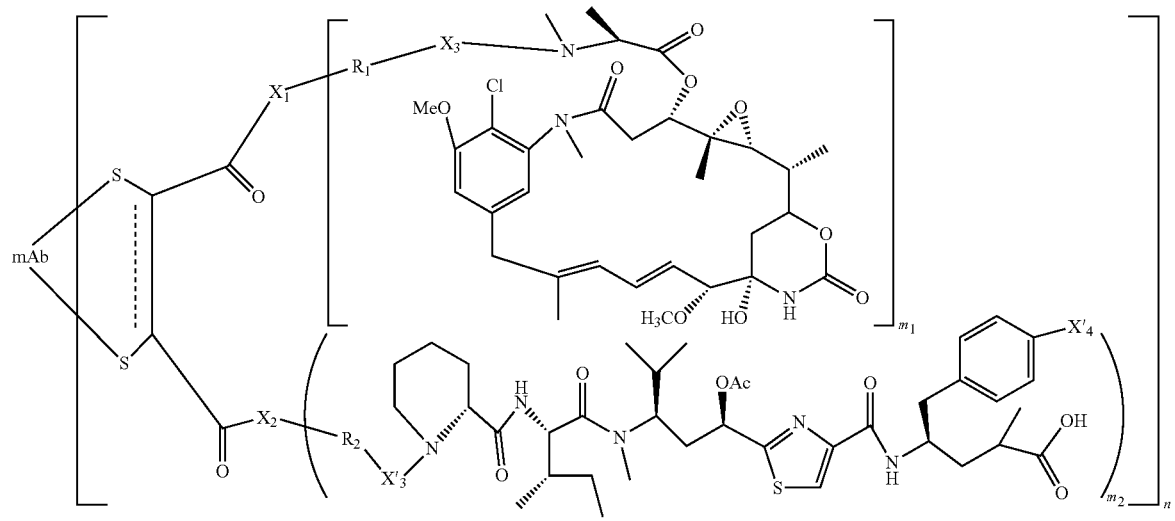
Z18

Wherein mAb is an antibody; $X_3$ and $X'_3$ are independently $CH_2$, O, NH, NHC(O), NHC(O)NH, C(O), OC(O), OC(O)($NR_3$), $R_1$, $NHR_1$, $NR_1$, C(O)$R_1$ or absent; $X_4$ and $X'_4$ are independently H, $CH_2$, OH, O, C(O), C(O)NH, C(O)N($R_1$), $R_1$, $NHR_1$, $NR_1$, C(O)$R_1$ or C(O)O; $M_1$ and $M_2$ are independently H, Na, K, Ca, Mg, $NH_4$, $NR_1R_2R_3$; n, $m_1$, $m_2$, " — ", " ═ ", $X_1$, $X_2$, $R_1$, $R_2$ and $R_3$ are the same defined in Formula (I) and (II). In addition, $R_1$ and/or $R_2$ can be absent independently.

In yet another embodiment, cell-binding ligands or cell receptor agonists can be conjugated to a cell-binding molecule via a bridge linker of this patent. These conjugated cell-binding ligands or cell receptor agonists, in particular, antibody-receptor conjugates, can be not only to work as a targeting conductor/director to deliver the conjugate to malignant cells, but also be used to modulate or co-stimulate a desired immune response or altering signaling pathways.

In the immunotherapy, the cell-binding ligands or receptor agonists are preferred to conjugate to an antibody of TCR (T cell receptors) T cell, or of CARs (chimeric antigen receptors) T cells, or of B cell receptor (BCR), or the cytotoxic cells. The cell-binding ligands or receptor agonists are selected, but not limited, from: Folate derivatives (binding to the folate receptor, a protein over-expressed in ovarian cancer and in other malignancies) (Low, P. S. et al 2008, Acc. Chem. Res. 41, 120-9); Glutamic acid urea derivatives (binding to the prostate specific membrane antigen, a surface marker of prostate cancer cells) (Hillier, S. M. et al, 2009, Cancer Res. 69, 6932-40); Somatostatin (also known as growth hormone-inhibiting hormone (GHIH) or somatotropin release-inhibiting factor (SRIF)) or somatotropin release-inhibiting hormone) and its analogues such as octreotide (Sandostatin) and lanreotide (Somatuline) (particularly for neuroendocrine tumors, GH-producing pituitary adenoma, paraganglioma, nonfunctioning pituitary adenoma, pheochromocytomas) (Ginj, M., et al, 2006, Proc. Natl. Acad. Sci. U.S.A. 103, 16436-41). In general, Somatostatin and its receptor subtypes (sst1, sst2, sst3, sst4, and sst5) have been found in many types of tumors, such as neuroendocrine tumors, in particular in GH-secreting pituitary adenomas (Reubi J. C., Landolt, A. M. 1984 J. Clin. Endocrinol Metab 59: 1148-51; Reubi J. C., Landolt A. M. 1987 J Clin Endocrinol Metab 65: 65-73; Moyse E, et al, J Clin Endocrinol Metab 61: 98-103) and gastroenteropancreatic tumors (Reubi J. C., et al, 1987 J Clin Endocrinol Metab 65: 1127-34; Reubi, J. C, et al, 1990 Cancer Res 50: 5969-77), pheochromocytomas (Epel-baum J, et al 1995 J Clin Endocrinol Metab 80:1837-44; Reubi J. C., et al, 1992 J Clin Endocrinol Metab 74: 1082-9), neuroblastomas (Prevost G, 1996 Neuroendocrinology 63:188-197; Moertel, C. L, et al 1994 Am J Clin Path 102:752-756), medullary thyroid cancers (Reubi, J. C, et al 1991 Lab Invest 64:567-573) small cell lung cancers (Sagman U, et al, 1990 Cancer 66:2129-2133), nonneuroendocrine tumors including brain tumors such as meningiomas, medulloblastomas, or gliomas (Reubi J. C., et al 1986 J Clin Endocrinol Metab 63: 433-8; Reubi J. C., et al 1987 Cancer Res 47: 5758-64; Fruhwald, M. C, et al 1999 Pediatr Res 45: 697-708), breast carcinomas (Reubi J. C., et al 1990 Int J Cancer 46: 416-20; Srkalovic G, et al 1990 J Clin Endocrinol Metab 70: 661-669), lymphomas (Reubi J. C., et al 1992, Int J Cancer 50: 895-900), renal cell cancers (Reubi J. C., et al 1992, Cancer Res 52: 6074-6078), mesenchymal tumors (Reubi J. C., et al 1996 Cancer Res 56: 1922-31), prostatic (Reubi J. C., et al 1995, J. Clin. Endocrinol Metab 80: 2806-14; et al 1989, Prostate 14:191-208; Halmos G, et al J. Clin. Endo-crinol Metab 85: 2564-71), ovarian (Halmos, G, et al, 2000 J Clin Endocrinol Metab 85: 3509-12; Reubi J. C., et al 1991 Am J Pathol 138:1267-72), gastric (Reubi J. C., et al 1999, Int J Cancer 81: 376-86; Miller, G. V, 1992 Br J Cancer 66: 391-95), hepatocellular (Kouroumalis E, et al 1998 Gut 42: 442-7; Reubi J. C., et al 1999 Gut 45: 66-774) and nasopharyngeal carcinomas (Loh K. S, et al, 2002 Virchows Arch 441: 444-8); certain Aromatic sulfonamides, specific to carbonic anhydrase IX (a marker of hypoxia and of renal cell carcinoma) (Neri, D., et al, Nat. Rev. Drug Discov. 2011, 10, 767-7); Pituitary adenylate cyclase activating peptides (PACAP) (PAC1) for pheochromocytomas and paragangliomas; Vasoactive intestinal peptides (VIP) and their receptor subtypes (VPAC1, VPAC2) for cancers of lung, stomach, colon, rectum, breast, prostate, pancreatic ducts, liver, urinary bladder and epithelial tumors; α-Melanocyte-stimulating hormone (α-MSH) receptors for various tumors; Cholecystokinin (CCK)/gastrin receptors and their receptor subtypes (CCK1 (formerly CCK-A) and CCK2 for small cell lung cancers, medullary thyroid carcinomas, astrocytomas, insulinomas and ovarian cancers; Bombesin(Pyr-Gln-Arg-Leu-Gly-Asn-Gln-Trp-Ala-Val-Gly-His-Leu-Met-$NH_2$)/gastrin-releasing peptide (GRP) and their receptor subtypes (BB1, GRP receptor subtype (BB2), the BB3 and BB4) for renal cell, breast, lung, gastric and prostate carcinomas, and neuroblastoma (and neuroblastoma (Ohlsson, B., et al, 1999, Scand. J. Gastroenterology 34 (12): 1224-9; Weber, H. C., 2009, Cur. Opin. Endocri. Diab. Obesity 16(1): 66-71, Gonzalez N, et al, 2008, Cur, Opin. Endocri. Diab. Obesity 15(1), 58-64); Neurotensin receptors and its receptor subtypes (NTR1, NTR2, NTR3) for small cell lung cancer, neuroblastoma, pancreatic, colonic cancer and Ewing sarcoma; Substance P receptors and their receptor subtypes (such as NK1 receptor for Glial tumors, Hennig I. M., et al 1995 Int. J. Cancer 61, 786-792); Neuropeptide Y (NPY) receptors and its receptor subtypes (Y1-Y6) for breast carcinomas; Homing Peptides include RGD (Arg-Gly-Asp), NGR (Asn-Gly-Arg), the dimeric and multimeric cyclic RGD peptides (e.g. cRGDfV) that recognize receptors (integrins) on tumor surfaces (Laakkonen P, Vuorinen K. 2010, Integr Biol (Camb). 2(7-8): 326-337; Chen K, Chen X. 2011, Theranostics. 1:189-200; Garanger E, et al, Anti-Cancer Agents Med Chem. 7 (5): 552-558; Kerr, J. S. et al, Anticancer Research, 19(2A), 959-968; Thumshim, G, et al, 2003 Chem. Eur. J. 9, 2717-2725), and TAASGVRSMH or LTLRWVGLMS (chondroitin sulfate proteoglycan NG2 receptor) and F3 peptides (31 amino acid peptide that binds to cell surface-expressed nucleolin receptor) (Zitzmann, S., 2002 Cancer Res., 62, 18, pp. 5139-5143, Temminga, K., 2005, Drug Resistance Updates, 8, 381-402; P. Laakkonen and K. Vuorinen, 2010 Integrative Biol, 2(7-8), 326-337; M. A. Burg, 1999 Cancer Res., 59(12), 2869-2874; K. Porkka, et al 2002, Proc. Nat. Acad. Sci. USA 99(11), 7444-9); Cell Penetrating Peptides (CPPs) (Nakase I, et al, 2012, J. Control Release. 159(2), 181-188); Peptide Hormones, such as luteinizing hormone-releasing hormone (LHRH) agonists and antagonists, and gonadotropin-releasing hormone (GnR1-1) agonist, acts by targeting follicle stimulating hormone (FSH) and luteinising hormone (LH), as well as testosterone production, e.g. buserelin (Pyr-His-Trp-Ser-Tyr-D-Ser(OtBu)-Leu-Arg-Pro-NHEt), Gonadorelin (Pyr-His-Trp-Ser-Tyr-Gly-Leu-Arg-Pro-Gly-$NH_2$), Goserelin (Pyr-His-Trp-Ser-Tyr-D-Ser(OtBu)-Leu-Arg-Pro-AzGly-$NH_2$), Histrelin (Pyr-His-Trp-Ser-Tyr-D-His(N-benzyl)-Leu-Arg-Pro-NHEt), leuprolide (Pyr-His-Trp-Ser-Tyr-D-Leu-Leu-Arg-Pro-NHEt), Nafarelin (Pyr-His-Trp-Ser-Tyr-2Nal-Leu-Arg-Pro-Gly-$NH_2$), Triptorelin (Pyr-His-Trp-Ser-Tyr-D-Trp-Leu-Arg-Pro-Gly-$NH_2$), Nafarelin, Deslorelin, Abarelix (Ac-D-2Nal-D-4-chloroPhe-D-3-(3-pyridyl)Ala-Ser-(N-Me)Tyr-D-Asn-Leu-isopropylLys-Pro-DAla-NH$_2$), Cetrorelix (Ac-D-2Nal-D-4-chloro-Phe-D-3-(3-pyridyl)Ala-Ser-Tyr-D-Cit-Leu-Arg-Pro-D-Ala-NH$_2$), Degarelix (Ac-D-2Nal-D-4-chloroPhe-D-3-(3-pyridyl)Ala-Ser-4-aminoPhe(L-hydroorotyl)-D-4-aminoPhe(carba-moyl)-Leu-isopropylLys-Pro-D-Ala-NH$_2$), and Ganirelix (Ac-D-2Nal-D-4-chloroPhe-D-3-(3-pyridyl)Ala-Ser-Tyr-D-(N9,N10-diethyl)-homoArg-Leu-(N9,N10-diethyl)-homoArg-Pro-D-Ala-NH$_2$) (Thundimadathil, J., J. Amino Acids, 2012, 967347, doi:10.1155/2012/967347; Boccon-Gibod, L.; et al, 2011, Therapeutic Advances in Urology 3(3): 127-140; Debruyne, F., 2006, Future Oncology, 2(6), 677-696; Schally A. V; Nagy, A. 1999 Eur J Endocrinol 141:1-14; Koppan M, et al 1999 Prostate 38:151-158); and Pattern Recognition Receptors (PRRs), such as Toll-like receptors (TLRs), C-type lectins and Nodlike Receptors (NLRs) (Fukata, M., et al, 2009, Semin. Immunol. 21, 242-253; Maisonneuve, C., et al, 2014, Proc. Natl. Acad. Sci. U.S.A 111, 1-6; Botos, I., et al, 2011, Structure 19, 447-459; Means, T. K., et al, 2000, Life Sci. 68, 241-258) that range in size from small molecules (imiquimod, guanisine and adenosine analogs) tolarge and complex biomacromolecules such as lipopolysaccharide (LPS), nucleic acids (CpG DNA, polyI:C) and lipopeptides (Pam3CSK4) (Kasturi, S. P., et al, 2011, Nature 470, 543-547; Lane, T., 2001, J. R. Soc. Med. 94, 316; Hotz, C., and Bourquin, C., 2012, Oncoimmunology 1, 227-228; Dudek, A. Z., et al, 2007, Clin. Cancer Res. 13, 7119-25); Calcitonin receptors which is a 32-amino-acid neuropeptide involved in the regulation of calcium levels largely through its effects on osteoclasts and on the kidney (Zaidi M, et al, 1990 Crit Rev Clin Lab Sci 28, 109-174; Gorn, A. H., et al 1995 J Clin Invest 95:2680-91); And integrin receptors and their receptor subtypes (such as $\alpha v\beta_1$, $\alpha v\beta_3$, $\alpha v\beta_5$, $\alpha v\beta_6$, $\alpha_6\beta_4$, $\alpha_7\beta_1$, $\alpha_L\beta_2$, $\alpha_{IIb}\beta_3$, etc) which generally play important roles in angiogenesis are expressed on the surfaces of a variety of cells, in particular, of osteoclasts, endothelial cells and tumor cells (Ruoslahti, E. et al, 1994 Cell 77, 477-8; Albelda, S. M. et al, 1990 Cancer Res., 50, 6757-64). Short peptides, GRGDSPK and Cyclic RGD pentapeptides, such as cyclo(RGDfV) (L1) and its derives [cyclo(-N(Me)R-GDfV), cyclo(R-Sar-DfV), cyclo-(RG-N(Me)D-fV), cyclo(RGD-N(Me)f-V), cyclo(RGDf-N(Me)V-)(Cilengitide)] have shown high binding affinities of the intergrin receptors (Dechantsreiter, M. A. et al, 1999 J. Med. Chem. 42, 3033-40, Goodman, S. L., et al, 2002 J. Med. Chem. 45, 1045-51).

The cell-binding ligands or cell receptor agonists can be Ig-based and non-Ig-based protein scaffold molecules. The Ig-Based scaffolds can be selected, but not limited, from Nanobody (a derivative of VHH (camelid Ig)) (Muyldermans S., 2013 Annu Rev Biochem. 82, 775-97); Domain antibodies (dAb, a derivative of VH or VL domain) (Holt, L. J, et al, 2003, Trends Biotechnol. 21, 484-90); Bispecific T cell Engager (BiTE, a bispecific diabody) (Baeuerle, P. A, et al, 2009, Curr. Opin. Mol. Ther. 11, 22-30); Dual Affinity ReTargeting (DART, a bispecific diabody) (Moore P. A. P, et al. 2011, Blood 117(17), 4542-51); Tetravalent tandem antibodies (TandAb, a dimerized bispecific diabody) (Cochlovius, B, et al. 2000, Cancer Res. 60(16):4336-4341). The Non-Ig scaffolds can be selected, but not limited, from Anticalin (a derivative of Lipocalins) (Skerra A. 2008, FEBS J., 275(11): 2677-83; Beste G, et al, 1999 Proc. Nat. Acad. USA. 96(5):1898-903; Skerra, A. 2000 Biochim Biophys Acta, 1482(1-2): 337-50; Skerra, A. 2007, Curr Opin Biotechnol. 18(4): 295-304; Skerra, A. 2008, FEBS J. 275(11): 2677-83); Adnectins (10th FN3 (Fibronectin)) (Koide, A, et al, 1998 J. Mol. Biol., 284(4):1141-51; Batori V, 2002, Protein Eng. 15(12): 1015-20; Tolcher, A. W, 2011, Clin. Cancer Res. 17(2): 363-71; Hackel, B. J, 2010, Protein Eng. Des. Sel. 23(4): 211-19); Designed Ankyrin Repeat Proteins (DARPins) (a derivative of ankrin repeat (AR) proteins) (Boersma, Y. L, et al, 2011 Curr Opin Biotechnol. 22(6): 849-57), e.g. DARPin C9, DARPin Ec4 and DARPin E69_LZ3_E01 (Winkler J, et al, 2009 Mol Cancer Ther. 8(9), 2674-83; Patricia M-K. M., et al, Clin Cancer Res. 2011; 17(1):100-10; Boersma Y. L, et al, 2011 J. Biol. Chem. 286(48), 41273-85); Avimers (a domain A/low-density lipoprotein (LDL) receptor) (Boersma Y. L, 2011 J. Biol. Chem. 286(48): 41273-41285; Silverman J, et al, 2005 Nat. Biotechnol., 23(12):1556-61).

Examples of the structures of the conjugate of the antibody-cell-binding ligands or cell receptor agonists via the bridge linker are as the following: LB01 (PMSA ligand conjugate), LB02 (Folate conjugate), LB03 (Somatostatin conjugate), LB04 (Octreotide, a Somatostatin analog conjugate), LB05 (Lanreotide, a Somatostatin analog conjugate), LB06 (Vapreotide (Sanvar), a Somatostatin analog conjugate), LB07 (CAIX ligand conjugate), LB08 (CAIX ligand conjugate), LB09 (luteinizing hormone-releasing hormone (LH-RH) ligand and GnRH conjugate), LB10 (luteinizing hormone-releasing hormone (LH-RH) and GnRH ligand conjugate), LB11 (GnRH antagonist, Abarelix conjugate), LB12 (cobalamin, VB12 analog conjugate), LB13 (Gastrin releasing peptide receptor (GRPr), MBA conjugate), LB14 (for $\alpha_v\beta_3$ integrin receptor, cyclic RGD pentapeptide conjugate), LB15 (hetero-bivalent peptide ligand conjugate for VEGF receptor), LB16 (Neuromedin B conjugate), LB17 (bombesin conjugate for a G-protein coupled receptor), LB18 (TLR$_2$ conjugate for a Toll-like receptor), LB19 (for an androgen receptor), LB20 (Cilengitide/cyclo(-RGDfV-) conjugate for an $\alpha_v$ intergrin receptor) and LB21-LB29 (Glucocorticoids' conjugates for glucocorticoid receptor (GR, or GCR) also known as NR3C1 (nuclear receptor subfamily 3, group C, member 1).

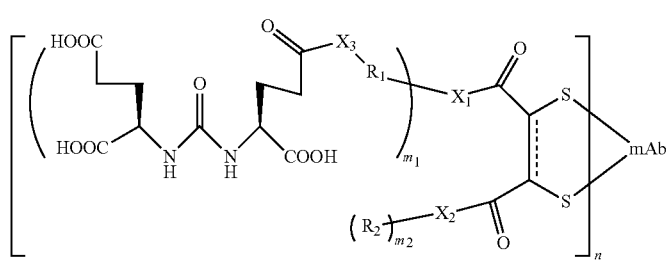

LB01

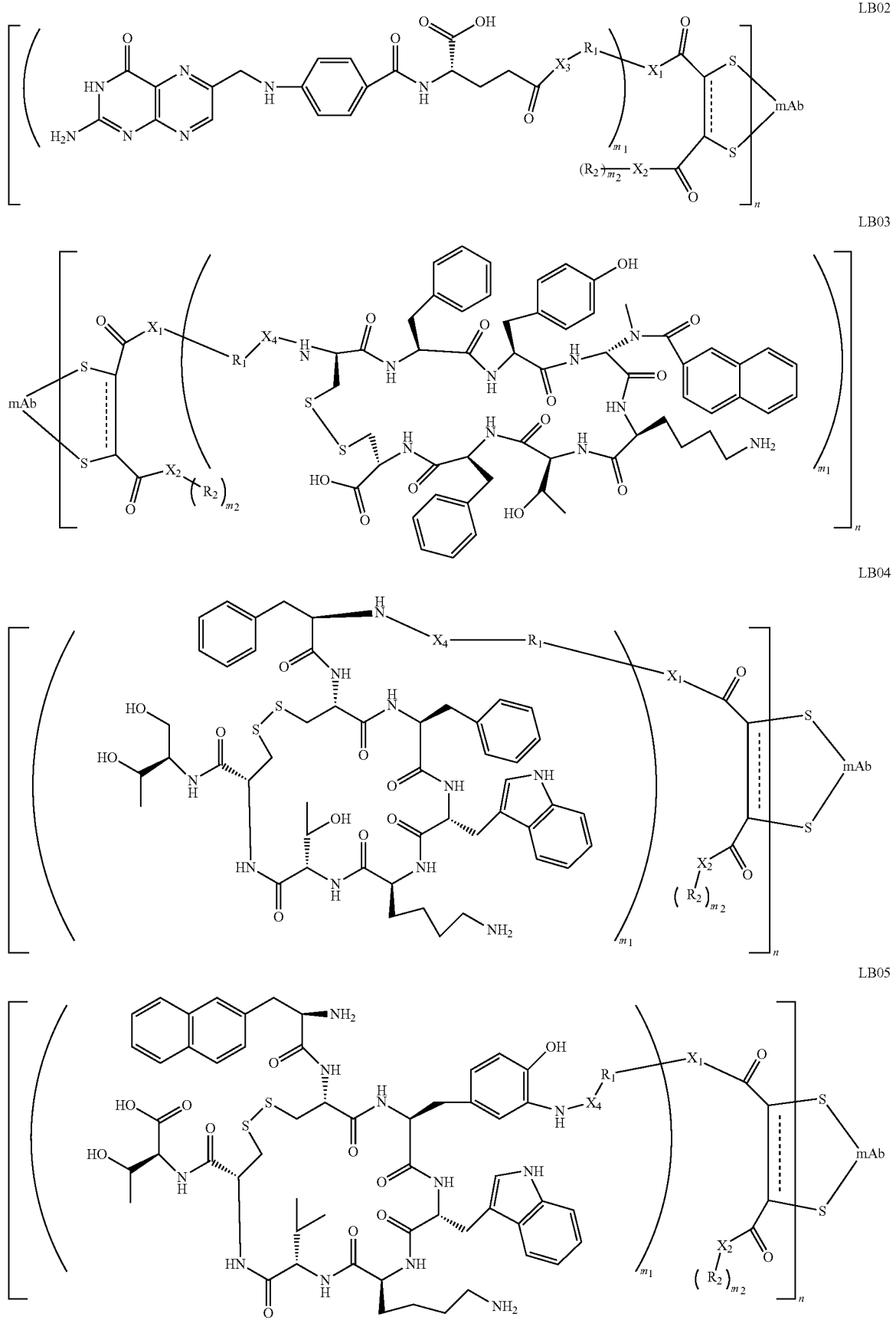

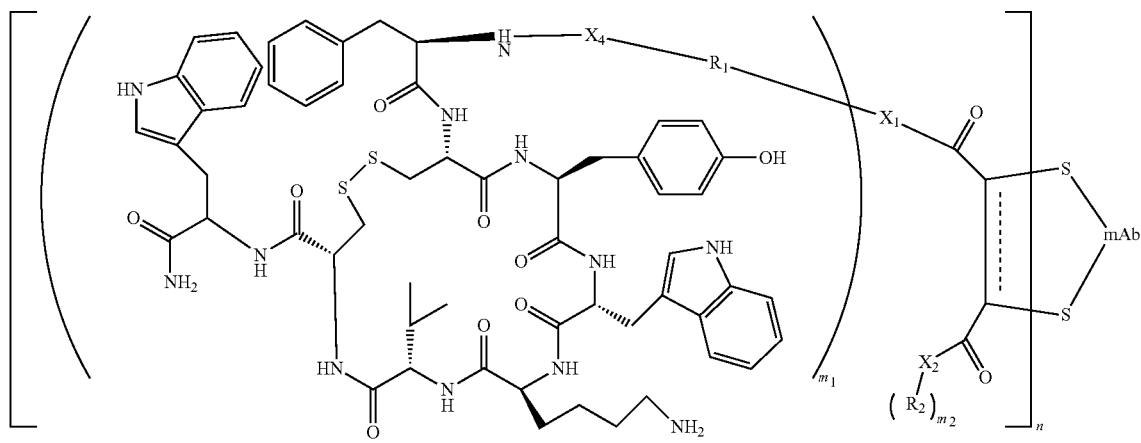
LB06
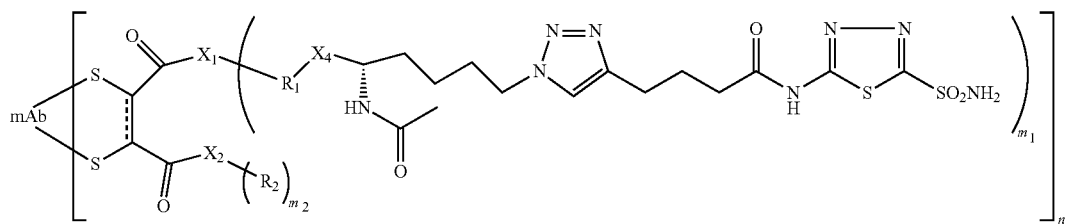
LB07
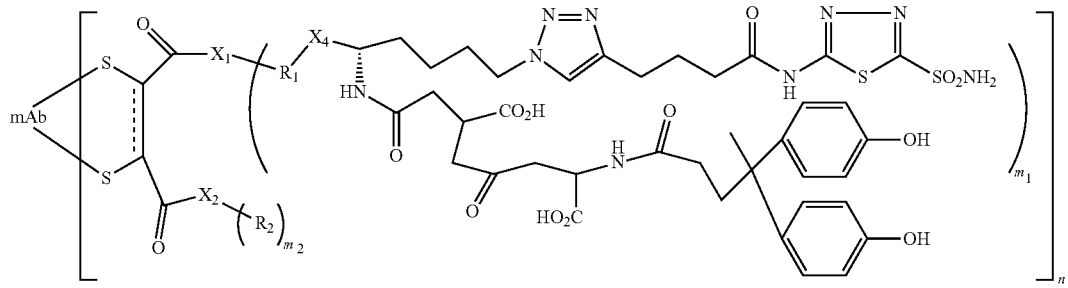
LB08
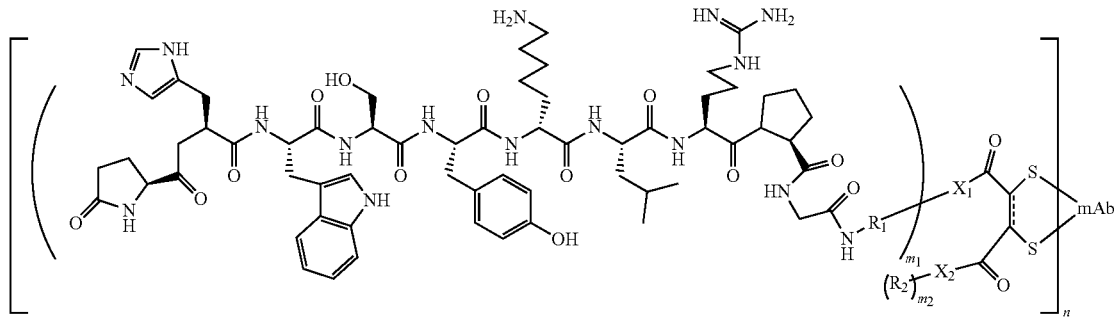
LB09

-continued
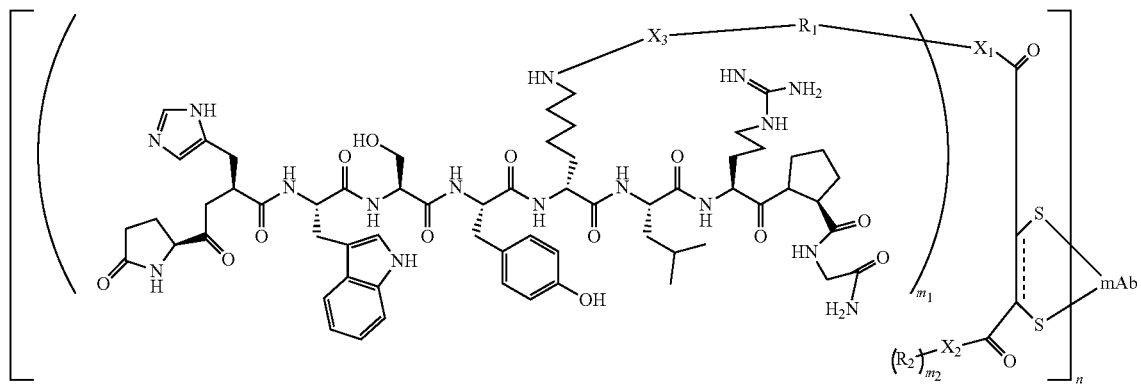
LB10
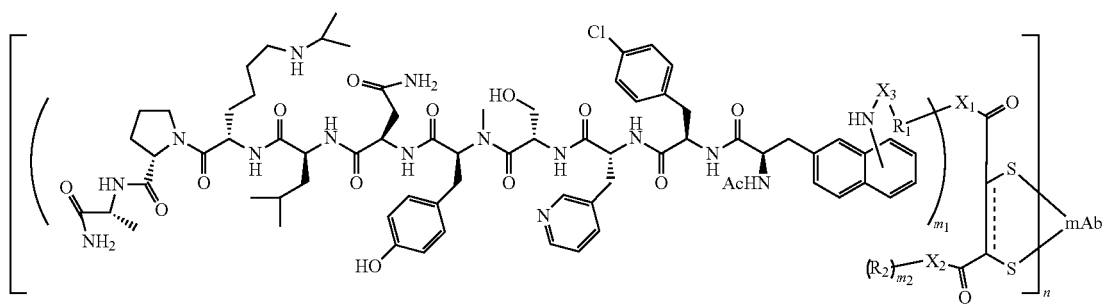
LB11
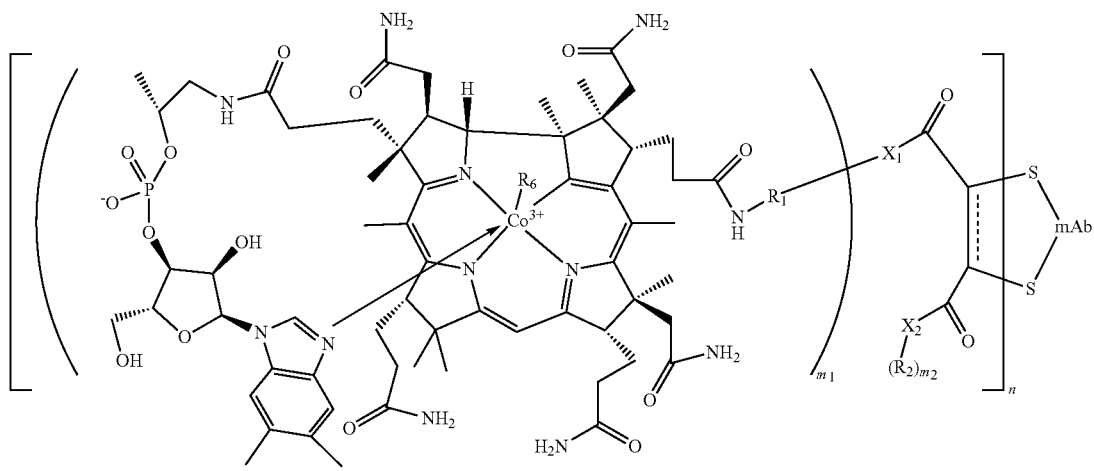
LB12
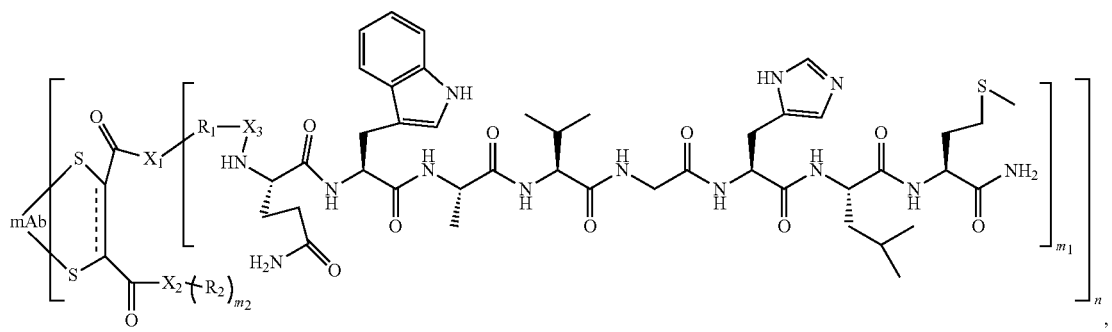
LB13
, -continued
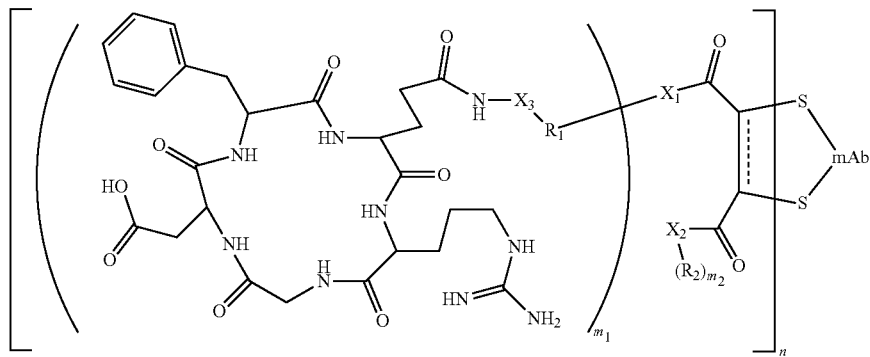
LB14
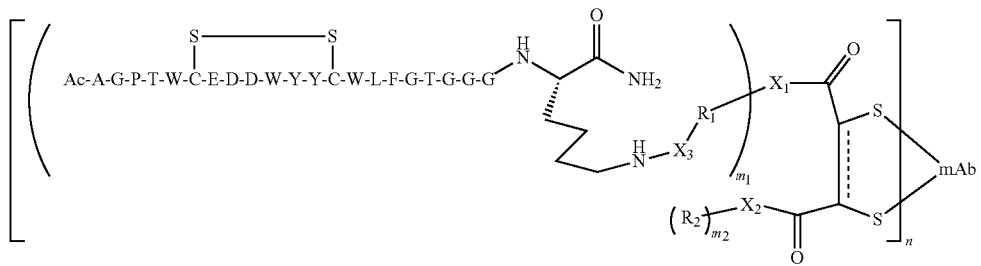
LB15
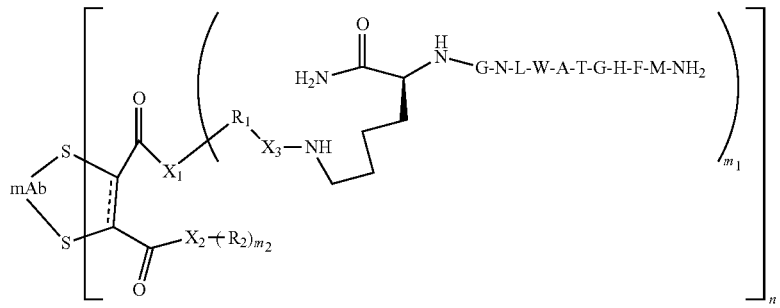
LB16
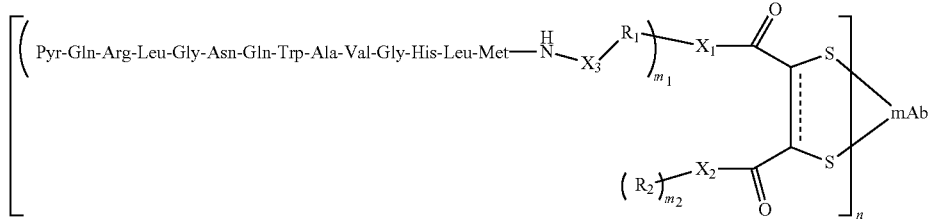
LB17
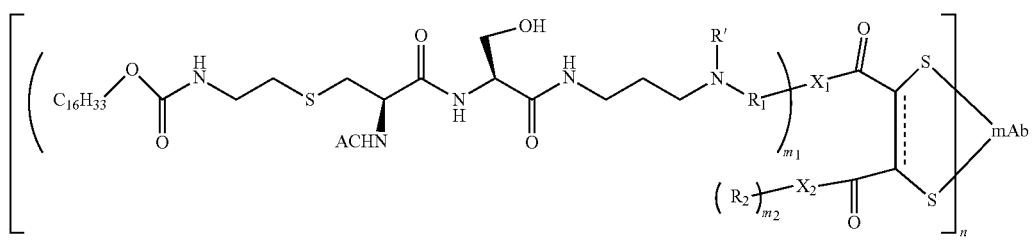
LB18

-continued
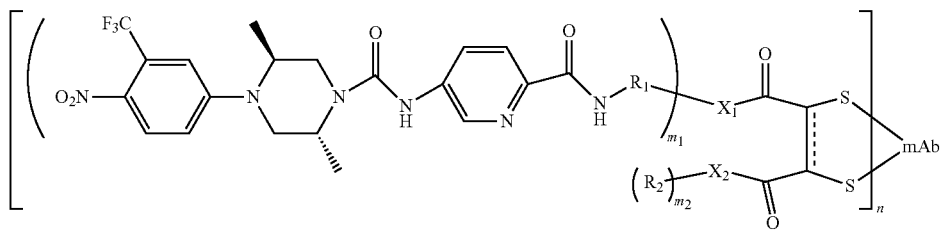
LB19
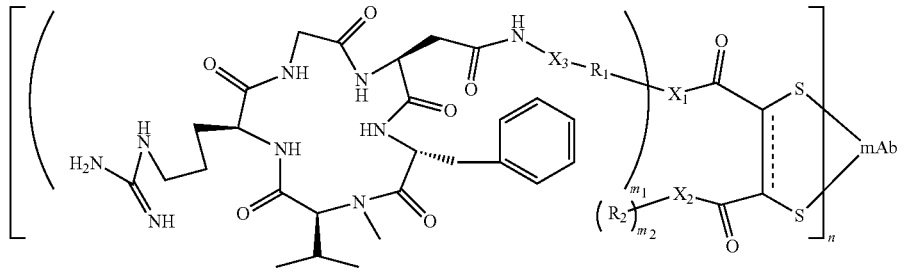
LB20
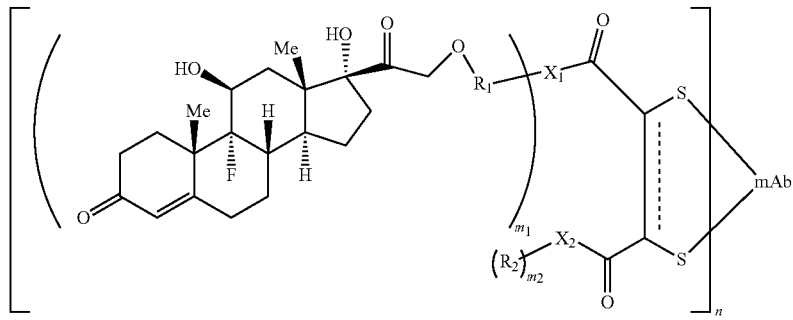
LB21
(Fludrocortisone conjugate)
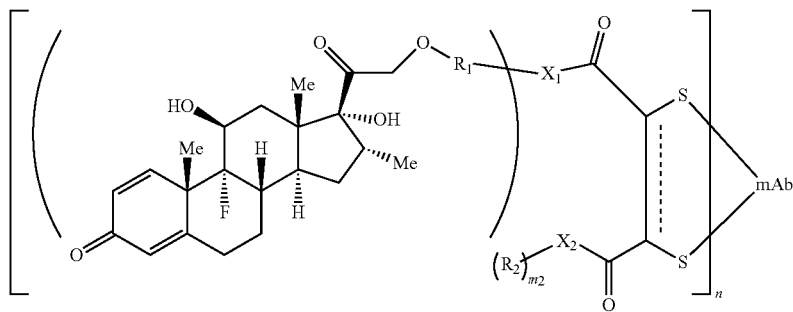
LB22
(Dexamethasone conjugate)
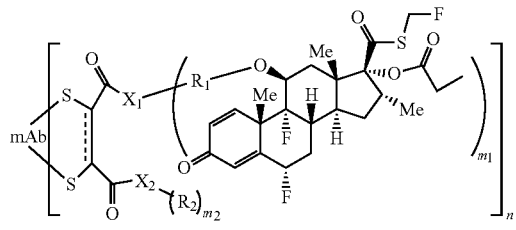
LB23
(fluticasone propionate conjugate)
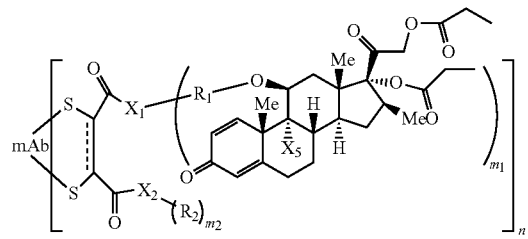
LB24
(Beclometasone dipropionate)

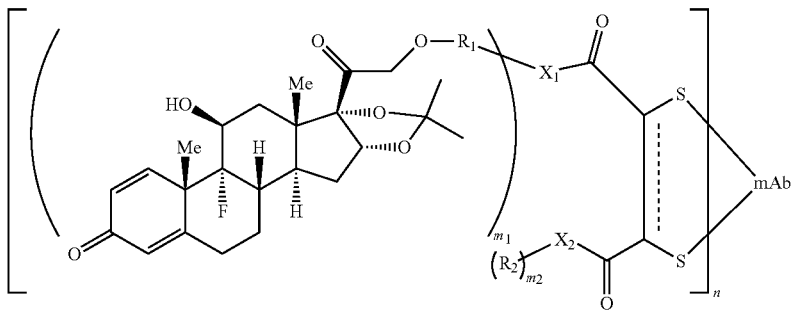
(Triamcinolone acetonide conjugate) LB25
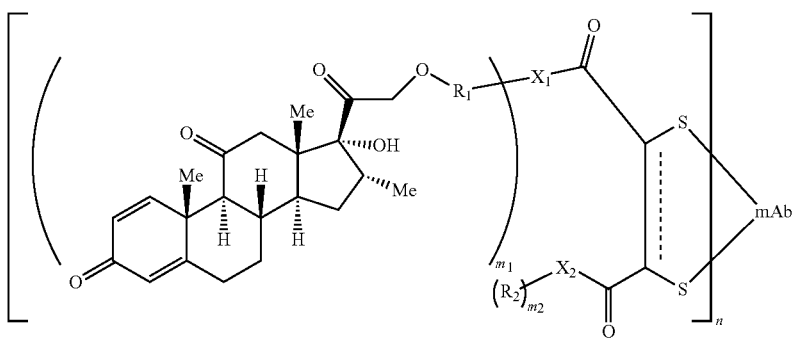
(Prednisone conjugate) LB26
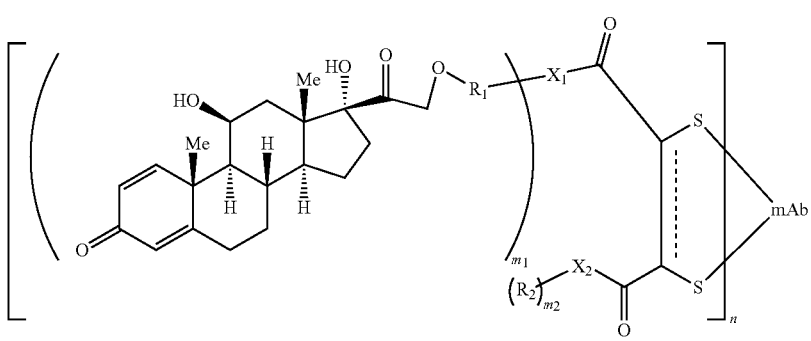
(Prednisolone conjugate) LB27
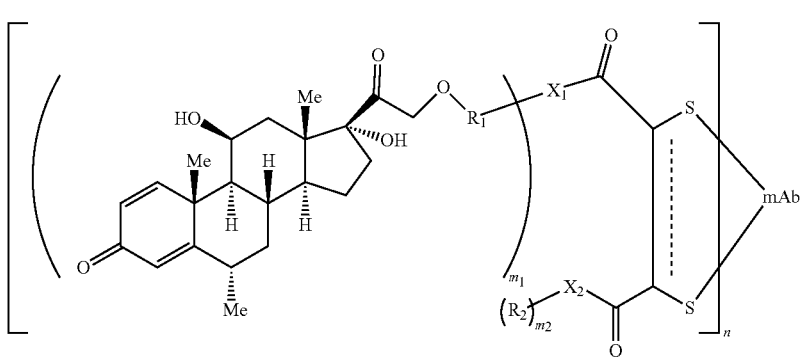
(Methylprednisolone conjugate) LB28

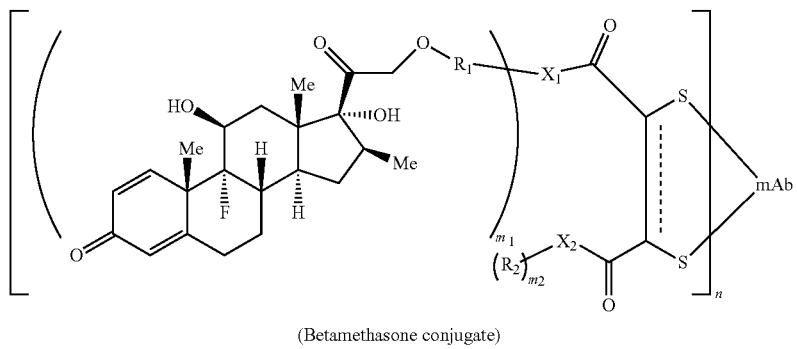

(Betamethasone conjugate)

LB29

Wherein mAb is an antibody; $X_3$ is $CH_2$, O, NH, NHC(O), NHC(O)NH, C(O), OC(O), OC(O)(NR$_3$), $R_1$, NHR$_1$, NR$_1$, C(O)R$_1$ or absent; $X_4$ is H, $CH_2$, OH, O, C(O), C(O)NH, C(O)N(R$_1$), $R_1$, NHR$_1$, NR$_1$, C(O)R$_1$ or C(O)O; $X_5$ is H, $CH_3$, F, or Cl; $M_1$ and $M_2$ are independently H, Na, K, Ca, Mg, $NH_4$, $NR_1R_2R_3$; $R_6$ is 5'-deoxyadenosyl, Me, OH, or CN; "═" represents either single bond or double bond; $m_1$, $m_2$, n, "—", $X_1$, $X_2$, $R_1$, and $R_2$ are the same defined in Formula (I). In addition, $R_1$ can be absent and $R_2$ can be H.

Figure 37A:
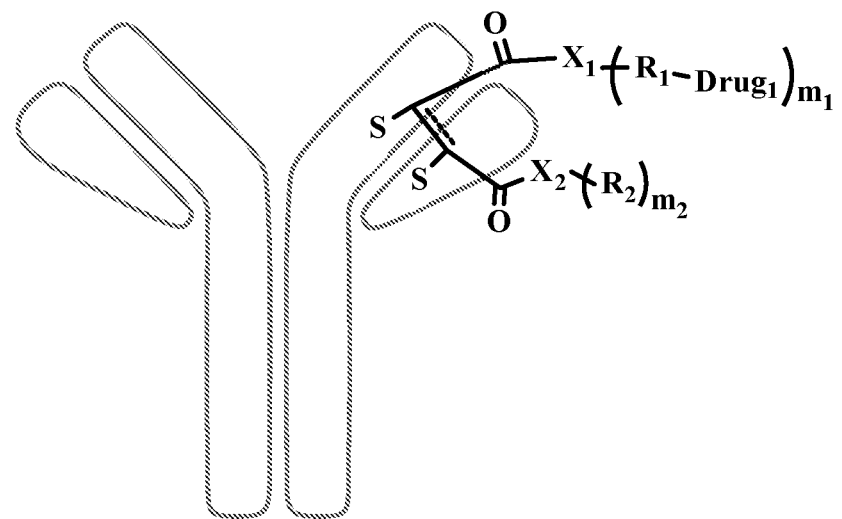
FIGS. 37A to 37C show exemplary conjugate structures ST1, ST2, ST3, ST4, ST5, ST6, ST7 and ST8.
Figure 37A:
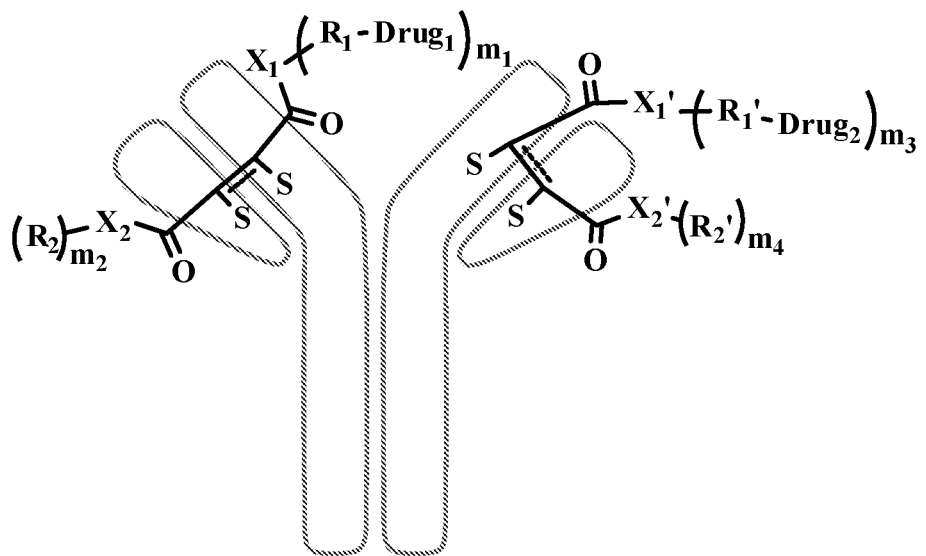
Figure 37A:
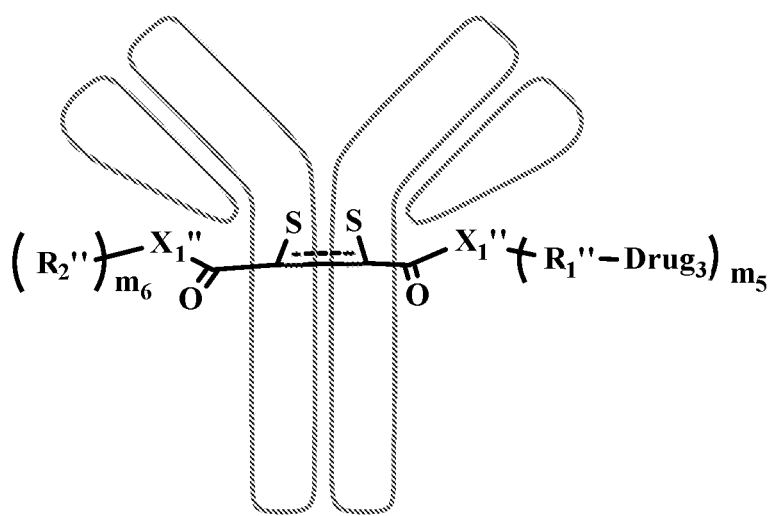
Figure 37B:
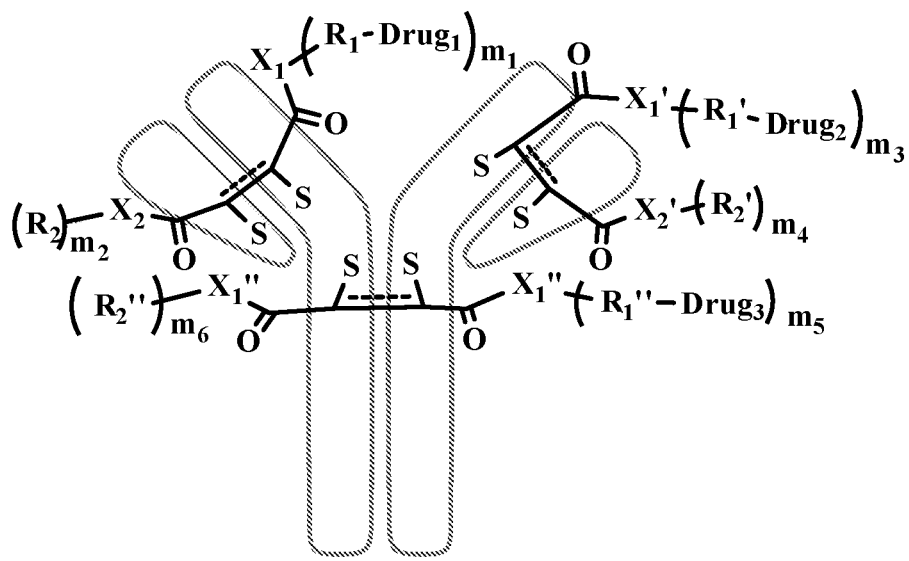
Figure 37B:
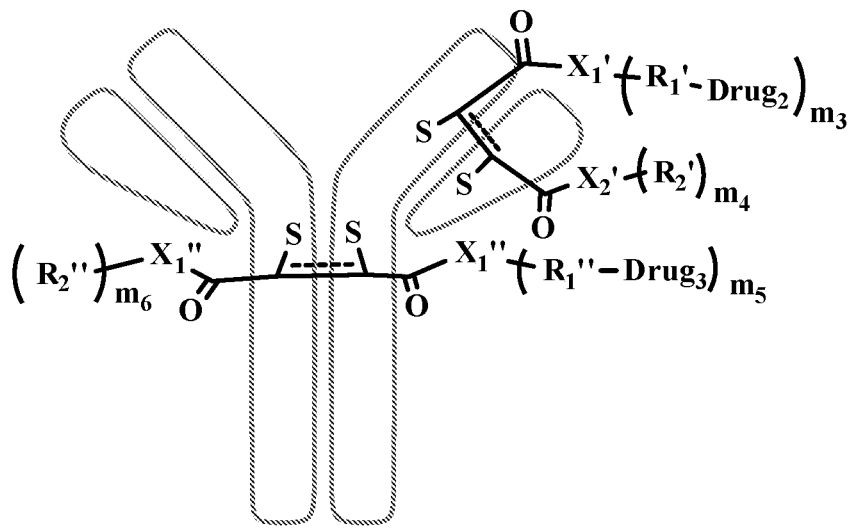
Figure 37B:
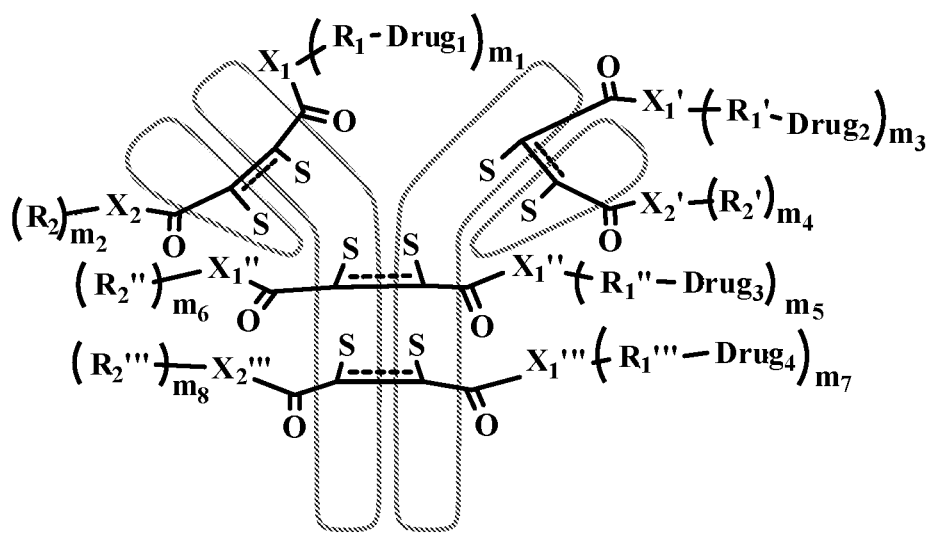
Figure 37C:
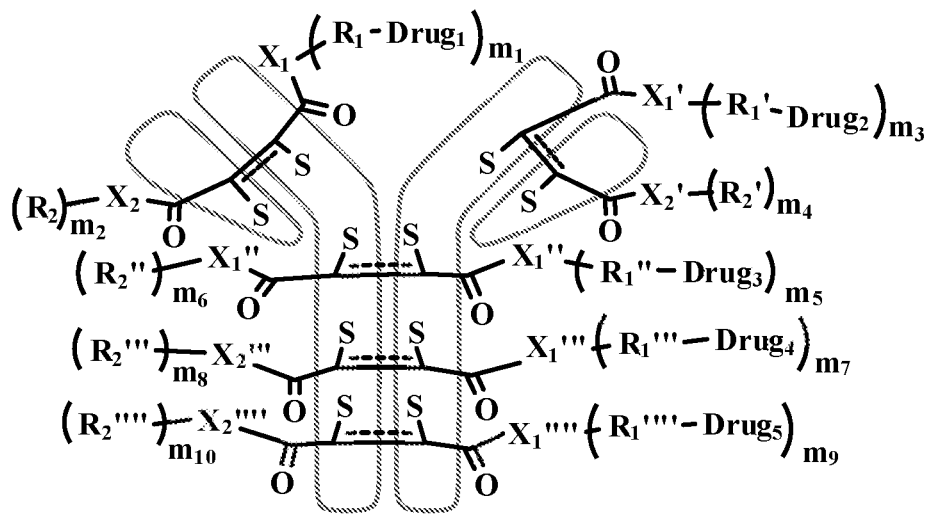
Figure 37C:
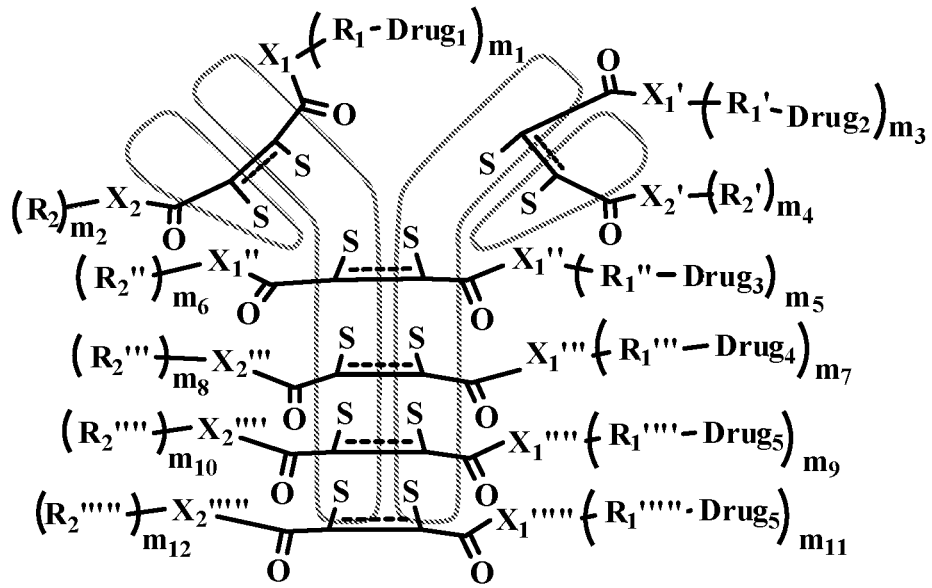

In yet another embodiment, IgG antibody conjugates conjugated with one, or two, or more differently function molecules or drugs are preferred to be conjugated specifically to a pair of thiols (through reduction of the disulfide bonds) between the light chain and heavy chain, the upper disulfide bonds between the two heavy chains, and the lower disulfide bonds between the two heavy chains as shown in structure, ST1, ST2, ST3, ST4, ST5, ST6, ST7 or ST8 of FIGS. 37A to 37C.

In structures ST1, ST2, ST3, ST4, ST5, ST6, ST7 and ST8, $R_1$, $R_1'$, $R_1''$, $R_1'''$, $R_1''''$, and $R_1'''''$ are independently defined as $R_1$ which is described the same in Formula (I); Wherein $R_2'$, $R_2''$, $R_2'''$, $R_2''''$, and $R_2'''''$ are independently defined as $R_2$ which is described the same in Formula (I); $X_1'$, $X_1''$, $X_1'''$, $X_1''''$, and $X_1'''''$ are independently defined as $X_1$ which is described in claim Formula (I); $X_2'$, $X_2''$, $X_2'''$, $X_2''''$, and $X_2'''''$ are independently defined as $X_2$ which is described the same in claim Formula (I); "═" represents either single bond or double bond; $m_1$, $m_2$, $m_3$, $m_4$, $m_5$, $m_6$, $m_7$ and $m_8$ are independently an integer from 1 to 30, preferably from 1 to 10; Drug$_1$, Drug$_2$, Drug$_3$, Drug$_4$, Drug$_5$ and Drug$_6$ is independently selected from tubulysins, maytansinoids, taxanoids (taxanes), CC-1065 analogs, daunorubicin and doxorubicin compounds, benzodiazepine dimers (e.g., dimers of pyrrolobenzodiazepine (PBD), tomaymycin, anthramycin, indolinobenzodiazepines, imidazobenzothiadiazepines, or oxazolidinobenzodiazepines), calicheamicins and the enediyne antibiotics, actinomycin, amanitin (amatoxins), azaserines, bleomycins, epirubicin, tamoxifen, idarubicin, dolastatins, auristatins (e.g. monomethyl auristatin E, MMAE, MMAF, auristatin PYE, auristatin TP, Auristatins 2-AQ, 6-AQ, EB (AEB), and EFP (AEFP)), duocarmycins, thiotepa, vincristines, hemiasterlins, nazumamides, microginins, radiosumins, alterobactins, microsclerodermins, theonellamides, esperamicins, PNU-159682, and their analogues and derivatives, as well as the function molecules described throughout this patent application. In addition, $R_1$, $R_1'$, $R_1''$, $R_1'''$, $R_1''''$ and/or $R_1'''''$ can be absent.

In yet another embodiment, a pharmaceutical composition comprising a therapeutically effective amount of the conjugate of Formula (II) or any conjugates described through the present patent can be administered concurrently with the other therapeutic agents such as the chemotherapeutic agent, the radiation therapy, immunotherapy agents, autoimmune disorder agents, anti-infectious agents or the other conjugates for synergistically effective treatment or prevention of a cancer, or an autoimmune disease, or an infectious disease. The synergistic agents are preferably selected from one or several of the following drugs: Abatacept (Orencia), Abiraterone acetate (Zytiga®), Acetaminophen/hydrocodone, Adalimumab, afatinib dimaleate (Gilotrif®), alemtuzumab (Campath®), Alitretinoin (Panretin®), ado-trastuzumab emtansine (Kadcyla™), Amphetamine mixed salts (Amphetamine/dextroamphetamine, or Adderall XR), anastrozole (Arimidex®), Aripiprazole, Atazanavir, Atezolizumab (MPDL3280A), Atorvastatin, axitinib (Inlyta®), AZD9291, belinostat (Beleodaq™), Bevacizumab (Avastin®), Cabazitaxel (Jevtana®), Cabozantinib (Cometriq™), bexarotene (Targrtin®), blinatumomab (Blincyto™) Bortezomib (Velcade®), bosutinib (Bosulif®), brentuximab vedotin (Adcetris®), Budesonide, Budesonide/formoterol, Buprenorphine, Capecitabine, carfilzomib (Kyprolis®), Celecoxib, ceritinib (LDK378/Zykadia), Cetuximab (Erbitux®), Ciclosporin, Cinacalcet, crizotinib (Xalkori®), Dabigatran, dabrafenib (Tafinlar®), Darbepoetin alfa, Darunavir, imatinib mesylate (Gleevec®), dasatinib (Sprycel®), denileukin diftitox (Ontak®), Denosumab (Xgeva®), Depakote, Dexlansoprazole, Dexmethylphenidate, Dinutuximab (Unituxin™), Doxycycline, Duloxetine, Durvalumab (MED14736), Emtricitabine/Rilpivirine/Tenofovir disoproxil fumarate, Emtricitbine/tenofovir/efavirenz, Enoxaparin, Enzalutamide (Xtandi®), Epoetin alfa, erlotinib (Tarceva®), Esomeprazole, Eszopiclone, Etanercept, Everolimus (Afinitor®), exemestane (Aromasin®), everolimus (Afinitor®), Ezetimibe, Ezetimibe/simvastatin, Fenofibrate, Filgrastim, fingolimod, Fluticasone propionate, Fluticasone/salmeterol, fulvestrant (Faslodex®), gefitinib (Iressa®), Glatiramer, Goserelin acetate (Zoladex), Icotinib, Imatinib (Gleevec), Ibritumomab tiuxetan (Zevalin®), ibrutinib (Imbruvica™), idelalisib (Zydelig®), Infliximab, Insulin aspart, Insulin detemir, Insulin glargine, Insulin lispro, Interferon beta 1a, Interferon beta 1b, lapatinib (Tykerb®), Ipilimumab (Yervoy®), Ipratropium bromide/salbutamol, Lanreotide acetate (Somatuline® Depot), lenalidomide (Revlimid®), lenvatinib mesylate (Lenvima™), letrozole (Femara®), Levothyroxine, Levothyroxine, Lidocaine, Linezolid, Liraglutide, Lisdexamfetamine, MED14736 (AstraZeneca, Celgene), Memantine, Methylphenidate, Metoprolol, Modafinil, Mometasone, Nilotinib (Tasigna®), Nivolumab (Opdivo®), ofatumumab (Arzerra®), obinutuzumab (Gazyva™), olaparib (Lynparza™), Olmesartan, Olmesartan/hydrochlorothiazide, Omalizumab, Omega-3 fatty acid ethyl esters, Oseltamivir, Oxycodone, palbociclib (Ibrance®), Palivizumab, panitumumab (Vectibix®), panobinostat (Farydak®), pazopanib (Votrient®), pembrolizumab (Keytruda®), Pemetrexed (Alimta), pertuzumab (Perjeta™), Pneumococcal conjugate vaccine, pomalidomide (Pomalyst®), Pregabalin, Quetiapine, Rabeprazole, radium 223 chloride (Xofigo®), Raloxifene, Raltegravir, ramucirumab (Cyramza®), Ranibizumab, regorafenib (Stivarga®), Rituximab (Rituxan®), Rivaroxaban, romidepsin (Istodax®), Rosuvastatin, ruxolitinib phosphate (Jakafi™) Salbutamol, Sevelamer, Sildenafil, siltuximab (Sylvant™), Sitagliptin, Sitagliptin/metformin, Solifenacin, Sorafenib (Nexavar®), Sunitinib (Sutent®), Tadalafil, tamoxifen, Telaprevir, temsirolimus (Torisel®), Tenofovir/emtricitabine, Testosterone gel, Thalidomide (Immunoprin, Talidex), Tiotropium bromide, toremifene (Fareston®), trametinib (Mekinist®), Trastuzumab, Tretinoin (Vesanoid®), Ustekinumab, Valsartan, vandetanib (Caprelsa®), vemurafenib (Zelboraf®), vorinostat (Zolinza®), ziv-aflibercept (Zaltrap®), Zostavax, and their analogs, derivatives, pharmaceutically acceptable salts, carriers, diluents, or excipients thereof, or a combination above thereof.

The drugs/cytotoxic agents used for conjugation via a bridge linker of the present patent can be any analogues and/or derivatives of drugs/molecules described in the present patent. One skilled in the art of drugs/cytotoxic agents will readily understand that each of the drugs/cytotoxic agents described herein can be modified in such a manner that the resulting compound still retains the specificity and/or activity of the starting compound. The skilled artisan will also understand that many of these compounds can be used in place of the drugs/cytotoxic agents described herein. Thus, the drugs/cytotoxic agents of the present invention include analogues and derivatives of the compounds described herein.

All references cited herein and in the examples that follow are expressly incorporated by reference in their entireties.

EXAMPLES

The invention is further described in the following examples, which are not intended to limit the scope of the invention. Cell lines described in the following examples were maintained in culture according to the conditions specified by the American Type Culture Collection (ATCC) or Deutsche Sammlung von Mikroorganismen und Zellkulturen GmbH, Braunschweig, Germany (DMSZ), or The Shanghai Cell Culture Institute of Chinese Academy of Science, unless otherwise specified. Cell culture reagents were obtained from Invitrogen Corp., unless otherwise specified. All anhydrous solvents were commercially obtained and stored in Sure-seal bottles under nitrogen. All other reagents and solvents were purchased as the highest grade available and used without further purification. The preparative HPLC separations were performed with Varain PreStar HPLC. NMR spectra were recorded on Varian Mercury 400 MHz Instrument. Chemical shifts (.delta.) are reported in parts per million (ppm) referenced to tetramethylsilane at 0.00 and coupling constants (J) are reported in Hz. The mass spectral data were acquired on a Waters Xevo QTOF mass spectrum equipped with Waters Acquity UPLC separations module and Acquity TUV detector.

Example 1. Synthesis of 2,3-dibromosuccinic anhydride (7)

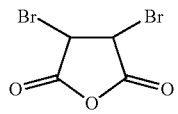

To a solution of 2,3-dibromosuccinic acid (10.00 g, 36.51 mmol) in dry $CH_2Cl_2$ (100 ml) at 0° C. was added phosphorus pentoxide (12.21 g, 85.84 mmol). The mixture was stirred at 0° C. for 2 h and then r.t. for 5 h, filtered through short $SiO_2$ column, and rinsed the column with EtOAc/$CH_2Cl_2$ (1:6). The filtrate was concentrated and triturated with EtOAc/hexane to afford the title compound (6.63 g, 71% yield). ESI MS m/z $C_4H_2Br_2O_3[M+H]^+$, cacld. 256.85, found 256.70.

Example 2. Synthesis of (S,E)-2-methyl-N-(3-methylbutan-2-ylidene)propane-2-sulfonamide (122)

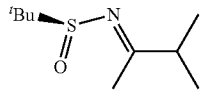

To a solution of (S)-2-methylpropane-2-sulfinamide (100 g, 0.825 mol, 1.0 eq.) in 1 L THF was added $Ti(OEt)_4$ (345 mL, 1.82 mol, 2.2 eq.) and 3-methyl-2-butanone (81 mL, 0.825 mol, 1.0 eq.) under $N_2$ at r.t. The reaction mixture was refluxed for 16 h, then cooled to r.t. and poured onto iced water. The mixture was filtered and the filter cake was washed with EtOAc. The organic layer was separated, dried over anhydrous $Na_2SO_4$ and concentrated to give a residue which was purified by vacuum distillation (15-20 torr, 95° C.) to afforded product 122 (141 g, 90% yield) as a yellow oil. 1H NMR (500 MHz, $CDCl_3$) δ 2.54-2.44 (m, 1H), 2.25 (s, 3H), 1.17 (s, 9H), 1.06 (dd, J=6.9, 5.1 Hz, 6H). MS ESI m/z calcd for $C_9H_{19}NaNOS [M+Na]^+$ 212.12; found 212.11.

Example 3. Synthesis of (2S,3S)-2-azido-3-methylpentanoic acid (124)

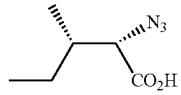

To a solution of $NaN_3$ (20.0 g, 308 mmol) in a mixture of water (50 mL) and dichloromethane (80 mL), cooled at 0° C., $Tf_2O$ (10 mL, 59.2 mmol, 2.0 eq.) was added slowly. After addition, the reaction was stirred at 0° C. for 2 h, then the organic phase was separated and the aqueous phase was extracted with dichloromethane (2×40 mL). The combined organic phases were washed with saturated $NaHCO_3$ solution and used as is. The dichloromethane solution of triflyl azide was added to a mixture of (L)-isoleucine (4.04 g, 30.8 mmol, 1.0 eq.), $K_2CO_3$ (6.39 g, 46.2 mmol, 1.5 eq.), CuSO$_4$·5H$_2$O (77.4 mg, 0.31 mmol, 0.01 eq.) in water (100 ml) and methanol (200 ml). The mixture was stirred at r.t. for 16 h. The organic solvents were removed under reduced pressure and the aqueous phase was diluted with water (250 mL) and acidified to pH 6 with concentrated HCl and diluted with phosphate buffer (0.25 M, pH 6.2, 250 mL). The aqueous layer was washed with EtOAc (5×100 mL) to remove the sulfonamide by-product, and then acidified to pH 2 with concentrated HCl, extracted with EtOAc (3×150 mL). The combined organic layers were dried over anhydrous Na$_2$SO$_4$, filtered and concentrated to give product 124 (4.90 g, 99% yield) as a colorless oil. $^1$H NMR (500 MHz, CDCl$_3$) δ 12.01 (s, 1H), 3.82 (d, J=5.9 Hz, 1H), 2.00 (ddd, J=10.6, 8.6, 5.5 Hz, 1H), 1.54 (dqd, J=14.8, 7.5, 4.4 Hz, 1H), 1.36-1.24 (m, 1H), 1.08-0.99 (m, 3H), 0.97-0.87 (m, 3H).

Example 4. Synthesis of D-N-methyl pipecolinic acid (126)

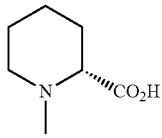

To a solution of D-pipecolinic acid (10.0 g, 77.4 mmol, 1.0 eq.) in methanol (100 mL) was added formaldehyde (37% aqueous solution, 30.8 mL, 154.8 mmol, 2.0 eq.), followed by Pd/C (10 wt %, 1.0 g). The reaction mixture was stirred under H$_2$ (1 atm) overnight, and then filtered through Celite, with washing of the filter pad with methanol. The filtrate was concentrated under reduced pressure to afford compound 126 (10.0 g, 90% yield) as a white solid.

Example 5. Synthesis of (R)-perfluorophenyl 1-methylpiperidine-2-carboxylate (127)

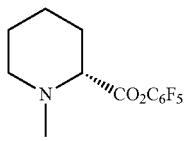

To a solution of D-N-methyl pipecolinic acid (2.65 g, 18.5 mmol) in EtOAc (50 mL) were added pentafluorophenol (3.75 g, 20.4 mmol) and DCC (4.21 g, 20.4 mmol). The reaction mixture was stirred at r.t. for 16 h, and then filtered over Celite. The filter pad was washed with 10 mL of EtOAc. The filtrate was used immediately without further purification or concentration.

Example 6. Synthesis of 2,2-diethoxyethanethioamide (129)

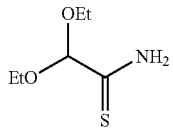

2,2-diethoxyacetonitrile (100 g, 0.774 mol, 1.0 eq.) was mixed with (NH$_4$)$_2$S aqueous solution (48%, 143 mL, 1.05 mol, 1.36 eq.) in methanol (1.5 L) at room temperature. After stirring for 16 h, the reaction mixture was concentrated and the residue was taken up in dichloromethane, washed with saturated NaHCO$_3$ solution and brine, dried over anhydrous Na$_2$SO$_4$ and concentrated. The residue was triturated with a solvent mixture of petroleum ether and dichloromethane. After filtration, the desired product 2 as a white solid was collected (100 g, 79% yield). $^1$H NMR (500 MHz, CDCl$_3$) δ 7.81 (d, J=71.1 Hz, 2H), 5.03 (s, 1H), 3.73 (dq, J=9.4, 7.1 Hz, 2H), 3.64 (dq, J=9.4, 7.0 Hz, 2H), 1.25 (t, J=7.1 Hz, 6H).

Example 7. Synthesis of ethyl 2-(diethoxymethyl)thiazole-4-carboxylate (130)

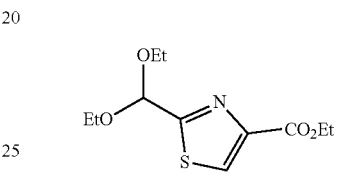

90 g of molecular sieves (3 Å) was added to a mixture of thioamide 129 (100 g, 0.61 mol, 1.0 eq.) and ethyl bromopyruvate (142 mL, 1.1 mol, 1.8 eq.) in 1 L EtOH. The mixture was refluxed (internal temperature about 60° C.) for 1 h, then ethanol was removed on rotovap and the residue was taken up in dichloromethane. The solid was filtered off and the filtrate was concentrated and purified by column chromatography (PE/EtOAc 5:1-3:1) to give thiazole carboxylate 130 (130 g, 82% yield) as a yellow oil.

Example 8. Synthesis of ethyl 2-formylthiazole-4-carboxylate (131)

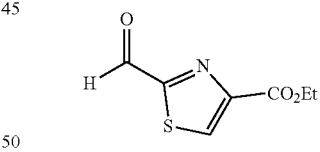

To a solution of compound 130 (130 g, 0.50 mol) in acetone (1.3 L) was added 2 N HCl (85 mL, 0.165 mol, 0.33 eq.). The reaction mixture was refluxed (internal temperature about 60° C.), monitored by TLC analysis until starting material was completely consumed (about 1-2 h). Acetone was removed under reduced pressure and the residue was taken up in dichloromethane (1.3 L), washed with saturated NaHCO$_3$ solution, water and brine, and then dried over anhydrous Na$_2$SO$_4$. The solution was filtered and concentrated under reduced pressure. The crude product was purified by recrystallization from petroleum ether and diethyl ether to afford a white solid 131 (40 g, 43% yield). $^1$H NMR (500 MHz, CDCl$_3$) δ 10.08-10.06 (m, 1H), 8.53-8.50 (m, 1H), 4.49 (q, J=7.1 Hz, 2H), 1.44 (t, J=7.1 Hz, 3H). MS ESI m/z calcd for C$_7$H$_8$NO$_3$S [M+H]$^+$ 186.01; found 186.01.

Example 9. Synthesis of ethyl 2-((R,E)-3-(((S)-tert-butylsulfinyl)imino)-1-hydroxy-4-methylpentyl)thiazole-4-carboxylate (132)

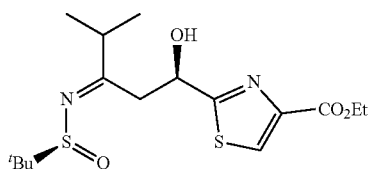 [SMILES: CCOC(=O)c1csc([C@H](O)C/C(=N\[S@@](=O)C(C)(C)C)C(C)C)n1]

To a solution of diisopropylamine (121 mL, 0.86 mol, 4.0 eq.) in dry THF (300 mL) was added n-butyllithium (2.5 M, 302 mL, 0.76 mol 3.5 eq.) at −78° C. under N$_2$. The reaction mixture was warmed to 0° C. over 30 min and then cooled back to −78°. Compound 122 (57 g, 0.3 mol, 1.4 eq.) in THF (200 mL) was added. The reaction mixture was stirred for 1 h before ClTi(O$^i$Pr)$_3$ (168.5 g, 0.645 mol, 3.0 eq.) in THF (350 mL) was added dropwise. After stirring for 1 h, compound 131 (40 g, 0.215 mol, 1.0 eq.) dissolved in THF (175 mL) was added dropwise and the resulting reaction mixture was stirred for 2 h. The completion of the reaction was indicated by TLC analysis. The reaction was quenched by a mixture of acetic acid and THF (v/v 1:4, 200 mL), then poured onto iced water, extracted with EtOAc (4×500 mL). The organic phase was washed with water and brine, dried over anhydrous Na$_2$SO$_4$, filtered and concentrated. The residue was purified by column chromatography (DCM/EtOAc/PE 2:1:2) to afforded the compound 132 (60 g, 74% yield) as a colorless oil. $^1$H NMR (500 MHz, CDCl$_3$) δ 8.13 (s, 1H), 6.63 (d, J=8.2 Hz, 1H), 5.20-5.11 (m, 1H), 4.43 (q, J=7.0 Hz, 2H), 3.42-3.28 (m, 2H), 2.89 (dt, J=13.1, 6.5 Hz, 1H), 1.42 (t, J=7.1 Hz, 3H), 1.33 (s, 9H), 1.25-1.22 (m, 6H). MS ESI m/z calcd for C$_{16}$H$_{26}$NaN$_2$O$_4$S$_2$ [M+Na]$^+$ 397.13, found 397.11.

Example 10. Synthesis of ethyl 2-((1R,3R)-3-((S)-1,1-dimethylethylsulfinamido)-1-hydroxy-4-methylpentyl)thiazole-4-carboxylate (133)

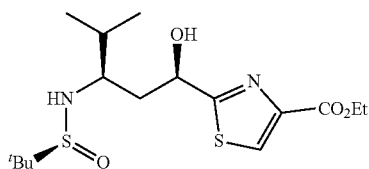 [SMILES: CCOC(=O)c1csc([C@H](O)C[C@@H](N[S@@](=O)C(C)(C)C)C(C)C)n1]

A solution of compound 132 (23.5 g, 62.7 mmol) dissolved in THF (200 mL) was cooled to −45° C. Ti(OEt)$_4$ (42.9 mL, 188 mmol, 3.0 eq.) was added slowly. After the completion of addition, the mixture was stirred for 1 h, before NaBH$_4$ (4.75 g, 126 mmol, 2.0 eq.) was added in portions. The reaction mixture was stirred at −45° C. for 3 h. TLC analysis showed some starting material still remained. The reaction was quenched with HOAc/THF (v/v 1:4, 25 mL), followed by EtOH (25 mL). The reaction mixture was poured onto ice (100 g) and warmed to r.t. After filtration over Celite, the organic phase was separated and washed with water and brine, dried over anhydrous Na$_2$SO$_4$, filtered, and concentrated. The residue was purified by column chromatography (EtOAc/PE 1:1) to deliver product 133 (16.7 g, 71% yield) as a white solid. $^1$H NMR (500 MHz, CDCl$_3$) δ 8.10 (s, 1H), 5.51 (d, J=5.8 Hz, 1H), 5.23-5.15 (m, 1H), 4.41 (q, J=7.0 Hz, 2H), 3.48-3.40 (m, 1H), 3.37 (d, J=8.3 Hz, 1H), 2.29 (t, J=13.0 Hz, 1H), 1.95-1.87 (m, 1H), 1.73-1.67 (m, 1H), 1.40 (t, J=7.1 Hz, 3H), 1.29 (s, 9H), 0.93 (d, J=7.3 Hz, 3H), 0.90 (d, J=7.2 Hz, 3H). MS ESI m/z calcd for C$_{16}$H$_{28}$NaN$_2$O$_4$S$_2$ [M+Na]$^+$ 399.15, found 399.14.

Example 11. Synthesis of ethyl 2-((1R,3R)-3-amino-1-hydroxy-4-methylpentyl)thiazole-4-carboxylate hydrochloride (134)

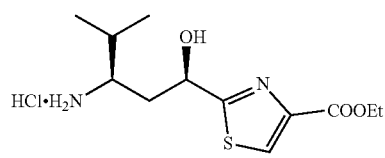

To a solution of compound 133 (6.00 g, 16.0 mmol, 1.0 eq.) in ethanol (40 mL) was added 4 N HCl in dioxane (40 mL) slowly at 0° C. The reaction was allowed to warm to r.t. and stirred for 2.5 h then concentrated and triturated with petroleum ether. A white solid (4.54 g, 92% yield) was collected and used in the next step.

Example 12. Synthesis of ethyl 2-((1R,3R)-3-((2S,3S)-2-azido-3-methylpentanamido)-1-hydroxy-4-methylpentyl)thiazole-4-carboxylate (135)

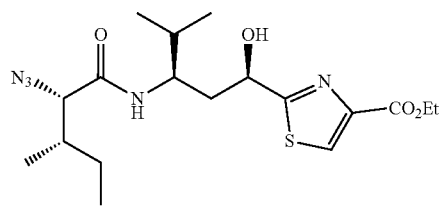 [SMILES: CCOC(=O)c1csc([C@H](O)C[C@@H](NC(=O)[C@@H](N=[N+]=[N-])[C@@H](C)CC)C(C)C)n1]

Azido-Ile-OH 124 (5.03 g, 28.8 mmol, 2.0 eq.) was dissolved in THF (120 mL) and cooled to 0° C., to which NMM (6.2 mL, 56.0 mmol, 4.0 eq.) and isobutylchloroformate (3.7 mL, 28.8 mmol, 2.0 eq.) were added in sequence. The reaction was stirred at 0° C. for 30 min and r.t. 1.0 h, and then cooled back to 0° C. Compound 134 (4.54 g, 14.7 mmol, 1.0 eq.) was added in portions. After stirring at 0° C. for 30 min, the reaction was warmed to r.t. and stirred for 2 h. Water was added at 0° C. to quenched the reaction and the resulting mixture was extracted with ethyl acetate for three times. The combined organic layers were washed with 1N HCl, saturated NaHCO$_3$ and brine, dried over anhydrous Na$_2$SO$_4$, filtered and concentrated. The residue was purified by column chromatography (0-30% EtOAc/PE) to give a white solid 135 (4.55 g, 74% yield).

Example 13. Synthesis of ethyl 2-((1R,3R)-3-((2S, 3S)-2-azido-3-methylpentanamido)-4-methyl-1-((triethylsilyl)oxy)pentyl)thiazole-4-carboxylate (136)

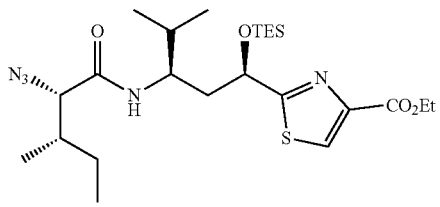

To a solution of compound 135 (5.30 g, 12.8 mmol, 1.0 eq.) in $CH_2Cl_2$ (50 mL) was added imidazole (1.75 g, 25.6 mmol, 2.0 eq.), followed by chlorotriethylsilane (4.3 mL, 25.6 mmol, 2.0 eq.) at 0° C. The reaction mixture was allowed to warm to r.t. over 1 hour and stirred for an additional hour. Brine was added to the reaction mixture, the organic layer was separated and the aqueous layer was extracted with EtOAc. The combined organic phases were dried, filtered, concentrated under reduced pressure, and purified by column chromatography with a gradient of 15-35% EtOAc in petroleum ether to afford product 136 (6.70 g, 99% yield) as a white solid. $^1$H NMR (500 MHz, $CDCl_3$) δ 8.12 (s, 1H), 6.75 (d, J=8.0 Hz, 1H), 5.20-5.12 (m, 1H), 4.44 (q, J=7.0 Hz, 2H), 4.06-3.97 (m, 1H), 3.87 (d, J=3.8 Hz, 1H), 2.14 (d, J=3.8 Hz, 1H), 2.01-1.91 (m, 3H), 1.42 (t, J=7.1 Hz, 3H), 1.34-1.25 (m, 2H), 1.06 (d, J=6.8 Hz, 3H), 1.00-0.93 (m, 18H), 0.88 (dd, J=19.1, 6.8 Hz, 6H). MS ESI m/z calcd for $C_{24}H_{44}N_5O_4SSi$ [M+H]$^+$ 526.28, found 526.28.

Example 14. Synthesis of ethyl 2-((1R,3R)-3-((2S, 3S)-2-azido-N,3-dimethyl pentanamido)-4-methyl-1-((triethylsilyl)oxy)pentyl)thiazole-4-carboxylate (137)

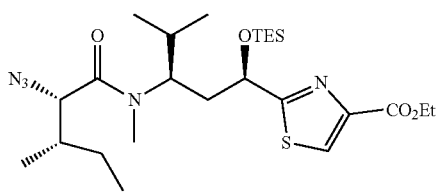

A solution of 136 (5.20 g, 9.9 mmol, 1.0 eq.) in THF (50 mL) was cooled to −45° C. and KHMDS (1M in toluene, 23.8 mL, 23.8 mmol, 2.4 eq.) was added. The resulting mixture was stirred at −45° C. for 20 min. Methyl iodide (1.85 mL, 29.7 mmol, 3.0 eq.) was then added, and the reaction mixture was allowed to warm to r.t. over 4.5 h, at which time the reaction was quenched with EtOH (10 mL). The crude product was diluted with EtOAc (250 mL) and washed with brine (100 mL). The aqueous layer was extracted with EtOAc (3×50 ml). The organic layers were dried, filtered, concentrated and purified by column chromatography with a gradient of 15-35% EtOAc in petroleum ether to afford product 137 (3.33 g, 63% yield) as a light yellow oil. $^1$H NMR (500 MHz, $CDCl_3$) δ 8.09 (s, 1H), 4.95 (d, J=6.6 Hz, 1H), 4.41 (q, J=7.1 Hz, 2H), 3.56 (d, J=9.5 Hz, 1H), 2.98 (s, 3H), 2.27-2.06 (m, 4H), 1.83-1.70 (m, 2H), 1.41 (t, J=7.2 Hz, 3H), 1.29 (ddd, J=8.9, 6.8, 1.6 Hz, 3H), 1.01 (d, J=6.6 Hz, 3H), 0.96 (dt, J=8.0, 2.9 Hz, 15H), 0.92 (d, J=6.6 Hz, 3H), 0.90 (d, J=6.7 Hz, 3H). MS ESI m/z calcd for $C_{25}H_{46}N_5O_4SSi$ [M+H]$^+$ 540.30, found 540.30.

Example 15. Synthesis of ethyl 2-((3S,6R,8R)-3-((S)-sec-butyl)-10,10-diethyl-6-isopropyl-5-methyl-1-((R)-1-methylpiperidin-2-yl)-1,4-dioxo-9-oxa-2,5-diaza-10-siladodecan-8-yl)thiazole-4-carboxylate (138)

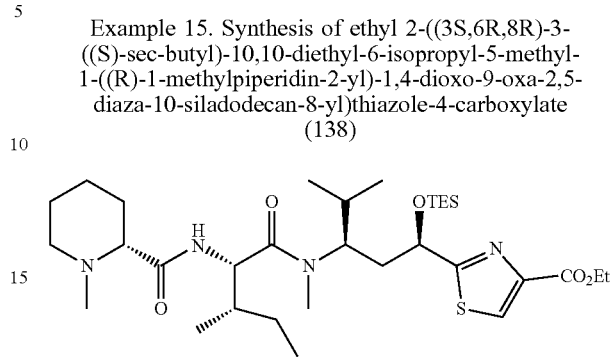

Dry Pd/C (10 wt %, 300 mg) and azide compound 137 (3.33 g, 6.61 mmol) were added to the above pentafluorophenyl ester 127 in EtOAc. The reaction mixture was stirred under hydrogen atmosphere for 27 h, and then filtered through a plug of Celite, with washing of the filter pad with EtOAc. The combined organic portions were concentrated and purified by column chromatography with a gradient of 0-5% methanol in EtOAc to deliver product 138 (3.90 g, 86% yield). MS ESI m/z calcd for $C_{32}H_{59}N_4O_5SSi$ [M+H]$^+$ 639.39, found 639.39.

Example 16. Synthesis of ethyl 2-((1R,3R)-3-((2S, 3S)—N,3-dimethyl-2-((R)-1-methyl piperidine-2-carboxamido)pentanamido)-1-hydroxy-4-methylpentyl)thiazole-4-carboxylate (139)

The coupling product 138 (3.90 g, 6.1 mmol) was dissolved in deoxygenated AcOH/water/THF (v/v/v 3:1:1, 100 mL), and stirred at r.t. for 48 h. The reaction was then concentrated and purified by column chromatography (2:98 to 15:85 MeOH/EtOAc) to afford compound 139 (2.50 g, 72% yield over 2 steps). MS ESI m/z calcd for $C_{26}H_{45}N_4O_5S$ [M+H]$^+$ 525.30, found 525.33.

Example 17. Synthesis of 2-((1R,3R)-3-((2S,3S)—N,3-dimethyl-2-((R)-1-methylpiperidine-2-carboxamido)pentanamido)-1-hydroxy-4-methylpentyl) thiazole-4-carboxylic acid (140)

An aqueous solution of LiOH (0.4 N, 47.7 mL, 19.1 mmol, 4.0 eq.) was added to a solution of compound 139 (2.50 g, 4.76 mmol, 1.0 eq.) in dioxane (47.7 mL) at 0° C. The reaction mixture was stirred at r.t. for 2 h and then concentrated. Column chromatography (100% CH$_2$Cl$_2$ then CH$_2$Cl$_2$/MeOH/NH$_4$OH 80:20:1) afforded compound 140 (2.36 g, 99% yield) as an amorphous solid. MS ESI m/z calcd for C$_{24}$H$_{41}$N$_4$O$_5$S [M+H]$^+$ 497.27, found 497.28.

Example 18. Synthesis of 2-((1R,3R)-1-acetoxy-3-((2S,3S)—N,3-dimethyl-2-((R)-1-methylpiperidine-2-carboxamido)pentanamido)-4-methylpentyl)thiazole-4-carboxylic acid (141)

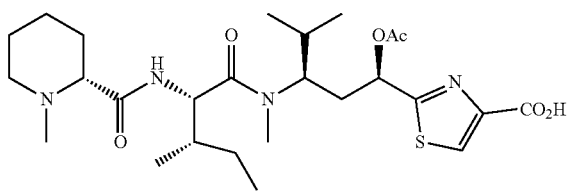 [SMILES: CC[C@H](C)[C@H](NC(=O)[C@H]1CCCCN1C)C(=O)N(C)[C@H](C[C@@H](OC(C)=O)c1nc(C(=O)O)cs1)C(C)C]

To a solution of compound 140 (2.36 g, 4.75 mmol) in pyridine (50 mL) at 0° C., acetic anhydride (2.25 mL, 24 mmol) was added slowly. The reaction mixture was allowed to warm to r.t. over 2 h and stirred at r.t. for 24 h. The reaction was concentrated and the residue was purified by reverse phase HPLC (C$_{18}$ column, 10-90% acetonitrile/water) to afford compound 141 (2.25 g, 88% yield) as an amorphous white solid. MS ESI m/z calcd for C$_{26}$H$_{43}$N$_4$O$_6$S [M+H]$^+$ 539.28, found 539.28.

Example 19. Synthesis of (1R,3R)-3-((2S,3S)—N,3-dimethyl-2-((R)-1-methylpiperidine-2-carboxamido)pentanamido)-4-methyl-1-(4-(perfluorobenzoyl)thiazol-2-yl)pentyl acetate (142)

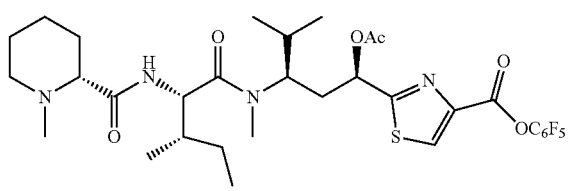

To a solution of compound 141 (86 mg, 0.16 mmol, 1.0 eq.) in dichloromethane (2 mL) was added pentafluorophenol (44 mg, 0.24 mmol, 1.5 eq.) and N,N'-diisopropylcarbodiimide (22 mg, 0.175 mmol, 1.1 eq.) at 0° C. The reaction mixture was warmed to room temperature and stirred over night. After the solvent was removed under reduced pressure, the reaction mixture was diluted with EtOAc (2 mL) then filtered over Celite. The filtrate was concentrated to afford crude pentafluorophenyl ester 142, which was used directly without further purification.

Example 20. Synthesis of tert-butyl 3-(2-(2-(2-hydroxyethoxy)ethoxy)ethoxy) propanoate (145)

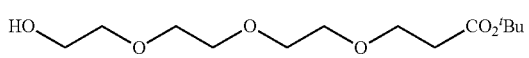

To a solution of 2,2'-(ethane-1,2-diylbis(oxy))diethanol (55.0 mL, 410.75 mmol, 3.0 eq.) in anhydrous THF (200 mL) was added sodium (0.1 g). The mixture was stirred until Na disappeared and then tert-butyl acrylate (20.0 mL, 137.79 mmol, 1.0 eq.) was added dropwise. The mixture was stirred overnight and then quenched by HCl solution (20.0 mL, 1N) at 0° C. THF was removed by rotary evaporation, brine (300 mL) was added and the resulting mixture was extracted with EtOAc (3×100 mL). The organic layers were washed with brine (3×300 mL), dried over anhydrous Na$_2$SO$_4$, filtered and concentrated to afford a colourless oil (30.20 g, 79.0% yield), which was used without further purification. MS ESI m/z calcd for C$_{13}$H$_{27}$O$_6$ [M+H]$^+$ 278.1729, found 278.1730.

Example 21. Synthesis of tert-butyl 3-(2-(2-(2-(tosyloxy)ethoxy)ethoxy)ethoxy) propanoate (146)

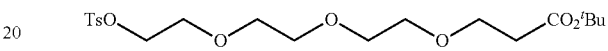

To a solution of tert-butyl 3-(2-(2-(2-hydroxyethoxy)ethoxy)ethoxy) propanoate (30.20 g, 108.5 mmol, 1.0 eq.) and TsCl (41.37 g, 217.0 mmol, 2.0 eq.) in anhydrous DCM (220 mL) at 0° C. was added TEA (30.0 mL, 217.0 mmol, 2.0 eq.). The mixture was stirred at room temperature overnight, and then washed with water (3×300 mL) and brine (300 mL), dried over anhydrous Na$_2$SO$_4$, filtered, concentrated and purified by SiO$_2$ column chromatography (3:1 hexanes/EtOAc) to give a colorless oil (39.4 g, 84.0% yield). MS ESI m/z calcd for C$_{20}$H$_{33}$O$_8$S [M+H]$^+$ 433.1818, found 433.2838.

Example 22. Synthesis of tert-butyl 3-(2-(2-(2-azidoethoxy)ethoxy)ethoxy) propanoate (147)

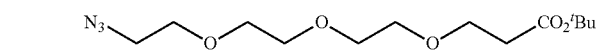 [SMILES: CC(C)(C)OC(=O)CCOCCOCCOCCN=[N+]=[N-]]

To a solution of tert-butyl 3-(2-(2-(2-(tosyloxy)ethoxy)ethoxy)ethoxy) propanoate (39.4 g, 91.1 mmol, 1.0 eq.) in anhydrous DMF (100 mL) was added NaN$_3$ (20.67 g, 316.6 mmol, 3.5 eq.). The mixture was stirred at room temperature overnight. Water (500 mL) was added and extracted with EtOAc (3×300 mL). The combined organic layers were washed with water (3×900 mL) and brine (900 mL), dried over anhydrous Na$_2$SO$_4$, filtered, concentrated and purified by SiO$_2$ column chromatography (5:1 hexanes/EtOAc) to give a light yellow oil (23.8 g, 85.53% yield). MS ESI m/z calcd for C$_{13}$H$_{25}$O$_3$N$_5$Na [M+Na]$^+$326.2, found 326.2.

Example 23. Synthesis of tert-butyl 3-(2-(2-(2-aminoethoxy)ethoxy)ethoxy) propanoate (148)

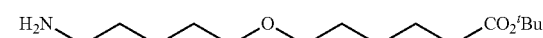

Raney-Ni (7.5 g, suspended in water) was washed with water (three times) and isopropyl alcohol (three times) and mixed with compound 147 (5.0 g, 16.5 mmol) in isopropyl alcohol. The mixture was stirred under a H$_2$ balloon at r.t. for 16 h and then filtered over a Celite pad, with washing of the pad with isopropyl alcohol. The filtrate was concentrated and purified by column chromatography (5-25% MeOH/DCM) to give a light yellow oil (2.60 g, 57% yield). MS ESI m/z calcd for C$_{13}$H$_{28}$NO$_5$ [M+H]$^+$ 279.19; found 279.19.

Example 24. Synthesis of di-tert-butyl 14,17-dioxo-4,7,10,21,24,27-hexaoxa-13,18-diazatriacont-15-yne-1,30-dioate (149)

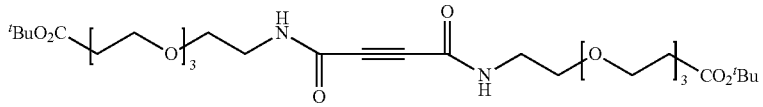

Acetylenedicarboxylic acid (0.35 g, 3.09 mmol, 1.0 eq.) was dissolved in NMP (10 mL) and cooled to 0° C., to which compound 148 (2.06 g, 7.43 mmol, 2.4 eq.) was added, followed by DMTMM (2.39 g, 8.65 mmol, 2.8 eq.) in portions. The reaction was stirred at 0° C. for 6 h and then diluted with ethyl acetate and washed with water and brine. The organic solution was concentrated and triturated with a mixture solvent of ethyl acetate and petroleum ether. The solid was filtered off and the filtrate was concentrated and purified by column chromatography (80-90% EA/PE) to give a light yellow oil (2.26 g, >100% yield), which was used without further purification. MS ESI m/z calcd for $C_{30}H_{53}N_2O_{12}$ [M+H]$^+$ 633.35; found 633.30.

Example 25. Synthesis of 14,17-dioxo-4,7,10,21,24,27-hexaoxa-13,18-diazatriacont-15-yne-1,30-dioic acid (150)

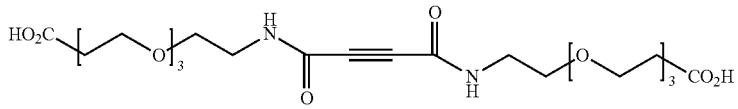

Compound 149 (2.26 g) was dissolved in dichloromethane (15 mL) and cooled to 0° C. then treated with TFA (15 mL). The reaction was warmed to r.t. and stirred for 45 min, and then the solvent and residual TFA was removed on rotovap. The crude product was purified by column chromatography (0-15% MeOH/DCM) to give a light yellow oil (1.39 g, 86% yield for two steps). MS ESI m/z calcd for $C_{22}H_{37}N_2O_{12}$ [M+H]$^+$ 521.23; found 521.24.

Example 26. Synthesis of 2-(2-(dibenzylamino)ethoxy)ethanol (152)

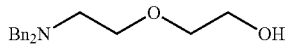

2-(2-aminoethoxy)ethanol (21.00 g, 200 mmol, 1.0 eq.) and $K_2CO_3$ (83.00 g, 600 mmol, 3.0 eq.) in acetonitrile (350 mL) was added BnBr (57.0 mL, 480 mmol, 2.4 eq.). The mixture was refluxed overnight. Water (1 L) was added and extracted with EtOAc (3×300 mL). The combined organic layers were washed with brine (1000 mL), dried over anhydrous $Na_2SO_4$, filtered, concentrated and purified by $SiO_2$ column chromatography (4:1 hexanes/EtOAc) to give a colorless oil (50.97 g, 89.2% yield). MS ESI m/z calcd for $C_{18}H_{23}NO_2Na$ [M+Na]$^+$ 309.1729, found 309.1967.

Example 27. Synthesis of tert-butyl 3-(2-(2-(dibenzylamino)ethoxy)ethoxy) propanoate (153)

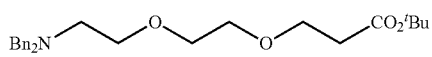

To a mixture of 2-(2-(dibenzylamino)ethoxy)ethanol (47.17 g, 165.3 mmol, 1.0 eq.), tert-butyl acrylate (72.0 mL, 495.9 mmol, 3.0 eq.) and n-Bu$_4$NI (6.10 g, 16.53 mmol, 0.1 eq.) in DCM (560 mL) was added sodium hydroxide solution (300 mL, 50%). The mixture was stirred overnight. The organic layer was separated and the water layer was extracted with EtOAc (3×100 mL). The organic layers were washed with water (3×300 mL) and brine (300 mL), dried over anhydrous $Na_2SO_4$, filtered, concentrated and purified by $SiO_2$ column chromatography (7:1 hexanes/EtOAc) to give a colorless oil (61.08 g, 89.4% yield). MS ESI m/z calcd for $C_{25}H_{36}NO_4$ [M+H]$^+$ 414.2566, found 414.2384.

Example 28. Synthesis of tert-butyl 3-(2-(2-aminoethoxy)ethoxy)propanoate (154)

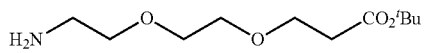

To a solution of tert-butyl 3-(2-(2-(dibenzylamino)ethoxy)ethoxy) propanoate (20.00 g, 48.36 mmol, 1.0 eq.) in THF (30 mL) and MeOH (60 mL) was added Pd/C (2.00 g, 10 wt %, 50% wet) in a hydrogenation bottle. The mixture was shaken overnight, filtered through Celite (filter aid), and the filtrate was concentrated to afford a colorless oil (10.58 g, 93.8% yield). MS ESI m/z calcd for $C_{11}H_{24}NO_4$ [M+H]$^+$ 234.1627, found 234.1810.

Example 29. Synthesis of tert-butyl 3-(2-(2-hydroxyethoxy)ethoxy)propanoate (156)

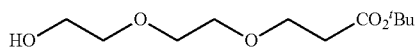

To a solution of 2,2'-oxydiethanol (19.7 mL, 206.7 mmol, 3.0 eq.) in anhydrous THF (100 mL) was added sodium (0.1 g). The mixture was stirred until Na disappeared and then tert-butyl acrylate (10.0 mL, 68.9 mmol, 1.0 eq.) was added dropwise. The mixture was stirred overnight, and brine (200 mL) was added and extracted with EtOAc (3×100 mL). The organic layers were washed with brine (3×300 mL), dried over anhydrous $Na_2SO_4$, filtered, concentrated and purified by $SiO_2$ column chromatography (1:1 hexanes/EtOAc) to give to a colorless oil (8.10 g, 49.4% yield). MS ESI m/z calcd for $C_{11}H_{23}O_5[M+H]^+$ 235.1467, found 235.1667.

Example 30. Synthesis of tert-butyl 3-(2-(2-(tosyloxy)ethoxy)ethoxy)propanoate (157)

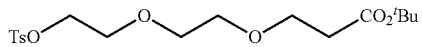 [SMILES: Cc1ccc(S(=O)(=O)OCCOCCOCCC(=O)OC(C)(C)C)cc1]

To a solution of tert-butyl 3-(2-(2-hydroxyethoxy)ethoxy) propanoate (6.24 g, 26.63 mmol, 1.0 eq.) and TsCl (10.15 g, 53.27 mmol, 2.0 eq.) in anhydrous DCM (50 mL) at 0° C. was added pyridine (4.3 mL, 53.27 mmol, 2.0 eq.). The mixture was stirred at room temperature overnight, and then washed with water (100 mL) and the water layer was extracted with DCM (3×50 mL). The combined organic layers were washed with brine (300 mL), dried over anhydrous $Na_2SO_4$, filtered, concentrated and purified by $SiO_2$ column chromatography (5:1 hexanes/EtOAc) to give a colorless oil (6.33 g, 61.3% yield). MS ESI m/z calcd for $C_{18}H_{27}O_7S$ $[M+H]^+$ 389.1556, found 389.2809.

Example 31. Synthesis of tert-butyl 3-(2-(2-azidoethoxy)ethoxy)propanoate (158)

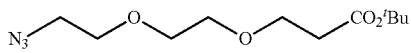 [SMILES: CC(C)(C)OC(=O)CCOCCOCCN=[N+]=[N-]]

To a solution of tert-butyl 3-(2-(2-(tosyloxy)ethoxy) ethoxy)propanoate (5.80 g, 14.93 mmol, 1.0 eq.) in anhydrous DMF (20 mL) was added $NaN_3$ (5.02 g, 77.22 mmol, 5.0 eq.). The mixture was stirred at room temperature overnight. Water (120 mL) was added and extracted with EtOAc (3×50 mL). The combined organic layers were washed with water (3×150 mL) and brine (150 mL), dried over anhydrous $Na_2SO_4$, filtered, concentrated and purified by $SiO_2$ column chromatography (5:1 hexanes/EtOAc) to give a colorless oil (3.73 g, 69.6% yield). MS ESI m/z calcd for $C_{11}H_{22}O_3N_4Na[M+H]^+$ 260.1532, found 260.2259.

Example 32. Synthesis of tert-butyl 3-(2-(2-aminoethoxy)ethoxy)propanoate (159)

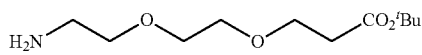

Compound 158 (0.18 g, 0.69 mmol) was dissolved in MeOH (3.0 mL, with 60 µL concentrated HCl) and hydrogenated with Pd/C (10 wt %, 20 mg) under a $H_2$ balloon for 30 min. The catalyst was filtered through a Celite pad, with washing of the pad with MeOH. The filtrate was concentrated to give a colorless oil (0.15 g, 93% yield). MS ESI m/z calcd for $C_{11}H_{24}NO_4$ $[M+H]^+$ 234.16; found 234.14.

Example 33. Synthesis of di-tert-butyl 11,14-dioxo-4,7,18,21-tetraoxa-10,15-diazatetracos-12-yne-1,24-dioate (160)

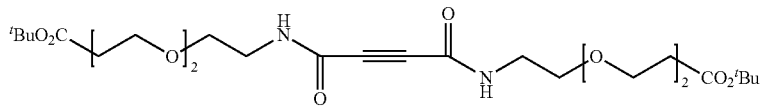

Acetylenedicarboxylic acid (26.5 mg, 0.232 mmol, 1.0 eq.) was dissolved in NMP (1.0 mL) and cooled to 0° C., to which compound 159 (0.15 g, 0.557 mmol, 2.4 eq.) was added, followed by DMTMM (0.18 g, 0.65 mmol, 2.8 eq.) in portions. The reaction was stirred at 0° C. for 5 h and then diluted with ethyl acetate and washed with water and brine. The organic solution was concentrated and purified by column chromatography (80-90% EA/PE). The appropriate fractions were concentrated and kept in refrigerator overnight. A solid formed and was filtered off. The filtrate was concentrated to give a light yellow oil (0.37 g, >100% yield), which was used without further purification. MS ESI m/z calcd for $C_{26}H_{45}N_2O_{10}$ $[M+H]^+$ 545.30; found 545.30.

Example 34. Synthesis of 11,14-dioxo-4,7,18,21-tetraoxa-10,15-diaza tetracos-12-yne-1,24-dioic acid (161)

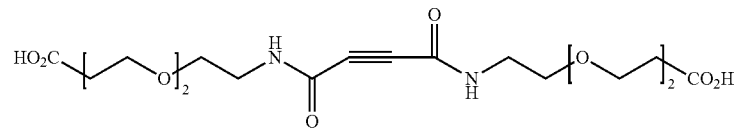

Compound 160 (0.21 g) was dissolved in dichloromethane (2.5 mL) and cooled to 0° C. then treated with TFA (2.5 mL). The reaction was warmed to r.t. and stirred for 45 min, and then the solvent and residual TFA was removed on rotovap. The crude product was purified by column chromatography (0-15% MeOH/DCM) to give a corlorless oil (58.7 mg, 99% yield for two steps). MS ESI m/z calcd for $C_{18}H_{29}N_2O_{10}$ [M+H]$^+$ 433.17; found 433.17.

Example 35. 3-(2-(2-azidoethoxy)ethoxy)propanoic acid (165)

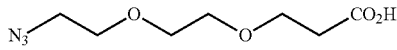

The azide compound 158 (2.51 g, 9.68 mmol) dissolved in 1,4-dioxane (30 mL) was treated with 10 ml of HCl (conc.) at r.t. The mixture was stirred for 35 min, diluted with EtOH (30 ml) and toluene (30 ml) and concentrated under vacuum. The crude mixture was purified on silica gel using a mixture of methanol (from 5% to 10%) and 1% formic acid in methylene chloride as the eluant to give title compound 165 (1.63 g, 83% yield), ESI MS m/z $C_7H_{12}N_3O_4$ [M−H]$^−$, cacld. 202.06, found 202.30.

Example 36. 2,5-dioxopyrrolidin-1-yl 3-(2-(2-azido-ethoxy)ethoxy)propanoate (166)

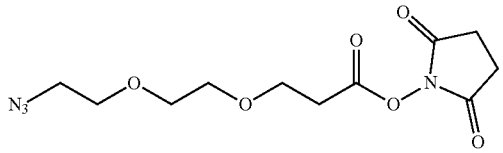 [SMILES: [N-]=[N+]=NCCOCCOCCC(=O)ON1C(=O)CCC1=O]

To compound 165 (1.60 g, 7.87 mmol) in 30 mL of dichloromethane was added NHS (1.08 g, 9.39 mmol) and EDC (3.60 g, 18.75 mmol) with stirring. After 8 h TLC analysis revealed that the reaction was complete, the reaction mixture was concentrated and purified on silica gel using a mixture of ethyl acetate (from 5% to 10%) in methylene chloride as the eluant to give title compound 166 (1.93 g, 82% yield). ESI MS m/z $C_{11}H_{17}N_4O_6$ [M+H]$^+$, cacld. 301.11, found 301.20.

Example 37. Synthesis of (E)-16-bromo-2,2-dimethyl-4,14-dioxo-3,7,10-trioxa-13-azaheptadec-15-en-17-oic acid (167)

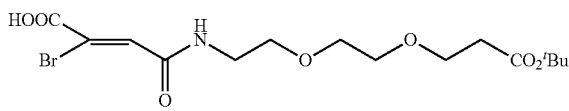 [SMILES: CC(C)(C)OC(=O)CCOCCOCCNC(=O)/C=C(\Br)C(=O)O]

To a solution of 3-bromofuran-2,5-dione (89 mg, 0.5 mmol) in THF (5 mL), tert-butyl 3-(2-(2-aminoethoxy) ethoxy)propanoate (117 mg, 0.5 mmol) was added. The resulting solution was stirred at r.t. for 4 h. The solvent was removed under vacuum to afford compound 167 (205 mg, theoretical yield). MS ESI m/z calcd for $C_{15}H_{25}BrNO_7$ [M+H]$^+$ 410.07, found 410.03.

Example 38. Synthesis of (E)-1-tert-butyl 18-methyl 13-bromo-11,14-dioxo-4,7-dioxa-10,15-diazaoctadec-12-ene-1,18-dioate (169)

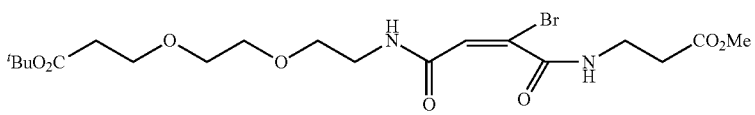 [SMILES: COC(=O)CCNC(=O)/C(Br)=C\C(=O)NCCOCCOCCC(=O)OC(C)(C)C]

Compound 167 (205 mg, 0.5 mmol) and methyl 3-aminopropanoate hydrochloride (70 mg, 0.5 mmol) were dissolved in DCM (20 mL), to which DIPEA (0.26 mL, 1.5 mmol) and EDC (144 mg, 0.75 mmol) were added. The resulting solution was stirred at r.t. overnight, and then washed with brine (50 mL), dried over anhydrous $Na_2SO_4$. Concentration and purification by column chromatography (0 to 10% MeOH/DCM) yielded compound 169 (88 mg, 36% yield). MS ESI m/z calcd for $C_{19}H_{32}BrN_2O_8$ [M+H]$^+$ 495.13, found 495.25.

Example 39. Synthesis of (E)-8-bromo-3,7,10-trioxo-2,14,17-trioxa-6,11-diazaicos-8-en-20-oic acid (170)

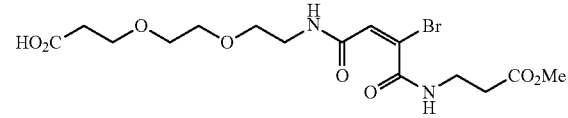 [SMILES: COC(=O)CCNC(=O)/C(Br)=C\C(=O)NCCOCCOCCC(=O)O]

Compound 169 (88 mg, 0.18 mmol) in DCM (3 mL) was treated with formic acid (6 ml) at 38° C. overnight. All volatiles were removed under vacuum to yield compound 170 (about 78 mg, ~90% yield).

Example 40. Synthesis of 4-(((benzyloxy)carbonyl)amino)butanoic acid (172)

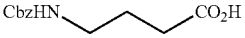

A solution of 4-aminobutyric acid (7.5 g, 75 mmol) and NaOH (6 g, 150 mmol) in $H_2O$ (40 mL) was cooled to 0° C. and treated with a solution of CbzCl (16.1 g, 95 mmol) in THF (32 ml) dropwise. After 1 h, the reaction was allowed to warm to r.t. and stirred for 3 h. THF was removed under vacuum, the pH of the aqueous solution was adjusted to 1.5 by addition of 6 N HCl. Extracted with ethyl acetate, and the organic layer was washed with brine, dried and concentrated to give compound 172 (16.4 g, 92% yield). MS ESI m/z calcd for $C_{12}H_{16}NO_5$ [M+H]$^+$ 238.10, found 238.08.

Example 41. Synthesis of tert-butyl 4-(((benzyloxy)carbonyl)amino)butanoate (173)

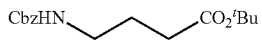

DMAP (0.8 g, 6.56 mmol) and DCC (17.1 g, 83 mmol) were added to a solution of 4-(((benzyloxy)carbonyl)amino)butanoic acid (16.4 g, 69.2 mmol) and t-BuOH (15.4 g, 208 mmol) in DCM (100 mL). After stirring at r.t. overnight, the reaction was filtered and filtrate concentrated. The residue was dissolved in ethyl acetate and the washed with 1N HCl, brine and dried over $Na_2SO_4$. Concentration and purification by column chromatography (10 to 50% EtOAc/hexanes) yielded compound 173 (7.5 g, 37% yield). MS ESI m/z calcd for $C_{16}H_{23}NO_4Na$ $[M+Na]^+$ 316.16, found 316.13.

Example 42. Synthesis of tert-butyl 4-aminobutanoate (174)

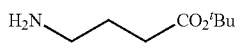

tert-Butyl 4-(((benzyloxy)carbonyl)amino)butanoate (560 mg, 1.91 mmol) was dissolved in MeOH (50 mL), and mixed with Pd/C catalyst (10 wt %, 100 mg) then hydrogenated (1 atm) at room temperature for 3 h. The catalyst was filtered off and all volatiles were removed under vacuum to afford compound 174 (272 mg, 90% yield). MS ESI m/z calcd for $C_8H_{18}NO_2$ $[M+H]^+$ 160.13, found 160.13.

Example 43. Synthesis of (E)-2-bromo-4-((4-(tert-butoxy)-4-oxobutyl)amino)-4-oxobut-2-enoic acid (175)

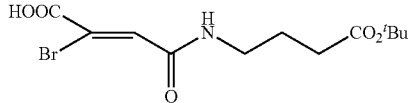 [SMILES: CC(C)(C)OC(=O)CCCNC(=O)/C=C(\Br)C(=O)O]

3-Bromofuran-2,5-dione (300 mg, 1.71 mmol) was dissolved in THF (20 mL), to which tert-butyl 4-aminobutanoate (272 mg, 1.71 mmol) was added and the resulting solution was stirred at r.t. for 3 h. The solvent was removed under vacuum to afford compound 175 (572 mg, theoretical yield). MS ESI m/z calcd for $C_{12}H_{19}BrNO_5$ $[M+H]^+$ 338.03, found 338.04.

Example 44. Synthesis of (E)-tert-butyl 4-(3-bromo-4-((2-methoxyethyl) amino)-4-oxobut-2-enamido)butanoate (177)

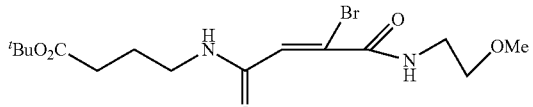

2-Bromo-4-((4-(tert-butoxy)-4-oxobutyl)amino)-4-oxobut-2-enoic acid (286 mg, 0.85 mmol) and 2-methoxyethanamine (128 mg, 1.7 mmol) were dissolved in DCM (40 mL), to which DIPEA (329 mg, 2.55 mmol) and EDC (490 mg, 2.55 mmol) were added. The resulting solution was stirred at r.t. for 24 h and then washed with brine, dried over $Na_2SO_4$. Concentration and purification by column chromatography (0 to 10% MeOH/DCM) yielded compound 177 (102 mg 31% yield). MS ESI m/z calcd for $C_{15}H_{26}BrN_2O_5$ $[M+H]^+$ 393.09, found 393.11.

Example 45. Synthesis of (E)-4-(3-bromo-4-((2-methoxyethyl)amino)-4-oxobut-2-enamido)butanoic acid (178)

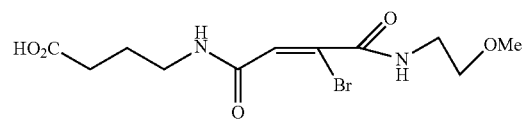

Compound 177 (52 mg, 0.132 mmol) was dissolved in DCM (3 mL), to which formic acid (6 ml) was added. The resulting solution was stirred at 38° C. overnight then concentrated to afford compound 178 (45 mg, theoretical yield). MS ESI m/z calcd for $C_{11}H_{18}BrN_2O_5$ $[M+H]^+$ 339.03, found 339.05.

Example 46. Synthesis of (E)-2,5-dioxopyrrolidin-1-yl 4-(3-bromo-4-((2-methoxyethyl)amino)-4-oxobut-2-enamido)butanoate (179)

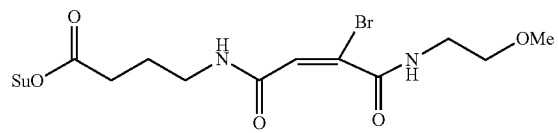

To a solution of compound 178 (45 mg, 0.132 mmol) in DCM (10 ml) NHS (23 mg, 0.199 mmol) and EDC (38 mg, 0.199 mmol) were added. After stirring at r.t. for 3 h, the reaction was concentrated and purified by column chromatography (10 to 50% EtOAc/hexanes) to yield compound 179 (57 mg, 99% yield). MS ESI m/z calcd for $C_{15}H_{21}BrN_3O_7[M+H]^+$ 436.05, found 436.06.

Example 47. Synthesis of (Z)-di-tert-butyl 4,4'-((2-bromofumaroyl)bis(azane diyl))dibutanoate (180)

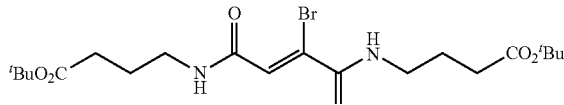

tert-Butyl 4-aminobutanoate (174) (477 mg, 3 mmol) and 2,3-dibromosuccinic acid (414 mg, 1.5 mmol) was dissolved in DCM (35 mL), to which DIPEA (1.16 g, 9 mmol) and EDC (0.86 g, 4.5 mmol) were added. The resulting solution was stirred at r.t. overnight and then washed with brine, dried over $Na_2SO_4$. Filtration, concentration and purification by column chromatography (0 to 10% MeOH/DCM) yielded compound 180 (160 mg, 22% yield). MS ESI m/z calcd for $C_{20}H_{34}BrN_2O_6[M+H]^+$ 477.15, found 477.16.

Example 48. Synthesis of (Z)-4,4'-((2-bromofumaroyl)bis(azanediyl))dibutanoic acid (181)

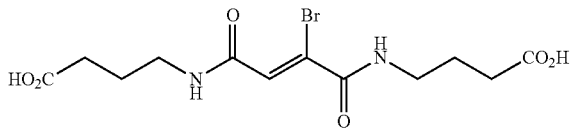 [SMILES: O=C(O)CCCNC(=O)/C=C(\Br)C(=O)NCCCC(=O)O]

Compound 180 (80 mg, 0.168 mmol) was dissolved in DCM (5 mL) and treated with formic acid (8 mL) at 38° C. overnight. All volatiles were removed under vacuum to afford compound 181 (61 mg, 99% yield). MS ESI m/z calcd for $C_{12}H_{18}BrN_2O_6[M+H]^+$ 365.03, found 365.05.

Example 49. Synthesis of (Z)-bis(2,5-dioxopyrrolidin-1-yl) 4,4'-((2-bromo fumaroyl)bis(azanediyl)) dibutanoate (182)

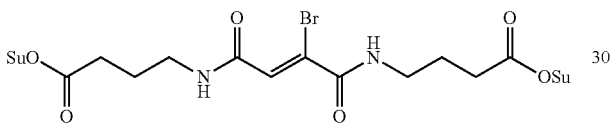

NHS (60 mg, 0.504 mmol) and EDC (97 mg, 0.504 mmol) were added to a solution of compound 181 (61 mg, 0.168 mmol) in DCM (10 mL). After stirring at r.t. overnight, the reaction mixture was concentrated and purified by column chromatography (0 to 10% MeOH/DCM) to afford compound 182 (72 mg, 77% yield). MS ESI m/z calcd for $C_{20}H_{24}BrN_4O_{10}$ [M+H]$^+$ 559.06, found 559.78.

Example 50. Synthesis of tert-butyl 2-(triphenylphosphoranylidene)propanoate (184)

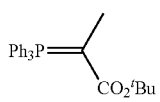

A mixture of tert-butyl-2-bromopropanoate 183 (15.5 g, 74.1 mmol, 1.0 eq.) and triphenyl phosphine (19.4 g, 74.1 mmol, 1.0 eq.) in dry acetonitrile (45 mL) was stirred at room temperature for 18 h. Acetonitrile was removed under reduced pressure and toluene was added to crash out a white precipitate. Toluene was then decanted off and the white solid was dissolved in dichloromethane (100 mL) and transferred to a separatory funnel. 10% NaOH (100 mL) was added to the funnel, and the organic layer immediately turned yellow after shaking. The organic layer was separated and the aqueous layer was extracted with dichloromethane (30 mL) once. The dichloromethane layers were combined and washed with brine (50 mL) once, then dried over $Na_2SO_4$, filtered and concentrated, giving the ylide as a yellow solid (16.8 g, 58%).

Example 51. Synthesis of (S)-methyl 3-(4-(benzyloxy)phenyl)-2-((tert-butoxy carbonyl)amino)propanoate (186)

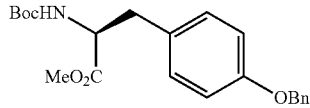 [SMILES: COC(=O)[C@H](Cc1ccc(OCc2ccccc2)cc1)NC(=O)OC(C)(C)C]

To a mixture of Boc-L-Tyr-OMe (20.0 g, 67.7 mmol, 1.0 eq.), $K_2CO_3$ (14.0 g, 101.6 mmol, 1.5 eq.) and KI (1.12 g, 6.77 mmol, 0.1 eq.) in acetone (100 mL) was added BnBr (10.5 mL, 81.3 mmol, 1.2 eq.) slowly. The mixture was then refluxed overnight. Water (250 mL) was added and the reaction mixture was extracted with EtOAc (3×100 mL). The combined organic layers were washed with brine (300 mL), dried over anhydrous $Na_2SO_4$, filtered, concentrated and purified by $SiO_2$ column chromatography (4:1 hexanes/EtOAc) to give a white solid 186 (26.12 g, 99% yield). $^1$H NMR (500 MHz, CDCl$_3$) δ 7.44-7.41 (m, 2H), 7.41-7.36 (m, 2H), 7.35-7.30 (m, 1H), 7.04 (d, J=8.5 Hz, 2H), 6.93-6.89 (m, 2H), 5.04 (s, 2H), 4.97 (d, J=7.7 Hz, 1H), 4.55 (d, J=6.9 Hz, 1H), 3.71 (s, 3H), 3.03 (dd, J=14.4, 5.7 Hz, 2H), 1.44 (d, J=18.6 Hz, 10H). MS ESI m/z calcd for $C_{22}H_{27}NO_5Na$ [M+Na]$^+$ 408.18, found 408.11.

Example 52. Synthesis of (S)-tert-butyl (1-(4-(benzyloxy)phenyl)-3-oxopropan-2-yl)carbamate (187)

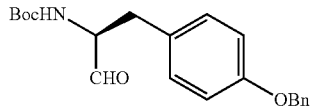 [SMILES: CC(C)(C)OC(=O)N[C@H](C=O)Cc1ccc(OCc2ccccc2)cc1]

To a solution of ester 186 (26.1 g, 67.8 mmol, 1.0 eq.) in anhydrous dichloromethane (450 mL) at −78° C. was added DIBAL (1.0 M in hexanes, 163 mL, 2.2 eq.) in 1 h. The mixture was stirred at −78° C. for 3 h and then quenched with 50 mL of ethanol. 1N HCl was added dropwise until pH 4 was reached. The resulting mixture was allowed to warm to 0° C. Layers were separated and the aqueous layer was further extracted with EtOAc (3×100 mL). The combined organic solution was washed with brine, dried over anhydrous $Na_2SO_4$, and concentrated. Trituration with PE/EtOAc and filtration gave a white solid 187 (18.3 g, 76% yield). MS ESI m/z calcd for $C_{22}H_{27}NO_5Na$ [M+Na]$^+$378.11, found 378.11.

Example 53. Synthesis of (S,Z)-tert-butyl 5-(4-(benzyloxy)phenyl)-4-((tert-but oxycarbonyl)amino)-2-methylpent-2-enoate (188)

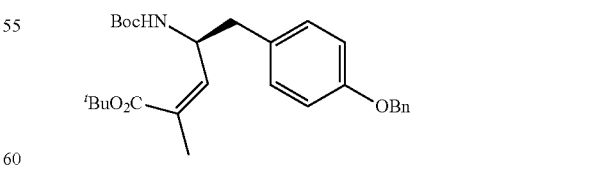

Aldehyde 187 (0.84 g, 2 mmol, 1.0 eq.) was dissolved in dry dichloromethane (50 mL), to which tert-butyl ester ylide 184 (1.6 g, 4 mmol, 2.0 eq.) was added and the solution was stirred at r.t. for 1.5 h as determined complete by TLC. Purification by column chromatography (10-50% EtOAc/hexanes) afforded compound 188 (1.16 g, 98% yield).

Example 54. Synthesis of (4R)-tert-butyl 4-((tert-butoxycarbonyl)amino)-5-(4-hydroxyphenyl)-2-methylpentanoate (189)

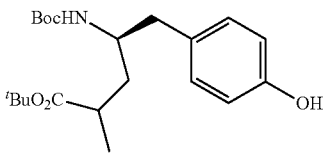 [SMILES: CC(C[C@H](Cc1ccc(O)cc1)NC(=O)OC(C)(C)C)C(=O)OC(C)(C)C]

Compound 188 (467 mg, 1 mmol) was dissolved in methanol (30 mL) and hydrogenated (1 atm) with Pd/C catalyst (10 wt %, 250 mg) at r.t. overnight. The catalyst was filtered off and the filtrate were concentrated under reduced pressure to afford compound 189 (379 mg, 99% yield).

Example 55. Synthesis of (4R)-tert-butyl 4-((tert-butoxycarbonyl)amino)-5-(4-hydroxy-3-nitrophenyl)-2-methylpentanoate (190)

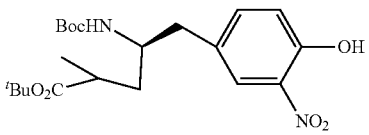 [SMILES: CC(C[C@H](Cc1ccc(O)c([N+](=O)[O-])c1)NC(=O)OC(C)(C)C)C(=O)OC(C)(C)C]

Compound 189 (379 mg, 1 mmol, 1.0 eq.) was dissolved in THF (20 mL), to which a solution of tert-butyl nitrite (315 mg, 3 mmol, 3.0 eq.) in THF (2 mL) was added. The reaction was stirred at r.t. for 3 h and then poured onto water, extracted with EtOAc (2×50 mL) and the combined organic phases were washed with brine (50 mL), dried over anhydrous $Na_2SO_4$, filtered and concentrated. Purification by column chromatography (10-50% EtOAc/hexanes) afforded compound 190 (300 mg, 71% yield).

Example 56. Synthesis of (4R)-tert-butyl 4-((tert-butoxycarbonyl)amino)-5-(4-((tert-butyldimethylsilyl)oxy)-3-nitrophenyl)-2-methylpentanoate (191)

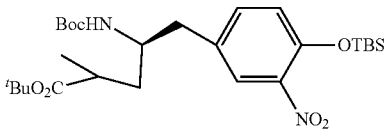

To a solution of compound 190 (424 mg, 1 mmol) in DCM (20 mL), imidazole (408 mg, 6 mmol) and tert-butylchlorodimethylsilane (602 mg, 4 mmol) were added. The resulting solution was stirred at r.t. for 3 h. Afterwards, the reaction mixture was washed with brine (50 mL), dried over anhydrous $Na_2SO_4$, concentrated and purified by column chromatography (10% to 30% EtOAc/hexanes) to yield compound 191 (344 mg, 64% yield).

Example 57. Synthesis of (4R)-tert-butyl 5-(3-amino-4-((tert-butyldimethylsilyl) oxy)phenyl)-4-((tert-butoxycarbonyl)amino)-2-methylpentanoate (192)

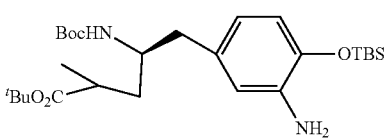 [SMILES: CC(C[C@H](Cc1ccc(O[Si](C)(C)C(C)(C)C)c(N)c1)NC(=O)OC(C)(C)C)C(=O)OC(C)(C)C]

Compound 191 (200 mg, 0.37 mmol) was dissolved in EtOAc (30 mL), mixed with palladium catalyst (10 wt % on carbon, 100 mg) and hydrogenated (1 atm) at r.t. for 2 h. The catalyst was filtered off and all volatiles were removed under vacuum to afford compound 192 (187 mg, 99% yield).

Example 58. Synthesis of (E)-methyl 13-bromo-1-((5-((2R)-5-(tert-butoxy)-2-((tert-butoxycarbonyl)amino)-4-methyl-5-oxopentyl)-2-((tert-butyldimethylsilyl)oxy)phenyl)-amino)-1,11,14-trioxo-4,7-dioxa-10,15-diazaoctadec-12-en-18-oate (193)

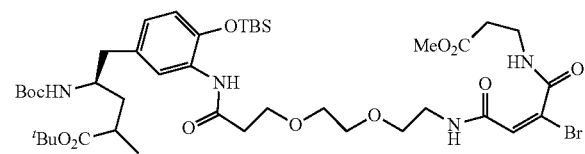 [SMILES: COC(=O)CCNC(=O)/C(Br)=C\C(=O)NCCOCCOCCC(=O)Nc1cc(C[C@@H](CC(C)C(=O)OC(C)(C)C)NC(=O)OC(C)(C)C)ccc1O[Si](C)(C)C(C)(C)C]

Compound 192 (90 mg, 0.178 mmol) and compound 170 (78 mg, 0.178 mmol) were dissolved in DCM (5 mL) and DMA (5 mL). To which TEA (36 mg, 0.356 mmol) and HATU (102 mg, 0.267 mmol) were added. The resulting mixture was stirred at r.t. for 4 h, and then diluted with EA and washed with brine, dried over anhydrous $Na_2SO_4$. Filtration and purification by column chromatography (0 to 10% MeOH/DCM) yielded compound 193 (87 mg, 53% yield).

Example 59. Synthesis of (E)-methyl 13-bromo-1-((5-((2R)-5-(tert-butoxy)-2-((tert-butoxycarbonyl)amino)-4-methyl-5-oxopentyl)-2-hydroxyphenyl)amino)-1,11,14-trioxo-4,7-dioxa-10,15-diazaoctadec-12-en-18-oate (194)

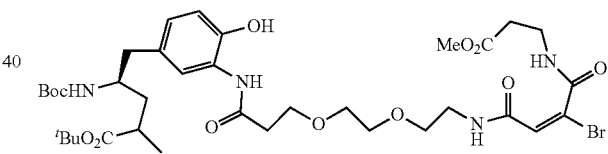

Compound 193 (87 mg, 0.0936 mmol) was dissolved in DCM (10 mL) and treated with TBAF (1M in THF, 0.3 mL). The resulting mixture was stirred at r.t. for 0.5 h and washed with brine, dried over anhydrous $Na_2SO_4$. Filtration and purification by column chromatography (0 to 10% MeOH/DCM) yielded compound 194 (53 mg, 69% yield). MS ESI m/z calcd for $C_{36}H_{56}BrN_4O_{12}$ $[M+H]^+$ 817.30, found 817.51.

Example 60. Synthesis of (4R)-4-amino-5-(3-((E)-8-bromo-3,7,10-trioxo-2,14,17-trioxa-6,11-diaza-icos-8-enamido)-4-hydroxyphenyl)-2-methylpentanoic acid (195)

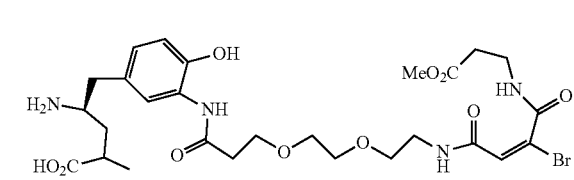 [SMILES: COC(=O)CCNC(=O)/C(Br)=C\C(=O)NCCOCCOCCC(=O)Nc1cc(C[C@H](N)CC(C)C(=O)O)ccc1O]

Compound 194 (18 mg, 0.022 mmol) was dissolved in DCM (2 mL) and treated with TFA (2 mL) at r.t. for 3 h. All volatiles were removed under vacuum to afford compound 195 (14.5 mg, theoretical yield). MS ESI m/z calcd for $C_{27}H_4OBrN_4O_{10}$ [M+H]$^+$ 659.18, found 659.18.

Example 61. Synthesis of (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-((E)-8-bromo-3,7,10-trioxo-2,14,17-trioxa-6,11-diazaicos-8-enamido)-4-hydroxyphenyl)-2-methylpentanoic acid (196)

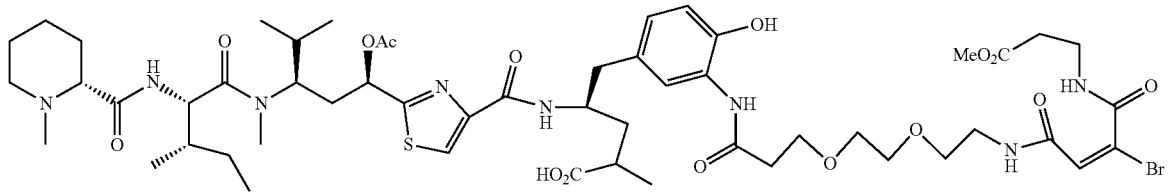 [SMILES: CC[C@H](C)[C@H](NC(=O)[C@H]1CCCCN1C)C(=O)N(C)[C@H](C[C@@H](OC(C)=O)c1nc(C(=O)N[C@@H](Cc2ccc(O)c(NC(=O)CCOCCOCCNC(=O)/C=C(/Br)C(=O)NCCC(=O)OC)c2)CC(C)C(=O)O)cs1)C(C)C]

To a solution of compound 195 (14.5 mg, 0.022 mmol) and perfluorophenyl ester 142 (18.5 mg, 0.026 mmol) in DMA (2.5 mL) was DIPEA (15 mg, 0.116 mmol) added. The resulting mixture was stirred at r.t. for 1.5 h and then the solvent was removed under vacuum. The residue was purified on reverse phase preparative HPLC (Cis column, 10-90% MeCN/H$_2$O) to afford compound 196 (12.6 mg, 49% yield). MS ESI m/z calcd for $C_{53}H_{80}BrN_8O_{15}$ [M+H]$^+$ 1181.45, found 1181.45.

Example 62. Synthesis of (4R)-tert-butyl 5-(3-amino-4-hydroxyphenyl)-4-((tert-butoxycarbonyl)amino)-2-methylpentanoate (197)

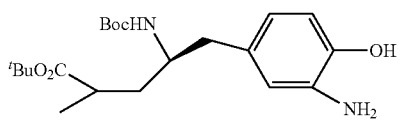

Compound 190 (56 mg, 0.132 mmol) was dissolved in EtOAc (20 mL) and mixed with Pd/C catalyst (10 wt %, 50 mg) and hydrogenated (1 atm) at r.t. for 3 h. The catalyst was filtered off and all volatiles were removed under vacuum to afford compound 197 (52 mg, 99% yield). MS ESI m/z calcd for $C_{21}H_{35}N_2O_5$ [M+H]$^+$ 395.25, found 395.26.

Example 63. Synthesis of (4R)-tert-butyl 5-(3-(4-((E)-3-bromo-4-((2-methoxy ethyl)amino)-4-oxobut-2-enamido)butanamido)-4-hydroxyphenyl)-4-((tert-butoxycarbonyl)amino)-2-methylpentanoate (198)

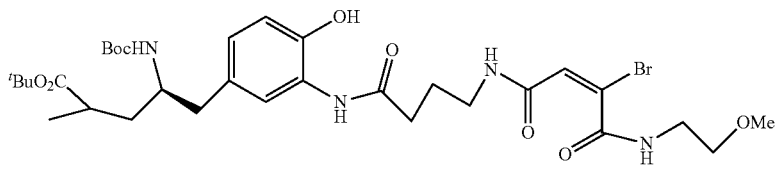 [SMILES: COCCNC(=O)/C(Br)=C\C(=O)NCCCC(=O)Nc1cc(C[C@@H](CC(C)C(=O)OC(C)(C)C)NC(=O)OC(C)(C)C)ccc1O]

$NaH_2PO_4$ (0.1M in water, 2 ml) was added to a solution of compound 179 (57 mg, 0.1323 mmol) and compound 197 (52 mg, 0.1323 mmol) in EtOH (10 mL). The resulting solution was stirred at r.t. for 72 h, concentrated and purified by column chromatography (30 to 100% EtOAc/hexanes) to yield compound 198 (50 mg, 53% yield). MS ESI m/z calcd for $C_{32}H_{50}BrN_4O_9$[M+H]$^+$ 715.27, found 715.27.

Example 64. Synthesis of (4R)-4-amino-5-(3-(4-((E)-3-bromo-4-((2-methoxy ethyl) amino)-4-oxobut-2-enamido)butanamido)-4-hydroxyphenyl)-2-methylpentanoic acid (199)

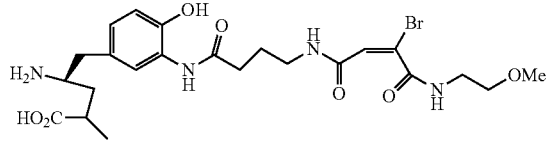 [SMILES: COCCNC(=O)/C(Br)=C\C(=O)NCCCC(=O)Nc1cc(C[C@@H](N)CC(C)C(=O)O)ccc1O]

Compound 198 (25 mg, 0.035 mmol) in DCM (2 mL) was treated with TFA (2 mL) at r.t. for 1 h. All volatiles were removed under vacuum to afford compound 199 (19 mg, 99% yield). MS ESI m/z calcd for $C_{23}H_{34}BrN_4O_7$[M+H]$^+$ 557.15, found 557.27.

Example 65. Synthesis of (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-(4-((E)-3-bromo-4-((2-methoxyethyl)amino)-4-oxobut-2-enamido)butanamido)-4-hydroxyphenyl)-2-methylpentanoic acid (200)

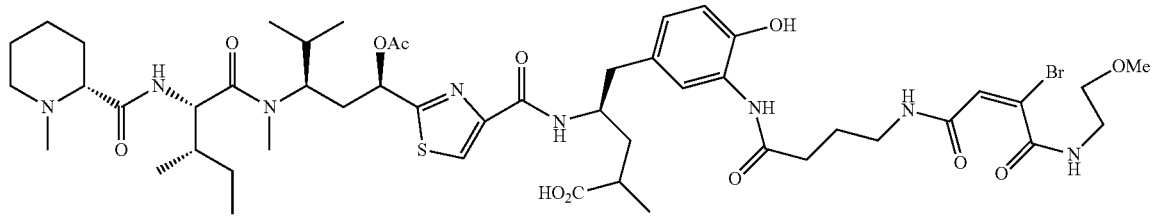 [SMILES: CC[C@H](C)[C@H](NC(=O)[C@H]1CCCCN1C)C(=O)N(C)[C@H](C[C@@H](OC(C)=O)c1nc(C(=O)N[C@@H](Cc2ccc(O)c(NC(=O)CCCNC(=O)/C=C(/Br)C(=O)NCCOC)c2)CC(C)C(=O)O)cs1)C(C)C]

Compound 199 (19 mg, 0.035 mmol) and perfluorophenyl ester 142 (33 mg, 0.046 mmol) was dissolved in DMA (5 mL), to which DIPEA (10 mg, 0.077 mmol) was added. The reaction mixture was stirred at r.t. for 2 h then concentrated and purified on preparative HPLC (Cis column, 10-90% MeCN/H$_2$O) to afford the compound 200 (9 mg, 24% yield). MS ESI m/z calcd for C$_{49}$H$_{74}$BrN$_8$O$_{12}$S [M+H]$^+$ 1079.43, found 1079.66.

Example 66. Synthesis of (4R)-tert-butyl 5-(3-((Z)-79-bromo-1-hydroxy-73,78,81-trioxo-3,6,9,12,15,18,21,24,27,30,33,36,39,42,45,48,51,54,57,60,63,66,69-tricosaoxa-72,77,82-triazahexaoctacont-79-enamido)-4-hydroxyphenyl)-4-((tert-butoxycarbonyl)amino)-2-methylpentanoate (203)

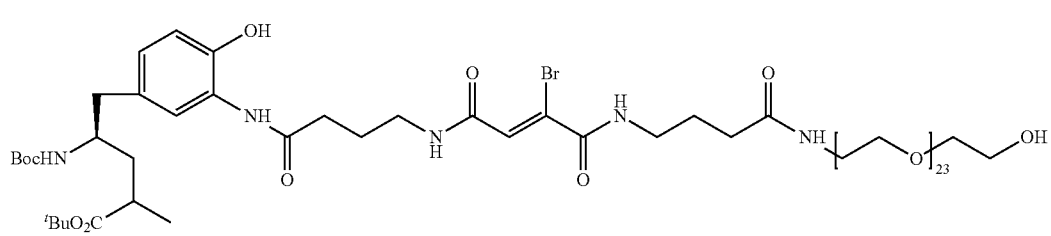

NaH$_2$PO$_4$ (0.1M in water, 1 mL) was added to a solution of compound 182 (36 mg, 0.065 mmol) and compound 197 (25 mg, 0.063 mmol) in EtOH (5 mL). The resulting solution was stirred at r.t. overnight and then HO-(PEG)$_{24}$-NH$_2$ (95 mg) was added to the mixture and stirred at r.t. overnight. All volatiles were removed under vacuum and the residue was purified by column chromatography (0 to 10% MeOH/DCM) to yield compound 203 (28 mg, 24% yield). MS ESI m/z 1798.93 ([M+H]$^+$).

Example 67. Synthesis of (4R)-4-amino-5-(3-((Z)-79-bromo-1-hydroxy-73,78,81-trioxo-3,6,9,12,15,18,21,24,27,30,33,36,39,42,45,48,51,54,57,60,63,66,69-tricosaoxa-72,77,82-triazahexaoctacont-79-enamido)-4-hydroxyphenyl)-2-methylpentanoic acid (204)

for 1.5 h then poured onto ice water and extracted with ethyl acetate. The organic layer was washed with brine (50 mL), dried over anhydrous Na$_2$SO$_4$, and concentrated under reduced pressure to give known compound 208 (8.50 g, 91% yield) as a white solid. $^1$H NMR (500 MHz, CDCl$_3$) δ 3.94 (dd, J=4.9, 2.7 Hz, 2H), 3.60 (ddd, J=18.7, 11.9, 9.3 Hz, 2H),

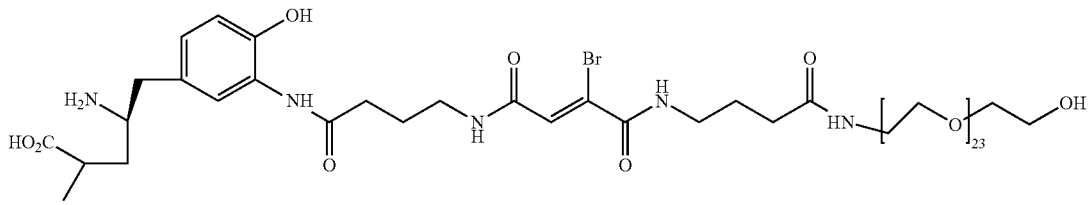

Compound 203 (28 mg, 0.0156 mmol) was dissolved in DCM (2 mL) and treated with TFA (2 mL) at r.t. for 2 h. All volatiles were removed under vacuum to afford compound 204 (25 mg, 98% yield). MS ESI m/z 1642.82 ([M+H]$^+$).

Example 68. Synthesis of (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-((Z)-79-bromo-1-hydroxy-73,78,81-trioxo-3,6,9,12,15,18,21,24,27,30,33,36,39,42,45,48,51,54,57,60,63,66,69-tricosaoxa-72,77,82-triazahexaoctacont-79-enamido)-4-hydroxyphenyl)-2-methylpentanoic acid (205)

3.49-3.37 (m, 1H), 3.34-3.23 (m, 1H), 2.06-1.91 (m, 1H), 1.89-1.69 (m, 2H), 1.65-1.51 (m, 1H), 1.49-0.40 (m, 9H).

Example 70. Synthesis of (S)-tert-butyl 2-formylpyrrolidine-1-carboxylate (209)

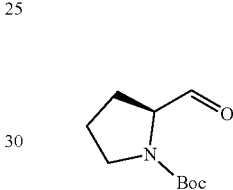

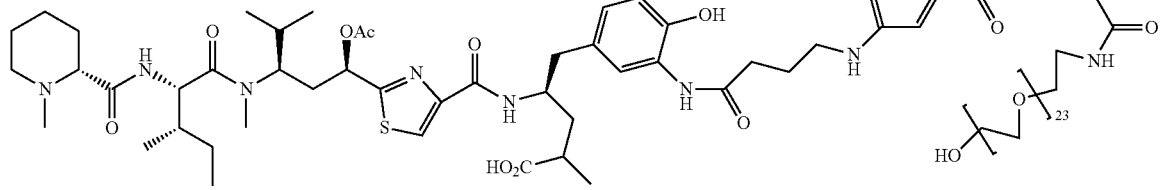

Compound 204 (25 mg, 0.0152 mmol) and perfluorophenyl ester 142 (15 mg, 0.0213 mmol) were dissolved in DMA (5 mL). To the mixture, DIPEA (10 mg, 0.077 mmol) was added. The resulting mixture was stirred at r.t. overnight, concentrated and purified by preparative HPLC (C$_{18}$ column, 10-90% MeCN/H$_2$O) to afford compound 205 (13 mg, 40% yield). MS ESI m/z 2163.82 ([M+H]$^+$).

Example 69. Synthesis of (S)-tert-butyl 2-(hydroxymethyl)pyrrolidine-1-carboxylate (208)

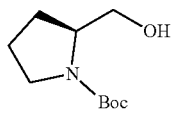

Boc-L-proline (10.0 g, 46.4 mmol) dissolved in 50 mL THF was cooled to 0° C., to which BH$_3$ in THF (1.0 M, 46.4 mL) was added carefully. The mixture was stirred at 0° C.

To a solution of alcohol 208 (13.0 g, 64.6 mmol) in dimethyl sulfoxide (90 mL) was added triethylamine (40 mL) and the stirring was continued for 15 min. The mixture was cooled over ice bath and sulfur trioxide-pyridine complex (35.98 g, 226 mmol) was added in portions over a 40 min period. The reaction was warmed to r.t. and stirred for 2.5 h. After addition of ice (250 g), the mixture was extracted with dichloromethane (150 mL×3). The organic phase was washed with 50% citric acid solution (150 mL), water (150 mL), saturated sodium bicarbonate solution (150 mL), and brine (150 mL), dried over anhydrous Na$_2$SO$_4$. Removal of solvent in vacuo yielded aldehyde 209 (10.4 g, 81% yield) as a dense oil which was used without further purification. $^1$H NMR (500 MHz, CDCl$_3$) δ 9.45 (s, 1H), 4.04 (s, 1H), 3.53 (dd, J=14.4, 8.0 Hz, 2H), 2.00-1.82 (m, 4H), 1.44 (d, J=22.6 Hz, 9H).

Example 71. Synthesis of (4R,5S)-4-methyl-5-phenyl-3-propionyloxazolidin-2-one (211)

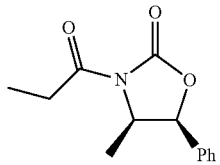

n-Butyllithium in hexane (21.6 mL, 2.2 M, 47.43 mmol) was added dropwise at −78° C. to a stirred solution of 4-methyl-5-phenyloxazolidin-2-one (8.0 g, 45.17 mmol) in THF (100 mL) under N$_2$. The solution was maintained at −78° C. for 1 h then propionyl chloride (4.4 mL, 50.59 mmol) was added slowly. The reaction mixture was warmed to −50° C., stirred for 2 h then quenched by addition of a saturated solution of ammonium chloride (100 mL). The organic solvent was removed in vacuo and the resultant solution was extracted with ethyl acetate (3×100 mL). The organic layer was washed with saturated sodium bicarbonate solution (100 mL) and brine (100 mL), dried over Na$_2$SO$_4$, filtered and concentrated in vacuo. The residue was purified by column chromatography (20% ethyl acetate/hexanes) to afford the compound 211 as a dense oil (10.5 g, 98% yield). 1H NMR (500 MHz, CDCl$_3$) δ 7.45-7.34 (m, 3H), 7.30 (d, J=7.0 Hz, 2H), 5.67 (d, J=7.3 Hz, 1H), 4.82-4.70 (m, 1H), 2.97 (dd, J=19.0, 7.4 Hz, 2H), 1.19 (t, J=7.4 Hz, 3H), 0.90 (d, J=6.6 Hz, 3H).

Example 72. Synthesis of (S)-tert-butyl 2-((1R,2R)-1-hydroxy-2-methyl-3-((4R,5S)-4-methyl-2-oxo-5-phenyloxazolidin-3-yl)-3-oxopropyl)pyrrolidine-1-carboxylate (212)

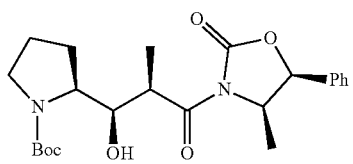 [SMILES: C[C@@H]1[C@H](c2ccccc2)OC(=O)N1C(=O)[C@H](C)[C@@H](O)[C@@H]1CCCN1C(=O)OC(C)(C)C]

To a solution of 209 (9.40 g, 40.4 mmol) in dichloromethane (60 mL) was added Et$_3$N (6.45 mL, 46.64 mmol) at 0° C., followed by 1M dibutylboron triflate in dichloromethane (42 mL, 42 mmol). The mixture was stirred at 0° C. for 45 min, cooled to −70° C., aldehyde 211 (4.58 g, 22.97 mmol) in dichloromethane (40 mL) was then added slowly over a 30 min period. The reaction was stirred at −70° C. for 2 h, 0° C. 1 h, and r.t. 15 min, and then quenched with phosphate buffer solution (pH 7, 38 mL). After the addition of MeOH-30% H$_2$O$_2$ (2:1, 100 mL) at below 10° C. and stirring for 20 min, water (100 mL) was added and the mixture was concentrated in vacuo. More water (200 mL) was added to the residue and the mixture was extracted with ethyl acetate (3×100 mL). The organic layer was washed with 1N KHSO$_4$ (100 mL), sodium bicarbonate solution (100 mL) and brine (100 mL), dried over anhydrous Na$_2$SO$_4$ and concentrated in vacuo. The residue was purified by flash column chromatography (10%-50% ethyl acetate/hexanes) to afford the compound 212 as a white solid (7.10 g, 71% yield). 1H NMR (500 MHz, CDCl$_3$) δ 7.39 (dt, J=23.4, 7.1 Hz, 3H), 7.30 (d, J=7.5 Hz, 2H), 5.67 (d, J=7.1 Hz, 1H), 4.84-4.67 (m, 1H), 4.08-3.93 (m, 3H), 3.92-3.84 (m, 1H), 3.50 (d, J=9.0 Hz, 1H), 3.24 (d, J=6.7 Hz, 1H), 2.15 (s, 1H), 1.89 (dd, J=22.4, 14.8 Hz, 3H), 1.48 (d, J=21.5 Hz, 9H), 1.33 (d, J=6.9 Hz, 3H), 0.88 (d, J=6.4 Hz, 3H).

Example 73. Synthesis of (S)-tert-butyl 2-((1R,2R)-1-methoxy-2-methyl-3-((4R,5S)-4-methyl-2-oxo-5-phenyloxazolidin-3-yl)-3-oxopropyl)pyrrolidine-1-carboxylate (213)

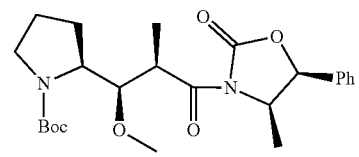 [SMILES: CO[C@H]([C@@H](C)C(=O)N1C(=O)O[C@@H](c2ccccc2)[C@H]1C)[C@@H]1CCCN1C(=O)OC(C)(C)C]

To a mixture of 212 (5.1 g 11.9 mmol) and molecular sieves (4 Å, 5 g) was added anhydrous dichloroethane (30 mL) under N$_2$. The mixture was stirred at room temperature for 20 min and cooled to 0° C. Proton sponge (6.62 g, 30.9 mmol) was added, followed by trimethyloxonium tetrafluoroborate (4.40 g, 29.7 mmol). Stirring was continued for 2 h at 0° C. and 48 h at r.t. The reaction mixture was filtrated and the filtrate was concentrated and purified by column chromatography (20-70% ethyl acetate/hexanes) to afford compound 213 as a white solid (1.80 g, 35% yield). 1H NMR (500 MHz, CDCl$_3$) δ 7.46-7.27 (m, 5H), 5.65 (s, 1H), 4.69 (s, 1H), 3.92 (s, 1H), 3.83 (s, 1H), 3.48 (s, 3H), 3.17 (s, 2H), 2.02-1.68 (m, 5H), 1.48 (d, J=22.3 Hz, 9H), 1.32 (t, J=6.0 Hz, 3H), 0.91-0.84 (m, 3H).

Example 74. Synthesis of (2R,3R)-3-((S)-1-(tert-butoxycarbonyl)pyrrolidin-2-yl)-3-methoxy-2-methylpropanoic acid (214)

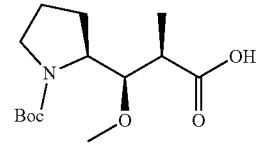 [SMILES: CO[C@H]([C@@H](C)C(=O)O)[C@@H]1CCCN1C(=O)OC(C)(C)C]

To a solution of 213 (1.80 g, 4.03 mmol) in THF (30 mL) and H$_2$O (7.5 mL), 30% H$_2$O$_2$ (1.44 mL, 14.4 mmol) was added over a 5 min period at 0° C., followed by a solution of LiOH (0.27 g, 6.45 mmol) in water (5 mL). After stirring at 0° C. for 3 h, 1 N sodium sulfite (15.7 mL) was added and the mixture was allowed to warm to r.t. and stirred overnight. THF was removed in vacuo and the aqueous phase was wash with dichloromethane (3×50 mL) to remove the oxazolidinone auxiliary. The aqueous phase was acidified to pH 3 with TN HCl and extracted with ethyl acetate (3×50 mL). The organic layer was washed with brine (50 mL), dried over Na$_2$SO$_4$, filtered and concentrated in vacuo to afford the compound 214 as a colorless oil (1.15 g, 98% yield). 1H NMR (500 MHz, CDCl$_3$) δ 3.99-3.74 (m, 2H), 3.44 (d, J=2.6 Hz, 3H), 3.23 (s, 1H), 2.60-2.45 (m, 1H), 1.92 (tt, J=56.0, 31.5 Hz, 3H), 1.79-1.69 (m, 1H), 1.58-1.39 (m, 9H), 1.30-1.24 (m, 3H).

Example 75. Synthesis of (4S,5S)-ethyl 4-((tert-butoxycarbonyl)amino)-5-methyl-3-oxo heptanoate (217)

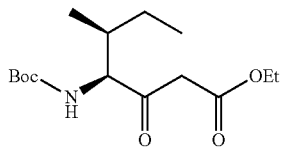 [SMILES: CCOC(=O)CC(=O)[C@@H](NC(=O)OC(C)(C)C)[C@@H](C)CC]

To an ice-cooled solution of N-Boc-L-isoleucine (4.55 g, 19.67 mmol) in THF (20 mL) was added 1,1'-carbonyldiimidazole (3.51 g, 21.63 mmol). After evolution of gas ceased, the resultant mixture was stirred at r.t. for 3.5 h.

A solution of freshly prepared isopropylmagnesium bromide in THF (123 mmol, 30 mL) was added dropwise to a pre-cooled (0° C.) solution of ethyl hydrogen malonate (6.50 g, 49.2 mmol) at such a rate to keep the internal temperature below 5° C. The mixture was stirred at r.t. for 1.5 h. This solution of the magnesium enolate was then cooled over an ice-water bath, followed by the gradual addition of the imidazolide solution over a 1 h period via a double-ended needle at 0° C. The resultant mixture was stirred at 0° C. for 30 min then r.t. 64 h. The reaction mixture was quenched by addition of 10% aqueous citric acid (5 mL), and acidified to pH 3 with an additional 10% aqueous citric acid (110 mL). The mixture was extracted with ethyl acetate (3×150 mL). The organic extracts were washed with water (50 mL), saturated aqueous sodium hydrogen carbonate (50 mL), and saturated aqueous sodium chloride (50 mL), dried over $Na_2SO_4$, and concentrated in vacuo. The residue was purified by column chromatography on silica gel using ethyl acetate/hexane (1:4) as an eluent to give compound 217 (5.50 g, 93% yield). $^1$H NMR (500 MHz, CDCl$_3$) δ 5.04 (d, J=7.8 Hz, 1H), 4.20 (p, J=7.0 Hz, 3H), 3.52 (t, J=10.7 Hz, 2H), 1.96 (d, J=3.7 Hz, 1H), 1.69 (s, 2H), 1.44 (s, 9H), 1.28 (dd, J=7.1, 2.9 Hz, 3H), 0.98 (t, J=6.9 Hz, 3H), 0.92-0.86 (m, 3H).

Example 76. Synthesis of (3R,4S,5S)-ethyl 4-((tert-butoxycarbonyl)amino)-3-hydroxy-5-methylheptanoate (218)

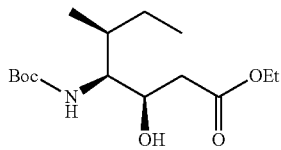 [SMILES: CCOC(=O)C[C@@H](O)[C@@H](NC(=O)OC(C)(C)C)[C@@H](C)CC]

To a solution of the compound 217 (5.90 g, 19.83 mmol) in ethanol (6 mL) at −60° C. was added sodium borohydride (3.77 g, 99.2 mmol) in one portion. The reaction mixture was stirred for 5.5 h below −55° C. then quenched with 10% aqueous citric acid (100 mL). The resultant solution was acidified to pH 2 with an additional 10% aqueous citric acid, followed by extraction with ethyl acetate (3×100 mL). The organic extracts were washed with saturated aqueous sodium chloride (100 mL), dried over $Na_2SO_4$, and concentrated in vacuo. The residue was purified by column chromatography (10-50% ethyl acetate/hexane) to give pure diastereomer 218 (2.20 g, 37% yield) and a mixture of two diastereomers (2.0 g, 34% yield, about 9:1 ratio). $^1$H NMR (500 MHz, CDCl$_3$) δ 4.41 (d, J=9.3 Hz, 1H), 4.17 (tt, J=7.1, 3.6 Hz, 2H), 4.00 (t, J=6.9 Hz, 1H), 3.55 (dd, J=11.7, 9.3 Hz, 1H), 2.56-2.51 (m, 2H), 2.44 (dd, J=16.4, 9.0 Hz, 1H), 1.79 (d, J=3.8 Hz, 1H), 1.60-1.53 (m, 1H), 1.43 (s, 9H), 1.27 (dd, J=9.3, 5.0 Hz, 3H), 1.03-0.91 (m, 7H).

Example 77. Synthesis of (3R,4S,5S)-4-((tert-butoxycarbonyl)amino)-3-hydroxy-5-methyl heptanoic acid (219)

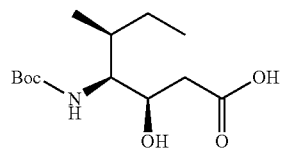 [SMILES: CC[C@H](C)[C@H](NC(=O)OC(C)(C)C)[C@H](O)CC(=O)O]

To a solution of compound 218 (2.20 g, 7.20 mmol) in ethanol (22 mL) was added 1 N aqueous sodium hydroxide (7.57 mL, 7.57 mmol). The mixture was stirred at 0° C. for 30 min then r.t. 2 h. The resultant solution was acidified to pH 4 by addition of 1 N aqueous hydrochloric acid, which was then extracted with ethyl acetate (3×50 mL). The organic extracts were washed with 1 N aqueous potassium hydrogen sulfate (50 mL), and saturated aqueous sodium chloride (50 mL), dried over $Na_2SO_4$, and concentrated in vacuo to give compound 219 (1.90 g, 95% yield). $^1$H NMR (500 MHz, CDCl$_3$) δ 4.50 (d, J=8.7 Hz, 1H), 4.07 (d, J=5.5 Hz, 1H), 3.59 (d, J=8.3 Hz, 1H), 2.56-2.45 (m, 2H), 1.76-1.65 (m, 1H), 1.56 (d, J=7.1 Hz, 1H), 1.45 (s, 9H), 1.26 (t, J=7.1 Hz, 3H), 0.93 (dd, J=14.4, 7.1 Hz, 6H).

Example 78. Synthesis of (3R,4S,5S)-4-((tert-butoxycarbonyl)(methyl)amino)-3-methoxy-5-methyl-heptanoic acid (220)

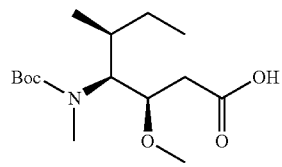 [SMILES: CC[C@H](C)[C@@H]([C@@H](CC(=O)O)OC)N(C)C(=O)OC(C)(C)C]

To a solution of compound 219 (1.90 g, 6.9 mmol) in THF (40 mL) was added sodium hydride (60% oil suspension, 1.93 g, 48.3 mmol) at 0° C. After stirring for 1 h, methyl iodide (6.6 mL, 103.5 mmol) was added. The stirring was continued at 0° C. for 40 h before saturated aqueous sodium hydrogen carbonate (50 mL) was added, followed by water (100 mL). The mixture was washed with diethyl ether (2×50 mL) and the aqueous layer was acidified to pH 3 by 1 N aqueous potassium hydrogen sulfate, then extracted with ethyl acetate (3×50 mL). The combined organic extracts were washed with 5% aqueous sodium thiosulfate (50 mL) and saturated aqueous sodium chloride (50 mL), dried over $Na_2SO_4$, and concentrated in vacuo to give compound 220 (1.00 g, 48% yield). $^1$H NMR (500 MHz, CDCl$_3$) δ 3.95 (d, J=75.4 Hz, 2H), 3.42 (d, J=4.4 Hz, 3H), 2.71 (s, 3H), 2.62 (s, 1H), 2.56-2.47 (m, 2H), 1.79 (s, 1H), 1.47 (s, 1H), 1.45 (d, J=3.3 Hz, 9H), 1.13-1.05 (m, 1H), 0.96 (d, J=6.7 Hz, 3H), 0.89 (td, J=7.2, 2.5 Hz, 3H).

Example 79. Synthesis of Boc-N-Me-L-Val-OH (222)

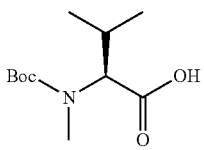

To a solution of Boc-L-Val-OH (2.00 g, 9.2 mmol) and methyl iodide (5.74 mL, 92 mmol) in anhydrous THF (40 mL) was added sodium hydride (3.68 g, 92 mmol) at 0° C. The reaction mixture was stirred at 0° C. for 1.5 h, then warmed to r.t. and stirred for 24 h. The reaction was quenched by ice water (50 mL). After addition of water (100 mL), the reaction mixture was washed with ethyl acetate (3×50 mL) and the aqueous solution was acidified to pH 3 then extracted with ethyl acetate (3×50 mL). The combined organic phase was dried over $Na_2SO_4$ and concentrated to afford Boc-N-Me-Val-OH (2.00 g, 94% yield) as a white solid. $^1H$ NMR (500 MHz, $CDCl_3$) δ 4.10 (d, J=10.0 Hz, 1H), 2.87 (s, 3H), 2.37-2.13 (m, 1H), 1.44 (d, J=26.7 Hz, 9H), 1.02 (d, J=6.5 Hz, 3H), 0.90 (t, J=8.6 Hz, 3H).

Example 80. Synthesis of (S)-tert-butyl 2-((1R,2R)-1-methoxy-3-(((S)-1-methoxy-1-oxo-3-phenylpropan-2-yl)amino)-2-methyl-3-oxopropyl)pyrrolidine-1-carboxylate (223)

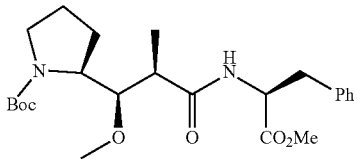 [SMILES: COC(=O)[C@H](Cc1ccccc1)NC(=O)[C@H](C)[C@@H](OC)[C@@H]1CCCN1C(=O)OC(C)(C)C]

To a solution of compound 214 (100 mg, 0.347 mmol) and L-phenylalanine methyl ester hydrochloride (107.8 mg, 0.500 mmol) in DMF (5 mL) at 0° C. was added diethyl cyanophosphate (75.6 μL, 0.451 mmol), followed by $Et_3N$ (131 μL, 0.94 mmol). The reaction mixture was stirred at 0° C. for 2 h, then warmed to r.t. and stirred overnight. The reaction mixture was then diluted with ethyl acetate (80 mL), washed with 1 N aqueous potassium hydrogen sulfate (40 mL), water (40 mL), saturated aqueous sodium hydrogen carbonate (40 mL), and saturated aqueous sodium chloride (40 mL), dried over $Na_2SO_4$, and concentrated in vacuo. The residue was purified by column chromatography (15-75% ethyl acetate/hexanes) to afford compound 223 (130 mg, 83% yield) as a white solid. $^1H$ NMR (500 MHz, $CDCl_3$) δ 7.28 (dd, J=7.9, 6.5 Hz, 2H), 7.23 (t, J=7.3 Hz, 1H), 7.16 (s, 2H), 4.81 (s, 1H), 3.98-3.56 (m, 5H), 3.50 (s, 1H), 3.37 (d, J=2.9 Hz, 3H), 3.17 (dd, J=13.9, 5.4 Hz, 2H), 3.04 (dd, J=14.0, 7.7 Hz, 1H), 2.34 (s, 1H), 1.81-1.69 (m, 2H), 1.65 (s, 3H), 1.51-1.40 (m, 9H), 1.16 (d, J=7.0 Hz, 3H).

Example 81. General procedure for the removal of the Boc function with trifluoroacetic acid. To a solution of the N-Boc amino acid (1.0 mmol) in methylene chloride (2.5 mL) was added trifluoroacetic acid (1.0 mL). After being stirred at room temperature for 1-3 h, the reaction mixture was concentrated in vacuo. Co-evaporation with toluene gave the deprotected product, which was used without any further purification.

Example 82. Synthesis of (S)-methyl 2-((2R,3R)-3-((S)-1-((3R,4S,5S)-4-((tert-butoxycarbonyl)(methyl)amino)-3-methoxy-5-methylheptanoyl)pyrrolidin-2-yl)-3-methoxy-2-methylpropanamido)-3-phenylpropanoate (225)

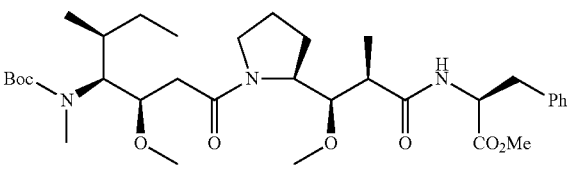 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)OC(C)(C)C]

To a solution of the Boc-deprotected product of compound 224 (0.29 mmol) and compound 220 (96.6 mg, 0.318 mmol) in DMF (5 mL) at 0° C. was added diethyl cyanophosphonate (58 μL, 0.347 mmol), followed by $Et_3N$ (109 μL, 0.78 mmol). The reaction mixture was stirred at 0° C. for 2 h, then warmed to r.t. and stirred overnight. The reaction mixture was diluted with ethyl acetate (80 mL), washed with 1 N aqueous potassium hydrogen sulfate (40 mL), water (40 mL), saturated aqueous sodium hydrogen carbonate (40 mL), and saturated aqueous sodium chloride (40 mL), dried over $Na_2SO_4$ and concentrated in vacuo. The residue was purified by column chromatography (15-75% ethyl acetate/hexanes) to afford compound 225 (150 mg, 81% yield) as a white solid. LC-MS (ESI) m/z calcd. for $C_{34}H_{55}N_3O_8$ $[M+H]^+$: 634.40, found: 634.40.

Example 83. Synthesis of (S)-methyl 2-((2R,3R)-3-((S)-1-((3R,4S,5S)-4-((S)-2-((tert-butoxycarbonyl)amino)-N,3-dimethylbutanamido)-3-methoxy-5-methylheptanoyl)pyrrolidin-2-yl)-3-methoxy-2-methylpropanamido)-3-phenylpropanoate (227)

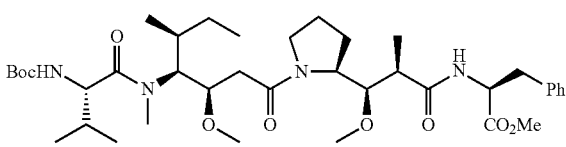 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)OC(C)(C)C)C(C)C]

To a solution of the Boc-deprotected product of compound 225 (0.118 mmol) and Boc-Val-OH (51.8 mg, 0.236 mmol) in DCM (5 mL) at 0° C. was added BroP (70.1 mg, 0.184 mmol), followed by diisopropylethylamine (70 μL, 0.425 mmol). The mixture was shielded from light and stirred at 0° C. for 30 min then at r.t. for 2 days. The reaction mixture was diluted with ethyl acetate (80 mL), washed with 1 N aqueous potassium hydrogen sulfate (40 mL), water (40 mL), saturated aqueous sodium hydrogen carbonate (40 mL), and saturated aqueous sodium chloride (40 mL), dried over $Na_2SO_4$ and concentrated in vacuo. The residue was purified by column chromatography (20-100% ethyl acetate/hexanes) to afford compound 227 (67 mg, 77% yield) as a white solid. LC-MS (ESI) m/z calcd. for $C_{39}H_{64}N_4O_9$ $[M+H]^+$: 733.47, found: 733.46.

Example 84. Synthesis of (S)-methyl 2-((2R,3R)-3-((S)-1-((6S,9S,12S,13R)-12-((S)-sec-butyl)-6,9-diisopropyl-13-methoxy-2,2,5,11-tetramethyl-4,7,10-trioxo-3-oxa-5,8,11-triazapentadecan-15-oyl)pyrrolidin-2-yl)-3-methoxy-2-methylpropanamido)-3-phenylpropanoate (229)

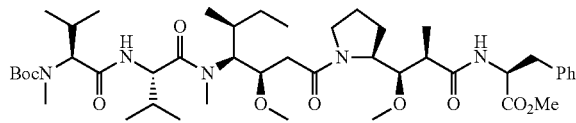 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)C(=O)OC(C)(C)C)C(C)C]

To a solution of the Boc-deprotected product of compound 227 (0.091 mmol) and Boc-N-Me-Val-OH (127 mg, 0.548 mmol) in DMF (5 mL) at 0° C. was added diethyl cyanophosphonate (18.2 µL, 0.114 mmol), followed by N-methylmorpholine (59 µL, 0.548 mmol). The reaction mixture was stirred at 0° C. for 2 h, then warmed to r.t. and stirred overnight. The reaction mixture was diluted with ethyl acetate (80 mL), washed with 1 N aqueous potassium hydrogen sulfate (40 mL), water (40 mL), saturated aqueous sodium hydrogen carbonate (40 mL), and saturated aqueous sodium chloride (40 mL), dried over sodium sulfate, and concentrated in vacuo. The residue was purified by column chromatography (20-100% ethyl acetate/hexanes) to afford compound 229 (30 mg, 39% yield) as a white solid. LC-MS (ESI) m/z calcd. for $C_{45}H_{75}N_5O_{10}$ [M+H]$^+$: 846.55, found: 846.56.

Example 85. Synthesis of (S)-methyl 2-((2R,3R)-3-((S)-1-((3R,4S,5S)-4-((S)—N,3-dimethyl-2-((S)-3-methyl-2-(methylamino)butanamido)butanamido)-3-methoxy-5-methyl-heptanoyl)pyrrolidin-2-yl)-3-methoxy-2-methylpropanamido)-3-phenylpropanoate (230)

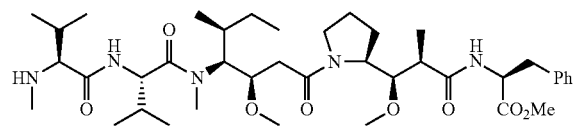

To a solution of compound 229 (75.0 mg, 0.0886 mmol) in methylene chloride (5 mL) was added trifluoroacetic acid (2 mL) at room temperature. After being stirred at room temperature for 1 h, the reaction mixture was concentrated in vacuo. Co-evaporation with toluene gave the deprotected product 230, which was used without further purification.

Example 86. Synthesis of (2S,4R)-methyl 4-hydroxypyrrolidine-2-carboxylate hydrochloric (232)

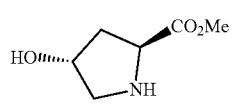

To a solution of trans-4-hydroxy-L-proline (15.0 g, 114.3 mmol) in dry methanol (250 mL) was added thionyl chloride (17 mL, 231 mmol) dropwise at 0 to 4° C. The resulting mixture was stirred for at r.t. overnight, concentrated, crystallized with EtOH/hexane to provide the title compound (18.0 g, 87% yield). ESI MS m/z 168.2 ([M+Na]$^+$).

Example 87. Synthesis of (2S,4R)-1-tert-butyl 2-methyl 4-hydroxypyrrolidine-1,2-dicarboxylate (233)

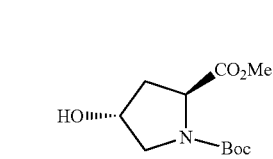

To a solution of trans-4-hydroxy-L-proline methyl ester (18.0 g, 107.0 mmol) in the mixture of MeOH (150 ml) and sodium bicarbonate solution (2.0 M, 350 ml) was added Boc$_2$O (30.0 g, 137.6 mmol) in three portions in 4 h. After stirring for an additional 4 h, the reaction was concentrated to ~350 ml and extracted with EtOAc (4×80 mL). The combined organic layers were washed with brine (100 mL), dried (MgSO$_4$), filtered, concentrated and purified by SiO$_2$ column chromatography (1:1 hexanes/EtOAc) to give the title compound (22.54 g, 86% yield). ESI MS m/z 268.2 ([M+Na]$^+$).

Example 88. Synthesis of (S)-1-tert-butyl 2-methyl 4-oxopyrrolidine-1,2-dicarboxylate (234)

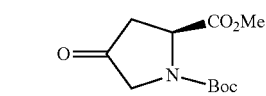

The title compound prepared through Dess-Martin oxidation was described in: Franco Manfre et al. J. Org. Chem. 1992, 57, 2060-2065. Alternatively Swern oxidation procedure is as following: To a solution of (COCl)$_2$ (13.0 ml, 74.38 mmol) in CH$_2$Cl$_2$ (350 ml) cooled to −78° C. was added dry DMSO (26.0 mL). The solution was stirred at −78° C. for 15 min and then compound 233 (8.0 g, 32.63 mmol) in CH$_2$Cl$_2$ (100 ml) was added. After stirring at −78° C. for 2 h, triethylamine (50 ml, 180.3 mmol) was added dropwise, and the reaction solution was warmed to room temperature. The mixture was diluted with aq. NaH$_2$PO$_4$ solution (1.0 M, 400 ml) and phases separated. The aqueous layer was extracted with CH$_2$Cl$_2$ (2×60 ml). The organic layers were combined, dried over MgSO$_4$, filtered, concentrated and purified by SiO$_2$ column chromatography (7:3 hexanes/EtOAc) to give the title compound (6.73 g, 85% yield). ESI MS m/z 266.2 ([M+Na]$^+$).

Example 89. Synthesis of (S)-1-tert-butyl 2-methyl 4-methylenepyrrolidine-1,2-dicarboxylate (235)

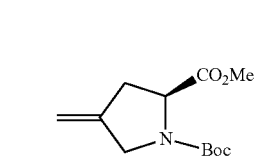 [SMILES: C=C1C[C@@H](C(=O)OC)N(C(=O)OC(C)(C)C)C1]

To a suspension of methyltriphenylphosphonium bromide (19.62 g, 55.11 mmol) in THF (150 mL) at 0° C. was added potassium-t-butoxide (6.20 g, 55.30 mmol) in anhydrous THF (80 mL). After stirring at 0° C. for 2 h, the resulting yellow ylide was added to a solution of compound 234 (6.70 g, 27.55 mmol) in THF (40 mL). After stirring at r.t. for 1 h, the reaction mixture was concentrated, diluted with EtOAc (200 mL), washed with H$_2$O (150 mL), brine (150 mL), dried over MgSO$_4$, concentrated and purified on SiO$_2$ column chromatography (9:1 hexanes/EtOAc) to yield the title compound (5.77 g, 87% yield). EI MS m/z 264 ([M+Na]$^+$).

Example 90. Synthesis of (S)-methyl 4-methylenepyrrolidine-2-carboxylate hydrochloride (236)

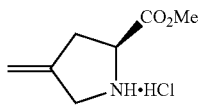

To a solution of compound 235 (5.70 g, 23.63 mmol) in EtOAc (40 ml) at 4° C. was added HCl (12 M, 10 ml). The mixture was stirred for 1 h, diluted with toluene (50 ml), concentrated, and crystallized with EtOH/hexane to yield the title compound as HCl salt (3.85 g, 92% yield). EI MS m/z 142.2 ([M+H]$^+$).

Example 91. Synthesis of 4-(benzyloxy)-3-methoxybenzoic acid (238)

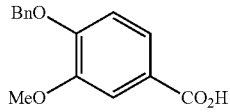

To a mixture of 4-hydroxy-3-methoxybenzoic acid (50.0 g, 297.5 mmol) in ethanol (350 ml) and aq. NaOH solution (2.0 M, 350 ml) was added BnBr (140.0 g, 823.5 mmol). The mixture was stirred at 65° C. for 8 h, concentrated, co-evaporated with water (2×400 ml) and concentrated to ~400 ml, acidified to pH 3.0 with 6 N HCl. The solid was collected by filtration, crystallized with EtOH, dried at 45° C. under vacuum to afford the title compound (63.6 g, 83% yield). ESI MS m/z 281.2 ([M+Na]$^+$).

Example 92. Synthesis of 4-(benzyloxy)-5-methoxy-2-nitrobenzoic acid (239)

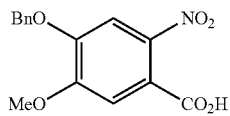

To a solution of compound 238 (63.5 g, 246.0 mmol) in CH$_2$Cl$_2$ (400 ml) and HOAc (100 m$_1$) was added HNO$_3$ (fuming, 25.0 ml, 528.5 mmol). The mixture was stirred for 6 h, concentrated, crystallized with EtOH, dried at 40° C. under vacuum to afford the title compound (63.3 g, 85% yield). ESI MS m/z 326.1 ([M+Na]$^+$).

Example 93. Synthesis of (S)-methyl 1-(4-(benzyloxy)-5-methoxy-2-nitro benzoyl)-4-methylenepyrrolidine-2-carboxylate (240)

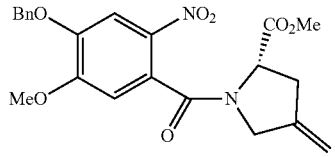 [SMILES: C=C1C[C@@H](C(=O)OC)N(C(=O)c2cc(OC)c(OCc3ccccc3)cc2[N+](=O)[O-])C1]

A catalytic amount of DMF (30 µl) was added to a solution of compound 239 (2.70 g, 8.91 mmol) and oxalyl chloride (2.0 mL, 22.50 mmol) in anhydrous CH$_2$Cl$_2$ (70 mL) and the resulting mixture was stirred at room temperature for 2 h. Excess CH$_2$Cl$_2$ and oxalyl chloride was removed with rotavap. The acetyl chloride was re-suspended in fresh CH$_2$Cl$_2$ (70 mL) and was added slowly to a pre-mixed solution of 236 (1.58 g, 8.91 mmol) and Et$_3$N (6 mL) in CH$_2$Cl$_2$ at 0° C. under N$_2$ atmosphere. The reaction mixture was allowed to warm to r.t. and stirring was continued for 8 h. After removal of CH$_2$Cl$_2$ and Et$_3$N, the residue was partitioned between H$_2$O and EtOAc (70/70 mL). The aqueous layer was further extracted with EtOAc (2×60 mL). The combined organic layers were washed with brine (40 mL), dried (MgSO$_4$) and concentrated. Purification of the residue with flash chromatography (silica gel, 2:8 hexanes/EtOAc) yielded compound 240 (2.88 g, 76% yield). EI MS m/z 449.1 ([M+Na]$^+$).

Example 94. Synthesis of (S)-1-(4-(benzyloxy)-5-methoxy-2-nitrobenzoyl)-4-methylenepyrro-lidine-2-carbaldehyde (241)

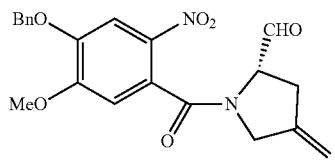 [SMILES: C=C1C[C@@H](C=O)N(C(=O)c2cc(OC)c(OCc3ccccc3)cc2[N+](=O)[O-])C1]

To a vigorously stirred solution of compound 240 (2.80 g, 6.57 mmol) in anhydrous CH$_2$C$_{12}$ (60 mL) was added DIBAL-H (1N in CH$_2$Cl$_2$, 10 mL) dropwise at −78° C. under N$_2$ atmosphere. After the mixture was stirred for an additional 90 min, excess reagent was decomposed by addition of 2 ml of methanol, followed by 5% HCl (10 mL). The resulting mixture was allowed to warm to 0° C. Layers were separated and the aqueous layer was further extracted with CH$_2$C$_{12}$ (3×50 mL). Combined organic layers were washed with brine, dried (MgSO$_4$) and concentrated. Purification of the residue with flash chromatography (silica gel, 95:5 CHCl$_3$/MeOH) yielded compound 241 (2.19 g, 84% yield). EIMS m/z 419.1 ([M+Na]$^+$).

Example 95. Synthesis of (S)-8-(benzyloxy)-7-methoxy-2-methylene-2,3-dihydro-1H-benzo[e]-pyrrolo[1,2-a]azepin-5(11aH)-one (242)

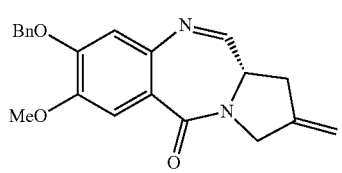 [SMILES: C=C1C[C@H]2C=Nc3cc(OCc4ccccc4)c(OC)cc3C(=O)N2C1]

A mixture of compound 241 (2.18 g, 5.50 mmol) and Na$_2$S$_2$O$_4$ (8.0 g, 45.97 mmol) in THF (60 ml) and H$_2$O (40 ml) was stirred at r.t. for 20 h. Solvents were removed under high vacuum. The residue was re-suspended in MeOH (60 mL), and HCl (6M) was added dropwise until pH 2 was reached. The resulting mixture was stirred at r.t. for 1 h. The reaction was worked-up by removing most of MeOH, then diluted with EtOAc (100 mL). The EtOAc solution was washed with sat. NaHCO$_3$, brine, dried (MgSO$_4$), and concentrated. Purification of the residue with flash chromatography (silica gel, 97:3 CHCl$_3$/MeOH) yielded compound 242 (1.52 g, 80%). EIMS m/z 372.1 ([M+Na]$^+$).

Example 96. Synthesis of (S)-8-hydroxy-7-methoxy-2-methylene-2,3-dihydro-1H-benzo[e]-pyrrolo[1,2-a]azepin-5(11aH)-one (243)

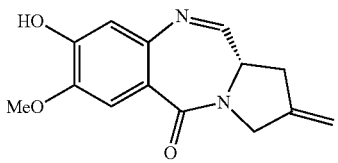 [SMILES: C=C1C[C@H]2C=Nc3cc(O)c(OC)cc3C(=O)N2C1]

To a solution of compound 242 (1.50 g, 4.32 mmol) in 70 ml of CH$_2$Cl$_2$ was added 25 ml of CH$_3$SO$_3$H at 0° C. The mixture was stirred at 0° C. for 10 min then r.t. for 2 h, diluted with CH$_2$Cl$_2$, pH adjusted with cold 1.0 N NaHCO$_3$ to 4 and filtered. The aqueous layer was extracted with CH$_2$Cl$_2$ (3×60 ml). The organic layers were combined, dried over Na$_2$SO$_4$, filtered, evaporated and purified on SiO$_2$ column chromatography (CH$_3$OH/CH$_2$Cl$_2$ 1:15) to afford 811 mg (73% yield) of the title product. EIMS m/z 281.1 ([M+Na]$^+$).

Example 97. Synthesis of (11aS,11a'S)-8,8'-(pentane-1,5-diylbis(oxy))bis(7-methoxy-2-methylene-2,3-dihydro-1H-benzo[e]pyrrolo[1,2-a][1,4]diazepin-5(11aH)-one) (244)

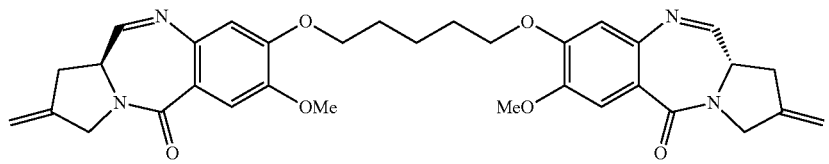

To a stirred suspended solution of Cs$_2$CO$_3$ (0.761 g, 2.33 mmol) in butanone (8 ml) were added compound C11 (401 mg, 1.55 mmol) and 1,5-diiodopentane (240 mg, 0.740 mmol). The mixture was stirred at r.t. overnight, concentrated, and purified on SiO$_2$ chromatography (EtOAc/CH$_2$Cl$_2$ 1:10) to afford 337 mg (78% yield) of the title product. EIMS m/z 607.2 ([M+Na]$^+$).

Example 98. Synthesis of (S)-7-methoxy-8-((5-(((S)-7-methoxy-2-methylene-5-oxo-2,3,5,10,11,11a-hexahydro-TH-benzo[e]pyrrolo[1,2-a][1,4]diazepin-8-yl)oxy)pentyl)oxy)-2-methylene-2,3-dihydro-1H-benzo[e]pyrrolo[1,2-a][1,4]diazepin-5(11aH)-one (245)

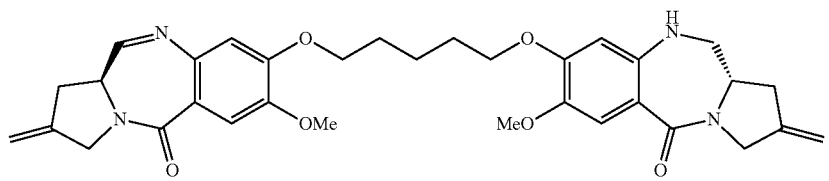

To a solution of compound 244 (150 mg, 0.256 mmol) in anhydrous dichloromethane (1 mL) and absolute ethanol (1.5 mL) was added sodium borohydride in methoxyethyl ether (85 μl, 0.5 M, 0.042 mmol) at 0° C. The ice bath was removed after 5 minutes and the mixture was stirred at room temperature for 3 hours, then cooled to 0° C., quenched with saturated ammonium chloride, diluted with dichloromethane, and phases separated. The organic layer was washed with brine, dried over anhydrous $Na_2SO_4$, filtered through Celite and concentrated. The residue was purified by reverse phase HPLC (Cis column, acetonitrile/water). The corresponding fractions were extracted with dichloromethane and concentrated to afford the title compound 245 (64.7 mg, 43%), MS m/z 609.2 ([M+Na]$^+$), 625.3 ([M+K]$^+$) and 627.2 ([M+Na+$H_2O$]$^+$); the fully reduced compound was obtained (16.5 mg, 11%), MS m/z 611.2 ([M+Na]$^+$), 627.2 ([M+K]$^+$), 629.2 ([M+Na+$H_2O$]$^+$); and the unreacted starting material was also recovered (10.2 mg, 7%), MS m/z 607.2 ([M+Na]$^+$), 625.2 ([M+Na+$H_2O$]$^+$).

Example 99. Synthesis of (S)-8-((5-(((S)-10-(3-(2-(2-azidoethoxy)ethoxy) propanoyl)-7-methoxy-2-methylene-5-oxo-2,3,5,10,11,11a-hexahydro-TH-benzo[e]pyrrolo[1,2-a][1,4]diazepin-8-yl)oxy) pentyl)oxy)-7-methoxy-2-methylene-2,3-dihydro-1H-benzo[e]pyrrolo[1,2-a][1,4]diazepin-5(11aH)-one (246)

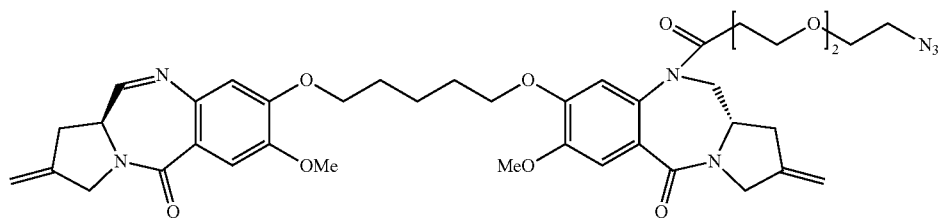

To the mixture of compound 245 (60.0 mg, 0.102 mmol) and compound 166 (40.5 mg, 0.134 mmol) in dichloromethane (5 ml) was added EDC (100.5 mg, 0.520 mmol). The mixture was stirred at r.t. overnight, concentrated and purified on $SiO_2$ column chromatography (EtOAc/$CH_2Cl_2$, 1:6) to afford 63.1 mg (81% yield) of the title product 246. ESI MS m/z $C_{40}H_{50}N_7O_9$[M+H]$^+$, cacld. 772.36, found 772.30.

Example 100. Synthesis of (S)-8-((5-(((S)-10-(3-(2-(2-aminoethoxy)ethoxy) propanoyl)-7-methoxy-2-methylene-5-oxo-2,3,5,10,11,11a-hexahydro-1H-benzo[e]pyrrolo[1,2-a][1,4]diazepin-8-yl)oxy) pentyl)oxy)-7-methoxy-2-methylene-2,3-dihydro-1H-benzo[e]pyrrolo[1,2-a][1,4]diazepin-5(11aH)-one (247)

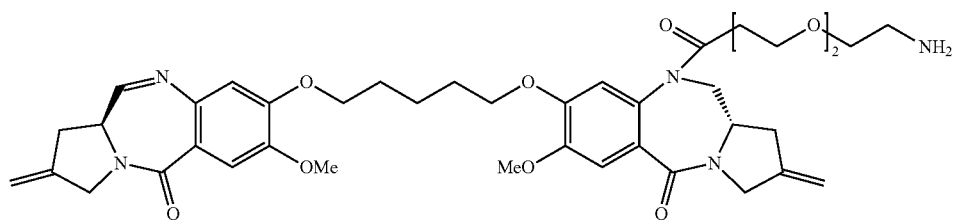

To a solution of compound 246 (60 mg, 0.078 mmol) in the mixture of THF (5 ml) and NaH$_2$PO$_4$ buffer solution (pH 7.5, 1.0 M, 0.7 ml) was added PPh$_3$ (70 mg, 0.267 mmol). The mixture was stirred at r.t. overnight, concentrated and purified on Cis preparative HPLC, eluted with water/CH$_3$CN (from 90% water to 35% water in 35 min) to afford 45.1 mg (79% yield) of the title product 247 after drying under high vacuum. ESI MS m/z C$_{40}$H$_{52}$N$_5$O$_9$ [M+H]$^+$, cacld. 746.37, found 746.50.

Example 101. Synthesis of (2S)-2-((2R,3R)-3-((2S)-1-((11S,14S,17S)-1-azido-17-((R)-sec-butyl)-11,14-diisopropyl-18-methoxy-10,16-dimethyl-9,12,15-trioxo-3,6-dioxa-10,13,16-triazai-cosan-20-oyl) pyrrolidin-2-yl)-3-methoxy-2-methylpropanamido)-3-phenylpropanoic acid (257)

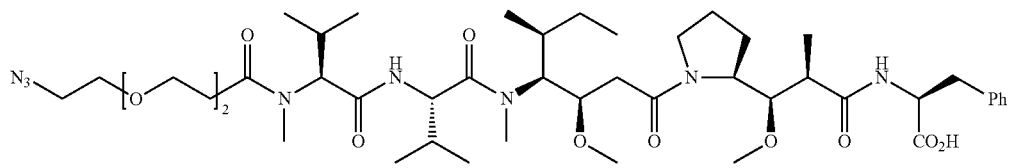

To the crude compound 331 (22 mg, 0.030 mmol) in a mixture of DMA (0.8 ml) and NaH$_2$PO$_4$ buffer solution (pH 7.5, 1.0 M, 0.7 ml) was added compound 166 (18.0 mg, 0.060 mmol) in four portions in 2 h. The mixture was stirred overnight, concentrated and purified on SiO$_2$ column chromatography (CH$_3$OH/CH$_2$Cl$_2$/HOAc 1:8:0.01) to afford the title compound (22.5 mg, 82% yield). LC-MS (ESI) m/z calcd. for C$_{46}$H$_{77}$N$_8$O$_{11}$ [M+H]$^+$: 917.56, found: 917.60.

Example 102. Synthesis of (2S)-2-((2R,3R)-3-((2S)-1-((11S,14S,17S)-1-amino-17-((R)-sec-butyl)-11,14-diisopropyl-18-methoxy-10,16-dimethyl-9,12,15-trioxo-3,6-dioxa-10,13,16-triazaicosan-20-oyl) pyrrolidin-2-yl)-3-methoxy-2-methylpropanamido)-3-phenylpropanoic acid (258)

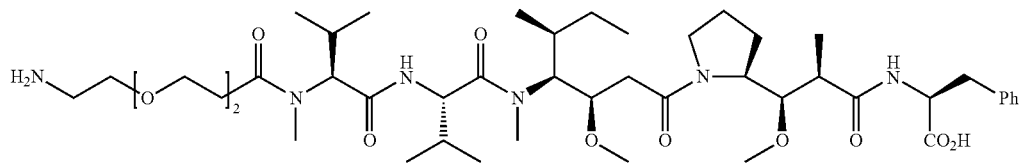

To compound 257 (22.0 mg, 0.024 mmol) in methanol (5 ml) in a hydrogenation bottle was added Pd/C (5 mg, 10% Pd, 50% wet). After air was vacuumed out and 25 psi H$_2$ was conducted in, the mixture was shaken for 4 h, filtered through celite. The filtrate was concentrated to afford the crude title product (~20 mg, 92% yield), which was used in the next step without further purification. ESI MS m/z+ C$_{46}$H$_{79}$N$_6$O$_{11}$ (M+H), cacld. 891.57, found 891.60.

Example 103. Synthesis of (S)-2-((2R,3R)-3-((S)-1-((6S,9S,12S,13R)-12-((S)-sec-butyl)-6,9-diisopropyl-13-methoxy-2,2,5,11-tetramethyl-4,7,10-trioxo-3-oxa-5,8,11-triazapenta-decan-15-oyl)pyrrolidin-2-yl)-3-methoxy-2-methylpropanamido)-3-phenylpropanoic acid (330)

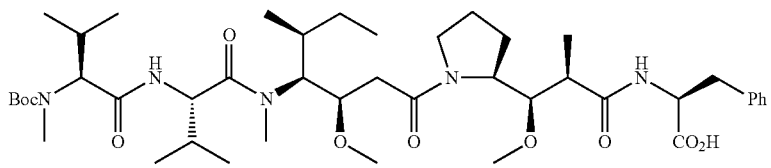 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)OC(C)(C)C)C(C)C]

To a solution of compound 229 (30 mg, 0.035 mmol) in THF (1.0 ml) was added LiOH in water (1.0 M, 0.8 ml). The mixture was stirred at r.t. for 35 min, neutralized with 0.5 M $H_3PO_4$ to pH 6, concentrated and purified on $SiO_2$ column chromatography ($CH_3OH/CH_2Cl_2$/HOAc 1:10:0.01) to afford the title compound 330 (25.0 mg, 85% yield). LC-MS (ESI) m/z calcd. for $C_{44}H_{74}N_5O_{10}$ [M+H]$^+$: 832.54, found: 832.60.

Example 104. Synthesis of (S)-2-((2R,3R)-3-((S)-1-((3R,4S,5S)-4-((S)—N,3-dimethyl-2-((S)-3-methyl-2-(methylamino)butanamido)butanamido)-3-methoxy-5-methylheptanoyl)-pyrrolidin-2-yl)-3-methoxy-2-methylpropanamido)-3-phenylpropanoic acid (331)

Compound 330 (25 mg, 0.030 mmol) in the mixture of conc. HCl (0.3 ml) and 1,4-dioxane (0.9 ml) was stirred at r.t. for 35 min. The mixture was diluted with EtOH (1.0 ml) and toluene (1.0 ml), concentrated and co-evaporated with EtOH/toluene (2:1) to afford the title compound 331 as a white solid (22 mg, ~100% yield), which was used in the next step without further purification. LC-MS (ESI) m/z calcd. for $C_{39}H_{66}N_5O_8$ [M+H]$^+$: 732.48, found: 732.60.

Example 105. Synthesis of (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-(3-(2-(2-azidoethoxy)ethoxy)propanamido)-4-hydroxyphenyl)-2-methylpentanoic acid (335)

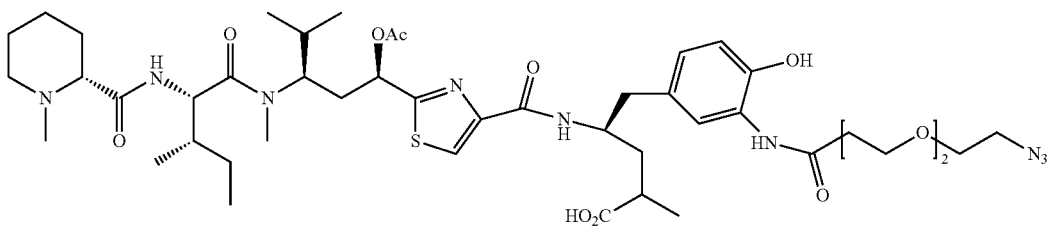

To a solution of (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-amino-4-hydroxyphenyl)-2-methylpentanoic acid 285 (Huang Y. et al, Med Chem. #44, 249th ACS National Meeting, Denver, CO, Mar. 22~26, 2015; WO2014009774) (100 mg, 0.131 mmol) in the mixture of DMA (10 ml) and NaH$_2$PO$_4$ buffer solution (pH 7.5, 1.0 M, 0.7 ml) was added compound 166 (80.0 mg, 0.266 mmol) in four portions in 2 h. The mixture was stirred overnight, concentrated and purified on Cis preparative HPLC (3.0×25 cm, 25 ml/min), eluted with from 80% water/methanol to 10% water/methanol in 45 min to afford the title compound (101.5 mg, 82% yield). LC-MS (ESI) m/z calcd. for C$_{45}$H$_{70}$N$_9$O$_{11}$S [M+H]$^+$: 944.48, found: 944.70.

Example 106. Synthesis of (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-(3-(2-(2-aminoethoxy)ethoxy)propanamido)-4-hydroxyphenyl)-2-methylpentanoic acid (336)

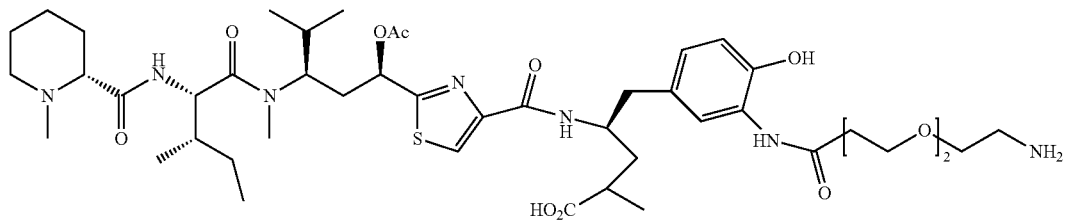

To a solution of compound 332 (100.0 mg, 0.106 mmol) in methanol (25 ml) containing 0.1% HCl in a hydrogenation bottle was added Pd/C (25 mg, 10% Pd, 50% wet). After air was vacuumed out in the vessel and 35 psi H$_2$ was conducted in, the mixture was shaken for 4 h, filtered through celite. The filtrate was concentrated and purified on Cis preparative HPLC (3.0×25 cm, 25 ml/min), eluted with from 85% water/methanol to 15% water/methanol in 45 min to afford the title compound (77.5 mg, 79% yield). LC-MS (ESI) m/z calcd. for C$_{45}$H$_{72}$N$_7$O$_{11}$S [M+H]$^+$: 918.49, found: 918.60.

Example 107. Synthesis of 2,3-dibromo-4-((2-(2-(3-((S)-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepin-10(5H)-yl)-3-oxopropoxy)ethoxy)ethyl)amino)-4-oxobutanoic acid (340)

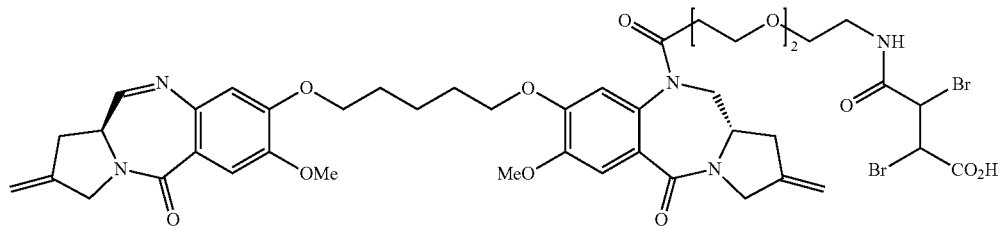

To a solution of compound 247 (40.0 mg, 0.068 mmol) in the mixture of DCM (4 ml) and DIPEA (12 uL, 0.069 mmol) was added 7 (38.0 mg, 0.148 mmol) at 0° C. The mixture was stirred at 0° C. for 2 h and then r.t. 5 h. The mixture was concentrated and purified on SiO$_2$ column eluted with CH$_3$OH/CH$_2$Cl$_2$/HOAc (1:6:0.01) to afford the title compound 340 (56.5 mg, 83% yield). ESI MS m/z calcd. for C$_{44}$H$_{53}$Br$_2$N$_5$O$_{12}$ [M+H]$^+$: 1002.21, found: 1002.40, 1004.40 [M+2+H]$^+$.

Example 108. Synthesis of 2,5-dioxopyrrolidin-1-yl 2,3-dibromo-4-((2-(2-(3-(((S)-7-methoxy-8-((5-(((S)-7-methoxy-2-methylene-5-oxo-2,3,5,11a-tetrahydro-1H-benzo[e]pyrrolo[1,2-a][1,4]-diazepin-8-yl)oxy)pentyl)oxy)-2-methylene-5-oxo-2,3,11,11a-tetrahydro-1H-benzo[e]pyr-rolo[1,2-a][1,4]diazepin-10(5H)-yl)-3-oxopropoxy)ethoxy)ethyl)amino)-4-oxobutanoate (341)

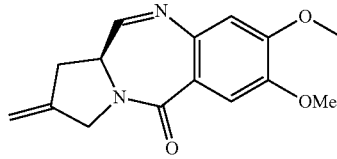
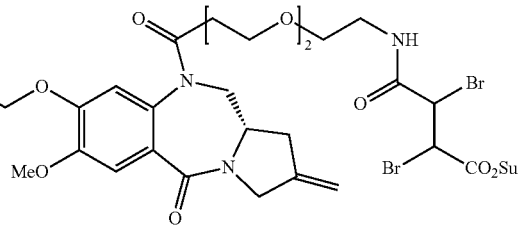

To a solution of 2,3-dibromo-4-((2-(2-(3-(((S)-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepin-10(5H)-yl)-3-oxopropoxy)ethoxy)ethyl)amino)-4-oxobutanoic acid (55.0 mg, 0.054 mmol) in CH$_2$Cl$_2$ (3 ml) was added NHS (10.0 mg, 0.086 mmol) and EDC (30.5 mg, 0.158 mmol). The mixture was stirred at r.t. overnight, concentrated and purified on SiO$_2$ column eluted with EtOAc/CH$_2$Cl$_2$ (1:5) to afford the title compound 341 (50.5 mg, 85% yield). ESI MS m/z calcd. for C$_{48}$H$_{56}$Br$_2$N$_6$O$_{14}$ [M+H]$^+$: 1099.22, found: 1099.40, 1101.40 [M+2+H]$^+$, 1119.50 [M+2+H+H$_2$O]$^+$.

Example 109. Synthesis of (2S)-2-((2R,3R)-3-((2S)-1-((13S,26S,29S,32S)-12,13-dibromo-32-((R)-sec-butyl)-26,29-diisopropyl-33-methoxy-1-((S)-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepin-10(5H)-yl)-25,31-dimethyl-1,11,14,24,27,30-hexaoxo-4,7,18,21-tetraoxa-10,15,25,28,31-pentaazapentatriacontan-35-oyl)pyrrolidin-2-yl)-3-methoxy-2-methylpropanamido)-3-phenylpropanoic acid (344)

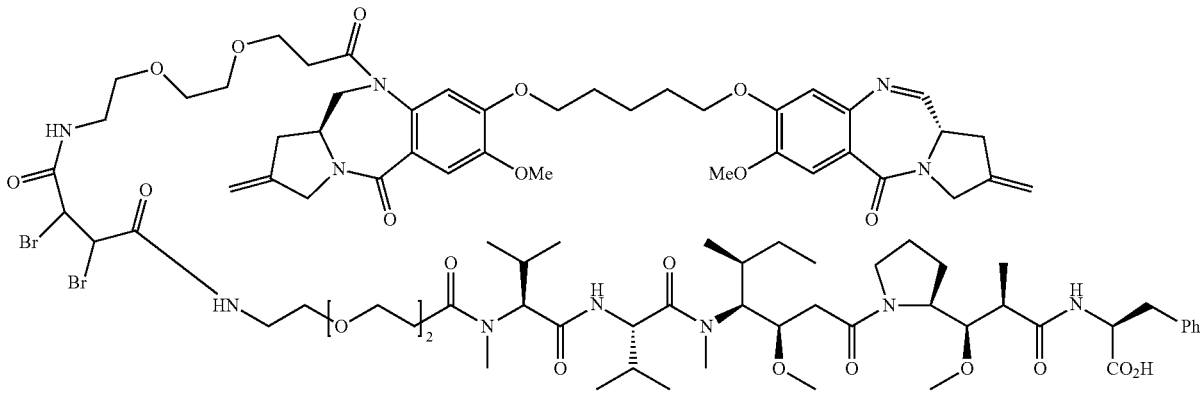

To a solution of compound 258 (~20 mg, 0.022 mmol) in the mixture of THF (1.5 mL) and $NaH_2PO_4$ buffer solution (0.9 mL, 0.15 M, pH 7.5) was added compound 2,5-dioxopyrrolidin-1-yl 2,3-dibromo-4-((2-(2-(3-(((S)-7-methoxy-8-((5-(((S)-7-methoxy-2-methylene-5-oxo-2,3,5,11a-tetrahydro-1H-benzo[e]pyrrolo[1,2-a][1,4]-diazepin-8-yl)oxy)pentyl)oxy)-2-methylene-5-oxo-2,3,11,11a-tetrahydro-1H-benzo[e]pyr-rolo[1,2-a][1,4]diazepin-10 (5H)-yl)-3-oxopropoxy)ethoxy)ethyl)amino)-4-oxobutanoate 341 (30.0 mg, 0.027 mmol). The mixture was stirred at r.t. for 7 h, concentrated, and purified on Cis preparative HPLC ((Φ 2.0 cm×25 cm) eluted with water/$CH_3CN$ (from 90% water to 15% water in 50 min at 10 ml/min) to afford the title product 344 (26.1 mg, 63% yield) after drying under high vacuum. ESI MS m/z $C_{90}H_{130}Br_2N_{11}O_{22}$ $[M+H]^+$, cacld. 1874.77, found 1874.50.

Example 110. Conjugated Compound 344 to an Antibody for 345

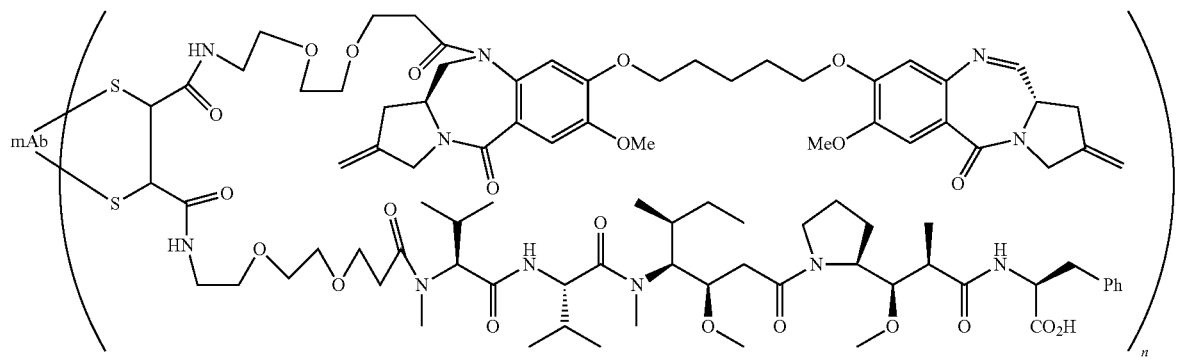

To a mixture of 2.0 mL of 10 mg/ml Herceptin in pH 6.0~8.0, were added 0.70~2.0 mL PBS buffer of 100 mM $NaH_2PO_4$, pH 6.5~7.5 buffers, TCEP (28 μL, 20 mM in water) and the compound 344 (14 μL, 20 mM in DMA). The mixture was incubated at RT for 4~16 h, then DHAA (135 μL, 50 mM) was added. After continuous incubation at RT overnight, the mixture was purified on G-25 column eluted with 100 mM $NaH_2PO_4$, 50 mM NaCl pH 6.0~7.5 buffer to afford 16.5~17.7 mg of conjugate compound 345 (82%~88% yield) in 13.1~15.0 ml buffer. The drug/antibody ratio (DAR) (the combination of PBD dimer and MMAF per antibody) was 3.85, determined by UPLC-QT of mass spectrum. The product was 96~99% monomer analyzed by SEC HPLC (Tosoh Bioscience, Tskgel G3000SW, 7.8 mm ID×30 cm, 0.5 ml/min, 100 min) and a single band measured by SDS-PAGE gel.

Example 111. Synthesis of (4R)-4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-(12,13-dibromo-24-((S)-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepin-10(5H)-yl)-11,14,24-trioxo-4,7,18,21-tetraoxa-10,15-diazatetracosanamido)-4-hydroxyphenyl)-2-methylpentanoic acid (346)

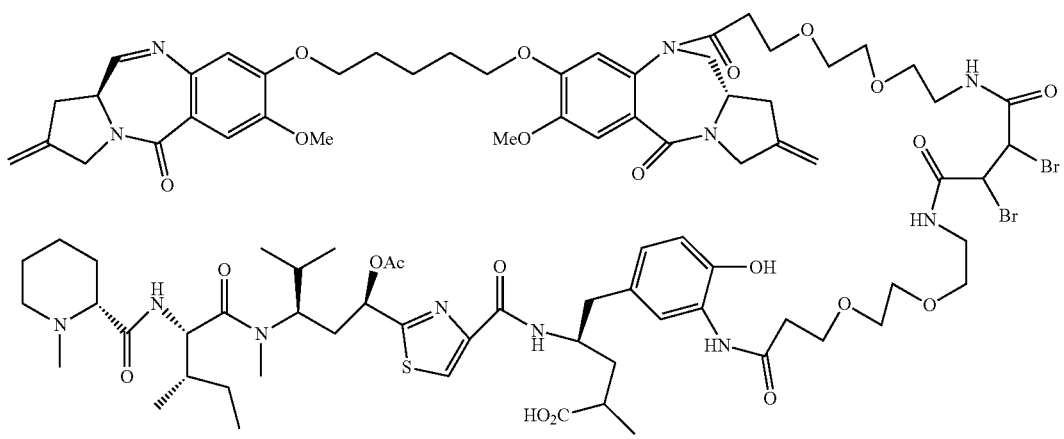

346

To a solution of compound 336 (20 mg, 0.021 mmol) in the mixture of THF (1 ml) and NaH$_2$PO$_4$ buffer solution (0.6 ml, 0.15 M, pH 7.5) was added compound 341 (30.0 mg, 0.027 mmol). The mixture was stirred at r.t. for 8 h, concentrated, and purified on Cis preparative HPLC ((Φ 2.0 cm×25 cm) eluted with water/CH$_3$CN (from 90% water to 20% water in 50 min at 10 ml/min) to afford the title product 346 (26.6 mg, 64% yield) after drying under high vacuum. ESI MS m/z C$_{89}$H$_{123}$Br$_2$N$_{12}$O$_{22}$S [M+H]$^+$, cacld. 1901.69, found 1901.90.

Example 112. Conjugated Compound 346 to an Antibody for 347

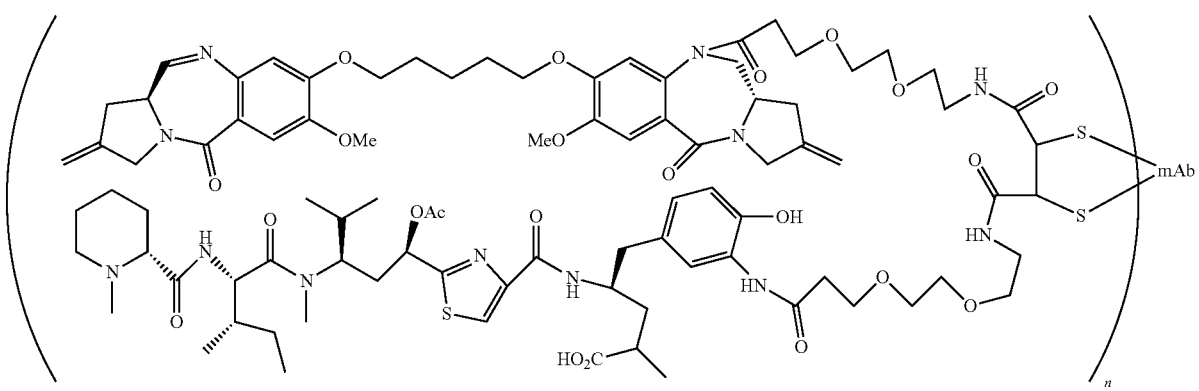

347

To a mixture of 2.0 mL of 10 mg/ml Herceptin in pH 6.0~8.0, were added 0.70~ 2.0 mL PBS buffer of 100 mM NaH$_2$PO$_4$, pH 6.5~7.5 buffers, TCEP (28 μL, 20 mM in water) and the compound 346 (14 μL, 20 mM in DMA). The mixture was incubated at RT for 4~16 h, then DHAA (135 μL, 50 mM) was added. After continuous incubation at RT overnight, the mixture was purified on G-25 column eluted with 100 mM NaH$_2$PO$_4$, 50 mM NaCl pH 6.0~7.5 buffer to afford 16.4~17.6 mg of the conjugate compound 347(82%-88% yield) in 13.2~15.1 ml buffer. The drug/antibody ratio (DAR) (the combination of PBD dimer and tubulysin analog per antibody) was 3.9, determined by UPLC-QT of mass spectrum. The product was 96~99% monomer analyzed by SEC HPLC (Tosoh Bioscience, Tskgel G3000SW, 7.8 mm ID×30 cm, 0.5 ml/min, 100 min) and a single band measured by SDS-PAGE gel.

Example 113. Synthesis of (4R)-tert-butyl 5-(4-acetoxy-3-nitrophenyl)-4-((tert-butoxycarbonyl)amino)-2-methylpentanoate (349)

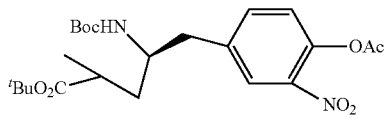 [SMILES: CC(=O)Oc1ccc(C[C@@H](CC(C)C(=O)OC(C)(C)C)NC(=O)OC(C)(C)C)cc1[N+](=O)[O-]]

To a solution of compound 190 (107.1 mg, 0.252 mmol) in dichloromethane (4.0 mL) at 0° C. was added acetic anhydride (0.11 mL, 1.17 mmol) and triethylamine (0.16 mL) in sequence. The reaction was then warmed to r.t. and stirred for 1 h, diluted with dichloromethane and washed with water and brine, dried over anhydrous Na$_2$SO$_4$, filtered and concentrated. The residue was purified by column chromatography (0-15% EA/PE) to give a colorless oil (120.3 mg, theoretical yield). MS ESI m/z calcd for C$_{23}$H$_{35}$N$_2$O$_8$ [M+H]$^+$ 467.23, found 467.23.

Example 114. Synthesis of (4R)-tert-butyl 5-(4-acetoxy-3-aminophenyl)-4-((tert-butoxycarbonyl)amino)-2-methylpentanoate (349)

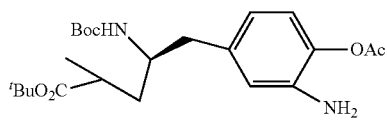 [SMILES: CC(=O)Oc1ccc(C[C@@H](CC(C)C(=O)OC(C)(C)C)NC(=O)OC(C)(C)C)cc1N]

Phenyl nitrile 348 (120.3 mg, 0.258 mmol) was dissolved in ethyl acetate (5 mL) and acetic acid (0.5 mL). To which Pd/C (10 wt %, 10 mg) was added and the mixture was stirred under H$_2$ balloon at r.t. for 30 min before filtration through a celite pad with washing of the pad with ethyl acetate. The filtrate was concentrated and purified by column chromatography (0-25% EA/PE) to give a yellow oil (120.9 mg, theoretical yield). MS ESI m/z calcd for C$_{23}$H$_{37}$N$_2$O$_6$ [M+H]$^+$ 437.26, found 437.28.

Example 115. Synthesis of 30-((2-acetoxy-5-((2R)-5-(tert-butoxy)-2-((tert-butoxycarbonyl)amino)-4-methyl-5-oxopentyl)phenyl)amino)-14,17,30-trioxo-4,7,10,21,24,27-hexaoxa-13,18-diazatriacont-15-yn-1-oic acid (350)

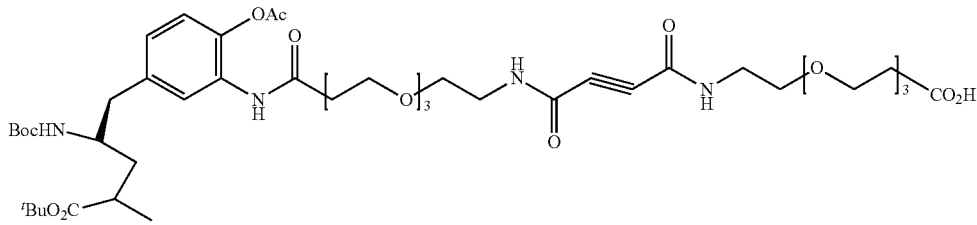

To a solution of aniline 349 (106.9 mg, 0.245 mmol) and diacid 150 (140.2 mg, 0.269 mmol) in DMF (4.5 mL) at 0° C. was added HATU (93.2 mg, 0.245 mmol) and DIPEA (0.13 mL) in sequence. The reaction was then warmed to r.t. and stirred for 18 h, diluted with ethyl acetate and washed with water for three times and brine, dried over anhydrous Na$_2$SO$_4$, filtered and concentrated. The residue was purified by column chromatography (0-15% MeOH/CH$_2$Cl$_2$) to give a light yellow oil (70.9 mg, 31% yield). MS ESI m/z calcd for C$_{45}$H$_{71}$N$_4$O$_{17}$ [M+H]$^+$ 939.47, found 939.47.

Example 116. Synthesis of 2,5-dioxopyrrolidin-1-yl 30-((2-acetoxy-5-((2R)-5-(tert-butoxy)-2-((tert-butoxycarbonyl)amino)-4-methyl-5-oxopentyl)phenyl)amino)-14,17,30-trioxo-4,7,10,21,24,27-hexaoxa-13,18-diazatriacont-15-yn-1-oate (351)

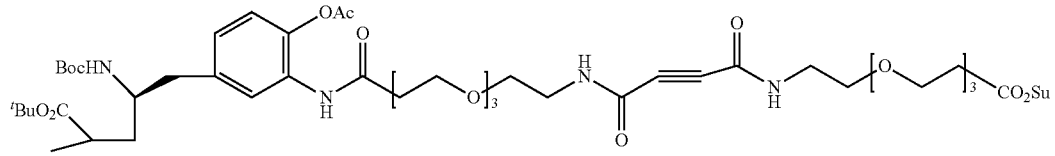

A mixture of acid 350 (22.3 mg, 0.0237 mmol), N-hydroxysuccinimide (13.7 mg, 0.119 mmol) and DCC (15.0 mg, 0.0728 mmol) were stirred at r.t. for 16 h. The solid was filtered off and the filtrate concentrated and purified by column chromatography (0-10% MeOH/CH$_2$Cl$_2$) to give colorless oil (14.7 mg, 60% yield). MS ESI m/z calcd for C$_{49}$H$_{74}$N$_5$O$_{19}$ [M+H]$^+$ 1036.49, found 1036.49.

Example 117. Synthesis of (4R)-butyl 5-(4-acetoxy-3-(1-hydroxy-73,86,89-trioxo-3,6,9,12,15,18,21,24,27,30,33,36,39,42,45,48,51,54,57,60,63,66,69,76,79,82,93,96,99-nonacosaoxa-72,85,90-triazadohect-87-ynamido)phenyl)-4-((tert-butoxycarbonyl)amino)-2-methylpentanoate (352)

To a solution of H$_2$N-PEG$_{24}$-OH (15.2 mg, 0.0142 mmol) in a mixture of EtOH/CH$_2$Cl$_2$/H$_2$O (v/v/v 5:3:1, 0.5 mL), triethylamine (25 μL) was added, followed by a solution of NHS ester 351 (14.7 mg, 0.0142 mmol) in EtOH/CH$_2$Cl$_2$/H$_2$O (v/v/v 5:3:1, 1.0 mL). After stirring at r.t. for 1 h, the reaction was concentrated and purified by column chromatography (0-15% MeOH/CH$_2$Cl$_2$) to give colorless oil. MS ESI m/z calcd for C$_{93}$H$_{168}$N$_5$O$_{40}$ [M+H]$^+$ 1995.12, found 1995.12.

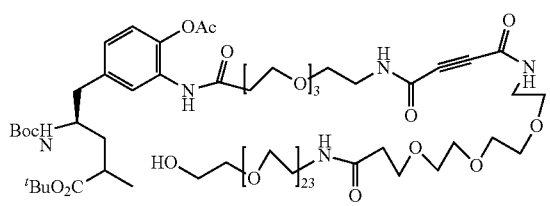

Example 118. Synthesis of (4R)-4-(2-((1R,3R)-1-acetoxy-3-((2S,3S)—N,3-di methyl-2-((R)-1-methylpiperidine-2-carboxamido)pentanamido)-4-methylpentyl)thiazole-4-carboxamido)-5-(4-acetoxy-3-(1-hydroxy-73,86,89-trioxo-3,6,9,12,15,18,21,24,27,30,33,36,39,42,45,48,51,54,57,60,63,66,69,76,79,82,93,96,99-nonacosaoxa-72,85,90-triazadohect-87-ynamido)phenyl)-2-methylpentanoic acid (353)

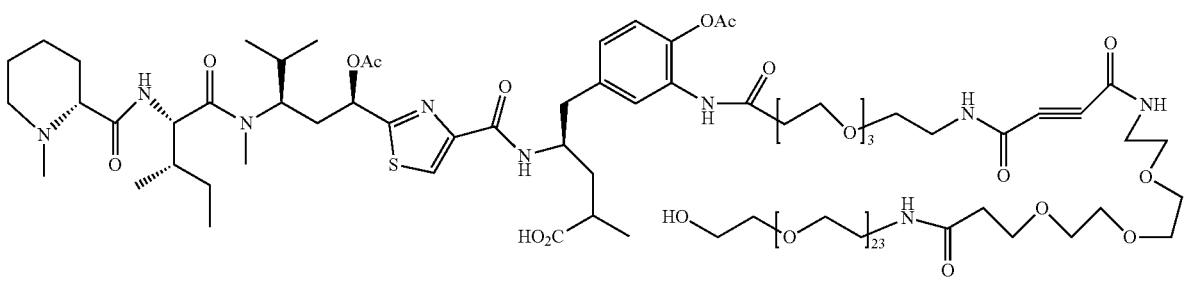

Compound 352 (0.005 mmol) was dissolved in $CH_2Cl_2$ (1.0 mL) and treated with TFA (1.0 mL) at r.t. for 1.5 h then concentrated and re-dissolved in DMF (0.5 mL), to which pentafluorophenyl ester 142 (0.02 mmol) in DMF (0.5 mL) and DIPEA (3.5 µL) were added. The reaction was stirred at r.t. for 2 h and then concentrated. The residue was purified by preparative reverse phase HPLC (Cis column, acetonitrile/water) to give a colorless oil (1.13 mg, 10% yield). MS ESI m/z calcd for $C_{110}H_{192}N_9O_{43}S$ [M+H]$^+$ 2359.28, found 2359.28.

Example 119. Synthesis of (3R,4S,7S,10S)-4-((S)-sec-butyl)-7,10-diisopropyl-3-(2-((S)-2-((1R,2R)-1-methoxy-3-(((S)-1-methoxy-1-oxo-3-phenylpropan-2-yl)amino)-2-methyl-3-oxopropyl)pyrrolidin-1-yl)-2-oxoethyl)-5,11-dimethyl-6,9,12,25,28-pentaoxo-2,15,18,21,32,35,38-heptaoxa-5,8,11,24,29-pentaazahentetracont-26-yn-41-oic acid (355)

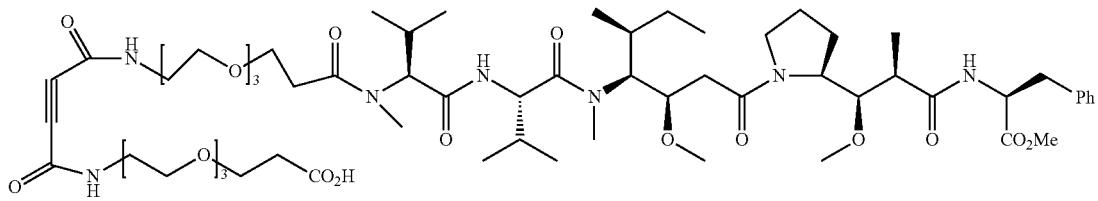

To a solution of 230 (26.1 mg, 0.035 mmol) and diacid 150 (55 mg, 0.106 mmol) in dichloromethane (2 mL) at 0° C. was added Brop (16 mg, 0.042 mmol), followed by diisopropylethylamine (22 µL, 0.12 mmol). The reaction mixture was stirred at 0° C. for 10 min, then warmed to r.t. and stirred overnight. The reaction mixture was diluted with ethyl acetate (50 mL), washed with water (10 mL), saturated aqueous sodium chloride (10 mL), dried over sodium sulfate, and concentrated in vacuo. The residue was purified by reverse phase HPLC with a gradient of MeCN/H$_2$O to afforded compound 355 (30 mg, 68% yield) as a white solid. MS ESI m/z calcd. for $C_{62}H_{101}N_7O_{19}$ [M+H]$^+$: 1248.72, found: 1248.72.

Example 120. Synthesis of (3R,4S,7S,10S)-perfluorophenyl4-((S)-sec-butyl)-7,10-diisopropyl-3-(2-((S)-2-((1R,2R)-1-methoxy-3-(((S)-1-methoxy-1-oxo-3-phenylpropan-2-yl)amino)-2-methyl-3-oxopropyl)pyrrolidin-1-yl)-2-oxoethyl)-5,11-dimethyl-6,9,12,25,28-pentaoxo-2,15,18,21,32,35,38-heptaoxa-5,8,11,24,29-pentaazahentetracont-26-yn-41-oate (356)

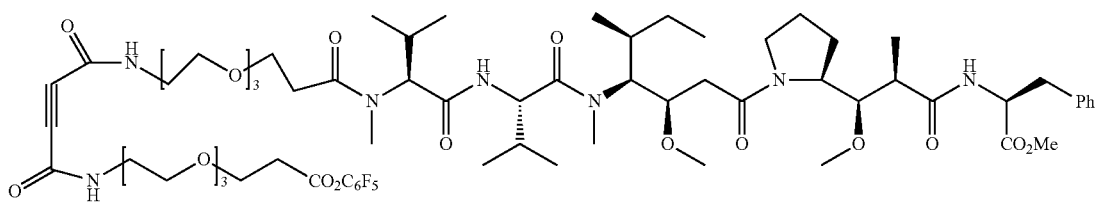

To a solution of compound 355 (15 mg, 0.012 mmol) dissolved in ethyl acetate (1 mL) was added pentafluorophenol (3.3 mg, 0.018 mmol) and DCC (3.7 mg, 0.018 mmol). The reaction mixture was stirred at room temperature overnight and then filtered, washing the filter cake with 2 mL of EtOAc. The filtrate was used immediately without further purification or concentration.

Example 121. Synthesis of (S)-methyl 2-((2R,3R)-3-((S)-1-((104S,107S,110S,111R)-110-((S)-sec-butyl)-1-hydroxy-104,107-diisopropyl-111-methoxy-103,109-dimethyl-73,86,89,102,105,108-hexaoxo-3,6,9,12,15,18,21,24,27,30,33,36,39,42,45,48,51,54,57,60,63,66,69,76,79,82,93,96,99-nonacosaoxa-72,85,90,103,106,109-hexaazatridecahect-87-yn-113-oyl)pyrrolidin-2-yl)-3-methoxy-2-methylpropanamido)-3-phenylpropanoate (357)

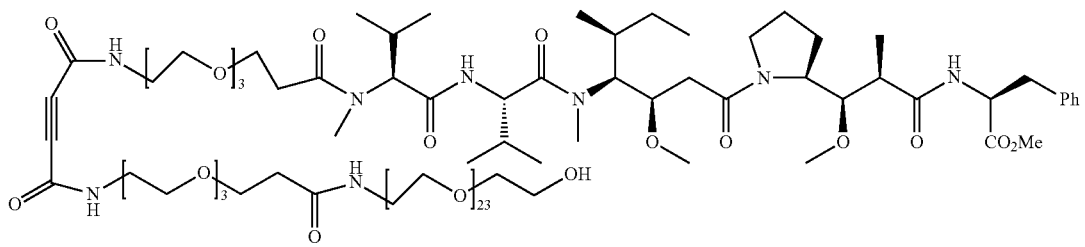

To a solution of compound 356 (0.012 mmol) dissolved in DMA (1 mL) was added HO-PEG$_{24}$-NH$_2$ (19 mg, 0.018 mmol) and diisopropylethylamine (4.2 µL, 0.024 mmol). The reaction mixture was stirred overnight and concentrated in vacuo. The residue was purified by reverse phase HPLC with a gradient of MeCN/H$_2$O to afforded compound 357 (5 mg, 18% yield) as a colorless oil. MS ESI m/z calcd. for C$_{110}$H$_{198}$N$_8$O$_{42}$ [M+H]$^+$ 2304.36, found 2304.36.

Example 122. Synthesis of Compound 361

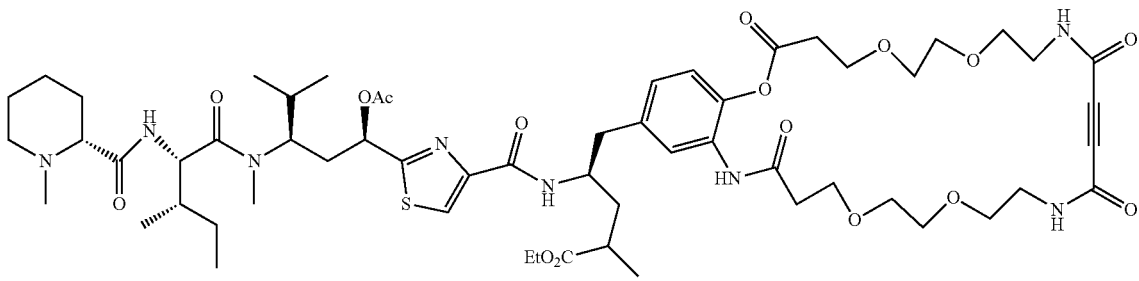

To a solution of compound 161 (4.7 mg, 0.011 mmol) dissolved in ethyl acetate (1 mL) was added pentafluorophenol (10.1 mg, 0.055 mmol) and DCC (11.3 mg, 0.055 mmol). The reaction mixture was stirred at room temperature overnight and then filtered through celite, washing the filter cake with 2 mL of EtOAc. The filtrate was concentrated and re-dissolved in DMA (2 mL), to which (4R)-ethyl 4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-(3-amino-4-hydroxyphenyl)-2-methylpentanoate 360 (8 mg, 0.0102 mmol) and DIPEA (3.8 µL, 0.022 mmol) were added. The reaction mixture was stirred at r.t. overnight, and then the solvent was removed under reduced pressure and the residue was purified by reverse phase HPLC with a gradient of MeCN/H$_2$O to give the title product 361 (4.5 mg, 38% yield). ESI MS m/z: calcd for C$_{58}$H$_{87}$N$_8$O$_{16}$S [M+H]$^+$ 1183.59, found 1183.58.

Example 123. Synthesis of Compound 364

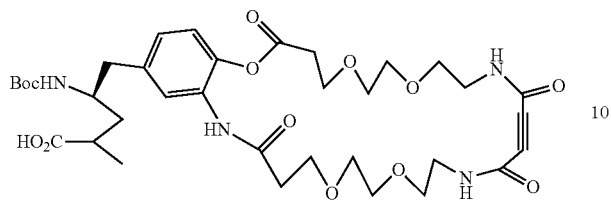

364

To a solution of compound 161 (0.43 g, 0.997 mmol) dissolved in ethyl acetate (20 mL) was added pentafluorophenol (0.92 g, 4.98 mmol) and DCC (1.02 g, 4.98 mmol). The reaction mixture was stirred at room temperature overnight and then filtered through celite, washing the filter cake EtOAc. The filtrate was concentrated and re-dissolved in DMA (10 mL), to which (4R)-5-(3-amino-4-hydroxyphenyl)-4-((tert-butoxycarbonyl)amino)-2-methylpentanoic acid 363 (0.34 g, 0.997 mmol) and DIPEA (0.35 mL, 2 mmol) were added. The reaction mixture was stirred at r.t. overnight and concentrated under reduced pressure. The residue was diluted with $H_2O$ and extracted with EtOAc. The combined the organic layers were dried over $Na_2SO_4$, concentrated and purified by $SiO_2$ column chromatography to give the title product 364 (0.3 g, 42% yield). ESI MS m/z: calcd for $C_{35}H_{51}N_4O_{13}$ [M+H]$^+$:735.34, found 735.34.

Example 124. Synthesis of Compound 365

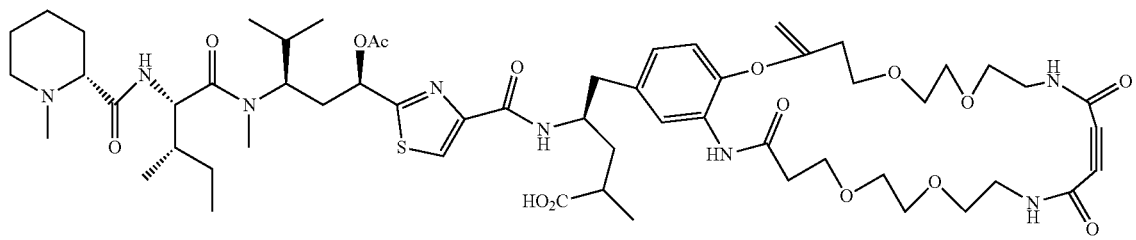 [SMILES: C=C1CCOCCOCCNC(=O)C#CC(=O)NCCOCCOCCC(=O)Nc2cc(C[C@@H](CC(C)C(=O)O)NC(=O)c3csc([C@@H](C[C@H](C(C)C)N(C)C(=O)[C@@H](NC(=O)[C@H]4CCCCN4C)[C@@H](C)CC)OC(C)=O)n3)ccc2O1]

Compound 364 (0.1 g, 0.14 mmol) was dissolved in DCM (10 mL), treated with TFA (5 mL) and stirred at r.t. for 2 h, then concentrated. The residue was dissolved in DMA (8 ml), to which pentafluorophenyl ester 142 (0.15 g, 0.21 mmol) and DIPEA (37 μl, 0.21 mmol) were added and the reaction was stirred overnight. The reaction solution was concentrated and purified by reverse phase HPLC with a gradient of MeCN/$H_2O$ to give the product 365 (47.2 mg, 30% yield). ESI MS m/z: calcd for $C_{56}H_{83}N_5O_{16}S$ [M+H]$^+$: 1155.56, found 1155.56.

Example 125. Synthesis of 24-((5-((2R)-5-(tert-butoxy)-2-((tert-butoxycarbonyl) amino)-4-methyl-5-oxopentyl)-2-((tert-butyldimethylsilyl)oxy)phenyl)amino)-11,14,24-trioxo-4,7,18,21-tetraoxa-10,15-diazatetracos-12-yn-1-oic acid (367)

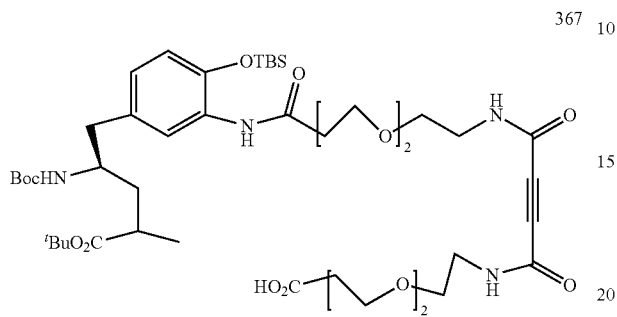

Compound 192 (0.085 g, 0.197 mmol), compound 161 (0.1 g, 0.197 mmol) and HATU (0.112 mg, 0.30 mmol) were mixed in DMF (6 ml), to which TEA (55 μL, 0.40 mmol) was added. The reaction mixture was stirred at r.t. overnight. The solvent was removed under reduced pressure and the residue purified by SiO₂ column chromatography to give the title product 367 (0.065 mg, 36% yield). ESI MS m/z: calcd for $C_{45}H_{75}N_4O_{14}Si$ [M+H]⁺ 923.50, found 923.50.

Example 126. Synthesis of 24-((5-((2R)-5-(tert-butoxy)-2-((tert-butoxycarbonyl) amino)-4-methyl-5-oxopentyl)-2-hydroxyphenyl)amino)-11,14,24-trioxo-4,7,18,21-tetraoxa-10,15-diazatetracos-12-yn-1-oic acid (368)

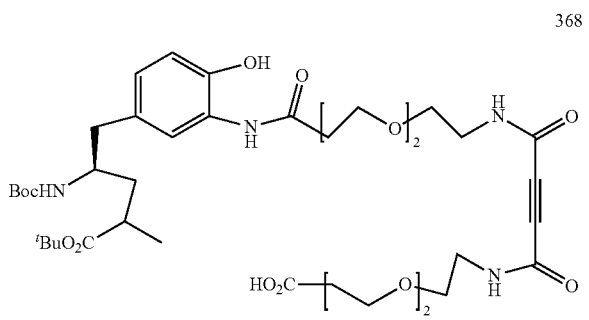

Compound 367 (64.8 mg, 0.070 mmol) was dissolved in DCM (3 mL), TBAF (1 M, 0.1 mL) was added, and the reaction was stirred at r.t. for 1 h, then concentrated and purified by SiO₂ column chromatography to give the title product 368 (34.5 mg, 61% yield). ESI MS m/z: calcd for $C_{39}H_{61}N_4O_{14}$ [M+H]⁺ 809.41, found 809.41.

Example 127. Synthesis of 24-((5-((2R)-2-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-4-carboxypentyl)-2-hydroxyphenyl)amino)-11,14,24-trioxo-4,7,18,21-tetraoxa-10,15-diazatetracos-12-yn-1-oic acid (369)

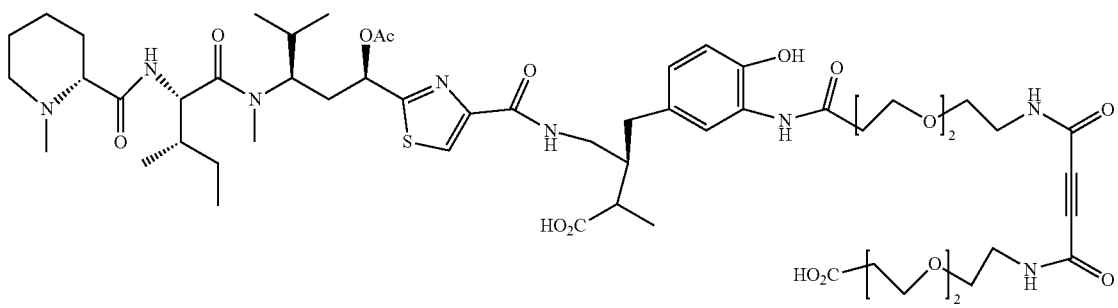

Compound 368 (34.5 mg, 0.043 mmol) was dissolved in DCM (1 mL), and then TFA (0.5 mL) was added. The reaction was stirred at r.t. for 2 h, then concentrated and re-dissolved in DMA (4 mL), to which pentafluorophenyl ester 142 (45 mg, 0.065 mmol) and DIPEA (15 μL, 0.09 mmol) were added and the reaction was stirred overnight and then concentrated and purified by reverse phase HPLC with a gradient of MeCN/H₂O to give the title product 369 (22.8 mg, 46% yield). ESI MS m/z: calcd for $C_{56}H_{85}N_8O_{17}S$ [M+H]⁺ 1173.57, found 1173.58.

Example 128. Synthesis of (4R)-ethyl 5-(3-(4-(((benzyloxy)carbonyl)amino) butanamido)-4-((tert-butyldimethylsilyl)oxy)phenyl)-4-((tert-butoxycarbonyl)amino)-2-methylpentanoate (372)

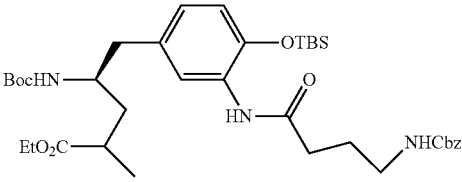 [SMILES: CCOC(=O)C(C)C[C@H](Cc1ccc(O[Si](C)(C)C(C)(C)C)c(NC(=O)CCCNC(=O)OCc2ccccc2)c1)NC(=O)OC(C)(C)C]

2,5-dioxopyrrolidin-1-yl 4-(((benzyloxy)carbonyl)amino) butanoate (0.396 g, 1.2 mmol) and (4R)-ethyl 5-(3-amino-4-hydroxyphenyl)-4-((tert-butoxycarbonyl) amino)-2-methylpentanoate (0.44 g, 1.2 mmol) were dissolved in EtOH (10 mL), and phosphate buffer solution (pH=7.5, 0.1M, 2 ml) was added. The reaction mixture was stirred at r.t. overnight and then the solvent was removed under reduced pressure and the residue purified by $SiO_2$ column chromatography to give the title product 372 (0.485 g, 70%). ESI: m/z: calcd for $C_{31}H_{44}N_3O_8$ $[M+H]^+$ 586.31, found 586.31.

Example 129. Synthesis of (4R)-ethyl 5-(3-(4-aminobutanamido)-4-((tert-butyl dimethylsilyl)oxy)phenyl)-4-((tert-butoxycarbonyl)amino)-2-methylpentanoate (373)

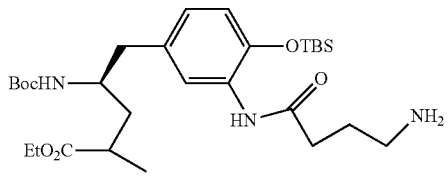

373

Compound 372 (0.35 g, 0.5 mmol) was dissolved in MeOH (5 ml), and Pd/C (10 wt %, 35 mg) was then added. The reaction mixture was stirred at r.t. under $H_2$ balloon overnight, then filtered through celite and the filtrate was concentrated under reduced pressure to give the title product 373 (0.22 g, 79% yield). ESI MS m/z: calcd for $C_{29}H_{52}N_3O_6Si$ $[M+H]^+$ 566.35, found 566.35.

Example 130. Synthesis of 4-((4-((5-((2R)-2-((tert-butoxycarbonyl)amino)-5-ethoxy-4-methyl-5-oxopentyl)-2-((tert-butyldimethylsilyl)oxy)phenyl)amino)-4-oxobutyl)amino)-4-oxobut-2-ynoic acid (374)

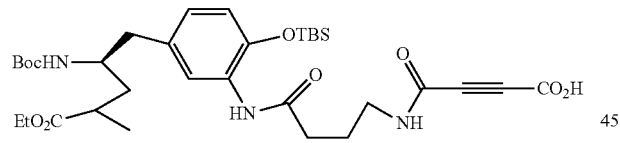

Compound 373 (0.22 g, 0.39 mmol) was dissolved in NMP (2 mL), and actylenedicarboxylic acid (0.089 g, 0.78 mmol) was added at 0° C. After stirring for 10 min, DMTMM (0.1 g, 0.39 mmol) was added. The mixture was stirred at 0° C. overnight. The reaction was washed with $H_2O$ (100 mL) and the aqueous layer was extracted with EtOAc. The combined organic layers were dried over $Na_2SO_4$, filtered, concentrated under reduced pressure and the residue was purified by $SiO_2$ column chromatography with a gradient of DCM/MeOH to give the title product 374 (0.05 g, 20% yield). ESI MS m/z: calcd for $C_{33}H_{52}N_3O_9Si$ $[M+H]^+$ 662.34, found 662.34.

Example 131. Synthesis of 4-((4-((5-((2R)-2-((tert-butoxycarbonyl)amino)-5-ethoxy-4-methyl-5-oxopentyl)-2-hydroxyphenyl)amino)-4-oxobutyl)amino)-4-oxobut-2-ynoic acid (375)

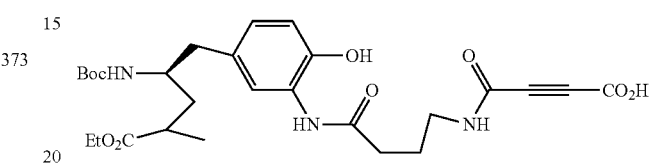

Compound 374 (50 mg, 0.076 mmol) was dissolved in DCM (2 mL), and then TBAF (1 M, 0.05 mL) was added. The reaction was stirred at r.t. for 1 h, and then concentrated and purified by $SiO_2$ column chromatography to give the title product 375 (10.5 mg, 25% yield). ESI MS m/z: calcd for $C_{27}H_{38}N_3O_9[M+H]^+$ 548.25, found 548.25.

Example 132. Synthesis of 4-((4-((5-((2R)-2-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-5-ethoxy-4-methyl-5-oxopentyl)-2-hydroxyphenyl)amino)-4-oxobutyl)amino)-4-oxobut-2-ynoic acid (376)

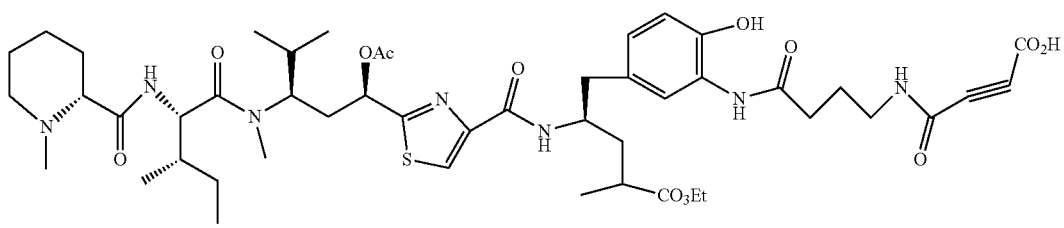

376

Compound 375 (10.5 mg, 0.02 mmol) was dissolved in DCM (1 mL), and TFA (0.5 mL) was added. The reaction was stirred at r.t. for 2 h, then concentrated and re-dissolved in DMA (2 mL), to which pentafluorophenyl ester 142 (21 mg, 0.03 mmol) and DIPEA (7 µl, 0.04 mmol) were added. The reaction was stirred overnight and then concentrated and the residue was purified by reverse phase HPLC with a gradient of MeCN/H$_2$O to give the title product 376 (9 mg, 47% yield). ESI MS m/z: calcd for C$_{48}$H$_{70}$N$_7$O$_{12}$S [M+H]$^+$ 968.47, found 968.47.

Example 133. Synthesis of 2-((6S,9S,12R,14R)-9-((S)-sec-butyl)-14-hydroxy-6,12-diisopropyl-2,2,5,11-tetramethyl-4,7,10-trioxo-3-oxa-5,8,11-triazatetradecan-14-yl)thiazole-4-carboxylic acid (381)

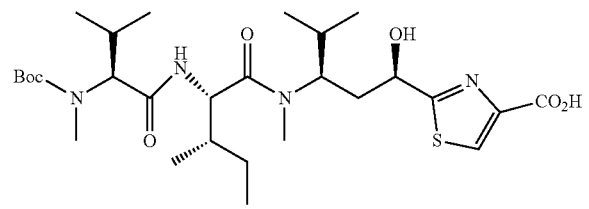 [SMILES: CC[C@H](C)[C@H](NC(=O)[C@H](C(C)C)N(C)C(=O)OC(C)(C)C)C(=O)N(C)[C@H](C[C@@H](O)c1nc(C(=O)O)cs1)C(C)C]

To a solution of Boc-N-Me-L-Val-OH (33 mg, 0.14 mmol) in EtOAc was added pentafluorophenol (39 mg, 0.21 mmol) and DCC (32 mg, 0.154 mmol). The reaction mixture was stirred at r.t. for 16 h and then filtered over a celite pad, with washing of the pad with EtOAc. The filtrate was concentrated and re-dissolved in DMA (2 mL), and then 2-((1R,3R)-3-((2S,3S)-2-amino-N,3-dimethylpentanamido)-1-hydroxy-4-methylpentyl)thiazole-4-carboxylic acid 380 (52 mg, 0.14 mmol) and DIPEA (48.5 µL, 0.28 mmol) were added. The reaction mixture was stirred at r.t. for 24 h and then concentrated and purified by reverse phase HPLC (C$_{18}$ column, 10-100% acetonitrile/water) to afford compound 381 (40.2 mg, 49% yield). ESI MS m/z: calcd for C$_{28}$H$_{49}$N$_4$O$_7$S [M+H]$^+$ 585.32, found 585.32.

Example 134. Synthesis of 2-((6S,9S,12R,14R)-9-((S)-sec-butyl)-6,12-di-isopropyl-2,2,5,11-tetramethyl-4,7,10,16-tetraoxo-3,15-dioxa-5,8,11-triazaheptadecan-14-yl)thiazole-4-carboxylic acid (382)

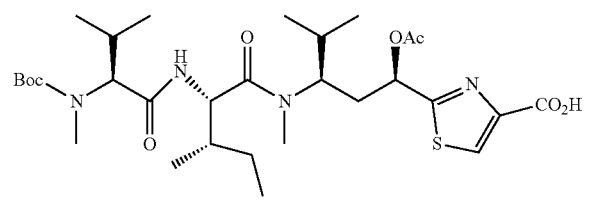

Compound 381 (40 mg, 0.069 mmol) was dissolved in pyridine (8 mL), to which acetic anhydride (20.4 mg, 0.2 mmol) was added at 0° C. and the reaction was allowed to warm to r.t. and stirred overnight. The mixture was concentrated and the residue purified by SiO$_2$ column chromatography with a gradient of DCM/MeOH to give the title product 382 (48.1 mg, ~100% yield). ESI MS m/z: calcd for C$_{30}$H$_{51}$N$_4$O$_8$S [M+H]$^+$ 627.33, found 627.33.

Example 135. Synthesis of (4R)-4-(2-((6S,9S,12R,14R)-9-((S)-sec-butyl)-6,12-diisopropyl-2,2,5,11-tetramethyl-4,7,10,16-tetraoxo-3,15-dioxa-5,8,11-triazaheptadecan-14-yl)thiazole-4-carboxamido)-2-methyl-5-phenylpentanoic acid (383)

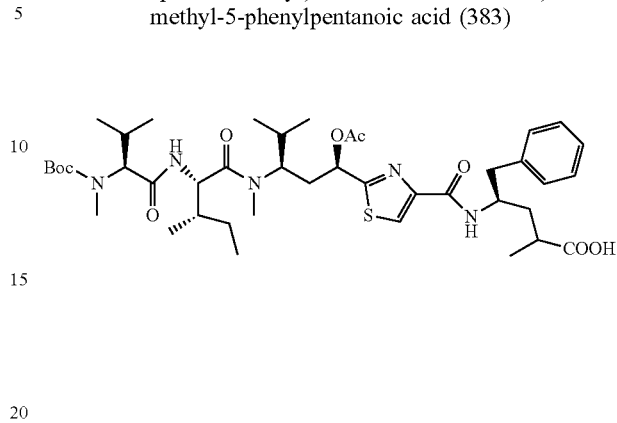

To a solution of compound 382 (48.1 mg, 0.077 mmol) in EtOAc was added pentafluorophenol (21.2 mg, 0.115 mmol) and DCC (17.4 mg, 0.085 mmol). The reaction mixture was stirred at r.t. for 16 h and then filtered over a celite pad, with washing of the pad with EtOAc. The filtrate was concentrated and re-dissolved in DMA (4 mL), and then (4R)-4-amino-2-methyl-5-phenylpentanoic acid (20.7 mg, 0.1 mmol) and DIPEA (26.8 µL, 0.154 mmol) were added. The reaction mixture was stirred at r.t. for 24 h and then concentrated and purified by reverse phase HPLC (Cis column, 10-100% acetonitrile/water) to afford compound 383 (63 mg, ~100% yield). ESI MS m/z: calcd for C$_{42}$H$_{66}$N$_5$O$_9$S [M+H]$^+$ 816.45, found 816.45.

Example 136. Synthesis of 11,14,24-trioxo-24-(perfluorophenoxy)-4,7,18,21-tetraoxa-10,15-diazatetracos-12-yn-1-oic acid (378)

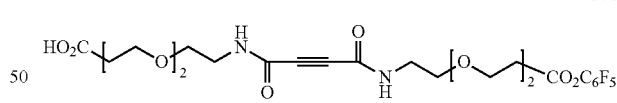

To a solution of compound 161 (45.4 mg, 0.11 mmol) in EtOAc was added pentafluorophenol (21.3 mg, 0.12 mmol) and DCC (24.7 mg, 0.12 mmol). The reaction mixture was stirred at r.t. for 16 h and then filtered over a Celite pad, with washing of the pad with EtOAc. The filtrate was concentrated and used for the next step without further purification.

Example 137. Synthesis of (4R,6R,9S,12S)-9-((S)-sec-butyl)-4-(4-(((2R)-4-carboxy-1-phenylpentan-2-yl)carbamoyl)thiazol-2-yl)-6,12-diisopropyl-7,13-dimethyl-2,8,11,14,24,27-hexaoxo-3,17,20,31,34-pentaoxa-7,10,13,23,28-pentaazaheptatriacont-25-yn-37-oic acid (384)

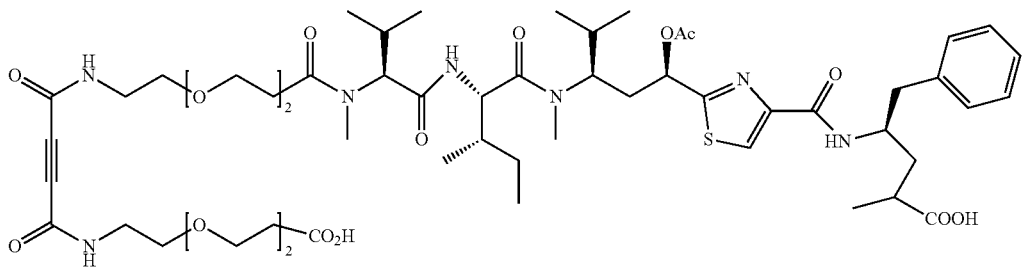

Compound 383 (63 mg, 0.077 mmol) was dissolved in DCM (5 mL), and TFA (2.5 mL) was then added. The reaction was stirred at r.t. for 2 h, then concentrated and re-dissolved in DMA (4 mL), to which compound 378 (65.8 mg, 0.11 mmol) and DIPEA (27 µL, 0.154 mmol) were added. The reaction mixture was stirred at r.t. overnight and then concentrated and the residue purified by reverse phase HPLC ($C_{18}$ column, 10-100% acetonitrile/water) to afford compound 384 (14 mg, 16% yield). ESI MS m/z: calcd for $C_{55}H_{84}N_7O_{16}S$ [M+H]$^+$ 1130.56, found 1130.57.

Example 138. General Method of Conjugation of Compound 196, 200, 205, 259, 267, 269, 271, 273, 274, 276, 288, 292, 299, 301, 307, 310, 313, 316, 318, 320, 325, 327, 328, 333, 337, 339, 342, 344, 346, 353, 355, 357, 361, 365, 369, 376, 384, 388, 393, 394, 397, 400, 401, 404, 406, 409, 411, or 413 Independently to an Antibody (Herceptin)

To a mixture of 2.0 mL of 10 mg/ml Herceptin in pH 6.0~8.0, were added of 0.70~ 2.0 mL PBS buffer of 100 mM $NaH_2PO_4$, pH 6.5~8.5 buffers, TCEP (14-35 µL, 20 mM in water) and the compound 196, 200, 205, 259, 260, 267, 269, 271, 273, 274, 276, 288, 292, 299, 301, 307, 310, 313, 316, 318, 320, 325, 327, 328, 333, 337, 339, 342, 344, 346, 353, 355, 357, 361, 365, 369, 376, 384, 388, 393, 394, 397, 400, 401, 404, 406, 409, 411, or 413 (14-28 µL, 20 mM in DMA). The mixture was incubated at RT for 4~16 h, then DHAA (135 µL, 50 mM) was added in. After continuous incubation at RT overnight, the mixture was purified on G-25 column eluted with 100 mM $NaH_2PO_4$, 50 mM NaCl pH 6.0~7.5 buffer to afford 12.0~18.4 mg of the conjugate compound 196a, 201, 206, 261, 267, 270, 272, 275, 277, 289, 293, 300, 302, 308, 311, 314, 317, 319, 321, 326, 329, 334, 338, 339a, 343, 345, 347, 354, 355a, 358, 362, 366, 370, 377, 385, 386, 389, 395, 396, 398, 402, 405, 407, 410, 412, or 414 (60%~91% yield) accordingly in 13.0~15.8 m₁ buffer. The drug/antibody ratio (DAR) was 1.9~4.0, which was determined via UPLC-QTOF mass spectrum. It was 94~99% monomer analyzed by SEC HPLC (Tosoh Bioscience, Tskgel G3000SW, 7.8 mm ID×30 cm, 0.5 ml/min, 100 min) and a single band measured by SDS-PAGE gel.

Example 139. General Method of Conjugation of Compound 248, 250, 252, 254, and 255, Independently to Herceptin (an Antibody)

To a mixture of 2.0 mL of 10 mg/ml Herceptin in pH 6.0~8.0, 0.70~ 2.0 mL of 100 mM $NaH_2PO_4$, 1 mM $Na_2SO_3$, pH 6.5~8.5 buffer, and the compound 248, 250, 252, 254 and 255 independently (21-28 µL, 20 mM in DMA) incubated for 1 h, was added TCEP (14-35 µL, 20 mM in water). After the mixture was continued to incubate at RT for 8~24 h, DHAA (135 µL, 50 mM) was added in. And the solution was continuously incubated for another 12 h. then purified on G-25 column eluted with 100 mM $NaH_2PO_4$, 50 mM NaCl pH 6.0~7.5 buffer to afford 13.8~17.6 mg of the conjugate compound 249, 251, 253, and 256 respectively (69%~88% yield) in 13.6~15.2 ml buffer. The drug/antibody ratio (DAR) was 1.9~4.0, which was determined via UPLC-QTOF mass spectrum. It was 96~99% monomer analyzed by SEC HPLC (Tosoh Bioscience, Tskgel G3000SW, 7.8 mm ID×30 cm, 0.5 ml/min, 100 min) and a single band measured by SDS-PAGE gel or two bands when a reduce reagent DTT was in the SDS Page.

Example 140. In Vitro Cytotoxicity Evaluation of Conjugates 196a, 201, 206, 354, 358, 362, 366, 370, 377, 385 and 407 in Comparison with T-DM1

The cell line used in the cytotoxicity assays was NCI-N87, a human gastric carcinoma cell line. The cells were grown in RPMI-1640 with 10% FBS. To run the assay, the cells (180 µl, 6000 cells) were added to each well in a 96-well plate and incubated for 24 hours at 37° C. with 5% $CO_2$. Next, the cells were treated with test compounds (20 µl) at various concentrations in appropriate cell culture medium (total volume, 0.2 mL). The control wells contain cells and the medium but lack the test compounds. The plates were incubated for 120 hours at 37° C. with 5% $CO_2$. MTT (5 mg/ml) was then added to the wells (20 µl) and the plates were incubated for 1.5 hr at 37° C. The medium was carefully removed and DMSO (180 µl) was added afterward. After it was shaken for 15 min, the absorbance was measured at 490 nm and 570 nm with a reference filter of 620 nm. The inhibition % was calculated according to the following equation: inhibition %=[1~(assay−blank)/(control−blank)]×100.

The cytotoxicity results:

| | DAR (drug ratio) | N87 cell (Ag+) $IC_{50}$(nM) |
|---|---|---|
| Conjugate 196a | 2.8 | 3.9 nM |
| Conjugate 201 | 2.7 | 1.3 nM |

| | DAR (drug ratio) | N87 cell (Ag+) IC$_{50}$(nM) |
|---|---|---|
| Conjugate 206 | 2.9 | 1.7 nM |
| Conjugate 354 | 2.1 | 28.4 nM |
| Conjugate 358 | 2.2 | 643.7 nM |
| Conjugate 362 | 2.8 | 3.1 nM |
| Conjugate 366 | 2.9 | 2.3 nM |
| Conjugate 370 | 3.2 | 1.3 nM |
| Conjugate 377 | 2.5 | 62.7 nM |
| Conjugate 385 | 2.8 | 561.6 nM |
| Conjugate 407 | 3.1 | 0.51 nM |
| T-DM1 | 3.5 | 0.07 nM |

The conjugates with the bridge linkers were less potent than T-DM1 in vitro.

Example 141. Antitumor Activity In Vivo

The in vivo efficacy of conjugates 196a, 201, 206, 354, 358, 370, 377, 385, and 407 along with T-DM1 were evaluated in a human gastric carcinoma N-87 cell line tumorxenograft models. Five-week-old female BALB/c Nude mice (30 animals) were inoculated subcutaneously in the area under the right shoulder with N-87 carcinoma cells (5×10$^6$ cells/mouse) in 0.1 mL of serum-free medium. The tumors were grown for 8 days to an average size of 130 mm$^3$. The animals were then randomly divided into 10 groups (6 animals per group). The first group of mice served as the control group and was treated with the phosphate-buffered saline vehicle. The remaining 9 groups were treated with conjugates 196a, 201, 206, 354, 358, 370, 377, 385, 407 and T-DM1 respectively at dose of 6 mg/Kg administered intravenously. Three dimensions of the tumor were measured every 4 days and the tumor volumes were calculated using the formula tumor volume=½ (length×width×height). The weight of the animals was also measured at the same time. A mouse was sacrificed when any one of the following criteria was met: (1) loss of body weight of more than 20% from pretreatment weight, (2) tumor volume larger than 1500 mm$^3$, (3) too sick to reach food and water, or (4) skin necrosis. A mouse was considered to be tumor-free if no tumor was palpable.

Figure 36:
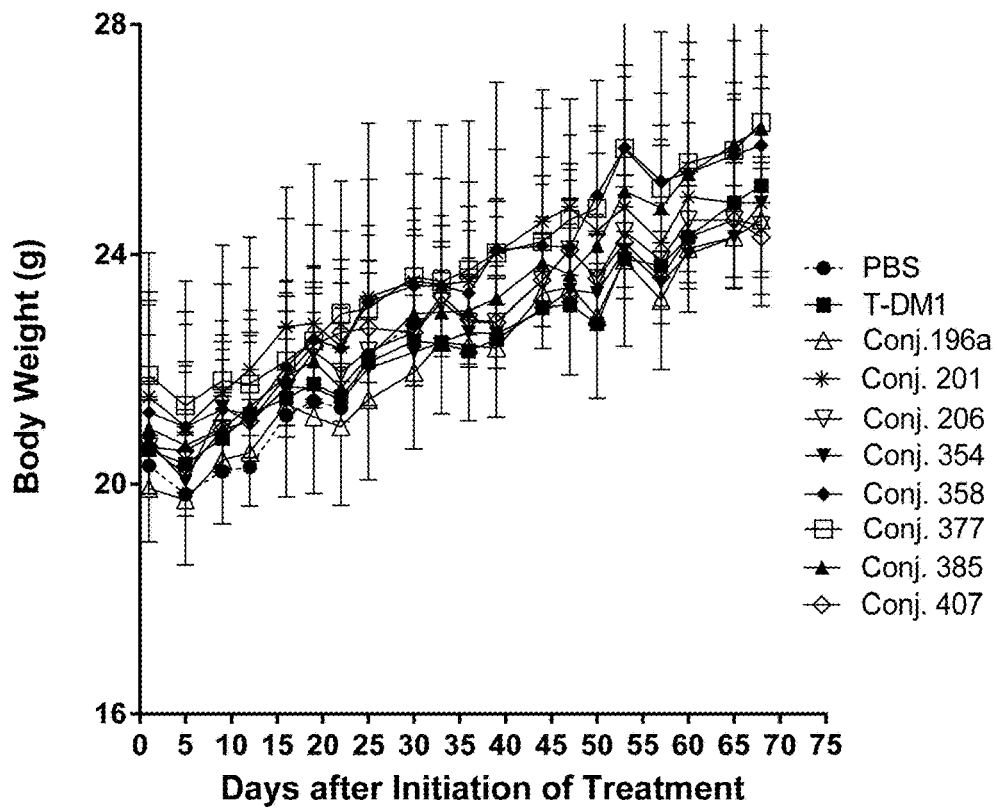
FIG. 36 shows the comparison of the anti-tumor effect of conjugate compounds 196a, 201, 206, 354, 358, 377, 385 and 407 with T-DM1 using human gastric tumor N87 cell model at dosing of 6 mg/kg, i.v., one injection. Top figure indicates that all the 9 conjugates did not cause the animal body weight loss. The bottom figure shows that conjugate compounds 196a, 201, 206, 277, 354, and 407 had better antitumor activity than T-DM1. In particular, compounds 201 and 407 were able to eliminate the tumors until the end of experiment.
Figure 36:
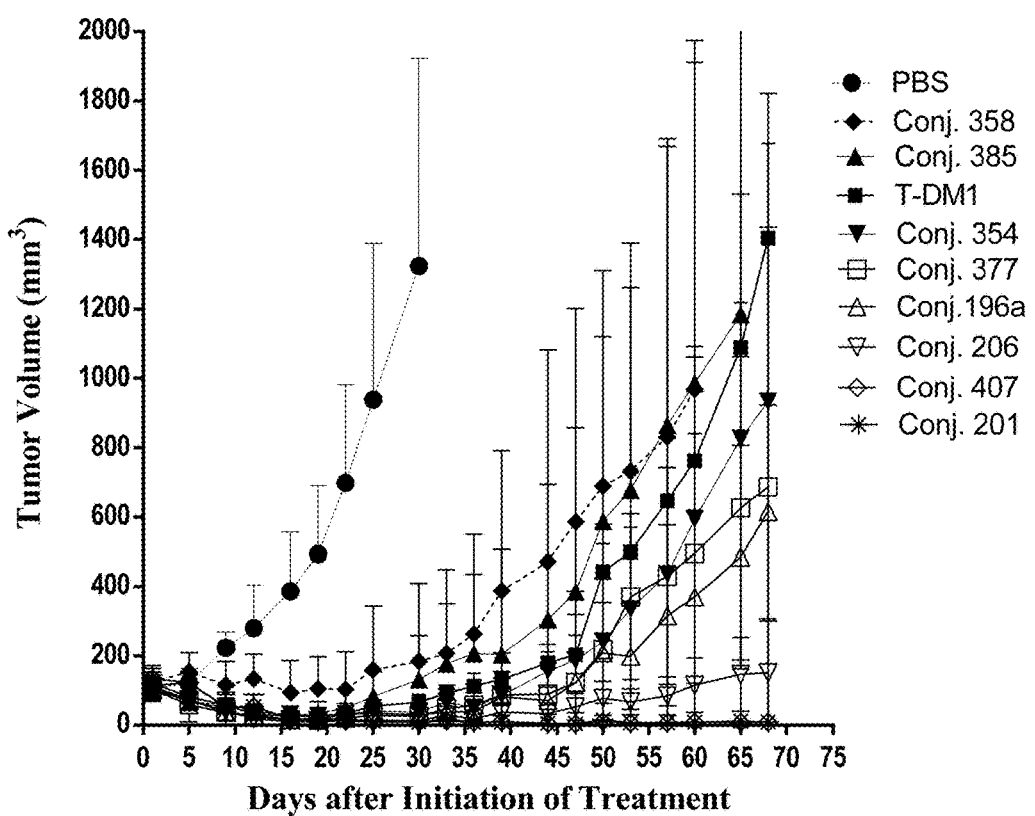

The results were plotted in FIG. 36. All the 9 conjugates did not cause the animal body weight loss. And the animals at control group were sacrificed at day 30 due to the tumor volume larger than 1200 mm$^3$ and they were too sick. All 6/6 animals at the groups of compounds 201 and 407 had completely no tumor measurable at day 18 till day 68 (the end of experiment). In contrast T-DM1 at dose of 6 mg/Kg was not able to eliminate the tumors and it only inhibited the tumor growth for 38 days. Conjugate compounds 196a, 206, 277, and 354 did not eradicate the tumor at dose of 6 mg/Kg, but had better antitumor activity than T-DM1. The conjugates 358 and 385 had worse antitumor activity than T-DM1. More importantly, all animals treated with conjugate compounds 196a, 201, 206, 277, 354, 358, 385 and 407 had no or less liver toxicities than the animals treated with T-DM1 when measured levels of alanine aminotransferase (ALT) and aspartame aminotransferase (AST) in serum at the end of experiment (data not shown). This demonstrates that the conjugates with the bridge linkers of this patent application would have broader therapeutical applications than the traditional conjugates.

The invention claimed is:
1. A bridge linker compound of Formula (I)

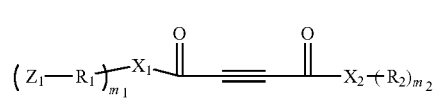

wherein:
" ≡ " represents a triple bond;
provided that the component:

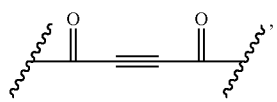

which is acetylenedicarboxyl group;
R$_1$ is selected from the group consisting of C$_1$-C$_8$ alkyl; C$_2$-C$_8$ heteroalkyl, alkylcycloalkyl, or heterocycloalkyl; C$_3$-C$_8$ aryl, Ar-alkyl, heterocyclic, carbocyclic, cycloalkyl, heteroalkylcycloalkyl, alkylcarbonyl, or heteroaryl; C$_1$-C$_8$ ester, ether, or amide; polyethyleneoxy unit of formula (OCH$_2$CH$_2$)$_p$ or (OCH$_2$CH(CH$_3$))$_p$, wherein p is an integer from 0 to about 1000, and a combination thereof,
or R$_1$ is a chain of atoms selected from the group consisting of C, N, O, S, Si, and P, which covalently connects to X$_1$ and Z$_1$;
X$_1$ and X$_2$ are independently absent or selected from the group consisting of NH; NHNH; N(R$_3$); N(R$_3$)N(R$_3$'); O; S; B(R$_3$); Si(R$_3$)N(R$_3$'); P(O)(R$_3$); C$_1$-C$_8$ alkyl; C$_2$-C$_8$ heteroalkyl, alkylcycloalkyl, or heterocycloalkyl; C$_3$-C$_8$ aryl, Ar-alkyl, heterocyclic, carbocyclic, cycloalkyl, heteroalkylcycloalkyl, alkylcarbonyl, or heteroaryl; 1-8 amino acids; wherein R$_3$ and R$_3$' are independently H; C$_1$-C$_8$ alkyl; C$_2$-C$_8$ heteroalkyl, alkylcycloalkyl, or heterocycloalkyl; C$_3$-C$_8$ aryl, Ar-alkyl, heterocyclic, carbocyclic, cycloalkyl, heteroalkylcycloalkyl, alkylcarbonyl, or heteroaryl; C$_1$-C$_8$ ester, ether, or amide; polyethyleneoxy unit of formula (OCH$_2$CH$_2$)$_p$ or (OCH$_2$CH(CH$_3$))$_p$, wherein p is an integer from 0 to about 1000, and a combination thereof,
R$_2$ is independently selected from the group consisting of OH, H, NH$_2$; SH; NHNH$_2$; N(R$_3$)(R$_3$'); N(R$_3$)NH(R$_3$'); polyethyleneoxy unit of formula (OCH$_2$CH$_2$)$_p$OR$_3$, (OCH$_2$CH(CH$_3$))$_p$OR$_3$, NH(CH$_2$CH$_2$O)$_p$R$_3$, NH(CH$_2$CH(CH$_3$)O)$_p$R$_3$, N[(CH$_2$CH$_2$O)$_p$R$_3$][(CH$_2$CH$_2$O)$_p$R$_3$'], (OCH$_2$CH$_2$)$_p$COOR$_3$, or CH$_2$CH$_2$(OCH$_2$CH$_2$)$_p$COOR$_3$, wherein p and p' are independently an integer selected from 0 to about 1000, or a combination thereof; C$_1$-C$_8$ alkyl; C$_2$-C$_8$ heteroalkyl, alkylcycloalkyl, or heterocycloalkyl; and C$_3$-C$_8$ aryl, Ar-alkyl, heterocyclic, carbocyclic, cycloalkyl, heteroalkylcycloalkyl, alkylcarbonyl, or heteroaryl; wherein R$_3$ and R$_3$' are independently H; C$_1$-C$_8$ alkyl; C$_2$-C$_8$ heteroalkyl, alkylcycloalkyl, or heterocycloalkyl; C$_3$-C$_8$ aryl, Ar-alkyl, heterocyclic, carbocyclic, cycloalkyl, heteroalkylcycloalkyl, alkylcarbonyl, or heteroaryl; C$_1$-C$_8$ ester, ether, or amide; 1-8 amino acids; polyethyleneoxy unit of formula (OCH$_2$CH$_2$)$_p$ or (OCH$_2$CH(CH$_3$))$_p$, wherein p is an integer from 0 to about 1000, or a combination thereof,
m$_1$ and m$_2$ are independently an integer from 1 to 30;
Z$_1$ is at least one of thiol, disulfide, amino, carboxyl, aldehyde, ketone, maleimido, haloacetyl, hydrazines, alkoxyamino, hydroxy, N-hydroxysuccinimide ester, p-nitrophenyl ester, dinitrophenyl ester, pentafluorophenyl ester, carboxylic acid chloride, carboxylic acid anhydride, pyridyldisulfide, nitropyridyldisulfide, maleimide, haloacetate, methylsulfonephenyloxadiazole, acyloxylamine, hydrazide, or alkyne.

2. The bridge linker compound according to claim 1, wherein $R_1$ is at least one of alkylene, alkenylene, alkynylene, ether, polyoxyalkylene, ester, amine, imine, polyamine, hydrazine, hydrazone, amide, urea, semicarbazide, carbazide, alkoxyamine, alkoxylamine, urethanes, amino acid, peptide, acyloxylamine, or hydroxamic acid.

3. The bridge linker compound according to claim 1, wherein $R_1$ or $R_2$ is independently a linear alkyl having from 1-6 carbon atoms, or polyethyleneoxy unit of formula $(OCH_2CH_2)_p$, p=1-100.

4. The bridge linker compound according to claim 1, wherein $R_1$ or $R_2$ is cleavable by a protease.

5. The bridge linker compound according to claim 1, wherein $R_1$ or $R_2$ has independently one or more, or repeating, or a combining thereof, of components depicted in the following:

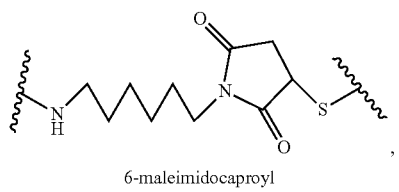

6-maleimidocaproyl

maleimido propanoyl

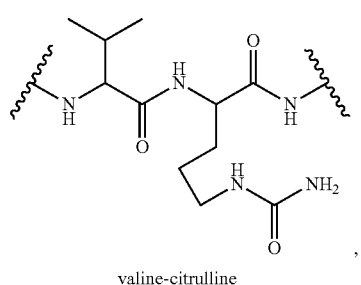

valine-citrulline

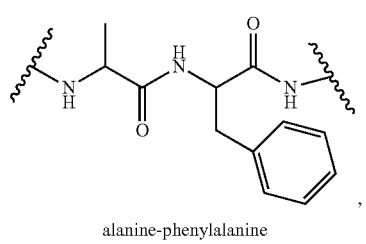

alanine-phenylalanine

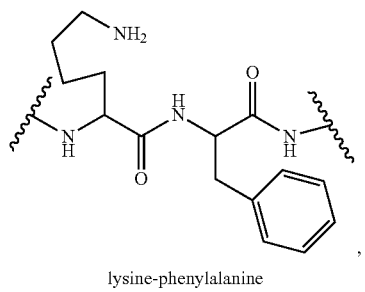

lysine-phenylalanine

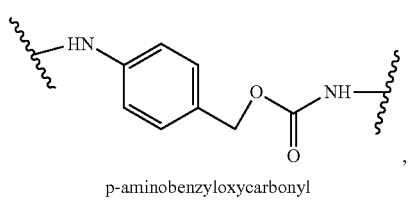

p-aminobenzyloxycarbonyl

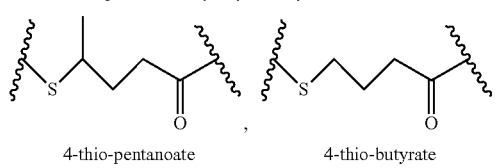

4-thio-pentanoate    4-thio-butyrate

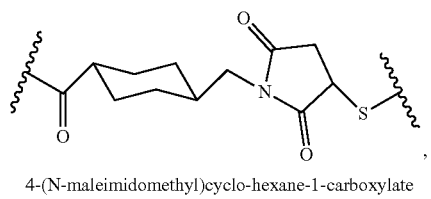

4-(N-maleimidomethyl)cyclo-hexane-1-carboxylate

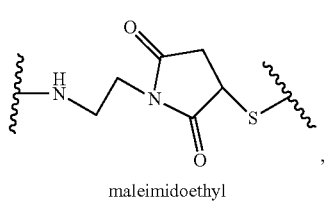

maleimidoethyl

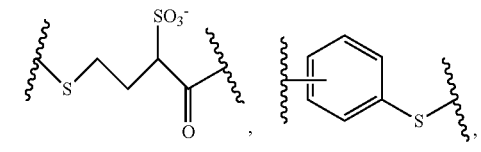

4-thio-2-hydroxysulfonyl-butyrate    aryl-thiol

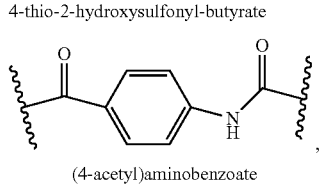

(4-acetyl)aminobenzoate

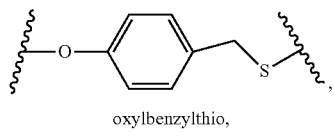

oxylbenzylthio,

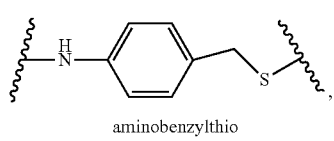

aminobenzylthio

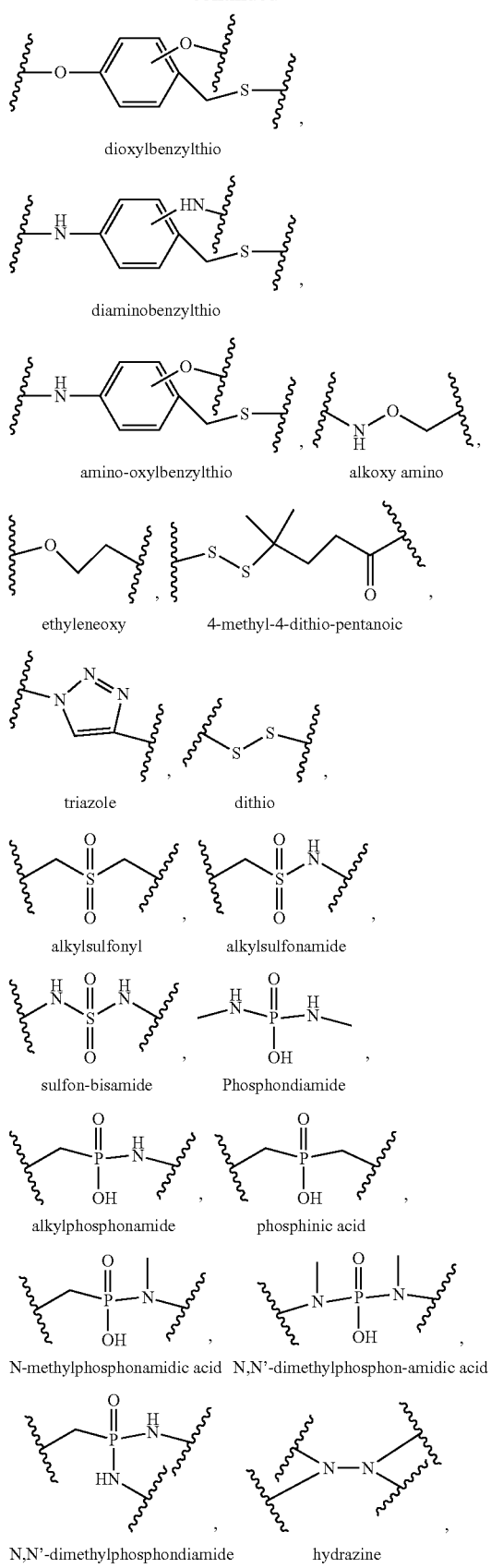
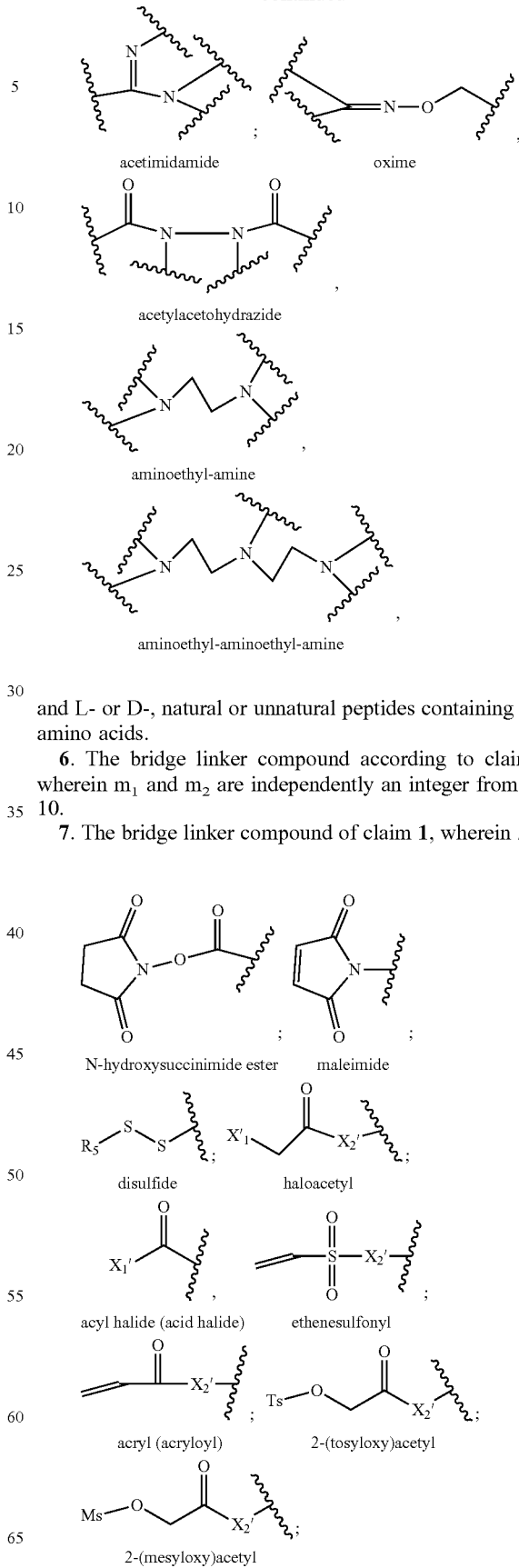
and L- or D-, natural or unnatural peptides containing 1-20 amino acids.
6. The bridge linker compound according to claim 1, wherein $m_1$ and $m_2$ are independently an integer from 1 to 10.
7. The bridge linker compound of claim 1, wherein $Z_1$ is -continued

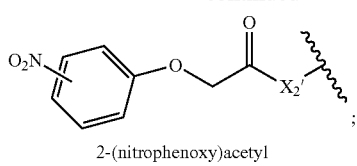
2-(nitrophenoxy)acetyl

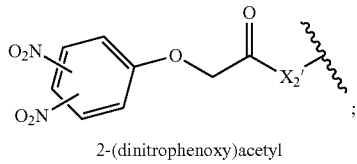
2-(dinitrophenoxy)acetyl

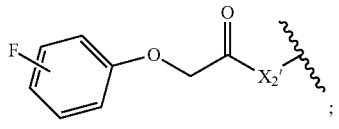
2-(fluorophenoxy)-acetyl

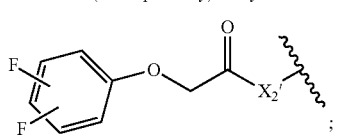
2-(difluorophenoxy)-acetyl

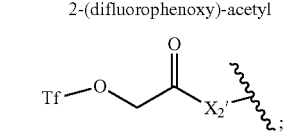
2-(((trifluoromethyl)-sulfonyl)oxy)acetyl

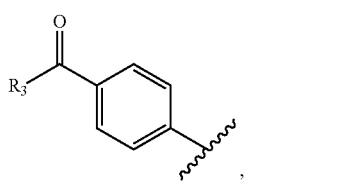
ketone or aldehyde

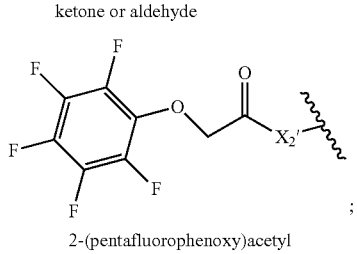
2-(pentafluorophenoxy)acetyl

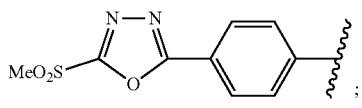
methylsulfone phenyloxadiazole (ODA)

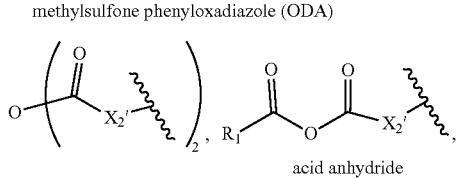
acid anhydride

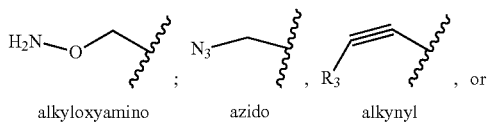
alkyloxyamino    azido    alkynyl

-continued

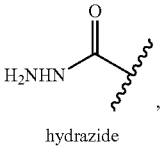
hydrazide wherein $X_1'$ is F, Cl, Br, I or $Lv_3$; $X_2'$ is O, NH, $N(R_1)$, or $CH_2$; $R_3$ and $R_5$ are H, $R_1$, aromatic, heteroaromatic, or aromatic group wherein one or several H atoms are replaced independently by —$R_1$, -halogen, —$OR_1$, —$SR_1$, —$NR_1R_2$, —$NO_2$, —$S(O)R_1$, —$S(O)_2R_1$, or —$COOR_1$; $Lv_3$ is a leaving group selected from the group consisting of methanesulfonyl, toluenesulfonyl, trifluoromethyl-sulfonyl, trifluoromethylsulfonate, nitrophenoxyl, N-succinimidyloxyl, phenoxyl; dinitrophenoxyl; pentafluorophenoxyl, tetrafluorophenoxyl, trifluorophenoxyl, difluorophenoxyl, monofluorophenoxyl, pentachlorophenoxyl, 1H-imidazole-1-yl, chlorophenoxyl, dichlorophenoxyl, trichlorophenoxyl, tetrachlorophenoxyl, N-(benzotriazolyl)oxyl, 2-ethyl-5-phenylisoxazolium-yl, phenyloxadiazol-yl, oxadiazol-yl, and an intermediate molecule generated with a condensation reagent for Mitsunobu reactions, wherein $R_1$ and $R_2$ are the same defined in claim 1.

8. A method for preparing the bridge linker compound of Formula (I) of claim 1, comprising a step of forming the acetylenedicarboxyl group, by condensation of an acetylenedicarboxyl compound, or an acid derivative thereof, with components containing a 1° or 2° amine, alcohol, or thiol, on their terminal as shown in the following scheme (Ia) or (Ib):

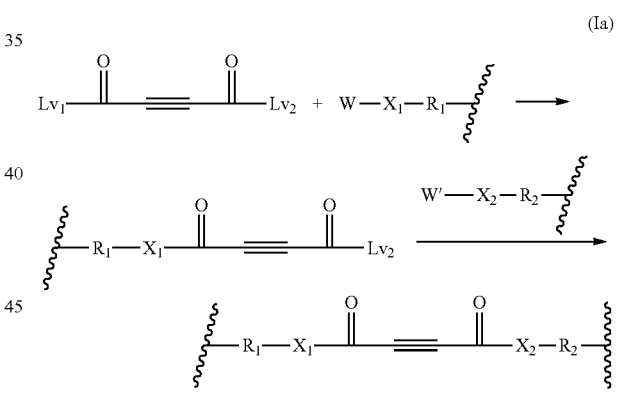

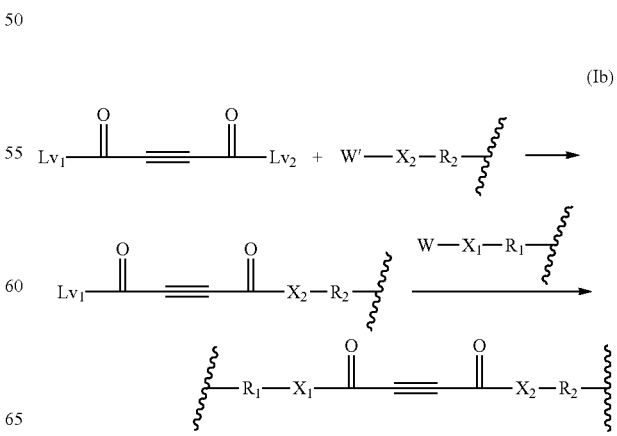

wherein $X_1$, $X_2$, $R_1$, and $R_2$ are described the same in claim 1;

W and W' are the same or independently a 1° or 2° amine, hydroxyl, or thiol;

$Lv_1$ and $Lv_2$ are the same or independently H, OH, F, Cl, Br, I, $NH_2$, $NHNH_2$, methane-sulfonyl, toluenesulfonyl, trifluoromethylsulfonyl, trifluoromethyl-sulfonate, nitrophenoxyl, N-succinimidyloxyl, phenoxyl; dinitrophenoxyl; pentafluo-rophenoxyl, tetrafluorophenoxyl, trifluorophenoxyl, difluorophenoxyl, monofluorophenoxyl, pentachlorophenoxyl, 1H-imidazole-1-yl, chlorophenoxyl, dichlorophenoxyl, trichlorophenoxyl, tetrachlorophenoxyl, N-(benzotriazol-yl)oxyl, 2-ethyl-5-phenylisoxazolium-3'-sulfonyl, phenyl-oxadiazole-sulfonyl, oxadiazol-yl, or an intermediate molecule generated with a condensation reagent for Mitsunobu reactions wherein the condensation reagents are: N-(3-dimethylaminopropyl)-N'-ethylcarbodiimide, dicyclohexyl-carbodiimide), N,N'-diisopropylcarbodiimide, N-cyclohexyl-N'-(2-morpholinoethyl)carbodiimide metho-p-toluenesulfonate, 1,1'-carbonyldiimidazole, O-(benzotria-zol-1-yl)-N,N,N',N'-tetramethyluronium tetrafluoroborate, N,N,N',N'-tetramethyl-O-(1H-benzotriazol-1-yl)uronium hexafluorophosphate, (benzotriazol-1-yloxy)tris(dimethyl-amino)phosphonium hexafluorophosphate, (benzotriazol-1-yloxy)tripyrrolidinophos-phonium hexafluorophosphate, diethyl cyanophosphonate, chloro-N,N,N',N'-tetramethylformamidinium hexafluorophosphate, 1-[bis(dimethylamino)-methylene]-1H-1,2,3-triazolo[4,5-b]pyridinium 3-oxide hexafluorophosphate, 1-[(dimethylamino) (morpholino) methylene]-1H-[1,2,3]triazolo[4,5-b]pyridine-1-ium 3-oxide hexafluorophos-phate, 2-chloro-1,3-dimethylimidazolidinium hexafluorophosphate, chlorotripyrrolidinophosphonium hexafluorophosphate, fluoro-N,N,N',N'-bis(tetramethylene)formamidinium hexafluorophosphate, N,N,N',N'-tetramethyl-S-(1-oxido-2-pyridyl)thiuronium hexafluorophosphate, 0-(2-oxo-1(2H)pyridyl)-N,N,N',N'-tetramethyl-uronium tetrafluoroborate, S-(1-oxido-2-pyridyl)-N,N,N',N'-tetramethyl-thiuronium tetrafluoroborate, O-[(ethoxycarbonyl) cyano-methylenamino]-N,N,N',N'-tetramethyluronium hexafluorophosphate, (1-cyano-2-ethoxy-2-oxoethylidenamino-oxy)dimethylamino-morpholinocarbenium hexafluorophosphate, O-(benzotriazol-1-yl)-N,N,N',N'-bis-(tetramethylene) uronium hexafluorophosphate, N-benzyl-N'-cyclohexylcarbodiimide with, or without polymer-bound, dipyrrolidino (N-succinimidyl-oxy) carbenium hexa-fluorophosphate, chlorodipyrrolidinocarbenium hexafluoro-phosphate, 2-chloro-1,3-dimethylimidazolidinium tetrafluoroborate, (benzotriazol-1-yloxy) dipiperidinocarbenium hexafluorophosphate, 0-(6-chlorobenzotriazol-1-yl)-N,N,N',N'-tetramethyluronium tetrafluoroborate, bromo-tris(dimethylamino)-phosphonium hexafluorophosphate, propylphosphonic anhydride, 2-morpholinoethyl isocyanide, N,N,N',N'-tetramethyl-O—(N-succinimidyl)uronium hexafluorophosphate, 2-bromo-1-ethyl-pyridinium tetrafluoroborate, O-[(ethoxycarbonyl)cyanome-thylenamino]-N,N,N',N'-tetramethyluronium tetrafluoroborate, 4-(4,6-dimethoxy-1,3,5-triazin-2-yl)-4-methylmorpholinium chloride, N,N,N',N'-tetramethyl-O—(N-succinimidyl) uronium tetrafluoro-borate, 0-(3,4-dihydro-4-oxo-1,2,3-ben-zotriazin-3-yl)-N,N,N',N'-tetramethyluronium tetrafluoroborate, 1,1'-(azodicarbonyl)dipiperidine, di-(4-chlorobenzyl) azodicarboxylate, di-tert-butyl azodi-carboxylate, diisopropyl azodicarboxylate, diethyl azodicarboxylate, or $Lv_1$ and $Lv_2$ are an anhydride, formed by an acid with itself or formed with another $C_1$-$C_8$ acid anhydride.

9. A bridge linker compound of Formula (I)

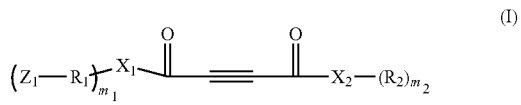

wherein:
" ≡ " represents a triple bond;
provided that the component:

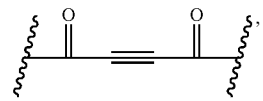

which is acetylenedicarboxyl group;

$R_1$ is absent, or selected from the group consisting of $C_1$-$C_8$ alkyl; $C_2$-$C_8$ heteroalkyl, alkylcycloalkyl, or heterocycloalkyl; $C_3$-$C_8$ aryl, Ar-alkyl, heterocyclic, carbocyclic, cycloalkyl, heteroalkylcycloalkyl, alkylcarbonyl, or heteroaryl; $C_1$-$C_8$ ester, ether, or amide; polyethyleneoxy unit of formula $(OCH_2CH_2)_p$ or $(OCH_2CH(CH_3))_p$, wherein p is an integer from 0 to about 1000, and a combination thereof, or $R_1$ is a chain of atoms selected from the group consisting of C, N, O, S, Si, and P, which covalently connects to $X_1$ and $Z_1$;

$X_1$ and $X_2$ are independently absent or selected from the group consisting of NH; NHNH; $N(R_3)$; $N(R_3)N(R_3')$; O; S; $B(R_3)$; $Si(R_3)N(R_3')$; $P(O)(R_3)$; $C_1$-$C_8$ alkyl; $C_2$-$C_8$ heteroalkyl, alkylcycloalkyl, or heterocycloalkyl; $C_3$-$C_8$ aryl, Ar-alkyl, heterocyclic, carbocyclic, cycloalkyl, heteroalkylcycloalkyl, alkylcarbonyl, or heteroaryl; 1-8 amino acids; wherein $R_3$ and $R_3'$ are independently H; $C_1$-$C_8$ alkyl; $C_2$-$C_8$ heteroalkyl, alkylcycloalkyl, or heterocycloalkyl; $C_3$-$C_8$ aryl, Ar-alkyl, heterocyclic, carbocyclic, cycloalkyl, heteroalkylcycloalkyl, alkylcarbonyl, or heteroaryl; $C_1$-$C_8$ ester, ether, or amide; polyethyleneoxy unit of formula $(OCH_2CH_2)_p$ or $(OCH_2CH(CH_3))_p$, wherein p is an integer from 0 to about 1000, and a combination thereof, provided that $X_1$ and $X_2$ are not absent at the same time;

$R_2$ is independently selected from the group consisting of OH, H, $NH_2$; SH; $NHNH_2$; $N(R_3)(R_3')$; $N(R_3)NH(R_3')$; polyethyleneoxy unit of formula $(OCH_2CH_2)_pOR_3$, $(OCH_2CH(CH_3))_pOR_3$, $NH(CH_2CH_2O)_pR_3$, $NH(CH_2CH(CH_3)O)_pR_3$, $N[(CH_2CH_2O)_pR_3][(CH_2CH_2O)_{p'}R_3']$, $(OCH_2CH_2)_pCOOR_3$, or $CH_2CH_2(OCH_2CH_2)_pCOOR_3$, wherein p and p' are independently an integer selected from 0 to about 1000, or a combination thereof; $C_1$-$C_8$ alkyl; $C_2$-$C_8$ heteroalkyl, alkylcycloalkyl, or heterocycloalkyl; and $C_3$-$C_8$ aryl, Ar-alkyl, heterocyclic, carbocyclic, cycloalkyl, heteroalkylcycloalkyl, alkylcarbonyl, or heteroaryl; wherein $R_3$ and $R_3'$ are independently H; $C_1$-$C_8$ alkyl; $C_2$-$C_8$ heteroalkyl, alkylcycloalkyl, or heterocycloalkyl; $C_3$-$C_8$ aryl, Ar-alkyl, heterocyclic, carbocyclic, cycloalkyl, heteroalkylcycloalkyl, alkylcarbonyl, or heteroaryl; $C_1$-$C_8$ ester, ether, or amide; 1-8 amino acids; polyethyleneoxy unit of formula $(OCH_2CH_2)_p$ or $(OCH_2CH(CH_3))_p$, wherein p is an integer from 0 to about 1000, or a combination thereof, $m_1$ and $m_2$ are independently an integer from 1 to 30;

$Z_1$ at least one of thiol, disulfide, amino, carboxyl, aldehyde, ketone, maleimido, haloacetyl, hydrazines, alkoxyamino, hydroxy, N-hydroxysuccinimide ester, p-nitrophenyl ester, dinitrophenyl ester, pentafluorophenyl ester, carboxylic acid chloride, carboxylic acid anhydride, pyridyldisulfide, nitropyridyldisulfide, maleimide, haloacetate, methylsulfonephenyloxadiazole, acyloxylamine, hydrazide, or alkyne.

10. A bridge linker compound of Formula (I)

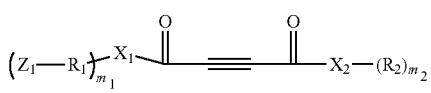
(I)

wherein:
' ≡ ' represents a triple bond;
provided that the component:

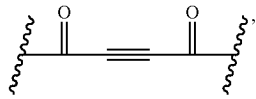 [SMILES: *C(=O)C#CC(*)=O]

which is acetylenedicarboxyl group;

$R_1$ is absent, or selected from the group consisting of $C_1$-$C_8$ alkyl; $C_2$-$C_8$ heteroalkyl, alkylcycloalkyl, or heterocycloalkyl; $C_3$-$C_8$ aryl, Ar-alkyl, heterocyclic, carbocyclic, cycloalkyl, heteroalkylcycloalkyl, alkylcarbonyl, or heteroaryl; $C_1$-$C_8$ ester, ether, or amide; polyethyleneoxy unit of formula $(OCH_2CH_2)_p$ or $(OCH_2CH(CH_3))_p$, wherein p is an integer from 0 to about 1000, and a combination thereof, or $R_1$ is a chain of atoms selected from the group consisting of C, N, O, S, Si, and P, which covalently connects to $X_1$ and $Z_1$;

$X_1$ and $X_2$ are independently absent or selected from the group consisting of NH; NHNH; $N(R_3)$; $N(R_3)N(R_3')$; O; S; $B(R_3)$; $Si(R_3)N(R_3')$; $P(O)(R_3)$; $C_1$-$C_8$ alkyl; $C_2$-$C_8$ heteroalkyl, alkylcycloalkyl, or heterocycloalkyl; $C_3$-$C_8$ aryl, Ar-alkyl, heterocyclic, carbocyclic, cycloalkyl, heteroalkylcycloalkyl, alkylcarbonyl, or heteroaryl; 1-8 amino acids; wherein $R_3$ and $R_3'$ are independently H; $C_1$-$C_8$ alkyl; $C_2$-$C_8$ heteroalkyl, alkylcycloalkyl, or heterocycloalkyl; $C_3$-$C_8$ aryl, Ar-alkyl, heterocyclic, carbocyclic, cycloalkyl, heteroalkylcycloalkyl, alkylcarbonyl, or heteroaryl; $C_1$-$C_8$ ester, ether, or amide; polyethyleneoxy unit of formula $(OCH_2CH_2)_p$ or $(OCH_2CH(CH_3))_p$, wherein p is an integer from 0 to about 1000, and a combination thereof, $R_2$ is independently selected from the group consisting of OH, H, $NH_2$; SH; $NHNH_2$; $N(R_3)(R_3')$; $N(R_3)NH(R_3')$; polyethyleneoxy unit of formula $(OCH_2CH_2)_pOR_3$, $(OCH_2CH(CH_3))_pOR_3$, $NH(CH_2CH_2O)_pR_3$, $NH(CH_2CH(CH_3)O)_pR_3$, $N[(CH_2CH_2O)_pR_3][(CH_2CH_2O)_pR_3']$, $(OCH_2CH_2)_pCOOR_3$, or $CH_2CH_2(OCH_2CH_2)_pCOOR_3$, wherein p and p' are independently an integer selected from 0 to about 1000, or a combination thereof; $C_1$-$C_8$ alkyl; $C_2$-$C_8$ heteroalkyl, alkylcycloalkyl, or heterocycloalkyl; and $C_3$-$C_8$ aryl, Ar-alkyl, heterocyclic, carbocyclic, cycloalkyl, heteroalkylcycloalkyl, alkylcarbonyl, or heteroaryl; wherein $R_3$ and $R_3'$ are independently H; $C_1$-$C_8$ alkyl; $C_2$-$C_8$ heteroalkyl, alkylcycloalkyl, or heterocycloalkyl; $C_3$-$C_8$ aryl, Ar-alkyl, heterocyclic, carbocyclic, cycloalkyl, heteroalkylcycloalkyl, alkylcarbonyl, or heteroaryl; $C_1$-$C_8$ ester, ether, or amide; 1-8 amino acids; polyethyleneoxy unit of formula $(OCH_2CH_2)_p$ or $(OCH_2CH(CH_3))_p$, wherein p is an integer from 0 to about 1000, or a combination thereof, $m_1$ and $m_2$ are independently an integer from 1 to 30;

$Z_1$ is thiol, disulfide, amino, carboxyl, aldehyde, ketone, maleimido, haloacetyl, hydrazines, alkoxyamino, hydroxy, N-hydroxysuccinimide ester, p-nitrophenyl ester, dinitrophenyl ester, pentafluorophenyl ester, carboxylic acid chloride, carboxylic acid anhydride, pyridyldisulfide, nitropyridyldisulfide, maleimide, haloacetate, methylsulfonephenyloxadiazole, acyloxylamine, hydrazide, or alkyne.

* * * * *